US010772906B2

(12) United States Patent
Freier

(10) Patent No.: US 10,772,906 B2
(45) Date of Patent: Sep. 15, 2020

(54) MODULATION OF FACTOR 11 EXPRESSION

(71) Applicant: Ionis Pharmaceuticals, Inc., Carlsbad, CA (US)

(72) Inventor: Susan M. Freier, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 16/273,922

(22) Filed: Feb. 12, 2019

(65) Prior Publication Data

US 2020/0000839 A1 Jan. 2, 2020

Related U.S. Application Data

(63) Continuation of application No. 15/075,545, filed on Mar. 21, 2016, now abandoned, which is a continuation of application No. 13/693,939, filed on Dec. 4, 2012, now abandoned, which is a continuation of application No. 12/580,241, filed on Oct. 15, 2009, now Pat. No. 8,334,372.

(60) Provisional application No. 61/174,461, filed on Apr. 30, 2009, provisional application No. 61/105,772, filed on Oct. 15, 2008.

(51) Int. Cl.

| | |
|---|---|
| ***C12N 15/11*** | (2006.01) |
| ***A61K 48/00*** | (2006.01) |
| ***C07H 21/02*** | (2006.01) |
| ***C07H 21/04*** | (2006.01) |
| ***A61K 31/7125*** | (2006.01) |
| ***C07H 21/00*** | (2006.01) |
| ***C12N 15/113*** | (2010.01) |
| ***A61K 31/366*** | (2006.01) |
| ***A61K 31/4365*** | (2006.01) |
| ***A61K 31/4545*** | (2006.01) |
| ***A61K 31/713*** | (2006.01) |
| ***A61K 31/737*** | (2006.01) |
| ***A61K 31/727*** | (2006.01) |

(52) U.S. Cl.

CPC ........ *A61K 31/7125* (2013.01); *A61K 31/366* (2013.01); *A61K 31/4365* (2013.01); *A61K 31/4545* (2013.01); *A61K 31/713* (2013.01); *A61K 31/727* (2013.01); *A61K 31/737* (2013.01); *C07H 21/00* (2013.01); *C12N 15/1137* (2013.01); *C12Y 304/21027* (2013.01); *C12N 2310/11* (2013.01); *C12N 2310/315* (2013.01); *C12N 2310/321* (2013.01); *C12N 2310/3341* (2013.01); *C12N 2310/341* (2013.01); *C12N 2310/346* (2013.01)

(58) Field of Classification Search

CPC ............ C12N 15/1137; C12N 2310/11; C12N 2310/321; C12N 2310/341; C12N 2310/346; C12N 2310/3341; A61K 31/7125; A61K 31/713

See application file for complete search history.

(56) References Cited

U.S. PATENT DOCUMENTS

| | | | |
|---|---|---|---|
| 3,687,808 | A | 8/1972 | Merigan et al. |
| 4,415,732 | A | 11/1983 | Caruthers et al. |
| 4,469,863 | A | 9/1984 | Ts'o et al. |
| 4,476,301 | A | 10/1984 | Imbach et al. |
| 4,500,707 | A | 2/1985 | Caruthers et al. |
| 4,725,677 | A | 2/1988 | Koster et al. |
| 4,845,205 | A | 7/1989 | Huynh Dinh et al. |
| 4,973,679 | A | 11/1990 | Caruthers et al. |
| 4,981,957 | A | 1/1991 | Lebleu et al. |
| 5,013,830 | A | 5/1991 | Ohutsuka et al. |
| 5,023,243 | A | 6/1991 | Tullis |
| 5,034,506 | A | 7/1991 | Summerton et al. |
| 5,118,800 | A | 6/1992 | Smith et al. |
| 5,130,302 | A | 7/1992 | Spielvogel et al. |
| 5,132,418 | A | 7/1992 | Caruthers et al. |
| 5,134,066 | A | 7/1992 | Rogers et al. |
| RE34,036 | E | 8/1992 | McGeehan |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,177,198 | A | 1/1993 | Spielvogel et al. |
| 5,188,897 | A | 2/1993 | Suhadolnik et al. |
| 5,194,599 | A | 3/1993 | Froehler et al. |
| 5,214,134 | A | 5/1993 | Weis et al. |

(Continued)

FOREIGN PATENT DOCUMENTS

| | | |
|---|---|---|
| WO | WO 1995/017420 | 6/1995 |
| WO | WO 2000/056885 | 9/2000 |

(Continued)

OTHER PUBLICATIONS

GenBank accession No. FW775436.1.

(Continued)

*Primary Examiner* — Terra C Gibbs

(74) *Attorney, Agent, or Firm* — Knobbe, Martens, Olson & Bear, LLP

(57) ABSTRACT

Disclosed herein are antisense compounds and methods for decreasing Factor 11 and treating or preventing thromboembolic complications in an individual in need thereof. Examples of disease conditions that can be ameliorated with the administration of antisense compounds targeted to Factor 11 include thrombosis, embolism, and thromboembolism, such as, deep vein thrombosis, pulmonary embolism, myocardial infarction, and stroke. Antisense compounds targeting Factor 11 can also be used as a prophylactic treatment to prevent individuals at risk for thrombosis and embolism.

20 Claims, No Drawings

Specification includes a Sequence Listing.

(56) References Cited

U.S. PATENT DOCUMENTS 5,216,141 A 6/1993 Benner
5,220,007 A 6/1993 Pederson et al.
5,223,618 A 6/1993 Cook et al.
5,235,033 A 8/1993 Summerton et al.
5,256,775 A 10/1993 Froehler
5,264,423 A 11/1993 Cohen et al.
5,264,562 A 11/1993 Matteucci
5,264,564 A 11/1993 Matteucci
5,185,444 A 12/1993 Summerton et al.
5,276,019 A 1/1994 Cohen et al.
5,286,717 A 2/1994 Cohen et al.
5,319,080 A 6/1994 Leumann
5,321,131 A 6/1994 Agrawal et al.
5,359,044 A 10/1994 Cook et al.
5,366,878 A 11/1994 Pederson et al.
5,367,066 A 11/1994 Urdea et al.
5,378,825 A 1/1995 Cook et al.
5,386,023 A 1/1995 Sanghvi et al.
5,393,878 A 2/1995 Leumann
5,399,676 A 3/1995 Froehler
5,403,711 A 4/1995 Walder et al.
5,405,938 A 4/1995 Sumerton et al.
5,405,939 A 4/1995 Suhadolnik et al.
5,432,272 A 7/1995 Benner
5,434,257 A 7/1995 Matteucci
5,446,137 A 8/1995 Maag et al.
5,453,496 A 9/1995 Caruthers et al.
5,455,233 A 10/1995 Spielvogel et al.
5,457,187 A 10/1995 Gmelner et al.
5,457,191 A 10/1995 Cook et al.
5,459,255 A 10/1995 Cook et al.
5,466,677 A 11/1995 Baxter et al.
5,466,786 A 11/1995 Burh et al.
5,470,967 A 11/1995 Huie et al.
5,476,925 A 12/1995 Letsinger et al.
5,484,908 A 1/1996 Froehler et al.
5,489,677 A 2/1996 Sanghvi et al.
5,491,133 A 2/1996 Walder et al.
5,502,177 A 3/1996 Matteucci et al.
5,508,270 A 4/1996 Baxter et al.
5,514,785 A 5/1996 Van Ness et al.
5,519,126 A 5/1996 Hecht
5,519,134 A 5/1996 Acevedo et al.
5,525,711 A 6/1996 Hawkins et al.
5,527,899 A 6/1996 Froehler
5,536,821 A 7/1996 Agrawal et al.
5,541,306 A 7/1996 Agrawal et al.
5,541,307 A 7/1996 Cook et al.
5,550,111 A 8/1996 Suhadolnik et al.
5,552,540 A 9/1996 Haralambidis
5,561,225 A 10/1996 Maddry et al.
5,563,253 A 10/1996 Agrawal et al.
5,565,350 A 10/1996 Kmiec
5,565,555 A 10/1996 Froehler et al.
5,567,811 A 10/1996 Mistura et al.
5,571,799 A 11/1996 Tkachuk et al.
5,576,427 A 11/1996 Cook et al.
5,587,361 A 12/1996 Cook et al.
5,587,469 A 12/1996 Cook et al.
5,587,470 A 12/1996 Cook et al.
5,591,722 A 1/1997 Montgomery et al.
5,594,121 A 1/1997 Froehler et al.
5,596,086 A 1/1997 Matteucci
5,596,091 A 1/1997 Switzer
5,597,909 A 1/1997 Urdea et al.
5,602,240 A 2/1997 De Mesmaeker et al.
5,608,046 A 3/1997 Cook et al.
5,610,289 A 3/1997 Cook et al.
5,610,300 A 3/1997 Altmann et al.
5,614,617 A 3/1997 Cook et al.
5,618,704 A 4/1997 Sanghvi et al.
5,623,065 A 4/1997 Cook et al.
5,623,070 A 4/1997 Cook et al.
5,625,050 A 4/1997 Beaton et al.
5,627,053 A 5/1997 Usman et al.
5,633,360 A 5/1997 Bishofberger et al.
5,639,873 A 6/1997 Barascut et al.
5,645,985 A 7/1997 Froehler et al.
5,646,265 A 7/1997 McGee
5,646,269 A 7/1997 Matteucci
5,652,355 A 7/1997 Metelev et al.
5,652,356 A 7/1997 Agrawal
5,663,312 A 9/1997 Chaturvedula
5,670,633 A 9/1997 Cook et al.
5,672,697 A 9/1997 Buhr et al.
5,677,437 A 10/1997 Teng et al.
5,677,439 A 10/1997 Weis et al.
5,681,941 A 10/1997 Cook et al.
5,698,685 A 12/1997 Summerton et al.
5,700,920 A 12/1997 Altmann et al.
5,700,922 A 12/1997 Cook
5,721,218 A 2/1998 Froehler
5,750,692 A 5/1998 Cook et al.
5,763,588 A 6/1998 Matteucci et al.
5,792,608 A 8/1998 Swaminathan et al.
5,792,847 A 8/1998 Burh et al.
5,808,027 A 9/1998 Cook et al.
5,830,653 A 11/1998 Froehler et al.
5,859,221 A 1/1999 Cook et al.
5,948,903 A 9/1999 Cook et al.
5,994,517 A 11/1999 Ts'O
6,005,087 A 12/1999 Cook et al.
6,005,096 A 12/1999 Matteucci et al.
6,166,199 A 12/2000 Cook et al.
6,300,319 B1 10/2001 Manoharan
6,426,220 B1 7/2002 Bennett et al.
6,525,191 B1 2/2003 Ramasamy
6,531,584 B1 3/2003 Cook et al.
6,600,032 B1 7/2003 Manoharan et al.
6,660,720 B2 12/2003 Manoharan
6,770,748 B2 8/2004 Imanishi et al.
7,015,315 B1 3/2006 Cook et al.
7,053,207 B2 5/2006 Wengel et al.
7,101,993 B1 9/2006 Cook et al.
7,262,177 B2 8/2007 Ts'o et al.
7,399,845 B2 7/2008 Seth et al.
7,427,672 B2 9/2008 Imanishi et al.
7,491,805 B2 2/2009 Vargeese et al.
7,547,684 B2 6/2009 Seth et al.
7,569,686 B1 8/2009 Bhat et al.
7,666,854 B2 2/2010 Seth et al.
7,696,345 B2 4/2010 Allerson et al.
7,723,509 B2 5/2010 Manoharan et al.
7,741,457 B2 6/2010 Swayze et al.
7,750,131 B2 7/2010 Seth et al.
7,875,733 B2 1/2011 Bhat et al.
7,939,677 B2 5/2011 Bhat et al.
8,022,193 B2 9/2011 Swayze et al.
8,030,467 B2 10/2011 Seth et al.
8,080,644 B2 12/2011 Wengel et al.
8,088,746 B2 1/2012 Seth et al.
8,088,904 B2 1/2012 Swayze et al.
8,106,022 B2 1/2012 Manoharan et al.
8,124,745 B2 2/2012 Allerson et al.
8,153,365 B2 4/2012 Wengel et al.
8,268,980 B2 9/2012 Seth et al.
8,278,283 B2 10/2012 Seth et al.
8,278,425 B2 10/2012 Prakash et al.
8,278,426 B2 10/2012 Seth et al.
8,440,803 B2 5/2013 Swayze et al.
8,501,805 B2 8/2013 Seth et al.
8,530,640 B2 9/2013 Seth et al.
8,546,556 B2 10/2013 Seth et al.
RE44,779 E 2/2014 Imanishi et al.
8,828,956 B2 9/2014 Manoharan et al.
9,005,906 B2 4/2015 Swayze et al.
9,012,421 B2 4/2015 Migawa et al.
9,127,276 B2 8/2015 Prakash et al.
9,290,760 B2 3/2016 Rajeev et al.
2003/0158403 A1 8/2003 Manoharan et al.
2003/0175906 A1 9/2003 Manoharan et al.
2004/0171570 A1 9/2004 Allerson et al.
2005/0130923 A1 6/2005 Bhat et al.
2006/0148740 A1 7/2006 Platenburg

(56) References Cited

U.S. PATENT DOCUMENTS

| | | | |
|---|---|---|---|
| 2008/0039618 | A1 | 2/2008 | Allerson et al. |
| 2010/0190837 | A1 | 7/2010 | Migawa et al. |
| 2010/0197762 | A1 | 8/2010 | Swayze et al. |
| 2013/0130378 | A1 | 5/2013 | Manoharan et al. |
| 2014/0107330 | A1 | 4/2014 | Freier et al. |
| 2015/0018540 | A1 | 1/2015 | Prakash et al. |
| 2015/0184153 | A1 | 7/2015 | Freier et al. |
| 2015/0191727 | A1 | 7/2015 | Migawa et al. |
| 2015/0267195 | A1 | 9/2015 | Seth et al. |
| 2015/0275212 | A1 | 10/2015 | Albaek et al. |

FOREIGN PATENT DOCUMENTS

| | | |
|---|---|---|
| WO | WO 2005/116204 | 12/2004 |
| WO | WO 2013/070771 | 5/2013 |
| WO | WO 2015/188194 | 12/2015 |

OTHER PUBLICATIONS

European Search Report for application EP 17201814.5 dated Jul. 6, 2018.

Crooke, ST., et al., “Antisense Drug Technology” Second Edition, CRC Press (2008) Chapters 1-28.

Egli, et al., “Synthesis, improved antisense activity and structural rationale for the divergent RNA affinities of 3'-fluoro hexitol nucleic acid (FHNA and Ara-FHNA) modified oligonucleotides.” J Am Chem (2011) 133(41):16642-16649.

Seth et al., “Short Antisense Oligonucleotides with Novel 2'-4' Conformationaly Restricted Nucleoside Analogues Show Improved Potency Without Increased Toxicity in Animals.” J Med Chem (2009) 52:10-13.

Woolf et al., “Specificity of antisense oligonucleotides in vivo” PNAS (1992) 89:7305-7309.

MODULATION OF FACTOR 11 EXPRESSION

SEQUENCE LISTING

The present application is being filed along with a Sequence Listing in electronic format. The Sequence Listing is provided as a file entitled BIOL0107USC3SEQ_ST25.txt created Feb. 7, 2019, which is 100 Kb in size. The information in the electronic format of the sequence listing is incorporated herein by reference in its entirety.

FIELD OF THE INVENTION

Embodiments of the present invention provide methods, compounds, and compositions for reducing expression of Factor 11 mRNA and protein in an animal. Such methods, compounds, and compositions are useful to treat, prevent, or ameliorate thromboembolic complications.

BACKGROUND OF THE INVENTION

The circulatory system requires mechanisms that prevent blood loss, as well as those that counteract inappropriate intravascular obstructions. Generally, coagulation comprises a cascade of reactions culminating in the conversion of soluble fibrinogen to an insoluble fibrin gel. The steps of the cascade involve the conversion of an inactive zymogen to an activated enzyme. The active enzyme then catalyzes the next step in the cascade.

Coagulation Cascade

The coagulation cascade may be initiated through two branches, the tissue factor pathway (also "extrinsic pathway"), which is the primary pathway, and the contact activation pathway (also "intrinsic pathway").

The tissue factor pathway is initiated by the cell surface receptor tissue factor (TF, also referred to as factor III), which is expressed constitutively by extravascular cells (pericytes, cardiomyocytes, smooth muscle cells, and keratinocytes) and expressed by vascular monocytes and endothelial cells upon induction by inflammatory cytokines or endotoxin. (Drake et al., *Am J Pathol* 1989, 134:1087-1097). TF is the high affinity cellular receptor for coagulation factor VIIa, a serine protease. In the absence of TF, VIIa has very low catalytic activity, and binding to TF is necessary to render VIIa functional through an allosteric mechanism. (Drake et al., *Am J Pathol* 1989, 134:1087-1097). The TF-VIIa complex activates factor X to Xa. Xa in turn associates with its co-factor factor Va into a prothrombinase complex which in turn activates prothrombin, (also known as factor II or factor 2) to thrombin (also known as factor IIa, or factor 2a). Thrombin activates platelets, converts fibrinogen to fibrin and promotes fibrin cross-linking by activating factor XIII, thus forming a stable plug at sites where TF is exposed on extravascular cells. In addition, thrombin reinforces the coagulation cascade response by activating factors V and VIII.

The contact activation pathway is triggered by activation of factor XII to XIIa. Factor XIIa converts XI to XIa, and XIa converts IX to IXa. IXa associates with its cofactor VIIIa to convert X to Xa. The two pathways converge at this point as factor Xa associates factor Va to activate prothrombin (factor II) to thrombin (factor IIa).

Inhibition of Coagulation.

At least three mechanisms keep the coagulation cascade in check, namely the action of activated protein C, antithrombin, and tissue factor pathway inhibitor. Activated protein C is a serine protease that degrades cofactors Va and VIIIa. Protein C is activated by thrombin with thrombomodulin, and requires coenzyme Protein S to function. Antithrombin is a serine protease inhibitor (serpin) that inhibits serine proteases: thrombin, Xa, XIIa, XIa and IXa. Tissue factor pathway inhibitor inhibits the action of Xa and the TF-VIIa complex. (Schwartz A L et al., *Trends Cardiovasc Med.* 1997; 7:234-239.)

Disease

Thrombosis is the pathological development of blood clots, and an embolism occurs when a blood clot migrates to another part of the body and interferes with organ function. Thromboembolism may cause conditions such as deep vein thrombosis, pulmonary embolism, myocardial infarction, and stroke. Significantly, thromboembolism is a major cause of morbidity affecting over 2 million Americans every year. (Adcock et al. *American Journal of Clinical Pathology.* 1997; 108:434-49). While most cases of thrombosis are due to acquired extrinsic problems, for example, surgery, cancer, immobility, some cases are due to a genetic predisposition, for example, antiphospholipid syndrome and the autosomal dominant condition, Factor V Leiden. (Bertina R M et al. *Nature* 1994; 369:64-67.)

Treatment.

The most commonly used anticoagulants, warfarin, heparin, and low molecular weight heparin (LMWH) all possess significant drawbacks.

Warfarin is typically used to treat patients suffering from atrial fibrillation. The drug interacts with vitamin K-dependent coagulation factors which include factors II, VII, IX and X. Anticoagulant proteins C and S are also inhibited by warfarin. Drug therapy using warfarin is further complicated by the fact that warfarin interacts with other medications, including drugs used to treat atrial fibrillation, such as amiodarone. Because therapy with warfarin is difficult to predict, patients must be carefully monitored in order to detect any signs of anomalous bleeding.

Heparin functions by activating antithrombin which inhibits both thrombin and factor X. (Bjork I, Lindahl U. *Mol Cell Biochem.* 1982 48: 161-182.) Treatment with heparin may cause an immunological reaction that makes platelets aggregate within blood vessels that can lead to thrombosis. This side effect is known as heparin-induced thrombocytopenia (HIT) and requires patient monitoring. Prolonged treatment with heparin may also lead to osteoporosis. LMWH can also inhibit Factor 2, but to a lesser degree than unfractioned heparin (UFH). LMWH has been implicated in the development of HIT.

Thus, current anticoagulant agents lack predictability and specificity and, therefore, require careful patient monitoring to prevent adverse side effects, such as bleeding complications. There are currently no anticoagulants which target only the intrinsic or extrinsic pathway.

SUMMARY OF THE INVENTION

Provided herein are methods, compounds, and compositions for modulating expression of Factor 11 mRNA and protein. In certain embodiments, Factor 11 specific inhibitors modulate expression of Factor 11 mRNA and protein. In certain embodiments, Factor 11 specific inhibitors are nucleic acids, proteins, or small molecules.

In certain embodiments, modulation can occur in a cell or tissue. In certain embodiments, the cell or tissue is in an animal. In certain embodiments, the animal is a human. In certain embodiments, Factor 11 mRNA levels are reduced. In certain embodiments, Factor 11 protein levels are reduced. Such reduction can occur in a time-dependent manner or in a dose-dependent manner.

Also provided are methods, compounds, and compositions useful for preventing, treating, and ameliorating diseases, disorders, and conditions. In certain embodiments, such diseases, disorders, and conditions are thromboembolic complications. Such thromboembolic complications include the categories of thrombosis, embolism, and thromboembolism. In certain embodiments such thromboembolic complications include deep vein thrombosis, pulmonary embolism, myocardial infarction, and stroke.

Such diseases, disorders, and conditions can have one or more risk factors, causes, or outcomes in common. Certain risk factors and causes for development of a thromboembolic complication include immobility, surgery (particularly orthopedic surgery), malignancy, pregnancy, older age, use of oral contraceptives, atrial fibrillation, previous thromboembolic complication, chronic inflammatory disease, and inherited or acquired prothrombotic clotting disorders. Certain outcomes associated with development of a thromboembolic complication include decreased blood flow through an affected vessel, death of tissue, and death.

In certain embodiments, methods of treatment include administering a Factor 11 specific inhibitor to an individual in need thereof.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O$(CH_2)_2$—$OCH_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to the 5' position. A 5-methylcytosine is a modified nucleobase.

"Active pharmaceutical agent" means the substance or substances in a pharmaceutical composition that provide a therapeutic benefit when administered to an individual. For example, in certain embodiments an antisense oligonucleotide targeted to Factor 11 is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Amelioration" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antidote compound" refers to a compound capable of decreasing the intensity or duration of any antisense-mediated activity.

"Antidote oligonucleotide" means an antidote compound comprising an oligonucleotide that is complementary to and capable of hybridizing with an antisense compound.

"Antidote protein" means an antidote compound comprising a peptide.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Coagulation factor" means any of factors I, II, III, IV, V, VII, VIII, IX, X, XI, XII, XIII, or TAFI in the blood coagulation cascade. "Coagulation factor nucleic acid" means any nucleic acid encoding a coagulation factor. For example, in certain embodiments, a coagulation factor nucleic acid includes, without limitation, a DNA sequence encoding a coagulation factor (including genomic DNA comprising introns and exons), an RNA sequence transcribed from DNA encoding a coagulation factor, and an mRNA sequence encoding a coagulation factor. "Coagulation factor mRNA" means an mRNA encoding a coagulation factor protein.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Factor 11 nucleic acid" or "Factor XI nucleic acid" or "F 11 nucleic acid" or "F XI nucleic acid" means any nucleic acid encoding Factor 11. For example, in certain embodiments, a Factor 11 nucleic acid includes a DNA sequence encoding Factor 11, an RNA sequence transcribed from DNA encoding Factor 11 (including genomic DNA comprising introns and exons), and an mRNA sequence encoding Factor 11. "Factor 11 mRNA" means an mRNA encoding a Factor 11 protein.

"Factor 11 specific inhibitor" refers to any agent capable of specifically inhibiting the expression of Factor 11 mRNA and/or Factor 11 protein at the molecular level. For example, Factor 11 specific inhibitors include nucleic acids (including antisense compounds), peptides, antibodies, small molecules, and other agents capable of inhibiting the expression of Factor 11 mRNA and/or Factor 11 protein. In certain embodiments, by specifically modulating Factor 11 mRNA expression and/or Factor 11 protein expression, Factor 11 specific inhibitors may affect other components of the coagulation cascade including downstream components. Similarly, in certain embodiments, Factor 11 specific inhibitors may affect other molecular processes in an animal.

"Factor 11 specific inhibitor antidote" means a compound capable of decreasing the effect of a Factor 11 specific inhibitor. In certain embodiments, a Factor 11 specific inhibitor antidote is selected from a Factor 11 peptide; a Factor 11 antidote oligonucleotide, including a Factor 11 antidote compound complementary to a Factor 11 antisense compound; and any compound or protein that affects the intrinsic or extrinsic coagulation pathway.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap segment" and the external regions may be referred to as "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Hybridization" means the annealing of complementary nucleic acid molecules. In certain embodiments, complementary nucleic acid molecules include an antisense compound and a target nucleic acid.

"Identifying an animal at risk for thromboembolic complications" means identifying an animal having been diagnosed with a thromboembolic complication or identifying an animal predisposed to develop a thromboembolic complication. Individuals predisposed to develop a thromboembolic complication include those having one or more risk factors for thromboembolic complications including immobility, surgery (particularly orthopedic surgery), malignancy, pregnancy, older age, use of oral contraceptives, and inherited or acquired prothrombotic clotting disorders. Such identification may be accomplished by any method including evaluating an individual's medical history and standard clinical tests or assessments.

"Immediately adjacent" means there are no intervening elements between the immediately adjacent elements.

"Individual" means a human or non-human animal selected for treatment or therapy.

"Internucleoside linkage" refers to the chemical bond between nucleosides.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising a modified internucleoside linkage, a modified sugar, or a modified nucleobase.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics e.g. non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(═O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Nucleotide" means a nucleoside having a phosphate group covalently linked to the sugar portion of the nucleoside.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage (P═S) is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Thromboembolic complication" means any disease, disorder, or condition involving an embolism caused by a thrombus. Examples of such diseases, disorders, and conditions include the categories of thrombosis, embolism, and thromboembolism. In certain embodiments, such disease disorders, and conditions include deep vein thrombosis, pulmonary embolism, myocardial infarction, and stroke.

"Treat" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Embodiments of the present invention provide methods, compounds, and compositions for decreasing Factor 11 mRNA and protein expression.

Embodiments of the present invention provide methods, compounds, and compositions for the treatment, prevention, or amelioration of diseases, disorders, and conditions associated with Factor 11 in an individual in need thereof. Also contemplated are methods and compounds for the preparation of a medicament for the treatment, prevention, or amelioration of a disease, disorder, or condition associated with Factor 11. Factor 11 associated diseases, disorders, and conditions include thromboembolic complications such as thrombosis, embolism, thromboembolism, deep vein thrombosis, pulmonary embolism, myocardial infarction, and stroke.

Embodiments of the present invention provide a Factor 11 specific inhibitor for use in treating, preventing, or ameliorating a Factor 11 associated disease. In certain embodiments, Factor 11 specific inhibitors are nucleic acids (including antisense compounds), peptides, antibodies, small molecules, and other agents capable of inhibiting the expression of Factor 11 mRNA and/or Factor 11 protein.

In certain embodiments of the present invention, Factor 11 specific inhibitors are peptides or proteins, such as, but not limited to, alpha 1 protease inhibitors, antithrombin III, C1 inhibitors, and alpha 2 plasmin inhibitors as described in *J Clin Invest* 1982, 69:844-852; alpha 1 antitrypsin (alpha 1AT) as described in *Thromb Res* 1987, 48:145-151; Factor 11 peptide inhibitors as described in USPPN 2008/021998 and Blood 1998, 92:4198-206; MAP4-RGKWC as described in *Thromb Res* 2001, 104:451-465; beta 2 GPI as described in *Proc Natl Acad Sci* 2004, 101:3939-44; Lentinus proteinase inhibitor as described in *Eur J Biochem* 1999, 262:915-923; protease nexin-2/amyloid beta protein precursor Kunitz domain inhibitor (APPI) and antithrombin (AT) as described in *J Biol Chem* 2004, 279:29485-29492; and aprotinin as described in *J Biol Chem* 2005, 280:23523-30.

In certain embodiments of the present invention, Factor 11 specific inhibitors are antibodies, such as, but not limited to, Winston-Salem (IgG3 kappa) and Baltimore (IgG1 kappa) as described in Blood 1988, 72:1748-54; 5F4, 3C1, and 1F1 as described in *J Biol Chem* 1985, 260:10714-719; monoclonal antibodies as described in Throm Haemost 1990, 63:417-23; XI-5108 as described in J Thromb Haem 2006, 4:1496-1501; monoclonal antibodies 4-1 as described in *Thromb Res* 1986, 42:225-34; and abcixmab antibody as described in Example 19 of U.S. Pat. No. 6,566,140.

In certain embodiments of the present invention, Factor 11 specific inhibitors are small molecules, such as, but not limited to, diisopropyl fluorophosphates (DFP); the small molecule inhibitors as described in Examples 1-7 of USPPN 2004/0180855; and p-aminobenzamidine (pAB) as described in *J Biol Chem* 2005, 280:23523-30.

Embodiments of the present invention provide a Factor 11 specific inhibitor, as described herein, for use in treating, preventing, or ameliorating thromboembolic complications such as thrombosis, embolism, thromboembolism, deep vein thrombosis, pulmonary embolism, myocardial infarction, and stroke.

Embodiments of the present invention provide the use of Factor 11 specific inhibitors as described herein in the manufacture of a medicament for treating, ameliorating, or preventing a thromboembolic complication such as thrombosis, embolism, thromboembolism, deep vein thrombosis, pulmonary embolism, myocardial infarction, and stroke.

Embodiments of the present invention provide a Factor 11 specific inhibitor as described herein for use in treating, preventing, or ameliorating a thromboembolic complication as described herein by combination therapy with an additional agent or therapy as described herein. Agents or therapies can be co-administered or administered concomitantly.

Embodiments of the present invention provide the use of a Factor 11 specific inhibitor as described herein in the manufacture of a medicament for treating, preventing, or ameliorating a thromboembolic complication as described herein by combination therapy with an additional agent or therapy as described herein. Agents or therapies can be co-administered or administered concomitantly.

Embodiments of the present invention provide the use of a Factor 11 specific inhibitor as described herein in the manufacture of a medicament for treating, preventing, or ameliorating a thromboembolic complication as described herein in a patient who is subsequently administered an additional agent or therapy as described herein.

Embodiments of the present invention provide a kit for treating, preventing, or ameliorating a thromboembolic complication as described herein wherein the kit comprises:

(i) a Factor 11 specific inhibitor as described herein; and alternatively (ii) an additional agent or therapy as described herein.

A kit of the present invention may further include instructions for using the kit to treat, prevent, or ameliorate a thromboembolic complication as described herein by combination therapy as described herein.

Embodiments of the present invention provide antisense compounds targeted to a Factor 11 nucleic acid. In certain embodiments, the Factor 11 nucleic acid is any of the sequences set forth in GENBANK Accession No. NM_000128.3 (incorporated herein as SEQ ID NO: 1), GENBANK Accession No. NT_022792.17, truncated from Ser. No. 19/598,000 to Ser. No. 19/624,000, (incorporated herein as SEQ ID NO: 2), GENBANK Accession No. NM_028066.1 (incorporated herein as SEQ ID NO: 6), exons 1-15 GENBANK Accession No. NW 001118167.1 (incorporated herein as SEQ ID NO: 274).

In certain embodiments, the invention provides a compound comprising a modified oligonucleotide. In certain embodiments, the compound of the invention comprises a modified oligonucleotide consisting of 12 to 30 linked nucleosides.

In certain embodiments, the compound of the invention may comprise a modified oligonucleotide comprising a nucleobase sequence at least 80%, at least 85%, at least 90%, at least 95%, at least 96%, at least 97%, at least 98%, or at least 99% complementary to an equal length portion of SEQ ID NO: 1. In certain embodiments, the compound of the invention may comprise a modified oligonucleotide comprising a nucleobase sequence 100% complementary to an equal length portion of SEQ ID NO: 1.

In certain embodiments, the invention provides a compound comprising a modified oligonucleotide comprising a nucleobase sequence complementary to at least a portion of nucleobases 656 to 676 of SEQ ID NO: 1. Said modified oligonucleotide may comprise at least 8, at least 10, at least 12, at least 14, at least 16, at least 18 or 20 contiguous nucleobases complementary to an equal length portion of nucleobases 656 to 676 of SEQ ID NO: 1. Said modified oligonucleotide may comprise a nucleobase sequence at least 80%, at least 85%, at least 90%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 80% inhibition of human mRNA levels as determined using an RT-PCR assay method, optionally in HepG2 cells (e.g. as described in Example 3).

In certain embodiments, the invention provides a compound comprising a modified oligonucleotide comprising a nucleobase sequence complementary to at least a portion of nucleobases 665 to 687 of SEQ ID NO: 1. Said modified oligonucleotide may comprise at least 8, at least 10, at least 12, at least 14, at least 16, at least 18 or 20 contiguous nucleobases complementary to an equal length portion of nucleobases 665 to 687 of SEQ ID NO: 1. Said modified oligonucleotide may comprise a nucleobase sequence at least 80%, at least 85%, at least 90%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 50% inhibition of human mRNA levels as determined using an RT-PCR assay method, optionally in HepG2 cells (e.g. as described in Example 3).

In certain embodiments, the invention provides a compound comprising a modified oligonucleotide comprising a nucleobase sequence complementary to at least a portion of nucleobases 675 to 704 of SEQ ID NO: 1. Said modified oligonucleotide may comprise at least 8, at least 10, at least 12, at least 14, at least 16, at least 18 or 20 contiguous nucleobases complementary to an equal length portion of nucleobases 675 to 704 of SEQ ID NO: 1. Said modified oligonucleotide may comprise a nucleobase sequence at least 80%, at least 85%, at least 90%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 50% inhibition of human mRNA levels as determined using an RT-PCR assay method, optionally in HepG2 cells (e.g. as described in Example 3).

In certain embodiments, the invention provides a compound comprising a modified oligonucleotide comprising a nucleobase sequence complementary to at least a portion of nucleobases 677 to 704 of SEQ ID NO: 1. Said modified oligonucleotide may comprise at least 8, at least 10, at least 12, at least 14, at least 16, at least 18 or 20 contiguous nucleobases complementary to an equal length portion of nucleobases 677 to 704 of SEQ ID NO: 1. Said modified oligonucleotide may comprise a nucleobase sequence at least 80%, at least 85%, at least 90%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 60% inhibition of human mRNA levels as determined using an RT-PCR assay method, optionally in HepG2 cells (e.g. as described in Example 3).

In certain embodiments, the invention provides a compound comprising a modified oligonucleotide comprising a nucleobase sequence complementary to at least a portion of nucleobases 678 to 697 of SEQ ID NO: 1. Said modified oligonucleotide may comprise at least 8, at least 10, at least 12, at least 14, at least 16, at least 18 or 20 contiguous nucleobases complementary to an equal length portion of nucleobases 678 to 697 of SEQ ID NO: 1. Said modified oligonucleotide may comprise a nucleobase sequence at least 80%, at least 85%, at least 90%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 70% inhibition of human mRNA levels as determined using an RT-PCR assay method, optionally in HepG2 cells (e.g. as described in Example 3).

In certain embodiments, the invention provides a compound comprising a modified oligonucleotide comprising a nucleobase sequence complementary to at least a portion of nucleobases 680 to 703 of SEQ ID NO: 1. Said modified oligonucleotide may comprise at least 8, at least 10, at least 12, at least 14, at least 16, at least 18 or 20 contiguous nucleobases complementary to an equal length portion of nucleobases 680 to 703 of SEQ ID NO: 1. Said modified oligonucleotide may comprise a nucleobase sequence at least 80%, at least 85%, at least 90%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 80% inhibition of human mRNA levels as determined using an RT-PCR assay method, optionally in HepG2 cells (e.g. as described in Example 3 and Example 30).

In certain embodiments, the invention provides a compound comprising a modified oligonucleotide comprising a nucleobase sequence complementary to at least a portion of nucleobases 683 to 702 of SEQ ID NO: 1. Said modified oligonucleotide may comprise at least 8, at least 10, at least 12, at least 14, at least 16, at least 18 or 20 contiguous nucleobases complementary to an equal length portion of nucleobases 683 to 702 of SEQ ID NO: 1. Said modified oligonucleotide may comprise a nucleobase sequence at least 80%, at least 85%, at least 90%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 90% inhibition of human mRNA levels as determined using an RT-PCR assay method, optionally in HepG2 cells (e.g. as described in Example 3).

In certain embodiments, the invention provides a compound comprising a modified oligonucleotide comprising a nucleobase sequence complementary to at least a portion of nucleobases 738 to 759 of SEQ ID NO: 1. Said modified oligonucleotide may comprise at least 8, at least 10, at least 12, at least 14, at least 16, at least 18 or 20 contiguous nucleobases complementary to an equal length portion of nucleobases 738 to 759 of SEQ ID NO: 1. Said modified oligonucleotide may comprise a nucleobase sequence at least 80%, at least 85%, at least 90%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 80% inhibition of human mRNA levels as determined using an RT-PCR assay method, optionally in HepG2 cells (e.g. as described in Example 3 and Example 30).

In certain embodiments, the invention provides a compound comprising a modified oligonucleotide comprising a nucleobase sequence complementary to at least a portion of nucleobases 738 to 760 of SEQ ID NO: 1. Said modified oligonucleotide may comprise at least 8, at least 10, at least 12, at least 14, at least 16, at least 18 or 20 contiguous nucleobases complementary to an equal length portion of nucleobases 738 to 760 of SEQ ID NO: 1. Said modified oligonucleotide may comprise a nucleobase sequence at least 80%, at least 85%, at least 90%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 60% inhibition of human mRNA levels as determined using an RT-PCR assay method, optionally in HepG2 cells (e.g. as described in Example 3).

In certain embodiments, the invention provides a compound comprising a modified oligonucleotide comprising a nucleobase sequence complementary to at least a portion of nucleobases 738 to 762 of SEQ ID NO: 1. Said modified oligonucleotide may comprise at least 8, at least 10, at least 12, at least 14, at least 16, at least 18 or 20 contiguous nucleobases complementary to an equal length portion of nucleobases 738 to 762 of SEQ ID NO: 1. Said modified oligonucleotide may comprise a nucleobase sequence at least 80%, at least 85%, at least 90%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 45% inhibition of human mRNA levels as determined using an RT-PCR assay method, optionally in HepG2 cells (e.g. as described in Example 3).

In certain embodiments, the invention provides a compound comprising a modified oligonucleotide comprising a nucleobase sequence complementary to at least a portion of nucleobases 1018 to 1042 of SEQ ID NO: 1. Said modified oligonucleotide may comprise at least 8, at least 10, at least 12, at least 14, at least 16, at least 18 or 20 contiguous nucleobases complementary to an equal length portion of nucleobases 1018 to 1042 of SEQ ID NO: 1. Said modified oligonucleotide may comprise a nucleobase sequence at least 80%, at least 85%, at least 90%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 80% inhibition of human mRNA levels as determined using an RT-PCR assay method, optionally in HepG2 cells (e.g. as described in Example 3).

In certain embodiments, the invention provides a compound comprising a modified oligonucleotide comprising a nucleobase sequence complementary to at least a portion of nucleobases 1062 to 1089 of SEQ ID NO: 1. Said modified oligonucleotide may comprise at least 8, at least 10, at least 12, at least 14, at least 16, at least 18 or 20 contiguous nucleobases complementary to an equal length portion of nucleobases 1062 to 1089 of SEQ ID NO: 1. Said modified oligonucleotide may comprise a nucleobase sequence at least 80%, at least 85%, at least 90%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 70% inhibition of human mRNA levels as determined using an RT-PCR assay method, optionally in HepG2 cells (e.g. as described in Example 3).

In certain embodiments, the invention provides a compound comprising a modified oligonucleotide comprising a nucleobase sequence complementary to at least a portion of nucleobases 1062 to 1090 of SEQ ID NO: 1. Said modified oligonucleotide may comprise at least 8, at least 10, at least 12, at least 14, at least 16, at least 18 or 20 contiguous nucleobases complementary to an equal length portion of nucleobases 1062 to 1090 of SEQ ID NO: 1. Said modified oligonucleotide may comprise a nucleobase sequence at least 80%, at least 85%, at least 90%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 60% inhibition of human mRNA levels as determined using an RT-PCR assay method, optionally in HepG2 cells (e.g. as described in Example 3).

In certain embodiments, the invention provides a compound comprising a modified oligonucleotide comprising a nucleobase sequence complementary to at least a portion of nucleobases 1062 to 1091 of SEQ ID NO: 1. Said modified oligonucleotide may comprise at least 8, at least 10, at least 12, at least 14, at least 16, at least 18 or 20 contiguous nucleobases complementary to an equal length portion of nucleobases 1062 to 1091 of SEQ ID NO: 1. Said modified oligonucleotide may comprise a nucleobase sequence at least 80%, at least 85%, at least 90%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 20% inhibition of human mRNA levels as determined using an RT-PCR assay method, optionally in HepG2 cells (e.g. as described in Example 3).

In certain embodiments, the invention provides a compound comprising a modified oligonucleotide comprising a nucleobase sequence complementary to at least a portion of nucleobases 1275 to 1301 of SEQ ID NO: 1. Said modified oligonucleotide may comprise at least 8, at least 10, at least 12, at least 14, at least 16, at least 18 or 20 contiguous nucleobases complementary to an equal length portion of nucleobases 1062 to 1091 of SEQ ID NO: 1. Said modified oligonucleotide may comprise a nucleobase sequence at least 80%, at least 85%, at least 90%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 80% inhibition of human mRNA levels as determined using an RT-PCR assay method, optionally in HepG2 cells (e.g. as described in Example 3).

In certain embodiments, the invention provides a compound comprising a modified oligonucleotide comprising a nucleobase sequence complementary to at least a portion of nucleobases 1276 to 1301 of SEQ ID NO: 1. Said modified oligonucleotide may comprise at least 8, at least 10, at least 12, at least 14, at least 16, at least 18 or 20 contiguous nucleobases complementary to an equal length portion of nucleobases 1062 to 1091 of SEQ ID NO: 1. Said modified oligonucleotide may comprise a nucleobase sequence at least 80%, at least 85%, at least 90%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 80% inhibition of human mRNA levels as determined using an RT-PCR assay method, optionally in HepG2 cells (e.g. as described in Example 30).

In certain embodiments, the invention provides a compound comprising a modified oligonucleotide comprising a nucleobase sequence complementary to at least a portion of nucleobases 1284 to 1308 of SEQ ID NO: 1. Said modified oligonucleotide may comprise at least 8, at least 10, at least 12, at least 14, at least 16, at least 18 or 20 contiguous nucleobases complementary to an equal length portion of nucleobases 1062 to 1091 of SEQ ID NO: 1. Said modified oligonucleotide may comprise a nucleobase sequence at least 80%, at least 85%, at least 90%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 80% inhibition of human mRNA levels as determined using an RT-PCR assay method, optionally in HepG2 cells (e.g. as described in Example 3).

In certain embodiments, the invention provides a compound comprising a modified oligonucleotide comprising a nucleobase sequence complementary to at least a portion of nucleobases 1291 to 1317 of SEQ ID NO: 1. Said modified oligonucleotide may comprise at least 8, at least 10, at least 12, at least 14, at least 16, at least 18 or 20 contiguous nucleobases complementary to an equal length portion of nucleobases 1062 to 1091 of SEQ ID NO: 1. Said modified oligonucleotide may comprise a nucleobase sequence at least 80%, at least 85%, at least 90%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 80% inhibition of human mRNA levels as determined using an RT-PCR assay method, optionally in HepG2 cells (e.g. as described in Example 3).

In certain embodiments, the invention provides a compound comprising a modified oligonucleotide comprising a nucleobase sequence complementary to at least a portion of nucleobases 1275 to 1318 of SEQ ID NO: 1. Said modified oligonucleotide may comprise at least 8, at least 10, at least 12, at least 14, at least 16, at least 18 or 20 contiguous nucleobases complementary to an equal length portion of nucleobases 1275 to 1318 of SEQ ID NO: 1. Said modified oligonucleotide may comprise a nucleobase sequence at least 80%, at least 85%, at least 90%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 70% inhibition of human mRNA levels as determined using an RT-PCR assay method, optionally in HepG2 cells (e.g. as described in Example 3).

Embodiments of the present invention provide compounds comprising a modified oligonucleotide consisting of 12 to 30 linked nucleosides and having a nucleobase sequence comprising at least 8, at least 10, at least 12, at least 14, at least 16, at least 18, or 20 contiguous nucleobases of a nucleobase sequence selected from among the nucleobase sequences recited in SEQ ID NOs: 15 to 241.

Embodiments of the present invention provide compounds comprising a modified oligonucleotide consisting of 12 to 30 linked nucleosides and having a nucleobase sequence comprising at least 8, at least 10, at least 12, at least 14, at least 16, at least 18, or 20 contiguous nucleobases of a nucleobase sequence selected from among the nucleobase sequences recited in SEQ ID NOs: 15 to 269.

Embodiments of the present invention provide compounds comprising a modified oligonucleotide consisting of 12 to 30 linked nucleosides and having a nucleobase sequence comprising at least 8, at least 10, at least 12, at least 14, at least 16, at least 18, or 20 contiguous nucleobases of a nucleobase sequence selected from among the nucleobase sequences recited in SEQ ID NOs: 242 to 269.

In certain embodiments, the modified oligonucleotide comprises at least 8, at least 10, at least 12, at least 14, at least 16, or at least 18 nucleobases of a nucleobase sequence selected from SEQ ID NOs: 22, 31, 32, 34, 36 to 38, 40, 41, 43, 51 to 53, 55, 56, 59, 60, 64, 66, 71, 73, 75, 96, 98 to 103, 105 to 109, 113 to 117, 119, 124, 127, 129, 171, 172, 174, 176, 178, 179, 181 to 197, 199 to 211, and 213 to 232. In certain embodiments, the modified oligonucleotide comprises a nucleobase sequence selected from SEQ ID NOs: 22, 31, 32, 34, 36 to 38, 40, 41, 43, 51 to 53, 55, 56, 59, 60, 64, 66, 71, 73, 75, 96, 98 to 103, 105 to 109, 113 to 117, 119, 124, 127, 129, 171, 172, 174, 176, 178, 179, 181 to 197, 199 to 211, and 213 to 232. In certain embodiments, the modified oligonucleotide consists of a nucleobase sequence selected from SEQ ID NOs: 22, 31, 32, 34, 36 to 38, 40, 41, 43, 51 to 53, 55, 56, 59, 60, 64, 66, 71, 73, 75, 96, 98 to 103, 105 to 109, 113 to 117, 119, 124, 127, 129, 171, 172, 174, 176, 178, 179, 181 to 197, 199 to 211, and 213 to 232. Said modified oligonucleotide may achieve at least 70% inhibition of human mRNA levels as determined using an RT-PCR assay method, optionally in HepG2 cells (e.g. as described in Example 3).

In certain embodiments, the modified oligonucleotide comprises at least 8, at least 10, at least 12, at least 14, at least 16, or at least 18 nucleobases of a nucleobase sequence selected from SEQ ID NOs: 22, 31, 34, 37, 40, 43, 51 to 53, 60, 98, 100 to 102, 105 to 109, 114, 115, 119, 171, 174, 176, 179, 181, 186, 188 to 193, 195, 196, 199 to 210, and 213 to 232. In certain embodiments, the modified oligonucleotide comprises a nucleobase sequence selected from SEQ ID NOs: 22, 31, 34, 37, 40, 43, 51 to 53, 60, 98, 100 to 102, 105 to 109, 114, 115, 119, 171, 174, 176, 179, 181, 186, 188 to 193, 195, 196, 199 to 210, and 213 to 232. In certain embodiments, the modified oligonucleotide consists of a nucleobase sequence selected from SEQ ID NOs: 22, 31, 34, 37, 40, 43, 51 to 53, 60, 98, 100 to 102, 105 to 109, 114, 115, 119, 171, 174, 176, 179, 181, 186, 188 to 193, 195, 196, 199 to 210, and 213 to 232. Said modified oligonucleotide may achieve at least 80% inhibition of human mRNA levels as determined using an RT-PCR assay method, optionally in HepG2 cells (e.g. as described in Example 3).

In certain embodiments, the modified oligonucleotide comprises at least 8, at least 10, at least 12, at least 14, at least 16, or at least 18 nucleobases of a nucleobase sequence selected from SEQ ID NOs: 31, 37, 100, 105, 179, 190 to 193, 196, 202 to 207, 209, 210, 214 to 219, 221 to 224, 226, 227, 229, and 231. In certain embodiments, the modified oligonucleotide comprises a nucleobase sequence selected from SEQ ID NOs: 31, 37, 100, 105, 179, 190 to 193, 196, 202 to 207, 209, 210, 214 to 219, 221 to 224, 226, 227, 229, and 231. In certain embodiments, the modified oligonucleotide consists of a nucleobase sequence selected from SEQ ID NOs: 31, 37, 100, 105, 179, 190 to 193, 196, 202 to 207, 209, 210, 214 to 219, 221 to 224, 226, 227, 229, and 231. Said modified oligonucleotide may achieve at least 90% inhibition of human mRNA levels as determined using an RT-PCR assay method, optionally in HepG2 cells (e.g. as described in Example 3).

In certain embodiments, the modified oligonucleotide comprises at least 8, at least 10, at least 12, at least 14, at least 16, or at least 18 nucleobases of a nucleobase sequence selected from SEQ ID NOs: 34, 52, 53, 114, 115, 190, 213 to 232, 242 to 260, and 262 to 266. In certain embodiments, the modified oligonucleotide comprises a nucleobase sequence selected from SEQ ID NOs: 34, 52, 53, 114, 115, 190, 213 to 232, 242 to 260, and 262 to 266. In certain embodiments, the modified oligonucleotide consists of a nucleobase sequence selected from SEQ ID NOs: 34, 52, 53, 114, 115, 190, 213 to 232, 242 to 260, and 262 to 266. Said modified oligonucleotides may achieve at least 70% inhibition of human mRNA levels as determined using an RT-PCR assay method, optionally in HepG2 cells (e.g. as described in Example 30).

In certain embodiments, the modified oligonucleotide comprises at least 8, at least 10, at least 12, at least 14, at least 16, or at least 18 nucleobases of a nucleobase sequence selected from SEQ ID NOs: 34, 52, 53, 114, 115, 190, 213 to 216, 218 to 226, 243 to 246, 248, 249, 252 to 259, 264, and 265. In certain embodiments, the modified oligonucleotide comprises a nucleobase sequence selected from SEQ ID NOs: 34, 52, 53, 114, 115, 190, 213 to 216, 218 to 226, 243 to 246, 248, 249, 252 to 259, 264, and 265. In certain embodiments, the modified oligonucleotide consists of a nucleobase sequence selected from SEQ ID NOs: 34, 52, 53, 114, 115, 190, 213 to 216, 218 to 226, 243 to 246, 248, 249, 252 to 259, 264, and 265. Said modified oligonucleotides may achieve at least 80% inhibition of human mRNA levels as determined using an RT-PCR assay method, optionally in HepG2 cells (e.g. as described in Example 30).

In certain embodiments, the modified oligonucleotide comprises at least 8, at least 10, at least 12, at least 14, at least 16, or at least 18 nucleobases of a nucleobase sequence selected from SEQ ID NOs: 34, 190, 215, 222, 223, 226, 246, and 254. In certain embodiments, the modified oligonucleotide comprises a nucleobase sequence selected from SEQ ID NOs: 34, 190, 215, 222, 223, 226, 246, and 254. In certain embodiments, the modified oligonucleotide consists of a nucleobase sequence selected from SEQ ID NOs: 34, 190, 215, 222, 223, 226, 246, and 254. Said modified oligonucleotides may achieve at least 90% inhibition of human mRNA levels as determined using an RT-PCR assay method, optionally in HepG2 cells (e.g. as described in Example 30).

In certain embodiments, the compound consists of a single-stranded modified oligonucleotide.

In certain embodiments, the modified oligonucleotide consists of 20 linked nucleosides.

In certain embodiments, the nucleobase sequence of the modified oligonucleotide is 100% complementary to a nucleobase sequence of SEQ ID NO: 1 or SEQ ID NO: 2 or SEQ ID NO: 6 or SEQ ID NO: 274.

In certain embodiments, the compound has at least one modified internucleoside linkage. In certain embodiments, the internucleoside linkage is a phosphorothioate internucleoside linkage.

In certain embodiments, the compound has at least one nucleoside comprising a modified sugar. In certain embodiments, the at least one modified sugar is a bicyclic sugar. In certain embodiments, the at least one modified sugar comprises a 2'-O-methoxyethyl.

Embodiments of the present invention provide compounds comprising a modified oligonucleotide consisting of 12 to 30 linked nucleosides and having a nucleobase sequence comprising at least 8, at least 10, at least 12, at least 14, at least 16, at least 18, or 20 contiguous nucleobases of a nucleobase sequence selected from among the nucleobase sequences recited in SEQ ID NOs: 15 to 241, SEQ ID NOs: 15 to 269, or SEQ ID NOs: 242 to 269, wherein at least one nucleoside comprises a modified sugar.

In certain embodiments, said at least one at least one modified sugar is a bicyclic sugar.

In certain embodiments, said at least one bicyclic sugar comprises a 4'-$(CH_2)_n$—O-2' bridge, wherein n is 1 or 2.

In certain embodiments, said at least one bicyclic sugar comprises a 4'-CH(CH3)-O-2' bridge.

In certain embodiments, said at least one modified sugar comprises a 2'-O-methoxyethyl group.

Embodiments of the present invention provide compounds comprising a modified oligonucleotide consisting of 12 to 30 linked nucleosides and having a nucleobase sequence comprising at least 8, at least 10, at least 12, at least 14, at least 16, at least 18, or 20 contiguous nucleobases of a nucleobase sequence selected from among the nucleobase sequences recited in SEQ ID NOs: 15 to 241, SEQ ID NOs: 15 to 269, or SEQ ID NOs: 242 to 269, comprising at least one tetrahydropyran modified nucleoside wherein a tetrahydropyran ring replaces the furanose ring.

In certain embodiments, said at least one tetrahydropyran modified nucleoside has the structure:

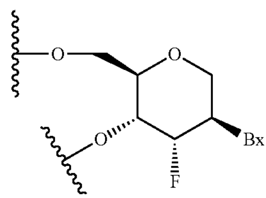

In certain embodiments, the compound has at least one nucleoside comprising a modified nucleobase. In certain embodiments, the modified nucleobase is a 5-methylcytosine.

In certain embodiments, the modified oligonucleotide of the compound comprises:
(i) a gap segment consisting of linked deoxynucleosides;
(ii) a 5' wing segment consisting of linked nucleosides;
(iii) a 3' wing segment consisting of linked nucleosides, wherein the gap segment is positioned immediately adjacent to and between the 5' wing segment and the 3' wing segment and wherein each nucleoside of each wing segment comprises a modified sugar. In some such embodiments, each cytosine in the modified oligonucleotide is a 5-methylcytosine.

In certain embodiments, the modified oligonucleotide of the compound comprises:
(i) a gap segment consisting of ten linked deoxynucleosides;
(ii) a 5' wing segment consisting of five linked nucleosides;
(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage. In some such embodiments, each cytosine in the modified oligonucleotide is a 5-methylcytosine.

In certain embodiments, the modified oligonucleotide of the compound comprises:
(i) a gap segment consisting of fourteen linked deoxynucleosides;
(ii) a 5' wing segment consisting of three linked nucleosides;
(iii) a 3' wing segment consisting of three linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage. In some such embodiments, each cytosine in the modified oligonucleotide is a 5-methylcytosine.

In certain embodiments, the modified oligonucleotide of the compound comprises:
(i) a gap segment consisting of thirteen linked deoxynucleosides;
(ii) a 5' wing segment consisting of two linked nucleosides;
(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage. In some such embodiments, each cytosine in the modified oligonucleotide is a 5-methylcytosine.

Embodiments of the present invention provide a composition comprising a modified oligonucleotide consisting of 12 to 30 linked nucleosides and having a nucleobase sequence comprising at least 12 contiguous nucleobases of a nucleobase sequence selected from among the nucleobase sequences recited in SEQ ID NOs: 15 to 241 or a salt thereof and a pharmaceutically acceptable carrier or diluent.

Embodiments of the present invention provide a composition comprising a modified oligonucleotide consisting of 12 to 30 linked nucleosides and having a nucleobase sequence comprising at least 12 contiguous nucleobases of a nucleobase sequence selected from among the nucleobase sequences recited in SEQ ID NOs: 15 to 269 or a salt thereof and a pharmaceutically acceptable carrier or diluent.

Embodiments of the present invention provide a composition comprising a modified oligonucleotide consisting of 12 to 30 linked nucleosides and having a nucleobase sequence comprising at least 12 contiguous nucleobases of a nucleobase sequence selected from among the nucleobase sequences recited in SEQ ID NOs: 241 to 269 or a salt thereof and a pharmaceutically acceptable carrier or diluent.

Embodiments of the present invention provide methods comprising administering to an animal a compound comprising a modified oligonucleotide consisting of 12 to 30 linked nucleosides and having a nucleobase sequence comprising at least 8 contiguous nucleobases of a nucleobase sequence selected from among the nucleobase sequences recited in SEQ ID NOs: 15 to 241.

Embodiments of the present invention provide methods comprising administering to an animal a compound comprising a modified oligonucleotide consisting of 12 to 30 linked nucleosides and having a nucleobase sequence comprising at least 8 contiguous nucleobases of a nucleobase sequence selected from among the nucleobase sequences recited in SEQ ID NOs: 15 to 269.

Embodiments of the present invention provide methods comprising administering to an animal a compound comprising a modified oligonucleotide consisting of 12 to 30 linked nucleosides and having a nucleobase sequence comprising at least 8 contiguous nucleobases of a nucleobase sequence selected from among the nucleobase sequences recited in SEQ ID NOs: 241 to 269.

In certain embodiments, the animal is a human.

In certain embodiments, the administering prevents deep vein thrombosis or pulmonary embolism.

In certain embodiments, the compound is co-administered with any of the group selected from aspirin, clopidogrel, dipyridamole, heparin, lepirudin, ticlopidine, warfarin, apixaban, rivaroxaban, and LOVENOX.

In certain embodiments, the compound is co-administered with any Factor Xa inhibitor.

In certain embodiment, the Factor Xa inhibitor is any of Rivaroxaban, LY517717, YM150, apixaban, PRT054021, and DU-176b.

In certain embodiments, the compound is administered concomitantly with any of the group selected from aspirin, clopidogrel, dipyridamole, heparin, lepirudin, ticlopidine, warfarin, apixaban, rivaroxaban, and LOVENOX are administered concomitantly.

In certain embodiments, the administering is parenteral administration. In certain embodiments, the parenteral administration is any of subcutaneous or intravenous administration.

Embodiments of the present invention provide methods comprising identifying an animal at risk for developing thromboembolic complications and administering to the at risk animal a therapeutically effective amount of a compound comprising a modified oligonucleotide consisting of 12 to 30 linked nucleosides, wherein the modified oligonucleotide is complementary to a Factor 11 nucleic acid.

In certain embodiments, the thromboembolic complication is deep vein thrombosis, pulmonary embolism, or a combination thereof.

Embodiments of the present invention provide methods comprising identifying an animal having a clotting disorder by administering to the animal a therapeutically effective amount of a compound comprising a modified oligonucleotide consisting of 12 to 30 linked nucleosides, wherein the modified oligonucleotide is complementary to a Factor 11 nucleic acid.

In certain embodiments, the compound is co-administered with any of the group selected from aspirin, clopidogrel, dipyridamole, heparin, lepirudin, ticlopidine, warfarin, apixaban, rivaroxaban, and LOVENOX.

In certain embodiments, the compound is administered concomitantly with any of the group selected from aspirin, clopidogrel, dipyridamole, heparin, lepirudin, ticlopidine, warfarin, apixaban, rivaroxaban, and LOVENOX are administered concomitantly.

Embodiments of the present invention provide methods comprising reducing the risk for thromboembolic complications in an animal by administering to the animal a therapeutically effective amount of a compound comprising a modified oligonucleotide consisting of 12 to 30 linked nucleosides, wherein the modified oligonucleotide is complementary to a Factor 11 nucleic acid.

Embodiments of the present invention provide methods comprising treating a clotting disorder in an animal by administering to the animal a therapeutically effective amount of a compound comprising a modified oligonucleotide consisting of 12 to 30 linked nucleosides, wherein the modified oligonucleotide is complementary to a Factor 11 nucleic acid.

Embodiments of the present invention provide methods comprising inhibiting Factor 11 expression in an animal by administering to the animal a therapeutically effective amount of a compound comprising a modified oligonucleotide consisting of 12 to 30 linked nucleosides, wherein the modified oligonucleotide is complementary to a Factor 11 nucleic acid.

In certain embodiments, the Factor 11 inhibition in the animal is reversed by administering an antidote to the modified oligonucleotide.

In certain embodiments, the antidote is an oligonucleotide complementary to the modified oligonucleotide.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a Factor 11 nucleic acid is 12 to 30 subunits in length. In other words, such antisense compounds are from 12 to 30 linked subunits. In other embodiments, the antisense compound is 8 to 80, 12 to 50, 15 to 30, 18 to 24, 19 to 22, or 20 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleotides.

In certain embodiments antisense oligonucleotides targeted to a Factor 11 nucleic acid may be shortened or truncated. For example, a single subunit may be deleted from the 5' end (5' truncation), or alternatively from the 3' end (3' truncation). A shortened or truncated antisense compound targeted to a Factor 11 nucleic acid may have two subunits deleted from the 5' end, or alternatively may have two subunits deleted from the 3' end, of the antisense compound.

Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a Factor 11 nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-(CH2)n-O-2' bridge, where n=1 or n=2). Preferably, each distinct region comprises uniform sugar moieties. The wing-gap-wing motif is frequently described as "X—Y—Z", where "X" represents the length of the 5' wing region, "Y" represents the length of the gap region, and "Z" represents the length of the 3' wing region. As used herein, a gapmer described as "X—Y—Z" has a configuration such that the gap segment is positioned immediately adjacent each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers of the present invention include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 5-8-5, or 6-8-6.

In certain embodiments, the antisense compound has a "wingmer" motif, having a wing-gap or gap-wing configuration, i.e. an X—Y or Y—Z configuration as described above for the gapmer configuration. Thus, wingmer configurations of the present invention include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, antisense compounds targeted to a Factor 11 nucleic acid possess a 5-10-5 gapmer motif.

In certain embodiments, antisense compounds targeted to a Factor 11 nucleic acid possess a 3-14-3 gapmer motif.

In certain embodiments, antisense compounds targeted to a Factor 11 nucleic acid possess a 2-13-5 gapmer motif.

In certain embodiments, antisense compounds targeted to a Factor 11 nucleic acid possess a 5-8-5 gapmer motif.

In certain embodiments, antisense compounds targeted to a Factor 11 nucleic acid possess a 6-8-6 gapmer motif.

In certain embodiments, an antisense compound targeted to a Factor 11 nucleic acid has a gap-widened motif.

In certain embodiments, a gap-widened antisense oligonucleotide targeted to a Factor 11 nucleic acid has a gap segment of fourteen 2'-deoxyribonucleotides positioned immediately adjacent to and between wing segments of three chemically modified nucleosides. In certain embodiments, the chemical modification comprises a 2'-sugar modification. In another embodiment, the chemical modification comprises a 2'-MOE sugar modification.

In certain embodiments, a gap-widened antisense oligonucleotide targeted to a Factor 11 nucleic acid has a gap segment of thirteen 2'-deoxyribonucleotides positioned immediately adjacent to and between a 5' wing segment of two chemically modified nucleosides and a 3' wing segment of five chemically modified nucleosides. In certain embodiments, the chemical modification comprises a 2'-sugar modification. In another embodiment, the chemical modification comprises a 2'-MOE sugar modification.

Target Nucleic Acids, Target Regions and Nucleotide Sequences

Nucleotide sequences that encode Factor 11 include, without limitation, the following: GENBANK Accession No. NM_000128.3, first deposited with GENBANK on Mar. 24, 1999 incorporated herein as SEQ ID NO: 1; NT_022792.17, truncated from Ser. No. 19/598,000 to Ser. No. 19/624,000, first deposited with GENBANK on Nov. 29, 2000, and incorporated herein as SEQ ID NO: 2; GENBANK Accession No. NM_028066.1, first deposited with GENBANK on Jun. 2, 2002, incorporated herein as SEQ ID NO: 6; and exons 1-15 GENBANK Accession No. NW_001118167.1, first deposited with GENBANK on Mar. 28, 2006, incorporated herein as SEQ ID NO: 274.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for Factor 11 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in Factor 11 mRNA levels are indicative of inhibition of Factor 11 expression. Reductions in levels of a Factor 11 protein are also indicative of inhibition of target mRNA expression. Further, phenotypic changes are indicative of inhibition of Factor 11 expression. For example, a prolonged aPTT time can be indicative of inhibition of Factor 11 expression. In another example, prolonged aPTT time in conjunction with a normal PT time can be indicative of inhibition of Factor 11 expression. In another example, a decreased quantity of Platelet Factor 4 (PF-4) can be indicative of inhibition of Factor 11 expression. In another example, reduced formation of thrombus or increased time for thrombus formation can be indicative of inhibition of Factor 11 expression.

Hybridization

In some embodiments, hybridization occurs between an antisense compound disclosed herein and a Factor 11 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a Factor 11 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a Factor 11 nucleic acid).

Non-complementary nucleobases between an antisense compound and a Factor 11 nucleic acid may be tolerated provided that the antisense compound remains able to specifically hybridize to a target nucleic acid. Moreover, an antisense compound may hybridize over one or more segments of a Factor 11 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a Factor 11 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound may be fully complementary to a Factor 11 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a Factor 11 nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a Factor 11 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a Factor 11 nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity or some other beneficial biological property to the antisense compounds. In certain embodiments, nucleosides comprise a chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or C(R1)(R)2 (R═H, C1-C12 alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH3 and 2'-O(CH2)2OCH3 substituent groups. The substituent at the 2' position can also be selected from allyl, amino, azido, thio, O-allyl, O—C1-C10 alkyl, OCF3, O(CH2)2SCH3, O(CH2)2-O—N(Rm)(Rn), and O—CH2-C(═O)—N(Rm)(Rn), where each Rm and Rn is, independently, H or substituted or unsubstituted C1-C10 alkyl.

Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-(CH2)-O-2' (LNA); 4'-(CH2)-S-2; 4'-(CH2)-O-2' (LNA); 4'-(CH2)2-O-2' (ENA); 4'-C(CH3)2-O-2' (see PCT/US2008/068922); 4'-CH(CH3)¬-O-2' and 4'-C¬H(CH2OCH3)¬-O-2' (see U.S. Pat. No. 7,399,845, issued on Jul. 15, 2008); 4'-CH2-N(OCH3)-2' (see PCT/US2008/064591); 4'-CH2-O—N(CH3)-2' (see published U.S. Patent Application US2004-0171570, published Sep. 2, 2004); 4'-CH2-N(R)—O-2' (see U.S. Pat. No. 7,427,672, issued on Sep. 23, 2008); 4'-CH2-C(CH3)-2' and 4'-CH2-C¬(═CH2)-2' (see PCT/US2008/066154); and wherein R is, independently, H, C1-C12 alkyl, or a protecting group. Each of the foregoing BNAs include various stereochemical sugar configurations including for example α-L-ribofuranose and β-D-ribofuranose (see PCT international application PCT/DK98/00393, published on Mar. 25, 1999 as WO 99/14226).

In certain embodiments, nucleosides are modified by replacement of the ribosyl ring with a sugar surrogate. Such modification includes without limitation, replacement of the ribosyl ring with a surrogate ring system (sometimes referred to as DNA analogs) such as a morpholino ring, a cyclohexenyl ring, a cyclohexyl ring or a tetrahydropyranyl ring such as one having one of the formula:

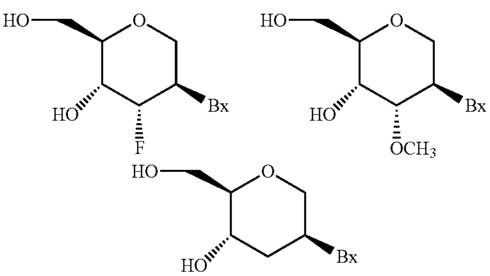

Many other bicyclo and tricyclo sugar surrogate ring systems are also know in the art that can be used to modify nucleosides for incorporation into antisense compounds (see for example review article: Leumann, J. C, *Bioorganic & Medicinal Chemistry,* 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds targeted to a MMP-13 nucleic acid comprise one or more nucleotides having modified sugar moieties. In certain embodiments, the modified sugar moiety is 2'-MOE. In certain embodiments, the 2'-MOE modified nucleotides are arranged in a gapmer motif Modified Nucleobases Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a Factor 11 nucleic acid comprise one or more modified nucleobases. In certain embodiments, gap-widened antisense oligonucleotides targeted to a Factor 11 nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a Factor 11 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a Factor 11 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of Factor 11 nucleic acids can be tested in vitro in a variety of cell types. Cell types used for such analyses are available from commercial vendors (e.g. American Type Culture Collection, Manassas, Va.; Zen-Bio, Inc., Research Triangle Park, NC; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides are mixed with LIPOFECTIN in OPTI-MEM 1 (Invitrogen, Carlsbad, Calif.) to achieve the desired final concentration of antisense oligonucleotide and a LIPOFECTIN concentration that typically ranges 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of anti sense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of a Factor 11 nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a Factor 11 nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of Factor 11 nucleic acids can be assessed by measuring Factor 11 protein levels. Protein levels of Factor 11 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of mouse, rat, monkey, and human Factor 11 are commercially available.

In Vivo Testing of Antisense Compounds

Antisense compounds, for example, antisense oligonucleotides, are tested in animals to assess their ability to inhibit expression of Factor 11 and produce phenotypic changes, such as, prolonged aPTT, prolonged aPTT time in conjunction with a normal PT, decreased quantity of Platelet Factor 4 (PF-4), and reduced formation of thrombus or increased time for thrombus formation. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from liver tissue and changes in Factor 11 nucleic acid expression are measured. Changes in Factor 11 protein levels are also measured using a thrombin generation assay. In addition, effects on clot times, e.g. PT and aPTT, are determined using plasma from treated animals.

Tolerability

In certain embodiments, the compounds provided herein display minimal side effects. Side effects include responses to the administration of the antisense compound that are typically unrelated to the targeting of factor 11, such as an inflammatory response in the animal. In certain embodiments compounds are well tolerated by the animal. Increased tolerability can depend on a number of factors, including, but not limited to, the nucleotide sequence of the antisense compound, chemical modifications to the nucleotides, the particular motif of unmodified and modified nucleosides in the antisense compound, or combinations thereof. Tolerability may be determined by a number of factors. Such factors include body weight, organ weight, liver function, kidney function, platelet count, white blood cell count.

In certain embodiments, the compounds provided herein demonstrate minimal effect on organ weight. In certain embodiments, the compounds demonstrate less than a 7-fold, 6-fold, 5-fold, 4-fold, 3-fold, 2-fold or no significant increase in spleen and/or liver weight.

In certain embodiments, the compounds provided herein demonstrate minimal effect on liver function. Factors for the evaluation of liver function include ALT levels, AST levels, plasma bilirubin levels and plasma albumin levels. In certain embodiments the compounds provided herein demonstrate less than a 7-fold, less than a 6-fold, less than a 5-fold, less than a 4-fold, less than a 3-fold or less than a 2-fold or no significant increase in ALT or AST. In certain embodiments the compounds provided herein demonstrate less than a 3-fold, less than a 2-fold or no significant increase in plasma bilirubin levels.

In certain embodiments, the compounds provided herein demonstrate minimal effect on kidney function. In certain embodiments, the compounds provided herein demonstrate less than a 3-fold, less than a 2-fold, or no significant increase in plasma concentrations of blood urea nitrogen (BUN). In certain embodiments, the compounds provided herein demonstrate less than a 6-fold, 5-fold, 4-fold, 3-fold, 2-fold, or no significant increase in the ratio of urine protein to creatinine.

In certain embodiments, the compounds provided herein demonstrate minimal effect on hematological factors. In certain embodiments, the compounds provided herein demonstrate less than a 60%, 50%, 40%, 30%, 20%, 10% or 5% decrease in platelet count. In certain embodiments, the compounds provided herein demonstrate less than a 4-fold, less than a 3-fold, less than a 2-fold or no significant increase in monocyte count.

In certain embodiments compounds further display favorable pharmacokinetics. In certain embodiments, antisense compounds exhibit relatively high half-lives in relevant biological fluids or tissues.

In certain embodiments, compounds or compositions further display favorable viscosity. In certain embodiments, the viscosity of the compound or composition is no more than 40 cP at a concentration of 165-185 mg/mL.

In other embodiments, the compounds display combinations of the characteristics above and reduce factor 11 mRNA expression in an animal model with high efficiency.

Certain Indications

In certain embodiments, the invention provides methods of treating an individual comprising administering one or more pharmaceutical compositions of the present invention. In certain embodiments, the individual has a thromboembolic complication. In certain embodiments, the individual is at risk for a blood clotting disorder, including, but not limited to, infarct, thrombosis, embolism, thromboembolism such as deep vein thrombosis, pulmonary embolism, myocardial infarction, and stroke. This includes individuals with an acquired problem, disease, or disorder that leads to a risk of thrombosis, for example, surgery, cancer, immobility, sepsis, atherosclerosis atrial fibrillation, as well as genetic predisposition, for example, antiphospholipid syndrome and the autosomal dominant condition, Factor V Leiden. In certain embodiments, the individual has been identified as in need of anticoagulation therapy. Examples of such individuals include, but are not limited to, those undergoing major orthopedic surgery (e.g., hip/knee replacement or hip fracture surgery) and patients in need of chronic treatment, such as those suffering from arterial fibrillation to prevent stroke. In certain embodiments the invention provides methods for prophylactically reducing Factor 11 expression in an individual. Certain embodiments include treating an individual in need thereof by administering to an individual a therapeutically effective amount of an antisense compound targeted to a Factor 11 nucleic acid.

In one embodiment, administration of a therapeutically effective amount of an antisense compound targeted to a Factor 11 nucleic acid is accompanied by monitoring of Factor 11 levels in the serum of an individual, to determine an individual's response to administration of the antisense compound. An individual's response to administration of the antisense compound is used by a physician to determine the amount and duration of therapeutic intervention.

In certain embodiments, administration of an antisense compound targeted to a Factor 11 nucleic acid results in reduction of Factor 11 expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a Factor 11 nucleic acid results in a change in a measure of blood clotting as measured by a standard test, for example, but not limited to, activated partial thromboplastin time (aPTT) test, prothrombin time (PT) test, thrombin time (TCT), bleeding time, or D-dimer. In certain embodiments, administration of a Factor 11 antisense compound increases the measure by at least 15, 20, 25, 30, 35, 40, 45, 50, 55, 60, 65, 70, 75, 80, 85, 90, 95 or 99%, or a range defined by any two of these values. In some embodiments, administration of a Factor 11 antisense compound decreases the measure by at least 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to Factor 11 are used for the preparation of a medicament for treating a patient suffering or susceptible to a thromboembolic complication.

Certain Combination Therapies

In certain embodiments, one or more pharmaceutical compositions of the present invention are co-administered with one or more other pharmaceutical agents. In certain embodiments, such one or more other pharmaceutical agents are designed to treat the same disease, disorder, or condition as the one or more pharmaceutical compositions of the present invention. In certain embodiments, such one or more other pharmaceutical agents are designed to treat a different disease, disorder, or condition as the one or more pharmaceutical compositions of the present invention. In certain embodiments, such one or more other pharmaceutical agents are designed to treat an undesired side effect of one or more pharmaceutical compositions of the present invention. In certain embodiments, one or more pharmaceutical compositions of the present invention are co-administered with another pharmaceutical agent to treat an undesired effect of that other pharmaceutical agent. In certain embodiments, one or more pharmaceutical compositions of the present invention are co-administered with another pharmaceutical agent to produce a combinational effect. In certain embodiments, one or more pharmaceutical compositions of the present invention are co-administered with another pharmaceutical agent to produce a synergistic effect.

In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

In certain embodiments, pharmaceutical agents that may be co-administered with a pharmaceutical composition of the present invention include anticoagulant or antiplatelet agents. In certain embodiments, pharmaceutical agents that may be co-administered with a pharmaceutical composition of the present invention include NSAID/Cyclooxygenase inhibitors, such as, aspirin. In certain embodiments, pharmaceutical agents that may be co-administered with a pharmaceutical composition of the present invention include adenosine diphosphate (ADP) receptor inhibitors, such as, clopidogrel (PLAVIX) and ticlopidine (TICLID). In certain embodiments, pharmaceutical agents that may be co-administered with a pharmaceutical composition of the present invention include phosphodiesterase inhibitors, such as, cilostazol (PLETAL). In certain embodiments, pharmaceutical agents that may be co-administered with a pharmaceutical composition of the present invention include, glycoprotein IIB/IIIA inhibitors, such as, abciximab (REOPRO), eptifibatide (INTEGRILIN), tirofiban (AGGRASTAT), and defibrotide. In certain embodiments, pharmaceutical agents that may be co-administered with a pharmaceutical composition of the present invention include, adenosine reuptake inhibitors, such as, to dipyridamole (PERSANTINE). In certain embodiments, pharmaceutical agents that may be co-administered with a pharmaceutical composition of the present invention include, but are not limited to warfarin (and related coumarins), heparin, direct thrombin inhibitors (such as lepirudin, bivalirudin), apixaban, LOVENOX, and small molecular compounds that interfere directly with the enzymatic action of particular coagulation factors (e.g. rivaroxaban, which interferes with Factor Xa). In certain embodiments, pharmaceutical agents that may be co-administered with a Factor 11 specific inhibitor of the present invention include, but are not limited to, an additional Factor 11 inhibitor. In certain embodiments, the anticoagulant or antiplatelet agent is administered prior to administration of a pharmaceutical composition of the present invention. In certain embodiments, the anticoagulant or antiplatelet agent is administered following administration of a pharmaceutical composition of the present invention. In certain embodiments the anticoagulant or antiplatelet agent is administered at the same time as a pharmaceutical composition of the present invention. In certain embodiments the dose of a co-administered anticoagulant or antiplatelet agent is the same as the dose that would be administered if the anticoagulant or antiplatelet agent was administered alone. In certain embodiments the dose of a co-administered anticoagulant or antiplatelet agent is lower than the dose that would be administered if the anticoagulant or antiplatelet agent was administered alone. In certain embodiments the dose of a co-administered anticoagulant or antiplatelet agent is greater than the dose that would be administered if the anticoagulant or antiplatelet agent was administered alone.

In certain embodiments, the co-administration of a second compound enhances the anticoagulant effect of a first compound, such that co-administration of the compounds results in an anticoagulant effect that is greater than the effect of administering the first compound alone. In other embodiments, the co-administration results in anticoagulant effects that are additive of the effects of the compounds when administered alone. In certain embodiments, the co-administration results in anticoagulant effects that are supra-additive of the effects of the compounds when administered alone. In certain embodiments, the co-administration of a second compound increases antithrombotic activity without increased bleeding risk. In certain embodiments, the first compound is an antisense compound. In certain embodiments, the second compound is an antisense compound.

In certain embodiments, an antidote is administered anytime after the administration of a Factor 11 specific inhibitor. In certain embodiments, an antidote is administered anytime after the administration of an antisense oligonucleotide targeting Factor 11. In certain embodiments, the antidote is administered minutes, hours, days, weeks, or months after the administration of an antisense compound targeting Factor 11. In certain embodiments, the antidote is a complementary (e.g. the sense strand) to the antisense compound targeting Factor 11. In certain embodiments, the antidote is a Factor 7, Factor 7a, Factor 11, or Factor 11a protein. In certain embodiments, the Factor 7, Factor 7a, Factor 11, or Factor 11a protein is a human Factor 7, human Factor 7a, human Factor 11, or human Factor 11a protein. In certain embodiments, the Factor 7 protein is NOVOSEVEN.

Certain Co Administered Antiplatelet Therapies

In certain embodiments, Factor 11 inhibitors are combined with antiplatelet therapies. In certain embodiments, administration of a Factor 11 inhibitor in combination with an antiplatelet therapy results in little to no appreciable or detectable increase in risk of bleeding as compared to antiplatelet therapy alone. In certain embodiments, the risk profile or risk indications are unchanged over antiplatelet therapy alone.

The combination of antiplatelet and anticoagulant therapy is used in clinical practice most frequently in patients diagnosed with, for example, thromboembolism, atrial fibrillation, a heart valve disorder, valvular heart disease, stroke, CAD, and in patients having a mechanical valve. The benefit of dual therapy relates to the probable additive effect of suppressing both platelet and coagulation factor activities. The risk of dual therapy is the potential for increased bleeding (Dowd, M. Plenary Sessions/Thrombosis Research 123 (2008)).

Prior combinations of antiplatelet and anticoagulant therapy have been shown to increase the risk of bleeding compared with anticoagulant or antiplatelet therapy alone. Such combinations include, FXa inhibitors (e.g., apixiban and rivaroxaban) with ADP receptor/P2Y12 inhibitors (Thienopyridines such as clopidogrel—also known as PLAVIX) and NSAIDs (e.g., aspirin and naproxen) (Kubitza, D. et al., *Br. J. Clin. Pharmacol.* 63:4 (2006); Wong, P. C. et al. *Journal of Thrombosis and Haemostasis* 6 (2008); FDA Advisory Committee Briefing Document for New Drug Application 22-406 (2009)). For example, Wong reports that addition of certain doses of apixaban to aspirin and to aspirin plus clopidogrel produced a significant increase in bleeding time compared with aspirin alone and asprin plus clopidogrel. Kubitza reports that the combination administration of rivaroxaban and naproxen significantly increased bleeding time over naproxen alone.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Human Factor 11 in HepG2 Cells

Antisense oligonucleotides targeted to a Factor 11 nucleic acid were tested for their effects on Factor 11 mRNA in vitro. Cultured HepG2 cells at a density of 10,000 cells per well were transfected using lipofectin reagent with 75 nM antisense oligonucleotide. After a treatment period of approximately 24 hours, RNA was isolated from the cells and Factor 11 mRNA levels were measured by quantitative real time PCR. Factor 11 mRNA levels were adjusted according to total RNA content, as measured by RIBOGREEN. Results are presented as percent inhibition of Factor 11, relative to untreated control cells.

The chimeric antisense oligonucleotides in Tables 1 and 2 were designed as 5-10-5 MOE gapmers. The gapmers are 20 nucleotides in length, wherein the central gap segment is comprised of 10 2'-deoxynucleotides and is flanked on both sides (in the 5' and 3' directions) by wings comprising 5 nucleotides each. Each nucleotide in the 5' wing segment and each nucleotide in the 3' wing segment has a 2'-MOE modification. The internucleoside linkages throughout each gapmer are phosphorothioate (P═S) linkages. All cytidine residues throughout each gapmer are 5-methylcytidines. "Target start site" indicates the 5'-most nucleotide to which the gapmer is targeted. "Target stop site" indicates the 3'-most nucleotide to which the gapmer is targeted. Each gapmer listed in Table 1 is targeted to SEQ ID NO: 1 (GENBANK Accession No. NM_000128.3) and each gapmer listed in Table 2 is targeted to SEQ ID NO: 2 (GENBANK Accession No. NT_022792.17, truncated from Ser. No. 19/598,000 to Ser. No. 19/624,000).

TABLE 1

Inhibition of human Factor 11 mRNA levels by chimeric antisense oligonucleotides having 5-10-5 MOE wings and deoxy gap targeted to SEQ ID NO: 1

| Oligo ID | Target Start Site | Target Stop Site | Sequence | % inhibition | SEQ ID NO |
|---|---|---|---|---|---|
| 412187 | 38 | 57 | TTCAAACAAGTGACATACAC | 21 | 15 |
| 412188 | 96 | 115 | TGAGAGAATTGCTTGCTTTC | 21 | 16 |
| 412189 | 106 | 125 | AAATATACCTTGAGAGAATT | 8 | 17 |
| 412190 | 116 | 135 | AGTATGTCAGAAATATACCT | 24 | 18 |
| 412191 | 126 | 145 | TTAAAATCTTAGTATGTCAG | 14 | 19 |
| 412192 | 146 | 165 | CAGCATATTTGTGAAAGTCG | 44 | 20 |
| 412193 | 222 | 241 | TGTGTAGGAAATGGTCACTT | 38 | 21 |
| 412194 | 286 | 305 | TGCAATTCTTAATAAGGGTG | 80 | 22 |
| 412195 | 321 | 340 | AAATCATCCTGAAAAGACCT | 22 | 23 |
| 412196 | 331 | 350 | TGATATAAGAAAATCATCCT | 25 | 24 |
| 412197 | 376 | 395 | ACACATTCACCAGAAACTGA | 45 | 25 |
| 412198 | 550 | 569 | TTCAGGACACAAGTAAACCA | 21 | 26 |
| 412199 | 583 | 602 | TTCACTCTTGGCAGTGTTTC | 66 | 27 |
| 412200 | 612 | 631 | AAGAATACCCAGAAATCGCT | 59 | 28 |
| 412201 | 622 | 641 | CATTGCTTGAAAGAATACCC | 66 | 29 |
| 412202 | 632 | 651 | TTGGTGTGAGCATTGCTTGA | 65 | 30 |
| 412203 | 656 | 675 | AATGTCTTTGTTGCAAGCGC | 91 | 31 |
| 412204 | 676 | 695 | TTCATGTCTAGGTCCACATA | 74 | 32 |
| 412205 | 686 | 705 | GTTTATGCCCTTCATGTCTA | 69 | 33 |
| 412206 | 738 | 757 | CCGTGCATCTTTCTTGGCAT | 87 | 34 |
| 412207 | 764 | 783 | CGTGAAAAAGTGGCAGTGGA | 64 | 35 |
| 412208 | 811 | 830 | AGACAAATGTTACGATGCTC | 73 | 36 |
| 412209 | 821 | 840 | GTGCTTCAGTAGACAAATGT | 91 | 37 |
| 412210 | 896 | 915 | TGCACAGGATTTCAGTGAAA | 73 | 38 |
| 412211 | 906 | 925 | GATTAGAAAGTGCACAGGAT | 64 | 39 |
| 412212 | 1018 | 1037 | CCGGGATGATGAGTGCAGAT | 88 | 40 |
| 412213 | 1028 | 1047 | AAACAAGCAACCGGGATGAT | 71 | 41 |
| 412214 | 1048 | 1067 | TCCTGGGAAAAGAAGGTAAA | 58 | 42 |
| 412215 | 1062 | 1081 | ATTCTTTGGGCCATTCCTGG | 81 | 43 |
| 412216 | 1077 | 1096 | AAAGATTTCTTTGAGATTCT | 43 | 44 |
| 412217 | 1105 | 1124 | AATCCACTCTCAGATGTTTT | 47 | 45 |
| 412218 | 1146 | 1165 | AACCAGAAAGAGCTTTGCTC | 27 | 46 |

TABLE 1-continued

Inhibition of human Factor 11 mRNA levels by chimeric antisense oligonucleotides having 5-10-5 MOE wings and deoxy gap targeted to SEQ ID NO: 1

| Oligo ID | Target Start Site | Target Stop Site | Sequence | % inhib-ition | SEQ ID NO |
|---|---|---|---|---|---|
| 412219 | 1188 | 1207 | GGCAGAACACTGGGATGCTG | 56 | 47 |
| 412220 | 1204 | 1223 | TGGTAAAATGAAGAATGGCA | 58 | 48 |
| 412221 | 1214 | 1233 | ATCAGTGTCATGGTAAAATG | 48 | 49 |
| 412222 | 1241 | 1263 | AACAATATCCAGTTCTTCTC | 5 | 50 |
| 412223 | 1275 | 1294 | ACAGTTTCTGGCAGGCCTCG | 84 | 51 |
| 412224 | 1285 | 1304 | GCATTGGTGCACAGTTTCTG | 87 | 52 |
| 412225 | 1295 | 1314 | GCAGCGGACGGCATTGGTGC | 86 | 53 |
| 412226 | 1371 | 1390 | TTGAAGAAAGCTTTAAGTAA | 17 | 54 |
| 412227 | 1391 | 1410 | AGTATTTTAGTTGGAGATCC | 75 | 55 |
| 412228 | 1425 | 1444 | ATGTGTATCCAGAGATGCCT | 71 | 56 |
| 412229 | 1456 | 1475 | GTACACTCATTATCCATTTT | 64 | 57 |
| 412230 | 1466 | 1485 | GATTTTGGTGGTACACTCAT | 52 | 58 |
| 412231 | 1476 | 1495 | TCCTGGGCTTGATTTTGGTG | 74 | 59 |
| 412232 | 1513 | 1532 | GGCCACTCACCACGAACAGA | 80 | 60 |
| 412233 | 1555 | 1574 | TGTCTCTGAGTGGGTGAGGT | 64 | 61 |
| 412234 | 1583 | 1602 | GTTTCCAATGATGGAGCCTC | 60 | 62 |
| 412235 | 1593 | 1612 | ATATCCACTGGTTTCCAATG | 57 | 63 |
| 412236 | 1618 | 1637 | CCATAGAAACAGTGAGCGGC | 72 | 64 |
| 412237 | 1628 | 1647 | TGACTCTACCCCATAGAAAC | 48 | 65 |
| 412238 | 1642 | 1661 | CGCAAAATCTTAGGTGACTC | 71 | 66 |
| 412239 | 1673 | 1692 | TTCAGATTGATTTAAAATGC | 43 | 67 |
| 412240 | 1705 | 1724 | TGAACCCCAAAGAAAGATGT | 32 | 68 |
| 412241 | 1715 | 1734 | TATTATTTCTTGAACCCCAA | 41 | 69 |
| 412242 | 1765 | 1784 | AACAAGGCAATATCATACCC | 49 | 70 |
| 412243 | 1775 | 1794 | TTCCAGTTTCAACAAGGCAA | 70 | 71 |
| 412244 | 1822 | 1841 | GAAGGCAGGCATATGGGTCG | 53 | 72 |
| 412245 | 1936 | 1955 | GTCACTAAGGGTATCTTGGC | 75 | 73 |
| 412246 | 1992 | 2011 | AGATCATCTTATGGGTTATT | 68 | 74 |
| 412247 | 2002 | 2021 | TAGCCGGCACAGATCATCTT | 75 | 75 |
| 412248 | 2082 | 2101 | CCAGATGCCAGACCTCATTG | 53 | 76 |
| 412249 | 2195 | 2214 | CATTCACACTGCTTGAGTTT | 55 | 77 |
| 412250 | 2268 | 2287 | TGGCACAGTGAACTCAACAC | 63 | 78 |
| 412251 | 2326 | 2345 | CTAGCATTTTCTTACAAACA | 58 | 79 |
| 412252 | 2450 | 2469 | TTATGGTAATTCTTGGACTC | 39 | 80 |
| 412253 | 2460 | 2479 | AAATATTGCCTTATGGTAAT | 20 | 81 |
| 412254 | 2485 | 2504 | TATCTGCCTATATAGTAATC | 16 | 82 |

TABLE 1-continued

Inhibition of human Factor 11 mRNA levels by chimeric antisense oligonucleotides having 5-10-5 MOE wings and deoxy gap targeted to SEQ ID NO: 1

| Oligo ID | Target Start Site | Target Stop Site | Sequence | % inhib-ition | SEQ ID NO |
|---|---|---|---|---|---|
| 412255 | 2510 | 2529 | GCCACTACTTGGTTATTTTC | 38 | 83 |
| 412256 | 2564 | 2583 | AACAAATCTATTTATGGTGG | 39 | 84 |
| 412257 | 2622 | 2641 | CTGCAAAATGGTGAAGACTG | 57 | 85 |
| 412258 | 2632 | 2651 | GTGTAGATTCCTGCAAAATG | 44 | 86 |
| 412259 | 2882 | 2901 | TTTTCAGGAAAGTGTATCTT | 37 | 87 |
| 412260 | 2892 | 2911 | CACAAATCATTTTTCAGGAA | 27 | 88 |
| 412261 | 2925 | 2944 | TCCCAAGATATTTTAAATAA | 3 | 89 |
| 412262 | 3168 | 3187 | AATGAGATAAATATTTGCAC | 34 | 90 |
| 412263 | 3224 | 3243 | TGAAAGCTATGTGGTGACAA | 33 | 91 |
| 412264 | 3259 | 3278 | CACACTTGATGAATTGTATA | 27 | 92 |
| 413460 | 101 | 120 | TACCTTGAGAGAATTGCTTG | 40 | 93 |
| 413461 | 111 | 130 | GTCAGAAATATACCTTGAGA | 39 | 94 |
| 413462 | 121 | 140 | ATCTTAGTATGTCAGAAATA | 12 | 95 |
| 413463 | 381 | 400 | GAGTCACACATTCACCAGAA | 74 | 96 |
| 413464 | 627 | 646 | GTGAGCATTGCTTGAAAGAA | 42 | 97 |
| 413465 | 637 | 656 | CTTATTTGGTGTGAGCATTG | 80 | 98 |
| 413466 | 661 | 680 | ACATAAATGTCTTTGTTGCA | 79 | 99 |
| 413467 | 666 | 685 | GGTCCACATAAATGTCTTTG | 91 | 100 |
| 413468 | 671 | 690 | GTCTAGGTCCACATAAATGT | 84 | 101 |
| 413469 | 681 | 700 | TGCCCTTCATGTCTAGGTCC | 84 | 102 |
| 413470 | 692 | 711 | GTTATAGTTTATGCCCTTCA | 72 | 103 |
| 413471 | 816 | 835 | TCAGTAGACAAATGTTACGA | 67 | 104 |
| 413472 | 826 | 845 | TGGGTGTGCTTCAGTAGACA | 99 | 105 |
| 413473 | 911 | 930 | AGCCAGATTAGAAAGTGCAC | 80 | 106 |
| 413474 | 1023 | 1042 | AGCAACCGGGATGATGAGTG | 84 | 107 |
| 413475 | 1053 | 1072 | GCCATTCCTGGGAAAAGAAG | 80 | 108 |
| 413476 | 1067 | 1086 | TTGAGATTCTTTGGGCCATT | 88 | 109 |
| 413477 | 1151 | 1170 | ACTGAAACCAGAAAGAGCTT | 54 | 110 |
| 413478 | 1193 | 1212 | AGAATGGCAGAACACTGGGA | 53 | 111 |
| 413479 | 1209 | 1228 | TGTCATGGTAAAATGAAGAA | 40 | 112 |
| 413480 | 1219 | 1238 | AAGAAATCAGTGTCATGGTA | 71 | 113 |
| 413481 | 1280 | 1299 | GGTGCACAGTTTCTGGCAGG | 86 | 114 |
| 413482 | 1290 | 1309 | GGACGGCATTGGTGCACAGT | 85 | 115 |
| 413483 | 1300 | 1319 | AACTGGCAGCGGACGGCATT | 78 | 116 |
| 413484 | 1430 | 1449 | CCTTAATGTGTATCCAGAGA | 74 | 117 |
| 413485 | 1461 | 1480 | TGGTGGTACACTCATTATCC | 68 | 118 |

TABLE 1-continued

Inhibition of human Factor 11 mRNA levels by chimeric antisense oligonucleotides having 5-10-5 MOE wings and deoxy gap targeted to SEQ ID NO: 1

| Oligo ID | Target Start Site | Target Stop Site | Sequence | % inhib-ition | SEQ ID NO |
|---|---|---|---|---|---|
| 413486 | 1471 | 1490 | GGCTTGATTTTGGTGGTACA | 83 | 119 |
| 413487 | 1481 | 1500 | AACGATCCTGGGCTTGATTT | 57 | 120 |
| 413488 | 1560 | 1579 | ACAGGTGTCTCTGAGTGGGT | 49 | 121 |
| 413489 | 1588 | 1607 | CACTGGTTTCCAATGATGGA | 68 | 122 |
| 413490 | 1623 | 1642 | CTACCCCATAGAAACAGTGA | 57 | 123 |
| 413491 | 1633 | 1652 | TTAGGTGACTCTACCCCATA | 73 | 124 |
| 413492 | 1647 | 1666 | AGACACGCAAAATCTTAGGT | 68 | 125 |
| 413493 | 1710 | 1729 | TTTCTTGAACCCCAAAGAAA | 65 | 126 |
| 413494 | 1780 | 1799 | GTGGTTTCCAGTTTCAACAA | 70 | 127 |
| 413495 | 1921 | 1940 | TTGGCTTTCTGGAGAGTATT | 58 | 128 |
| 413496 | 1997 | 2016 | GGCACAGATCATCTTATGGG | 72 | 129 |
| 413497 | 2627 | 2646 | GATTCCTGCAAAATGGTGAA | 39 | 130 |
| 413498 | 2637 | 2656 | GCAGAGTGTAGATTCCTGCA | 60 | 131 |
| 413499 | 2887 | 2906 | ATCATTTTTCAGGAAAGTGT | 52 | 132 |

TABLE 2

Inhibition of human Factor 11 mRNA levels by chimeric antisense oligonucleotides having 5-10-5 MOE wings and deoxy gap targeted to SEQ ID NO: 2

| Oligo ID | Target Start Site | Target Stop Site | Sequence | % inhib-ition | SEQ ID NO |
|---|---|---|---|---|---|
| 413500 | 1658 | 1677 | GTGAGACAAATCAAGACTTC | 15 | 133 |
| 413501 | 2159 | 2178 | TTAGTTTACTGACACTAAGA | 23 | 134 |
| 413502 | 2593 | 2612 | CTGCTTTATGAAAAACCAAC | 22 | 135 |
| 413503 | 3325 | 3344 | ATACCTAGTACAATGTAAAT | 29 | 136 |
| 413504 | 3548 | 3567 | GGCTTGTGTGTGGTCAATAT | 54 | 137 |
| 413505 | 5054 | 5073 | TGGGAAAGCTTTCAATATTC | 57 | 138 |
| 413506 | 6474 | 6493 | ATGGAATTGTGCTTATGAGT | 57 | 139 |
| 413507 | 7590 | 7609 | TTTCAAGCTCAGGATGGGAA | 55 | 140 |
| 413508 | 7905 | 7924 | GTTGGTAAAATGCAACCAAA | 64 | 141 |
| 413509 | 8163 | 8182 | TCAGGACACAAGTAAACCTG | 66 | 142 |
| 413510 | 9197 | 9216 | TGCAAGCTGGAAATAAAAGC | 17 | 143 |
| 413511 | 9621 | 9640 | TGCCAATTTAAAAGTGTAGC | 43 | 144 |
| 413512 | 9800 | 9819 | ATATTTCAAAATCCAGTATG | 39 | 145 |
| 413513 | 9919 | 9938 | TTCTGAATATACAAATTAAT | 27 | 146 |
| 413514 | 9951 | 9970 | TTTACTATGAAAATCTAAAT | 5 | 147 |
| 413515 | 11049 | 11068 | GGTATCCTGAGTGAGATCTA | 36 | 148 |

TABLE 2-continued

Inhibition of human Factor 11 mRNA levels by chimeric antisense oligonucleotides having 5-10-5 MOE wings and deoxy gap targeted to SEQ ID NO: 2

| Oligo ID | Target Start Site | Target Stop Site | Sequence | % inhib-ition | SEQ ID NO |
|---|---|---|---|---|---|
| 413516 | 11269 | 11288 | CCAGCTATCAGGAAAATTCC | 50 | 149 |
| 413517 | 12165 | 12184 | AAAGCTATTGGAGACTCAGA | 51 | 150 |
| 413518 | 12584 | 12603 | ATGGAATCTCTTCATTTCAT | 49 | 151 |
| 413519 | 12728 | 12747 | ATGGAGACATTCATTTCCAC | 59 | 152 |
| 413520 | 13284 | 13303 | GCTCTGAGAGTTCCAATTCA | 52 | 153 |
| 413521 | 14504 | 14523 | CTGGGAAGGTGAATTTTTAG | 62 | 154 |
| 413522 | 14771 | 14790 | TCAAGAGTCTTCATGCTACC | 42 | 155 |
| 413523 | 15206 | 15225 | TCAGTTTACCTGGGATGCTG | 61 | 156 |
| 413524 | 15670 | 15689 | GACATTATACTCACCATTAT | 7 | 157 |
| 413525 | 15905 | 15924 | GTATAAATGTGTCAAATTAA | 43 | 158 |
| 413526 | 16482 | 16501 | GTAAAGTTTTACCTTAACCT | 47 | 159 |
| 413527 | 17298 | 17317 | CCATAATGAAGAAGGAAGGG | 52 | 160 |
| 413528 | 17757 | 17776 | TTAAGTTACATTGTAGACCA | 48 | 161 |
| 413529 | 18204 | 18223 | TGTGTGGGTCCTGAAATTCT | 52 | 162 |
| 413530 | 18981 | 19000 | ATCTTGTAATTACACACCCC | 27 | 163 |
| 413531 | 19174 | 19193 | GTACACTCTGCAACAGAAGC | 47 | 164 |
| 413532 | 19604 | 19623 | AGGGAATAACATGAAGGCCC | 32 | 165 |
| 413533 | 20936 | 20955 | ATCCAGTTCACCATTGGAGA | 48 | 166 |
| 413534 | 21441 | 21460 | TTTTCCAGAAGAGACTCTTC | 31 | 167 |
| 413535 | 21785 | 21804 | GTCACATTTAAAATTTCCAA | 41 | 168 |
| 413536 | 23422 | 23441 | TTAATATACTGCAGAGAACC | 37 | 169 |
| 413537 | 25893 | 25912 | AGAAATATCCCCAGACAGAG | 16 | 170 |

Example 2: Dose-Dependent Antisense Inhibition of Human Factor 11 in HepG2 Cells Twelve gapmers, exhibiting over 84 percent or greater in vitro inhibition of human Factor 11, were tested at various doses in HepG2 cells. Cells were plated at a density of 10,000 cells per well and transfected using lipofectin reagent with 9.375 nM, 18.75 nM, 37.5 nM, 75 nM, and 150 nM concentrations of antisense oligonucleotide, as specified in Table 3. After a treatment period of approximately 16 hours, RNA was isolated from the cells and Factor 11 mRNA levels were measured by quantitative real-time PCR. Human Factor 11 primer probe set RTS 2966 (forward sequence: CAGCCTGGAGCATCGTAACA, incorporated herein as SEQ ID NO: 3; reverse sequence: TTTATCGAGCTTCGT-TATTCTGGTT, incorporated herein as SEQ ID NO: 4; probe sequence: TTGTCTACTGAAGCACACCCAAACA-GGGAX, incorporated herein as SEQ ID NO: 5) was used to measure mRNA levels. Factor 11 mRNA levels were adjusted according to total RNA content, as measured by RIBOGREEN. Results are presented as percent inhibition of Factor 11, relative to untreated control cells. As illustrated in Table 3, Factor 11 mRNA levels were reduced in a dose-dependent manner in antisense oligonucleotide treated cells.

TABLE 3

Dose-dependent antisense inhibition of human Factor 11 in HepG2 cells

| | 9.375 nM | 18.75 nM | 37.5 nM | 75 nM | 150 nM | $IC_{50}$ (nM) | SEQ ID No. |
|---|---|---|---|---|---|---|---|
| 412203 | 29 | 15 | 61 | 77 | 82 | 33 | 31 |
| 412206 | 28 | 44 | 68 | 80 | 89 | 22 | 34 |
| 412212 | 28 | 45 | 59 | 73 | 88 | 25 | 40 |
| 412223 | 33 | 48 | 62 | 76 | 81 | 21 | 51 |
| 412224 | 24 | 45 | 57 | 70 | 81 | 28 | 52 |
| 412225 | 32 | 42 | 65 | 78 | 73 | 23 | 53 |
| 413467 | 2 | 35 | 49 | 61 | 47 | 43 | 100 |
| 413468 | 14 | 34 | 56 | 78 | 75 | 35 | 101 |
| 413469 | 24 | 33 | 53 | 70 | 84 | 33 | 102 |
| 413476 | 26 | 44 | 64 | 73 | 82 | 25 | 109 |

TABLE 3-continued

| Dose-dependent antisense inhibition of human Factor 11 in HepG2 cells | | | | | | | |
|---|---|---|---|---|---|---|---|
| | 9.375 nM | 18.75 nM | 37.5 nM | 75 nM | 150 nM | $IC_{50}$ (nM) | SEQ ID No. |
| 413481 | 22 | 38 | 56 | 67 | 83 | 32 | 114 |
| 413482 | 26 | 39 | 59 | 74 | 82 | 28 | 115 |

Example 3: Antisense Inhibition of Human Factor 11 in HepG2 Cells by Oligonucleotides Designed by Microwalk Additional gapmers were designed based on the gapmers presented in Table 3. These gapmers were designed by creating gapmers shifted slightly upstream and downstream (i.e. "microwalk") of the original gapmers from Table 3. Gapmers were also created with various motifs, e.g. 5-10-5 MOE, 3-14-3 MOE, and 2-13-5 MOE. These gapmers were tested in vitro. Cultured HepG2 cells at a density of 10,000 cells per well were transfected using lipofectin reagent with 75 nM antisense oligonucleotide. After a treatment period of approximately 24 hours, RNA was isolated from the cells and Factor 11 mRNA levels were measured by quantitative real-time PCR. Factor 11 mRNA levels were adjusted according to total RNA content, as measured by RIBOGREEN. Results are presented as percent inhibition of Factor 11, relative to untreated control cells.

The in vitro inhibition data for the gapmers designed by microwalk were then compared with the in vitro inhibition data for the gapmers from Table 3, as indicated in Tables 4, 5, 6, 7, and 8. The oligonucleotides are displayed according to the region on the human mRNA (GENBANK Accession No. NM_000128.3) to which they map.

The chimeric antisense oligonucleotides in Table 4 were designed as 5-10-5 MOE, 3-14-3 MOE, and 2-13-5 MOE gapmers. The first listed gapmers in Table 4 are the original gapmers (see Table 3) from which the remaining gapmers were designed via microwalk and are designated by an asterisk. The 5-10-5 gapmers are 20 nucleotides in length, wherein the central gap segment is comprised of 10 2'-deoxynucleotides and is flanked on both sides (in the 5' and 3' directions) by wings comprising 5 nucleotides each. The 3-14-3 gapmers are 20 nucleotides in length, wherein the central gap segment is comprised of 14 2'-deoxynucleotides and is flanked on both sides (in the 5' and 3' directions) by wings comprising 3 nucleotides each. The 2-13-5 gapmers are 20 nucleotides in length, wherein the central gap segment is comprised of 13 2'-deoxynucleotides. The central gap is flanked on the 5' end with a wing comprising 2 nucleotides and on the 3' end with a wing comprising 5 nucleotides. For each of the motifs (5-10-5, 3-14-3, and 2-13-5), each nucleotide in the 5' wing segment and each nucleotide in the 3' wing segment has a 2'-MOE modification. The internucleoside linkages throughout each gapmer are phosphorothioate (P═S) linkages. All cytidine residues throughout each gapmer are 5-methylcytidines. "Target start site" indicates the 5'-most nucleotide to which the gapmer is targeted. "Target stop site" indicates the 3'-most nucleotide to which the gapmer is targeted. Each gapmer listed in Table 4 is targeted to SEQ ID NO: 1 (GENBANK Accession No. NM_000128.3).

As shown in Table 4, all of the 5-10-5 MOE gapmers, 3-14-3 MOE gapmers, and 2-13-5 MOE gapmers targeted to the target region beginning at target start site 656 and ending at the target stop site 704 (i.e. nucleobases 656-704) of SEQ ID NO: 1 exhibit at least 20% inhibition of Factor 11 mRNA. Many of the gapmers exhibit at least 60% inhibition. Several of the gapmers exhibit at least 80% inhibition, including ISIS numbers: 416806, 416809, 416811, 416814, 416821, 416825, 416826, 416827, 416828, 416868, 416869, 416878, 416879, 416881, 416883, 416890, 416891, 416892, 416893, 416894, 416895, 416896, 416945, 416946, 416969, 416970, 416971, 416972, 416973, 412203, 413467, 413468, and 413469. The following ISIS numbers exhibited at least 90% inhibition: 412203, 413467, 416825, 416826, 416827, 416868, 416878, 416879, 416892, 416893, 416895, 416896, 416945, 416972, and 416973. The following ISIS numbers exhibited at least 95% inhibition: 416878, 416892, 416895, and 416896.

TABLE 4

| Inhibition of human Factor 11 mRNA levels by chimeric antisense oligonucleotides targeted to nucleobases 656 to 704 of SEQ ID NO: 1 (GENBANK Accession No. NM_000128.3) | | | | | | |
|---|---|---|---|---|---|---|
| ISIS No. | Target Start Site | Target Stop Site | Sequence (5' to 3') | % inhib-ition | Motif | SEQ ID No. |
| *412203 | 656 | 675 | AATGTCTTTGTTGCAAGCGC | 97 | 5-10-5 | 31 |
| *413467 | 666 | 685 | GGTCCACATAAATGTCTTTG | 92 | 5-10-5 | 100 |
| *413468 | 671 | 690 | GTCTAGGTCCACATAAATGT | 83 | 5-10-5 | 101 |
| *413469 | 681 | 700 | TGCCCTTCATGTCTAGGTCC | 86 | 5-10-5 | 102 |
| 416868 | 656 | 675 | AATGTCTTTGTTGCAAGCGC | 93 | 3-14-3 | 31 |
| 416945 | 656 | 675 | AATGTCTTTGTTGCAAGCGC | 94 | 2-13-5 | 31 |
| 416806 | 657 | 676 | AAATGTCTTTGTTGCAAGCG | 86 | 5-10-5 | 171 |
| 416869 | 657 | 676 | AAATGTCTTTGTTGCAAGCG | 81 | 3-14-3 | 171 |
| 416946 | 657 | 676 | AAATGTCTTTGTTGCAAGCG | 86 | 2-13-5 | 171 |
| 416807 | 658 | 677 | TAAATGTCTTTGTTGCAAGC | 51 | 5-10-5 | 172 |

TABLE 4-continued

Inhibition of human Factor 11 mRNA levels by chimeric antisense oligonucleotides targeted to nucleobases 656 to 704 of SEQ ID NO: 1 (GENBANK Accession No. NM_000128.3)

| ISIS No. | Target Start Site | Target Stop Site | Sequence (5' to 3') | % inhib-ition | Motif | SEQ ID No. |
|---|---|---|---|---|---|---|
| 416870 | 658 | 677 | TAAATGTCTTTGTTGCAAGC | 76 | 3-14-3 | 172 |
| 416947 | 658 | 677 | TAAATGTCTTTGTTGCAAGC | 62 | 2-13-5 | 172 |
| 416808 | 659 | 678 | ATAAATGTCTTTGTTGCAAG | 55 | 5-10-5 | 173 |
| 416871 | 659 | 678 | ATAAATGTCTTTGTTGCAAG | 28 | 3-14-3 | 173 |
| 416948 | 659 | 678 | ATAAATGTCTTTGTTGCAAG | 62 | 2-13-5 | 173 |
| 416809 | 660 | 679 | CATAAATGTCTTTGTTGCAA | 86 | 5-10-5 | 174 |
| 416872 | 660 | 679 | CATAAATGTCTTTGTTGCAA | 20 | 3-14-3 | 174 |
| 416949 | 660 | 679 | CATAAATGTCTTTGTTGCAA | 64 | 2-13-5 | 174 |
| 416873 | 661 | 680 | ACATAAATGTCTTTGTTGCA | 51 | 3-14-3 | 99 |
| 416950 | 661 | 680 | ACATAAATGTCTTTGTTGCA | 71 | 2-13-5 | 99 |
| 416810 | 662 | 681 | CACATAAATGTCTTTGTTGC | 68 | 5-10-5 | 175 |
| 416874 | 662 | 681 | CACATAAATGTCTTTGTTGC | 49 | 3-14-3 | 175 |
| 416951 | 662 | 681 | CACATAAATGTCTTTGTTGC | 48 | 2-13-5 | 175 |
| 416811 | 663 | 682 | CCACATAAATGTCTTTGTTG | 84 | 5-10-5 | 176 |
| 416875 | 663 | 682 | CCACATAAATGTCTTTGTTG | 75 | 3-14-3 | 176 |
| 416952 | 663 | 682 | CCACATAAATGTCTTTGTTG | 51 | 2-13-5 | 176 |
| 416812 | 664 | 68 | TCCACATAAATGTCTTTGTT | 59 | 5-10-5 | 177 |
| 416876 | 664 | 683 | TCCACATAAATGTCTTTGTT | 37 | 3-14-3 | 177 |
| 416953 | 664 | 683 | TCCACATAAATGTCTTTGTT | 45 | 2-13-5 | 177 |
| 416813 | 665 | 684 | GTCCACATAAATGTCTTTGT | 70 | 5-10-5 | 178 |
| 416877 | 665 | 684 | GTCCACATAAATGTCTTTGT | 51 | 3-14-3 | 178 |
| 416954 | 665 | 684 | GTCCACATAAATGTCTTTGT | 61 | 2-13-5 | 178 |
| 416878 | 666 | 685 | GGTCCACATAAATGTCTTTG | 95 | 3-14-3 | 100 |
| 416955 | 666 | 685 | GGTCCACATAAATGTCTTTG | 75 | 2-13-5 | 100 |
| 416814 | 667 | 686 | AGGTCCACATAAATGTCTTT | 83 | 5-10-5 | 179 |
| 416879 | 667 | 686 | AGGTCCACATAAATGTCTTT | 92 | 3-14-3 | 179 |
| 416956 | 667 | 686 | AGGTCCACATAAATGTCTTT | 61 | 2-13-5 | 179 |
| 416815 | 668 | 687 | TAGGTCCACATAAATGTCTT | 63 | 5-10-5 | 180 |
| 416880 | 668 | 687 | TAGGTCCACATAAATGTCTT | 66 | 3-14-3 | 180 |
| 416957 | 668 | 687 | TAGGTCCACATAAATGTCTT | 59 | 2-13-5 | 180 |
| 416816 | 669 | 688 | CTAGGTCCACATAAATGTCT | 79 | 5-10-5 | 181 |
| 416881 | 669 | 688 | CTAGGTCCACATAAATGTCT | 81 | 3-14-3 | 181 |
| 416958 | 669 | 688 | CTAGGTCCACATAAATGTCT | 43 | 2-13-5 | 181 |
| 416817 | 670 | 689 | TCTAGGTCCACATAAATGTC | 74 | 5-10-5 | 182 |
| 416882 | 670 | 689 | TCTAGGTCCACATAAATGTC | 60 | 3-14-3 | 182 |
| 416959 | 670 | 689 | TCTAGGTCCACATAAATGTC | 25 | 2-13-5 | 182 |

TABLE 4-continued

Inhibition of human Factor 11 mRNA levels by chimeric antisense oligonucleotides targeted to nucleobases 656 to 704 of SEQ ID NO: 1 (GENBANK Accession No. NM_000128.3)

| ISIS No. | Target Start Site | Target Stop Site | Sequence (5' to 3') | % inhib- ition | Motif | SEQ ID No. |
|---|---|---|---|---|---|---|
| 416883 | 671 | 690 | GTCTAGGTCCACATAAATGT | 82 | 3-14-3 | 101 |
| 416960 | 671 | 690 | GTCTAGGTCCACATAAATGT | 60 | 2-13-5 | 101 |
| 416818 | 672 | 691 | TGTCTAGGTCCACATAAATG | 76 | 5-10-5 | 183 |
| 416884 | 672 | 691 | TGTCTAGGTCCACATAAATG | 69 | 3-14-3 | 183 |
| 416961 | 672 | 691 | TGTCTAGGTCCACATAAATG | 40 | 2-13-5 | 183 |
| 416819 | 673 | 692 | ATGTCTAGGTCCACATAAAT | 56 | 5-10-5 | 184 |
| 416885 | 673 | 692 | ATGTCTAGGTCCACATAAAT | 67 | 3-14-3 | 184 |
| 416962 | 673 | 692 | ATGTCTAGGTCCACATAAAT | 77 | 2-13-5 | 184 |
| 416820 | 674 | 693 | CATGTCTAGGTCCACATAAA | 77 | 5-10-5 | 185 |
| 416886 | 674 | 693 | CATGTCTAGGTCCACATAAA | 74 | 3-14-3 | 185 |
| 416963 | 674 | 693 | CATGTCTAGGTCCACATAAA | 48 | 2-13-5 | 185 |
| 416821 | 675 | 694 | TCATGTCTAGGTCCACATAA | 84 | 5-10-5 | 186 |
| 416964 | 675 | 694 | TCATGTCTAGGTCCACATAA | 69 | 2-13-5 | 186 |
| 412204 | 676 | 695 | TTCATGTCTAGGTCCACATA | 76 | 5-10-5 | 32 |
| 416888 | 676 | 695 | TTCATGTCTAGGTCCACATA | 76 | 3-14-3 | 32 |
| 416965 | 676 | 695 | TTCATGTCTAGGTCCACATA | 53 | 2-13-5 | 32 |
| 416822 | 677 | 696 | CTTCATGTCTAGGTCCACAT | 76 | 5-10-5 | 187 |
| 416889 | 677 | 696 | CTTCATGTCTAGGTCCACAT | 60 | 3-14-3 | 187 |
| 416966 | 677 | 696 | CTTCATGTCTAGGTCCACAT | 64 | 2-13-5 | 187 |
| 416823 | 678 | 697 | CCTTCATGTCTAGGTCCACA | 77 | 5-10-5 | 188 |
| 416890 | 678 | 697 | CCTTCATGTCTAGGTCCACA | 87 | 3-14-3 | 188 |
| 416967 | 678 | 697 | CCTTCATGTCTAGGTCCACA | 75 | 2-13-5 | 188 |
| 416824 | 679 | 698 | CCCTTCATGTCTAGGTCCAC | 64 | 5-10-5 | 189 |
| 416891 | 679 | 698 | CCCTTCATGTCTAGGTCCAC | 81 | 3-14-3 | 189 |
| 416968 | 679 | 698 | CCCTTCATGTCTAGGTCCAC | 73 | 2-13-5 | 189 |
| 416825 | 680 | 699 | GCCCTTCATGTCTAGGTCCA | 92 | 5-10-5 | 190 |
| 416892 | 680 | 699 | GCCCTTCATGTCTAGGTCCA | 100 | 3-14-3 | 190 |
| 416969 | 680 | 699 | GCCCTTCATGTCTAGGTCCA | 80 | 2-13-5 | 190 |
| 416893 | 681 | 700 | TGCCCTTCATGTCTAGGTCC | 90 | 3-14-3 | 102 |
| 416970 | 681 | 700 | TGCCCTTCATGTCTAGGTCC | 88 | 2-13-5 | 102 |
| 416826 | 682 | 701 | ATGCCCTTCATGTCTAGGTC | 94 | 5-10-5 | 191 |
| 416894 | 682 | 701 | ATGCCCTTCATGTCTAGGTC | 85 | 3-14-3 | 191 |
| 416971 | 682 | 701 | ATGCCCTTCATGTCTAGGTC | 83 | 2-13-5 | 191 |
| 416827 | 683 | 702 | TATGCCCTTCATGTCTAGGT | 93 | 5-10-5 | 192 |
| 416895 | 683 | 702 | TATGCCCTTCATGTCTAGGT | 95 | 3-14-3 | 192 |
| 416972 | 683 | 702 | TATGCCCTTCATGTCTAGGT | 90 | 2-13-5 | 192 |

TABLE 4-continued

| Inhibition of human Factor 11 mRNA levels by chimeric antisense oligonucleotides targeted to nucleobases 656 to 704 of SEQ ID NO: 1 (GENBANK Accession No. NM_000128.3) | | | | | | |
|---|---|---|---|---|---|---|
| ISIS No. | Target Start Site | Target Stop Site | Sequence (5' to 3') | % inhib-ition | Motif | SEQ ID No. |
| 416828 | 684 | 703 | TTATGCCCTTCATGTCTAGG | 87 | 5-10-5 | 193 |
| 416896 | 684 | 703 | TTATGCCCTTCATGTCTAGG | 95 | 3-14-3 | 193 |
| 416973 | 684 | 703 | TTATGCCCTTCATGTCTAGG | 92 | 2-13-5 | 193 |
| 416829 | 685 | 704 | TTTATGCCCTTCATGTCTAG | 72 | 5-10-5 | 194 |
| 416897 | 685 | 704 | TTTATGCCCTTCATGTCTAG | 66 | 3-14-3 | 194 |
| 416974 | 685 | 704 | TTTATGCCCTTCATGTCTAG | 73 | 2-13-5 | 194 |

The chimeric antisense oligonucleotides in Table 5 were designed as 5-10-5 MOE, 3-14-3 MOE, and 2-13-5 MOE gapmers. The first listed gapmer in Table 5 is the original gapmer (see Table 3) from which the remaining gapmers were designed via microwalk and is designated by an asterisk. The 5-10-5 gapmers are 20 nucleotides in length, wherein the central gap segment is comprised of 10 2'-deoxynucleotides and is flanked on both sides (in the 5' and 3' directions) by wings comprising 5 nucleotides each. The 3-14-3 gapmers are 20 nucleotides in length, wherein the central gap segment is comprised of 14 2'-deoxynucleotides and is flanked on both sides (in the 5' and 3' directions) by wings comprising 3 nucleotides each. The 2-13-5 gapmers are 20 nucleotides in length, wherein the central gap segment is comprised of 13 2'-deoxynucleotides. The central gap is flanked on the 5' end with a wing comprising 2 nucleotides and on the 3' end with a wing comprising 5 nucleotides. For each of the motifs (5-10-5, 3-14-3, and 2-13-5), each nucleotide in the 5' wing segment and each nucleotide in the 3' wing segment has a 2'-MOE modification. The internucleoside linkages throughout each gapmer are phosphorothioate (P═S) linkages. All cytidine residues throughout each gapmer are 5-methylcytidines. “Target start site” indicates the 5'-most nucleotide to which the gapmer is targeted. “Target stop site” indicates the 3'-most nucleotide to which the gapmer is targeted. Each gapmer listed in Table 5 is targeted to SEQ ID NO: 1 (GENBANK Accession No. NM_000128.3).

As shown in Table 5, all of the 5-10-5 MOE gapmers, 3-14-3 MOE gapmers, and 2-13-5 MOE gapmers targeted to the target region beginning at target start site 738 and ending at the target stop site 762 (i.e. nucleobases 738-762) of SEQ ID NO: 1 exhibit at least 45% inhibition of Factor 11 mRNA. Most of the gapmers exhibit at least 60% inhibition. Several of the gapmers exhibit at least 80% inhibition, including ISIS numbers: 412206, 416830, 416831, 416898, 416899, 416900, 416903, 416975, 416976, 416977, and 416980. The following ISIS numbers exhibited at least 90% inhibition: 412206, 416831, and 416900.

TABLE 5

| Inhibition of human Factor 11 mRNA levels by chimeric antisense oligonucleotides targeted to nucleobases 738 to 762 of SEQ ID NO: 1 (GENBANK Accession No. NM_000128.3) | | | | | | |
|---|---|---|---|---|---|---|
| ISIS No. | Target Start Site | Target Stop Site | Sequence (5' to 3') | % inhib-ition | Motif | SEQ ID No. |
| *412206 | 738 | 757 | CCGTGCATCTTTCTTGGCAT | 93 | 5-10-5 | 34 |
| 416898 | 738 | 757 | CCGTGCATCTTTCTTGGCAT | 88 | 3-14-3 | 34 |
| 416975 | 738 | 757 | CCGTGCATCTTTCTTGGCAT | 87 | 2-13-5 | 34 |
| 416830 | 739 | 758 | TCCGTGCATCTTTCTTGGCA | 81 | 5-10-5 | 195 |
| 416899 | 739 | 758 | TCCGTGCATCTTTCTTGGCA | 86 | 3-14-3 | 195 |
| 416976 | 739 | 758 | TCCGTGCATCTTTCTTGGCA | 83 | 2-13-5 | 195 |
| 416831 | 740 | 759 | ATCCGTGCATCTTTCTTGGC | 91 | 5-10-5 | 196 |
| 416900 | 740 | 759 | ATCCGTGCATCTTTCTTGGC | 90 | 3-14-3 | 196 |
| 416977 | 740 | 759 | ATCCGTGCATCTTTCTTGGC | 82 | 2-13-5 | 196 |
| 416832 | 741 | 760 | CATCCGTGCATCTTTCTTGG | 79 | 5-10-5 | 197 |
| 416901 | 741 | 760 | CATCCGTGCATCTTTCTTGG | 65 | 3-14-3 | 197 |

TABLE 5-continued

Inhibition of human Factor 11 mRNA levels by chimeric antisense oligonucleotides targeted to nucleobases 738 to 762 of SEQ ID NO: 1 (GENBANK Accession No. NM_000128.3)

| ISIS No. | Target Start Site | Target Stop Site | Sequence (5' to 3') | % inhib-ition | Motif | SEQ ID No. |
|---|---|---|---|---|---|---|
| 416978 | 741 | 760 | CATCCGTGCATCTTTCTTGG | 76 | 2-13-5 | 197 |
| 416833 | 742 | 761 | TCATCCGTGCATCTTTCTTG | 65 | 5-10-5 | 198 |
| 416902 | 742 | 761 | TCATCCGTGCATCTTTCTTG | 46 | 3-14-3 | 198 |
| 416979 | 742 | 761 | TCATCCGTGCATCTTTCTTG | 63 | 2-13-5 | 198 |
| 416834 | 743 | 762 | GTCATCCGTGCATCTTTCTT | 58 | 5-10-5 | 199 |
| 416903 | 743 | 762 | GTCATCCGTGCATCTTTCTT | 88 | 3-14-3 | 199 |
| 416980 | 743 | 762 | GTCATCCGTGCATCTTTCTT | 87 | 2-13-5 | 199 |

The chimeric antisense oligonucleotides in Table 6 were designed as 5-10-5 MOE, 3-14-3 MOE, and 2-13-5 MOE gapmers. The first listed gapmers in Table 6 are the original gapmers (see Table 3) from which the remaining gapmers were designed via microwalk and are designated by an asterisk. The 5-10-5 gapmers are 20 nucleotides in length, wherein the central gap segment is comprised of 10 2'-deoxynucleotides and is flanked on both sides (in the 5' and 3' directions) by wings comprising 5 nucleotides each. The 3-14-3 gapmers are 20 nucleotides in length, wherein the central gap segment is comprised of 14 2'-deoxynucleotides and is flanked on both sides (in the 5' and 3' directions) by wings comprising 3 nucleotides each. The 2-13-5 gapmers are 20 nucleotides in length, wherein the central gap segment is comprised of 13 2'-deoxynucleotides. The central gap is flanked on the 5' end with a wing comprising 2 nucleotides and on the 3' end with a wing comprising 5 nucleotides. For each of the motifs (5-10-5, 3-14-3, and 2-13-5), each nucleotide in the 5' wing segment and each nucleotide in the 3' wing segment has a 2'-MOE modification. The internucleoside linkages throughout each gapmer are phosphorothioate (P═S) linkages. All cytidine residues throughout each gapmer are 5-methylcytidines. “Target start site” indicates the 5'-most nucleotide to which the gapmer is targeted. “Target stop site” indicates the 3'-most nucleotide to which the gapmer is targeted. Each gapmer listed in Table 6 is targeted to SEQ ID NO: 1 (GENBANK Accession No. NM_000128.3).

As shown in Table 6, all of the 5-10-5 MOE gapmers, 3-14-3 MOE gapmers, and 2-13-5 MOE gapmers targeted to the target region beginning at target start site 1018 and ending at the target stop site 1042 (i.e. nucleobases 1018-1042) of SEQ ID NO: 1 exhibit at least 80% inhibition of Factor 11 mRNA. The following ISIS numbers exhibited at least 90% inhibition: 413474, 416837, 416838, 416904, 416907, and 416908.

TABLE 6

Inhibition of human Factor 11 mRNA levels by chimeric antisense oligonucleotides targeted to nucleobases 1018 to 1042 of SEQ ID NO: 1 (GENBANK Accession No. NM_000128.3)

| ISIS No. | Target Start Site | Target Stop Site | Sequence (5' to 3') | % inhib-ition | Motif | SEQ ID No. |
|---|---|---|---|---|---|---|
| *412212 | 1018 | 1037 | CCGGGATGATGAGTGCAGAT | 89 | 5-10-5 | 40 |
| 416904 | 1018 | 1037 | CCGGGATGATGAGTGCAGAT | 90 | 3-14-3 | 40 |
| 416981 | 1018 | 1037 | CCGGGATGATGAGTGCAGAT | 87 | 2-13-5 | 40 |
| 416835 | 1019 | 1038 | ACCGGGATGATGAGTGCAGA | 83 | 5-10-5 | 200 |
| 416905 | 1019 | 1038 | ACCGGGATGATGAGTGCAGA | 85 | 3-14-3 | 200 |
| 416982 | 1019 | 1038 | ACCGGGATGATGAGTGCAGA | 84 | 2-13-5 | 200 |
| 416836 | 1020 | 1039 | AACCGGGATGATGAGTGCAG | 89 | 5-10-5 | 201 |
| 416906 | 1020 | 1039 | AACCGGGATGATGAGTGCAG | 88 | 3-14-3 | 201 |
| 416983 | 1020 | 1039 | AACCGGGATGATGAGTGCAG | 86 | 2-13-5 | 201 |
| 416837 | 1021 | 1040 | CAACCGGGATGATGAGTGCA | 90 | 5-10-5 | 202 |
| 416907 | 1021 | 1040 | CAACCGGGATGATGAGTGCA | 90 | 3-14-3 | 202 |

TABLE 6-continued

Inhibition of human Factor 11 mRNA levels by chimeric antisense oligonucleotides targeted to nucleobases 1018 to 1042 of SEQ ID NO: 1 (GENBANK Accession No. NM_000128.3)

| ISIS No. | Target Start Site | Target Stop Site | Sequence (5' to 3') | % inhib-ition | Motif | SEQ ID No. |
|---|---|---|---|---|---|---|
| 416984 | 1021 | 1040 | CAACCGGGATGATGAGTGCA | 89 | 2-13-5 | 202 |
| 416838 | 1022 | 1041 | GCAACCGGGATGATGAGTGC | 94 | 5-10-5 | 203 |
| 416908 | 1022 | 1041 | GCAACCGGGATGATGAGTGC | 98 | 3-14-3 | 203 |
| 416985 | 1022 | 1041 | GCAACCGGGATGATGAGTGC | 88 | 2-13-5 | 203 |
| 413474 | 1023 | 1042 | AGCAACCGGGATGATGAGTG | 93 | 5-10-5 | 107 |

The chimeric antisense oligonucleotides in Table 7 were designed as 5-10-5 MOE, 3-14-3 MOE, and 2-13-5 MOE gapmers. The first listed gapmer in Table 7 is the original gapmer (see Table 3) from which the remaining gapmers were designed via microwalk and is designated by an asterisk. The 5-10-5 gapmers are 20 nucleotides in length, wherein the central gap segment is comprised of 10 2'-deoxynucleotides and is flanked on both sides (in the 5' and 3' directions) by wings comprising 5 nucleotides each. The 3-14-3 gapmers are 20 nucleotides in length, wherein the central gap segment is comprised of 14 2'-deoxynucleotides and is flanked on both sides (in the 5' and 3' directions) by wings comprising 3 nucleotides each. The 2-13-5 gapmers are 20 nucleotides in length, wherein the central gap segment is comprised of 13 2'-deoxynucleotides. The central gap is flanked on the 5' end with a wing comprising 2 nucleotides and on the 3' end with a wing comprising 5 nucleotides. For each of the motifs (5-10-5, 3-14-3, and 2-13-5), each nucleotide in the 5' wing segment and each nucleotide in the 3' wing segment has a 2'-MOE modification. The internucleoside linkages throughout each gapmer are phosphorothioate (P═S) linkages. All cytidine residues throughout each gapmer are 5-methylcytidines. "Target start site" indicates the 5'-most nucleotide to which the gapmer is targeted. "Target stop site" indicates the 3'-most nucleotide to which the gapmer is targeted. Each gapmer listed in Table 7 is targeted to SEQ ID NO: 1 (GENBANK Accession No. NM_000128.3).

As shown in Table 7, all of the 5-10-5 MOE gapmers, 3-14-3 MOE gapmers, and 2-13-5 MOE gapmers targeted to the target region beginning at target start site 1062 and ending at the target stop site 1091 (i.e. nucleobases 1062-1091) of SEQ ID NO: 1 exhibit at least 20% inhibition of Factor 11 mRNA. Many of the gapmers exhibit at least 50% inhibition, including: 412215, 413476, 413476, 416839, 416840, 416841, 416842, 416843, 416844, 416845, 416846, 416847, 416909, 416910, 416911, 416912, 416913, 416914, 416915, 416916, 416917, 416918, 416986, 416987, 416988, 416989, 416990, 416991, 416992, 416993, 416994, 416995. The following ISIS numbers exhibited at least 80% inhibition: 412215, 413476, 413476, 416839, 416840, 416841, 416842, 416843, 416844, 416845, 416910, 416911, 416912, 416913, 416914, 416916, 416917, 416986, 416987, 416989, 416991, 416992, 416993, and 416994. The following ISIS numbers exhibited at least 90% inhibition: 413476, 413476, 416842, 416844, 416910, 416911, 416912, 416913, 416916, 416917, and 416993.

TABLE 7

Inhibition of human Factor 11 mRNA levels by chimeric antisense oligonucleotides targeted to nucleobases 1062 to 1091 of SEQ ID NO: 1 (GENBANK Accession No. NM_000128.3)

| ISIS No. | Target Start Site | Target Stop Site | Sequence (5' to 3') | % inhib-ition | Motif | SEQ ID No. |
|---|---|---|---|---|---|---|
| *413476 | 1067 | 1086 | TTGAGATTCTTTGGGCCATT | 93 | 5-10-5 | 109 |
| 412215 | 1062 | 1081 | ATTCTTTGGGCCATTCCTGG | 82 | 5-10-5 | 43 |
| 416909 | 1062 | 1081 | ATTCTTTGGGCCATTCCTGG | 78 | 3-14-3 | 43 |
| 416986 | 1062 | 1081 | ATTCTTTGGGCCATTCCTGG | 88 | 2-13-5 | 43 |
| 416839 | 1063 | 1082 | GATTCTTTGGGCCATTCCTG | 89 | 5-10-5 | 204 |
| 416910 | 1063 | 1082 | GATTCTTTGGGCCATTCCTG | 90 | 3-14-3 | 204 |
| 416987 | 1063 | 1082 | GATTCTTTGGGCCATTCCTG | 80 | 2-13-5 | 204 |
| 416840 | 1064 | 1083 | AGATTCTTTGGGCCATTCCT | 85 | 5-10-5 | 205 |
| 416911 | 1064 | 1083 | AGATTCTTTGGGCCATTCCT | 90 | 3-14-3 | 205 |
| 416988 | 1064 | 1083 | AGATTCTTTGGGCCATTCCT | 76 | 2-13-5 | 205 |

TABLE 7-continued

Inhibition of human Factor 11 mRNA levels by chimeric antisense oligonucleotides targeted to nucleobases 1062 to 1091 of SEQ ID NO: 1 (GENBANK Accession No. NM_000128.3)

| ISIS No. | Target Start Site | Target Stop Site | Sequence (5' to 3') | % inhib-ition | Motif | SEQ ID No. |
|---|---|---|---|---|---|---|
| 416841 | 1065 | 1084 | GAGATTCTTTGGGCCATTCC | 87 | 5-10-5 | 206 |
| 416912 | 1065 | 1084 | GAGATTCTTTGGGCCATTCC | 92 | 3-14-3 | 206 |
| 416989 | 1065 | 1084 | GAGATTCTTTGGGCCATTCC | 88 | 2-13-5 | 206 |
| 416842 | 1066 | 1085 | TGAGATTCTTTGGGCCATTC | 94 | 5-10-5 | 207 |
| 416913 | 1066 | 1085 | TGAGATTCTTTGGGCCATTC | 93 | 3-14-3 | 207 |
| 416990 | 1066 | 1085 | TGAGATTCTTTGGGCCATTC | 76 | 2-13-5 | 207 |
| 413476 | 1067 | 1086 | TTGAGATTCTTTGGGCCATT | 93 | 5-10-5 | 109 |
| 416914 | 1067 | 1086 | TTGAGATTCTTTGGGCCATT | 87 | 3-14-3 | 109 |
| 416991 | 1067 | 1086 | TTGAGATTCTTTGGGCCATT | 87 | 2-13-5 | 109 |
| 416843 | 1068 | 1087 | TTTGAGATTCTTTGGGCCAT | 89 | 5-10-5 | 208 |
| 416915 | 1068 | 1087 | TTTGAGATTCTTTGGGCCAT | 79 | 3-14-3 | 208 |
| 416992 | 1068 | 1087 | TTTGAGATTCTTTGGGCCAT | 84 | 2-13-5 | 208 |
| 416844 | 1069 | 1088 | CTTTGAGATTCTTTGGGCCA | 90 | 5-10-5 | 209 |
| 416916 | 1069 | 1088 | CTTTGAGATTCTTTGGGCCA | 91 | 3-14-3 | 209 |
| 416993 | 1069 | 1088 | CTTTGAGATTCTTTGGGCCA | 91 | 2-13-5 | 209 |
| 416845 | 1070 | 1089 | TCTTTGAGATTCTTTGGGCC | 86 | 5-10-5 | 210 |
| 416917 | 1070 | 1089 | TCTTTGAGATTCTTTGGGCC | 92 | 3-14-3 | 210 |
| 416994 | 1070 | 1089 | TCTTTGAGATTCTTTGGGCC | 83 | 2-13-5 | 210 |
| 416846 | 1071 | 1090 | TTCTTTGAGATTCTTTGGGC | 72 | 5-10-5 | 211 |
| 416918 | 1071 | 1090 | TTCTTTGAGATTCTTTGGGC | 63 | 3-14-3 | 211 |
| 416995 | 1071 | 1090 | TTCTTTGAGATTCTTTGGGC | 64 | 2-13-5 | 211 |
| 416847 | 1072 | 1091 | TTTCTTTGAGATTCTTTGGG | 50 | 5-10-5 | 212 |
| 416919 | 1072 | 1091 | TTTCTTTGAGATTCTTTGGG | 27 | 3-14-3 | 212 |
| 416996 | 1072 | 1091 | TTTCTTTGAGATTCTTTGGG | 22 | 2-13-5 | 212 |

The chimeric antisense oligonucleotides in Table 8 were designed as 5-10-5 MOE, 3-14-3 MOE, and 2-13-5 MOE gapmers. The first listed gapmers in Table 8 are the original gapmers (see Table 3) from which the remaining gapmers were designed via microwalk and are designated by an asterisk. The 5-10-5 gapmers are 20 nucleotides in length, wherein the central gap segment is comprised of 10 2'-deoxynucleotides and is flanked on both sides (in the 5' and 3' directions) by wings comprising 5 nucleotides each. The 3-14-3 gapmers are 20 nucleotides in length, wherein the central gap segment is comprised of 14 2'-deoxynucleotides and is flanked on both sides (in the 5' and 3' directions) by wings comprising 3 nucleotides each. The 2-13-5 gapmers are 20 nucleotides in length, wherein the central gap segment is comprised of 13 2'-deoxynucleotides. The central gap is flanked on the 5' end with a wing comprising 2 nucleotides and on the 3' end with a wing comprising 5 nucleotides. For each of the motifs (5-10-5, 3-14-3, and 2-13-5), each nucleotide in the 5' wing segment and each nucleotide in the 3' wing segment has a 2'-MOE modification. The internucleoside linkages throughout each gapmer are phosphorothioate (P═S) linkages. All cytidine residues throughout each gapmer are 5-methylcytidines. “Target start site” indicates the 5'-most nucleotide to which the gapmer is targeted. “Target stop site” indicates the 3'-most nucleotide to which the gapmer is targeted. Each gapmer listed in Table 8 is targeted to SEQ ID NO: 1 (GENBANK Accession No. NM_000128.3).

As shown in Table 8, all of the 5-10-5 MOE gapmers, 3-14-3 MOE gapmers, and 2-13-5 MOE gapmers targeted to the target region beginning at target start site 1275 and ending at the target stop site 1318 (i.e. nucleobases 1275-1318) of SEQ ID NO: 1 exhibit at least 70% inhibition of Factor 11 mRNA. Many of the gapmers exhibit at least 80% inhibition, including: 412223, 412224, 412225, 413482, 416848, 416849, 416850, 416851, 416852, 416853, 416854, 416855, 416856, 416857, 416858, 416859, 416860, 416861, 416862, 416863, 416864, 416865, 416866, 416867, 416920, 416921, 416922, 416923, 416924, 416925, 416926, 416927, 416928, 416929, 416930, 416931, 416932, 416933, 416934, 416935, 416936, 416937, 416938, 416939, 416940, 416941, 416942, 416943, 416944, 416997, 416998, 416999, 417000, 417001, 417002, 417003, 417004, 417006, 417007, 417008, 417009, 417010, 417011, 417013, 417014, 417015, 417016, 417017, 417018, 417019, and 417020. The following ISIS numbers exhibited at least 90% inhibition: 412224, 416850, 416853, 416856, 416857, 416858, 416861, 416862, 416864, 416922, 416923, 416924, 416925, 416926, 416928, 416931, 416932, 416933, 416934, 416935, 416937, 416938, 416940, 416941, 416943, 416999, 417002, 416854, and 416859.

TABLE 8

Inhibition of human Factor 11 mRNA levels by chimeric antisense oligonucleotides targeted to nucleobases 1275 to 1318 of SEQ ID NO: 1 (GENBANK Accession No. NM_000128.3)

| ISIS No. | Target Start Site | Target Stop Site | Sequence (5' to 3') | % inhib-ition | Motif | SEQ ID No. |
|---|---|---|---|---|---|---|
| *412223 | 1275 | 1294 | ACAGTTTCTGGCAGGCCTCG | 85 | 5-10-5 | 51 |
| *412224 | 1285 | 1304 | GCATTGGTGCACAGTTTCTG | 93 | 5-10-5 | 52 |
| *413482 | 1290 | 1309 | GGACGGCATTGGTGCACAGT | 89 | 5-10-5 | 115 |
| *412225 | 1295 | 1314 | GCAGCGGACGGCATTGGTGC | 86 | 5-10-5 | 53 |
| 416920 | 1275 | 1294 | ACAGTTTCTGGCAGGCCTCG | 88 | 3-14-3 | 51 |
| 416997 | 1275 | 1294 | ACAGTTTCTGGCAGGCCTCG | 84 | 2-13-5 | 51 |
| 416848 | 1276 | 1295 | CACAGTTTCTGGCAGGCCTC | 86 | 5-10-5 | 213 |
| 416921 | 1276 | 1295 | CACAGTTTCTGGCAGGCCTC | 88 | 3-14-3 | 213 |
| 416998 | 1276 | 1295 | CACAGTTTCTGGCAGGCCTC | 88 | 2-13-5 | 213 |
| 416849 | 1277 | 1296 | GCACAGTTTCTGGCAGGCCT | 88 | 5-10-5 | 214 |
| 416922 | 1277 | 1294 | GCACAGTTTCTGGCAGGCCT | 94 | 3-14-3 | 214 |
| 416999 | 1277 | 1296 | GCACAGTTTCTGGCAGGCCT | 92 | 2-13-5 | 214 |
| 416850 | 1278 | 1297 | TGCACAGTTTCTGGCAGGCC | 93 | 5-10-5 | 215 |
| 416923 | 1278 | 1297 | TGCACAGTTTCTGGCAGGCC | 96 | 3-14-3 | 215 |
| 417000 | 1278 | 1297 | TGCACAGTTTCTGGCAGGCC | 89 | 2-13-5 | 215 |
| 416851 | 1279 | 1298 | GTGCACAGTTTCTGGCAGGC | 88 | 5-10-5 | 216 |
| 416924 | 1279 | 1298 | GTGCACAGTTTCTGGCAGGC | 96 | 3-14-3 | 216 |
| 417001 | 1279 | 1298 | GTGCACAGTTTCTGGCAGGC | 83 | 2-13-5 | 216 |
| 416925 | 1280 | 1299 | GGTGCACAGTTTCTGGCAGG | 98 | 3-14-3 | 114 |
| 417002 | 1280 | 1299 | GGTGCACAGTTTCTGGCAGG | 92 | 2-13-5 | 114 |
| 416852 | 1281 | 1300 | TGGTGCACAGTTTCTGGCAG | 84 | 5-10-5 | 217 |
| 416926 | 1281 | 1300 | TGGTGCACAGTTTCTGGCAG | 93 | 3-14-3 | 217 |
| 417003 | 1281 | 1300 | TGGTGCACAGTTTCTGGCAG | 89 | 2-13-5 | 217 |
| 416853 | 1282 | 1301 | TTGGTGCACAGTTTCTGGCA | 91 | 5-10-5 | 218 |
| 416927 | 1282 | 1301 | TTGGTGCACAGTTTCTGGCA | 87 | 3-14-3 | 218 |
| 417004 | 1282 | 1301 | TTGGTGCACAGTTTCTGGCA | 86 | 2-13-5 | 218 |
| 416854 | 1283 | 1302 | ATTGGTGCACAGTTTCTGGC | 90 | 5-10-5 | 219 |
| 416928 | 1283 | 1302 | ATTGGTGCACAGTTTCTGGC | 91 | 3-14-3 | 219 |
| 417005 | 1283 | 1302 | ATTGGTGCACAGTTTCTGGC | 79 | 2-13-5 | 219 |
| 416855 | 1284 | 1303 | CATTGGTGCACAGTTTCTGG | 87 | 5-10-5 | 220 |
| 416929 | 1284 | 1303 | CATTGGTGCACAGTTTCTGG | 83 | 3-14-3 | 220 |

TABLE 8-continued

Inhibition of human Factor 11 mRNA levels by chimeric antisense oligonucleotides targeted to nucleobases 1275 to 1318 of SEQ ID NO: 1 (GENBANK Accession No. NM_000128.3)

| ISIS No. | Target Start Site | Target Stop Site | Sequence (5' to 3') | % inhib-ition | Motif | SEQ ID No. |
|---|---|---|---|---|---|---|
| 417006 | 1284 | 1303 | CATTGGTGCACAGTTTCTGG | 81 | 2-13-5 | 220 |
| 416930 | 1285 | 1304 | GCATTGGTGCACAGTTTCTG | 87 | 3-14-3 | 52 |
| 417007 | 1285 | 1304 | GCATTGGTGCACAGTTTCTG | 82 | 2-13-5 | 52 |
| 416856 | 1286 | 1305 | GGCATTGGTGCACAGTTTCT | 95 | 5-10-5 | 221 |
| 416931 | 1286 | 1305 | GGCATTGGTGCACAGTTTCT | 96 | 3-14-3 | 221 |
| 417008 | 1286 | 1305 | GGCATTGGTGCACAGTTTCT | 82 | 2-13-5 | 221 |
| 416857 | 1287 | 1306 | CGGCATTGGTGCACAGTTTC | 92 | 5-10-5 | 222 |
| 416932 | 1287 | 1306 | CGGCATTGGTGCACAGTTTC | 92 | 3-14-3 | 222 |
| 417009 | 1287 | 1306 | CGGCATTGGTGCACAGTTTC | 85 | 2-13-5 | 222 |
| 416858 | 1288 | 1307 | ACGGCATTGGTGCACAGTTT | 93 | 5-10-5 | 223 |
| 416933 | 1288 | 1307 | ACGGCATTGGTGCACAGTTT | 92 | 3-14-3 | 223 |
| 417010 | 1288 | 1307 | ACGGCATTGGTGCACAGTTT | 81 | 2-13-5 | 223 |
| 416859 | 1289 | 1308 | GACGGCATTGGTGCACAGTT | 90 | 5-10-5 | 224 |
| 416934 | 1289 | 1308 | GACGGCATTGGTGCACAGTT | 90 | 3-14-3 | 224 |
| 417011 | 1289 | 1308 | GACGGCATTGGTGCACAGTT | 86 | 2-13-5 | 224 |
| 416935 | 1290 | 1309 | GGACGGCATTGGTGCACAGT | 92 | 3-14-3 | 115 |
| 417012 | 1290 | 1309 | GGACGGCATTGGTGCACAGT | 72 | 2-13-5 | 115 |
| 416860 | 1291 | 1310 | CGGACGGCATTGGTGCACAG | 88 | 5-10-5 | 225 |
| 416936 | 1291 | 1310 | CGGACGGCATTGGTGCACAG | 89 | 3-14-3 | 225 |
| 417013 | 1291 | 1310 | CGGACGGCATTGGTGCACAG | 86 | 2-13-5 | 225 |
| 416861 | 1292 | 1311 | GCGGACGGCATTGGTGCACA | 92 | 5-10-5 | 226 |
| 416937 | 1292 | 1311 | GCGGACGGCATTGGTGCACA | 93 | 3-14-3 | 226 |
| 417014 | 1292 | 1311 | GCGGACGGCATTGGTGCACA | 87 | 2-13-5 | 226 |
| 416862 | 1293 | 1312 | AGCGGACGGCATTGGTGCAC | 90 | 5-10-5 | 227 |
| 416938 | 1293 | 1312 | AGCGGACGGCATTGGTGCAC | 90 | 3-14-3 | 227 |
| 417015 | 1293 | 1312 | AGCGGACGGCATTGGTGCAC | 87 | 2-13-5 | 227 |
| 416863 | 1294 | 1313 | CAGCGGACGGCATTGGTGCA | 83 | 5-10-5 | 228 |
| 416939 | 1294 | 1313 | CAGCGGACGGCATTGGTGCA | 88 | 3-14-3 | 228 |
| 417016 | 1294 | 1313 | CAGCGGACGGCATTGGTGCA | 85 | 2-13-5 | 228 |
| 416940 | 1295 | 1314 | GCAGCGGACGGCATTGGTGC | 92 | 3-14-3 | 53 |
| 417017 | 1295 | 1314 | GCAGCGGACGGCATTGGTGC | 82 | 2-13-5 | 53 |
| 416864 | 1296 | 1315 | GGCAGCGGACGGCATTGGTG | 93 | 5-10-5 | 229 |
| 416941 | 1296 | 1315 | GGCAGCGGACGGCATTGGTG | 95 | 3-14-3 | 229 |
| 417018 | 1296 | 1315 | GGCAGCGGACGGCATTGGTG | 82 | 2-13-5 | 229 |
| 416865 | 1297 | 1316 | TGGCAGCGGACGGCATTGGT | 88 | 5-10-5 | 230 |
| 416942 | 1297 | 1316 | TGGCAGCGGACGGCATTGGT | 85 | 3-14-3 | 230 |

TABLE 8-continued

Inhibition of human Factor 11 mRNA levels by chimeric antisense oligonucleotides targeted to nucleobases 1275 to 1318 of SEQ ID NO: 1 (GENBANK Accession No. NM_000128.3)

| ISIS No. | Target Start Site | Target Stop Site | Sequence (5' to 3') | % inhib-ition | Motif | SEQ ID No. |
|---|---|---|---|---|---|---|
| 417019 | 1297 | 1316 | TGGCAGCGGACGGCATTGGT | 84 | 2-13-5 | 230 |
| 416866 | 1298 | 1317 | CTGGCAGCGGACGGCATTGG | 88 | 5-10-5 | 231 |
| 416943 | 1298 | 1317 | CTGGCAGCGGACGGCATTGG | 92 | 3-14-3 | 231 |
| 417020 | 1298 | 1317 | CTGGCAGCGGACGGCATTGG | 84 | 2-13-5 | 231 |
| 416867 | 1299 | 1318 | ACTGGCAGCGGACGGCATTG | 83 | 5-10-5 | 232 |
| 416944 | 1299 | 1318 | ACTGGCAGCGGACGGCATTG | 83 | 3-14-3 | 232 |
| 417021 | 1299 | 1318 | ACTGGCAGCGGACGGCATTG | 74 | 2-13-5 | 232 |

Example 4: Dose-Dependent Antisense Inhibition of Human Factor 11 in HepG2 Cells Gapmers from Example 3 (see Tables 4, 5, 6, 7, and 8), exhibiting in vitro inhibition of human Factor 11, were tested at various doses in HepG2 cells. Cells were plated at a density of 10,000 cells per well and transfected using lipofectin reagent with 9.375 nM, 18.75 nM, 37.5 nM and 75 nM concentrations of antisense oligonucleotide, as specified in Table 9. After a treatment period of approximately 16 hours, RNA was isolated from the cells and Factor 11 mRNA levels were measured by quantitative real-time PCR. Human Factor 11 primer probe set RTS 2966 was used to measure mRNA levels. Factor 11 mRNA levels were adjusted according to total RNA content, as measured by RIBOGREEN. Results are presented as percent inhibition of Factor 11, relative to untreated control cells. As illustrated in Table 9, Factor 11 mRNA levels were reduced in a dose-dependent manner in antisense oligonucleotide treated cells.

TABLE 9

Dose-dependent antisense inhibition of human Factor 11 in HepG2 cells via transfection of oligonucleotides with lipofectin

| | 9.375 nM | 18.75 nM | 37.5 nM | 75 nM | Motif | $IC_{50}$ (nM) | SEQ ID No. |
|---|---|---|---|---|---|---|---|
| 412203 | 33 | 40 | 62 | 74 | 5-10-5 | 24 | 31 |
| 412206 | 24 | 47 | 69 | 86 | 5-10-5 | 21 | 34 |
| 413467 | 35 | 51 | 62 | 69 | 5-10-5 | 20 | 100 |
| 413474 | 29 | 44 | 57 | 67 | 5-10-5 | 28 | 107 |
| 413476 | 24 | 58 | 62 | 77 | 5-10-5 | 21 | 109 |
| 416825 | 23 | 52 | 73 | 92 | 5-10-5 | 20 | 190 |
| 416826 | 8 | 36 | 58 | 84 | 5-10-5 | 29 | 191 |
| 416827 | 31 | 42 | 62 | 77 | 5-10-5 | 23 | 192 |
| 416838 | 31 | 51 | 64 | 86 | 5-10-5 | 19 | 203 |
| 416842 | 18 | 33 | 62 | 71 | 5-10-5 | 31 | 207 |
| 416850 | 4 | 30 | 67 | 84 | 5-10-5 | 29 | 215 |
| 416856 | 21 | 45 | 58 | 74 | 5-10-5 | 27 | 221 |
| 416858 | 0 | 28 | 54 | 82 | 5-10-5 | 33 | 223 |
| 416864 | 18 | 43 | 62 | 78 | 5-10-5 | 26 | 229 |
| 416878 | 22 | 34 | 60 | 82 | 5-10-5 | 27 | 100 |
| 416892 | 16 | 50 | 70 | 85 | 3-14-3 | 23 | 190 |
| 416895 | 39 | 57 | 66 | 71 | 3-14-3 | 15 | 192 |
| 416896 | 22 | 39 | 57 | 81 | 3-14-3 | 27 | 193 |
| 416908 | 36 | 57 | 67 | 76 | 3-14-3 | 16 | 203 |
| 416922 | 14 | 25 | 49 | 75 | 3-14-3 | 36 | 214 |
| 416923 | 36 | 47 | 60 | 67 | 3-14-3 | 23 | 215 |
| 416924 | 25 | 38 | 56 | 59 | 3-14-3 | 36 | 216 |
| 416925 | 13 | 38 | 59 | 75 | 3-14-3 | 30 | 114 |

TABLE 9-continued

Dose-dependent antisense inhibition of human Factor 11 in HepG2 cells via transfection of oligonucleotides with lipofectin

| | 9.375 nM | 18.75 nM | 37.5 nM | 75 nM | Motif | $IC_{50}$ (nM) | SEQ ID No. |
|---|---|---|---|---|---|---|---|
| 416926 | 31 | 43 | 63 | 82 | 3-14-3 | 22 | 217 |
| 416931 | 44 | 39 | 57 | 71 | 3-14-3 | 22 | 221 |
| 416941 | 33 | 54 | 63 | 78 | 3-14-3 | 19 | 229 |
| 416945 | 34 | 45 | 62 | 65 | 2-13-5 | 24 | 31 |
| 416969 | 17 | 39 | 61 | 76 | 2-13-5 | 28 | 190 |
| 416972 | 32 | 40 | 60 | 69 | 2-13-5 | 26 | 192 |
| 416973 | 60 | 75 | 85 | 87 | 2-13-5 | 3 | 193 |
| 416984 | 26 | 50 | 62 | 81 | 2-13-5 | 22 | 202 |
| 416985 | 17 | 30 | 47 | 57 | 2-13-5 | 49 | 203 |
| 416989 | 18 | 41 | 62 | 83 | 2-13-5 | 26 | 206 |
| 416993 | 15 | 37 | 50 | 68 | 2-13-5 | 36 | 209 |
| 416999 | 24 | 37 | 55 | 73 | 2-13-5 | 30 | 214 |
| 417000 | 35 | 47 | 58 | 70 | 2-13-5 | 23 | 215 |
| 417002 | 35 | 52 | 67 | 70 | 2-13-5 | 19 | 114 |
| 417003 | 26 | 44 | 60 | 56 | 2-13-5 | 33 | 217 |

The gapmers were also transfected via electroporation and their dose dependent inhibition of human Factor 11 mRNA was measured. Cells were plated at a density of 20,000 cells per well and transfected via electroporation with 0.7 μM, 2.2 μM, 6.7 μM, and 20 μM concentrations of antisense oligonucleotide, as specified in Table 10. After a treatment period of approximately 16 hours, RNA was isolated from the cells and Factor 11 mRNA levels were measured by quantitative real-time PCR. Human Factor 11 primer probe set RTS 2966 was used to measure mRNA levels. Factor 11 mRNA levels were adjusted according to total RNA content, as measured by RIBOGREEN. Results are presented as percent inhibition of Factor 11, relative to untreated control cells. As illustrated in Table 10, Factor 11 mRNA levels were reduced in a dose-dependent manner in antisense oligonucleotide treated cells.

TABLE 10

Dose-dependent antisense inhibition of human Factor 11 in HepG2 cells via transfection of oligonucleotides with electroporation

| | 0.7 μM | 2.2 μM | 6.7 μM | 20 μM | $IC_{50}$ (μM) | SEQ ID No. |
|---|---|---|---|---|---|---|
| 412203 | 11 | 60 | 70 | 91 | 2.7 | 31 |
| 412206 | 22 | 39 | 81 | 94 | 2.7 | 34 |

TABLE 10-continued

| Dose-dependent antisense inhibition of human Factor 11 in HepG2 cells via transfection of oligonucleotides with electroporation | | | | | | |
|---|---|---|---|---|---|---|
| | 0.7 μM | 2.2 μM | 6.7 μM | 20 μM | $IC_{50}$ (μM) | SEQ ID No. |
| 413467 | 5 | 31 | 65 | 89 | 4.2 | 100 |
| 413474 | 0 | 5 | 52 | 81 | 6.9 | 107 |
| 413476 | 40 | 69 | 88 | 93 | 0.9 | 109 |
| 416825 | 27 | 74 | 92 | 98 | 1.3 | 190 |
| 416826 | 2 | 47 | 86 | 82 | 3.2 | 191 |
| 416827 | 37 | 68 | 87 | 92 | 1.1 | 192 |
| 416838 | 5 | 30 | 55 | 83 | 5.1 | 203 |
| 416842 | 0 | 10 | 66 | 92 | 5.0 | 207 |
| 416850 | 14 | 25 | 81 | 91 | 3.4 | 215 |
| 416856 | 0 | 29 | 47 | 93 | 5.1 | 221 |
| 416858 | 5 | 20 | 56 | 86 | 5.3 | 223 |
| 416864 | 32 | 65 | 78 | 90 | 1.4 | 229 |
| 416878 | 1 | 26 | 75 | 85 | 4.3 | 100 |
| 416892 | 14 | 52 | 82 | 92 | 2.5 | 190 |
| 416895 | 0 | 62 | 70 | 91 | 3.0 | 192 |
| 416896 | 12 | 35 | 81 | 89 | 3.2 | 193 |
| 416908 | 7 | 58 | 74 | 89 | 2.8 | 203 |
| 416922 | 35 | 51 | 77 | 91 | 1.7 | 214 |
| 416923 | 15 | 30 | 60 | 90 | 4.0 | 215 |
| 416924 | 22 | 40 | 63 | 70 | 4.1 | 216 |
| 416925 | 0 | 40 | 76 | 80 | 3.9 | 114 |
| 416926 | 47 | 71 | 91 | 94 | 0.6 | 217 |
| 416931 | 7 | 24 | 60 | 82 | 5.1 | 221 |
| 416941 | 16 | 38 | 79 | 89 | 3.0 | 229 |
| 416945 | 48 | 70 | 81 | 88 | 0.6 | 31 |
| 416969 | 25 | 34 | 86 | 92 | 2.5 | 190 |
| 416972 | 25 | 30 | 48 | 88 | 4.3 | 192 |
| 416973 | 20 | 48 | 86 | 93 | 2.3 | 193 |
| 416984 | 43 | 54 | 88 | 90 | 1.1 | 202 |
| 416985 | 12 | 48 | 45 | 69 | 5.8 | 203 |
| 416989 | 32 | 65 | 88 | 94 | 1.3 | 206 |
| 416993 | 22 | 48 | 87 | 92 | 2.2 | 209 |
| 416999 | 20 | 42 | 77 | 88 | 2.8 | 214 |
| 417000 | 46 | 73 | 76 | 89 | 0.6 | 215 |
| 417002 | 32 | 38 | 82 | 91 | 2.2 | 114 |
| 417003 | 0 | 34 | 75 | 89 | 3.9 | 217 |

Example 5: Selection and Confirmation of Effective Dose-Dependent Antisense Inhibition of Human Factor 11 in HepG2 Cells Gapmers exhibiting significant dose-dependent inhibition of human Factor 11 in Example 4 were selected and tested at various doses in HepG2 cells. Cells were plated at a density of 10,000 cells per well and transfected using lipofectin reagent with 2.34 nM, 4.69 nM, 9.375 nM, 18.75 nM, 37.5 nM, and 75 nM concentrations of antisense oligonucleotide, as specified in Table 11. After a treatment period of approximately 16 hours, RNA was isolated from the cells and human Factor 11 mRNA levels were measured by quantitative real-time PCR. Human Factor 11 primer probe set RTS 2966 was used to measure mRNA levels. Factor 11 mRNA levels were adjusted according to total RNA content, as measured by RIBOGREEN. Results are presented as percent inhibition of human Factor 11, relative to untreated control cells. As illustrated in Table 11, Factor 11 mRNA levels were reduced in a dose-dependent manner in antisense oligonucleotide treated cells compared to the control.

TABLE 11

| Dose-dependent antisense inhibition of human Factor 11 in HepG2 cells via transfection of oligonucleotides with lipofectin | | | | | | | | | |
|---|---|---|---|---|---|---|---|---|---|
| | 2.34 nM | 4.69 nM | 9.375 nM | 18.75 nM | 37.5 nM | 75 nM | Motif | IC50 (nM) | SEQ ID No. |
| 416825 | 4 | 22 | 39 | 57 | 79 | 89 | 5-10-5 | 13 | 190 |
| 416826 | 15 | 22 | 32 | 54 | 76 | 90 | 5-10-5 | 15 | 191 |
| 416838 | 21 | 37 | 50 | 63 | 74 | 83 | 5-10-5 | 10 | 203 |
| 416850 | 24 | 31 | 49 | 55 | 70 | 77 | 5-10-5 | 13 | 215 |
| 416858 | 11 | 35 | 46 | 61 | 75 | 77 | 5-10-5 | 11 | 223 |
| 416864 | 13 | 34 | 42 | 65 | 68 | 80 | 5-10-5 | 15 | 229 |
| 416892 | 14 | 34 | 49 | 70 | 84 | 93 | 3-14-3 | 9 | 190 |
| 416925 | 24 | 34 | 45 | 56 | 67 | 72 | 3-14-3 | 13 | 114 |
| 416999 | 10 | 26 | 42 | 62 | 72 | 80 | 2-13-5 | 14 | 214 |
| 417002 | 17 | 26 | 49 | 61 | 81 | 84 | 2-13-5 | 12 | 114 |
| 417003 | 6 | 29 | 48 | 64 | 73 | 82 | 2-13-5 | 11 | 217 |

The gapmers were also transfected via electroporation and their dose dependent inhibition of human Factor 11 mRNA was measured. Cells were plated at a density of 20,000 cells per well and transfected via electroporation with 625 nM, 1250 nM, 2500 nM, 5,000 nM, 10,000 nM, and 20,000 nM concentrations of antisense oligonucleotide, as specified in Table 12. After a treatment period of approximately 16 hours, RNA was isolated from the cells and human Factor 11 mRNA levels were measured by quantitative real-time PCR. Human Factor 11 primer probe set RTS 2966 was used to measure mRNA levels. Factor 11 mRNA levels were adjusted according to total RNA content, as measured by RIBOGREEN. Results are presented as percent inhibition of human Factor 11, relative to untreated control cells. As illustrated in Table 12, Factor 11 mRNA levels were reduced in a dose-dependent manner in antisense oligonucleotide treated cells compared to the control.

TABLE 12

| Dose-dependent antisense inhibition of human Factor 11 in HepG2 cells via transfection of oligonucleotides with electroporation | | | | | | | | |
|---|---|---|---|---|---|---|---|---|
| | 625 nM | 1250 nM | 2500 nM | 5000 nM | 10000 nM | 20000 nM | IC50 (μM) | SEQ ID No. |
| 416825 | 69 | 84 | 91 | 94 | 96 | 97 | 19 | 190 |
| 416826 | 67 | 82 | 89 | 92 | 95 | 97 | 33 | 191 |
| 416838 | 66 | 79 | 87 | 90 | 93 | 96 | 43 | 203 |
| 416850 | 69 | 80 | 87 | 90 | 93 | 96 | 25 | 215 |
| 416858 | 65 | 77 | 87 | 89 | 93 | 93 | 44 | 223 |
| 416864 | 45 | 74 | 84 | 87 | 92 | 94 | 338 | 229 |
| 416892 | 66 | 86 | 96 | 97 | 100 | 100 | 31 | 190 |
| 416925 | 64 | 80 | 88 | 91 | 95 | 96 | 51 | 114 |
| 416999 | 61 | 82 | 89 | 94 | 94 | 97 | 67 | 214 |
| 417002 | 59 | 72 | 86 | 90 | 94 | 96 | 156 | 114 |
| 417003 | 60 | 74 | 86 | 90 | 95 | 95 | 123 | 217 |

Example 6: Selection and Confirmation of Effective Dose-Dependent Antisense Inhibition of Human Factor 11 in Cyano Primary Hepatocytes Gapmers from Example 4 exhibiting significant dose dependent in vitro inhibition of human Factor 11 were also tested at various doses in cyano primary hepatocytes. Cells were plated at a density of 35,000 cells per well and transfected via electroporation with 0.74 nM, 2.2 nM, 6.7 nM, 20 nM, 60 nM, and 180 nM concentrations of antisense oligonucleotide, as specified in Table 13. After a treatment period of approximately 16 hours, RNA was isolated from the cells and human Factor 11 mRNA levels were measured by quantitative real-time PCR. Human Factor 11 primer probe set RTS 2966 was used to measure mRNA levels. Factor 11 mRNA levels were adjusted according to total RNA content, as measured by RIBOGREEN. Results are presented as percent inhibition of human Factor 11, relative to untreated control cells. As illustrated in Table 13, Factor 11 mRNA levels were reduced in a dose-dependent manner in antisense oligonucleotide treated cells compared to the control.

TABLE 13

Dose-dependent antisense inhibition of human Factor 11 in cyano primary hepatocytes

| | 0.74 nM | 2.2 nM | 6.7 nM | 20 nM | 60 nM | 180 nM | $IC_{50}$ (μM) | SEQ ID No. |
|---|---|---|---|---|---|---|---|---|
| 416825 | 5 | 22 | 51 | 61 | 77 | 84 | 1.0 | 190 |
| 416826 | 13 | 24 | 34 | 67 | 69 | 71 | 1.3 | 191 |
| 416838 | 0 | 0 | 21 | 34 | 48 | 62 | 6.9 | 203 |
| 416850 | 2 | 20 | 24 | 65 | 69 | 67 | 1.6 | 215 |
| 416858 | 2 | 13 | 22 | 44 | 63 | 68 | 3.7 | 223 |
| 416864 | 0 | 1 | 15 | 23 | 47 | 64 | 7.7 | 229 |
| 416892 | 20 | 20 | 43 | 62 | 88 | 92 | 1.0 | 190 |
| 416925 | 0 | 9 | 1 | 48 | 55 | 76 | 4.4 | 114 |
| 416999 | 3 | 40 | 36 | 62 | 67 | 82 | 1.3 | 214 |
| 417002 | 32 | 16 | 28 | 38 | 55 | 71 | 4.0 | 114 |
| 417003 | 12 | 18 | 19 | 39 | 58 | 74 | 4.1 | 217 |

Example 7: Selection and Confirmation of Effective Dose-Dependent Antisense Inhibition of Human Factor 11 in HepB3 Cells by Gapmers Gapmers exhibiting in vitro inhibition of human Factor 11 in Example 4 were tested at various doses in human HepB3 cells. Cells were plated at a density of 4,000 cells per well and transfected using lipofectin reagent with 2.3 nM, 4.7 nM, 9.4 nM, 18.75 nM, 37.5 nM, and 75 nM concentrations of antisense oligonucleotide, as specified in Table 14. After a treatment period of approximately 16 hours, RNA was isolated from the cells and human Factor 11 mRNA levels were measured by quantitative real-time PCR. Human Factor 11 primer probe set RTS 2966 was used to measure mRNA levels. Factor 11 mRNA levels were adjusted according to total RNA content, as measured by RIBOGREEN. Results are presented as percent inhibition of Factor 11, relative to untreated control cells. As illustrated in Table 14, Factor 11 mRNA levels were reduced in a dose-dependent manner in antisense oligonucleotide treated cells compared to the control.

TABLE 14

Dose-dependent antisense inhibition of human Factor 11 in HepB3 cells

| ISIS No. | 2.3 nM | 4.7 nM | 9.4 nM | 18.75 nM | 37.5 nM | 75 nM | $IC_{50}$ (nM) | SEQ ID No. |
|---|---|---|---|---|---|---|---|---|
| 416825 | 0 | 15 | 34 | 36 | 53 | 59 | 35 | 190 |
| 416826 | 16 | 28 | 38 | 55 | 64 | 66 | 16 | 191 |
| 416838 | 23 | 34 | 43 | 59 | 71 | 56 | 11 | 203 |
| 416850 | 22 | 32 | 43 | 56 | 75 | 60 | 13 | 215 |
| 416858 | 17 | 34 | 43 | 57 | 74 | 62 | 12 | 223 |
| 416864 | 24 | 37 | 42 | 66 | 76 | 63 | 9 | 229 |
| 416892 | 28 | 34 | 50 | 68 | 82 | 72 | 9 | 190 |
| 416925 | 26 | 33 | 45 | 59 | 72 | 60 | 12 | 114 |
| 416999 | 19 | 33 | 42 | 60 | 71 | 59 | 12 | 214 |
| 417002 | 24 | 30 | 46 | 57 | 71 | 65 | 13 | 114 |
| 417003 | 11 | 28 | 40 | 40 | 63 | 58 | 17 | 217 |

The gapmers were also transfected via electroporation and their dose dependent inhibition of human Factor 11 mRNA was measured. Cells were plated at a density of 20,000 cells per well and transfected via electroporation with 41.15 nM, 123.457 nM, 370.37 nM, 1111.11 nM, 3333.33 nM, and 10,000 nM concentrations of antisense oligonucleotide, as specified in Table 15. After a treatment period of approximately 16 hours, RNA was isolated from the cells and human Factor 11 mRNA levels were measured by quantitative real-time PCR. Human Factor 11 primer probe set RTS 2966 was used to measure mRNA levels. Factor 11 mRNA levels were adjusted according to total RNA content, as measured by RIBOGREEN. Results are presented as percent inhibition of human Factor 11, relative to untreated control cells. As illustrated in Table 15, Factor 11 mRNA levels were reduced in a dose-dependent manner in antisense oligonucleotide treated cells compared to the control.

TABLE 15

Dose-dependent antisense inhibition of human Factor 11 in HepB3 cells

| | 41.15 nM | 123.457 nM | 370.37 nM | 1111.11 nM | 3333.33 nM | 10000 nM | $IC_{50}$ (μM) | SEQ ID No. |
|---|---|---|---|---|---|---|---|---|
| 416825 | 32 | 40 | 48 | 75 | 90 | 92 | 0.16 | 190 |
| 416826 | 0 | 0 | 34 | 61 | 87 | 92 | 0.78 | 191 |
| 416838 | 12 | 9 | 28 | 40 | 77 | 88 | 1.20 | 203 |
| 416850 | 26 | 38 | 51 | 73 | 90 | 95 | 0.30 | 215 |
| 416858 | 23 | 45 | 52 | 64 | 87 | 92 | 0.30 | 223 |
| 416864 | 4 | 3 | 6 | 35 | 75 | 87 | 2.20 | 229 |
| 416892 | 9 | 12 | 28 | 65 | 89 | 98 | 0.61 | 190 |
| 416925 | 27 | 39 | 50 | 73 | 88 | 96 | 0.20 | 114 |
| 416999 | 31 | 45 | 62 | 78 | 94 | 97 | 0.16 | 214 |
| 417002 | 19 | 0 | 31 | 47 | 86 | 93 | 1.20 | 114 |
| 417003 | 31 | 0 | 15 | 43 | 84 | 92 | 1.50 | 217 |

Example 8: Antisense Inhibition of Murine Factor 11 in Primary Mouse Hepatocytes Chimeric antisense oligonucleotides targeting murine Factor 11 were designed as 5-10-5 MOE gapmers targeting murine Factor 11 (GENBANK Accession No. NM_028066.1, incorporated herein as SEQ ID NO: 6). The gapmers are 20 nucleotides in length, wherein the central gap segment is comprised of 10 2'-deoxynucleotides and is flanked on both sides (in the 5' and 3' directions) by wings comprising 5 nucleotides each. Each nucleotide in each wing segment has a 2'-MOE modification. The internucleoside linkages throughout each gaper are phosphorothioate (P═S) linkages. All cytidine residues throughout each gapmer are 5-methylcytidines. The antisense oligonucleotides were evaluated for their ability to reduce murine Factor 11 mRNA in primary mouse hepatocytes.

Primary mouse hepatocytes were treated with 6.25 nM, 12.5 nM, 25 nM, 50 nM, 100 nM, and 200 nM of antisense oligonucleotides for a period of approximately 24 hours. RNA was isolated from the cells and murine Factor 11 mRNA levels were measured by quantitative real-time PCR. Murine Factor 11 primer probe set RTS 2898 (forward sequence ACATGACAGGCGCGATCTCT, incorporated herein as SEQ ID NO: 7; reverse sequence TCTAGGTTCACGTACACATCTTTGC, incorporated herein as SEQ ID NO: 8; probe sequence TTCCTTCAAGCAATGCCCTCAGCAATX, incorporated herein as SEQ ID NO: 9) was used to measure mRNA levels. Factor 11 mRNA levels were adjusted according to total RNA content as measured by RIBOGREEN. Several of the murine antisense oligonucleotides reduced Factor 11 mRNA levels in a dose-dependent manner.

The chimeric antisense oligonucleotides in Tables 16 were designed as 5-10-5 MOE gapmers. The gapmers are 20 nucleotides in length, wherein the central gap segment is comprised of 10 2'-deoxynucleotides and is flanked on both sides (in the 5' and 3' directions) by wings comprising 5 nucleotides each. Each nucleotide in the 5' wing segment and each nucleotide in the 3' wing segment has a 2'-MOE modification. The internucleoside linkages throughout each gapmer are phosphorothioate (P═S) linkages. All cytidine residues throughout each gapmer are 5-methylcytidines. "Mouse target start site" indicates the 5'-most nucleotide to which the gapmer is targeted. "Mouse target stop site" indicates the 3'-most nucleotide to which the gapmer is targeted. All the mouse oligonucleotides listed show cross-reactivity between the mouse Factor 11 mRNA (GENBANK Accession No. NM_028066.1), incorporated herein as SEQ ID NO: 6 and the human Factor 11 mRNA (GENBANK Accession No. NM_000128.3), incorporated herein as SEQ ID NO: 1. "Human Target Start Site" indicates the 5'-most nucleotide in the human mRNA (GENBANK Accession No. NM_000128.3) to which the antisense oligonucleotide is targeted. "Human Target Stop Site" indicates the 3'-most nucleotide in the human mRNA (GENBANK Accession No. NM_000128.3) to which the antisense oligonucleotide is targeted. "Number of mismatches" indicates the mismatches between the mouse oligonucleotide and the human mRNA sequence.

TABLE 16

Inhibition of mouse Factor 11 mRNA levels by chimeric antisense oligonucleotides having 5-10-5 MOE wings and deoxy gap targeted to SEQ ID NO: 1 and SEQ ID NO: 6

| ISIS No | Mouse Target Start Site | Mouse Target Stop Site | Sequence (5' to 3') | % Inhibition | SEQ ID No. | Human Target Start Site | Human Target Stop Site | No. of mismatches |
|---|---|---|---|---|---|---|---|---|
| 404050 | 379 | 398 | TGCTTGAAGGAATATCCAGA | 82 | 233 | 619 | 638 | 2 |
| 404054 | 448 | 467 | TAGTTCATGCCCTTCATGTC | 45 | 234 | 688 | 707 | 1 |
| 404055 | 453 | 472 | TGTTATAGTTCATGCCCTTC | 27 | 235 | 693 | 712 | 1 |
| 404066 | 686 | 705 | AATGTCCCTGATACAAGCCA | 37 | 236 | 926 | 945 | 1 |
| 404067 | 691 | 710 | GGGAAAATGTCCCTGATACA | 39 | 237 | 931 | 950 | 1 |
| 404083 | 1299 | 1318 | TGTGCAGAGTCACCTGCCAT | 47 | 238 | 1533 | 1552 | 2 |
| 404087 | 1466 | 1485 | TTCTTGAACCCTGAAGAAAG | 29 | 239 | 1709 | 1728 | 2 |
| 404089 | 1477 | 1496 | TGAATTATCATTTCTTGAAC | 6 | 240 | 1720 | 1739 | 2 |
| 404090 | 1483 | 1502 | TGATCATGAATTATCATTTC | 42 | 241 | 1726 | 1745 | 2 |

Example 9: Cross-Reactive Antisense Inhibition of Murine Factor 11 in Primary Mouse Hepatocytes Antisense oligonucleotides targeted to a murine factor 11 nucleic acid were tested for their effects on Factor 11 mRNA in vitro. Cultured primary mouse hepatocytes at a density of 10,000 cells per well were treated with 100 nM antisense oligonucleotide. After a treatment period of approximately 24 hours, RNA was isolated from the cells and mouse Factor 11 mRNA levels were measured by quantitative real-time PCR. Factor 11 mRNA levels were adjusted according to total RNA content, as measured by RIBOGREEN. Results are presented as percent inhibition of Factor 11, relative to untreated control cells.

Example 10: In Vivo Antisense Inhibition of Murine Factor 11

Several antisense oligonucleotides targeted to murine Factor 11 mRNA (GENBANK Accession No. NM_028066.1, incorporated herein as SEQ ID NO: 6) showing statistically significant dose-dependent inhibition were evaluated in vivo. BALB/c mice were treated with ISIS 404057 (TCCTGGCATTCTCGAGCATT, target start site 487, incorporated herein as SEQ ID NO: 10) and ISIS 404071 (TGGTAATCCACTTTCAGAGG, target start site 869, incorporated herein as SEQ ID NO: 11).

Treatment

BALB/c mice were injected with 5 mg/kg, 10 mg/kg, 25 mg/kg, or 50 mg/kg of ISIS 404057 or ISIS 404071 twice a week for 3 weeks. A control group of mice was injected with phosphate buffered saline (PBS) twice a week for 3 weeks. Mice were sacrificed 5 days after receiving the last dose. Whole liver was harvested for RNA analysis and plasma was collected for clotting analysis (PT and aPTT) and protein analysis.

RNA Analysis

RNA was extracted from liver tissue for real-time PCR analysis of Factor 11. As shown in Table 17, the antisense oligonucleotides achieved dose-dependent reduction of murine Factor 11 over the PBS control. Results are presented as percent inhibition of Factor 11, relative to control.

TABLE 17

Dose-dependent antisense inhibition of murine Factor 11 mRNA in BALB/c mice

| | mg/kg | % inhibition |
|---|---|---|
| 404057 | 5 | 40 |
| | 10 | 64 |
| | 25 | 85 |
| | 50 | 95 |
| 404071 | 5 | 72 |
| | 10 | 82 |
| | 25 | 93 |
| | 50 | 96 |

PT and aPTT Assay

Prothrombin Time (PT) and Activated Partial Thromboplastin Time (aPTT) were measured using platelet poor plasma (PPP) from mice treated with ISIS 404057 and ISIS 404071. PT and aPTT values provided in Table 18 are reported as International Normalized Ratio (INR) values. INR values for PT and aPTT were determined by dividing the PT or aPTT value for each experimental group (i.e. 5 mg/kg, 10 mg/kg, 25 mg/kg, and 50 mg/kg treatment with ISIS 404057 or ISIS 404071) by the PT or aPTT for the PBS treated group. This ratio was then raised to the power of the International Sensitivity Index (ISI) of the tissue factor used. As shown in Table 18, PT was not significantly prolonged in mice treated with ISIS 404057 or ISIS 404071. However, aPTT was prolonged in a dose-dependent manner in mice treated with ISIS 404057 and ISIS 404071. These data suggest that antisense reduction of Factor 11 affects the contact activation pathway, but not the extrinsic pathway of blood coagulation.

TABLE 18

Effect of ISIS 404071 and 404057 on PT and aPTT in BALB/c mice

| | Dose in mg/kg | PT INR | aPTT INR |
|---|---|---|---|
| ISIS 404057 | 5 | 1.00 | 1.07 |
| | 10 | 0.94 | 1.19 |
| | 25 | 1.02 | 1.27 |
| | 50 | 1.00 | 1.37 |
| ISIS 404071 | 5 | 1.06 | 1.09 |
| | 10 | 1.08 | 1.13 |
| | 25 | 1.06 | 1.35 |
| | 50 | 1.02 | 2.08 |

Protein Analysis

Factor 11 proenzyme from the plasma of mice treated with ISIS 404071, was measured using a F11 assay based on clotting time. Clotting times were determined in duplicate with a ST4 semi-automated coagulation instrument (Diagnostica Stago, NJ). Thirty μl of citrated sample plasma diluted 1/20 in HEPES-NaCl buffer with BSA was incubated with 30 μl aPTT reagent (Platelet Factor 3 reagent plus particulate activator) and 30 μl of citrated plasma deficient of Factor 11 (human congential, George King Bio-Medical Inc.) at 37° C. to initiate clotting. Results were interpolated on a standard curve of serially diluted citrated control murine plasma.

As shown in Table 19, treatment with ISIS 404071 resulted in a significant dose-dependent reduction of Factor 11 protein. Results are presented as percent inhibition of Factor 11, relative to PBS control.

TABLE 19

Dose-dependent inhibition of murine Factor 11 protein by ISIS 404071 in BALB/c mice

| Dose in mg/kg | % Inhibition |
|---|---|
| 5 | 39 |
| 10 | 67 |
| 25 | 89 |
| 50 | 96 |

Example 11: In Vivo Effect of Antisense Inhibition of Murine Factor 11 in the $FeCl_3$ Induced Venous Thrombosis (VT) Model as Compared to Warfarin Treatment ISIS 404071 and warfarin (COUMADIN) were evaluated in the $FeCl_3$ induced VT mouse model. Six groups of BALB/c mice were treated with 1.25 mg/kg, 2.5 mg/kg, 5 mg/kg, 10 mg/kg, 20 mg/kg, or 40 mg/kg of ISIS 404071, administered subcutaneously twice a week for 3 weeks. Two days after receiving the last dose of ISIS 404071, mice were anesthetized with 150 mg/kg ketamine mixed with 10 mg/kg xylazine administered by intraperitoneal injection. An additional 6 groups of BALB/c mice were treated with 0.5 mg/kg, 1 mg/kg, 2 mg/kg, 3 mg/kg, 4 mg/kg, and 5 mg/kg of warfarin, administered intraperioneally daily for 6 days. Four hours after the last dose of warfarin, mice were anesthetized with 150 mg/kg ketamine mixed with 10 mg/kg xylazine administered by intraperitoneal injection. Two control groups of BALB/c mice were treated with PBS, administered subcutaneously twice a week for 3 weeks. Two days after the last dose of PBS, mice in both groups were anesthetized with 150 mg/kg ketamine mixed with 10 mg/kg xylazine administered by intraperitoneal injection. Thrombus formation was induced with $FeCl_3$ in all groups of mice except the first control group.

In mice undergoing $FeCl_3$ treatment, thrombus formation was induced by applying a piece of filter paper (2×4 mm) pre-saturated with 10% $FeCl_3$ solution directly on the vena cava. After 3 minutes of exposure, the filter paper was removed. Thirty minutes after the filter paper application, a fixed length of the vein containing the thrombus was dissected out for platelet analysis. Liver was collected for RNA analysis.

RNA Analysis

RNA was extracted from liver tissue for real-time PCR analysis of Factor 11. Results are presented as percent inhibition of Factor 11, relative to PBS control. As shown in Table 20, treatment with ISIS 404071 resulted in significant dose-dependent reduction of Factor 11 mRNA in comparison to the PBS control. Conversely, treatment with warfarin did not result in significant reduction of Factor 11 as compared to the PBS control.

TABLE 20

Dose-dependent reduction of Factor 11 mRNA in the $FeCl_3$ induced venous thrombosis model

| Treatment | Dose in mg/kg | % inhibition |
|---|---|---|
| Warfarin | 0.5 | 0 |
| | 1 | 0 |
| | 2 | 1 |
| | 3 | 5 |
| | 4 | 8 |
| | 5 | 11 |
| ISIS 404071 | 1.25 | 0 |
| | 2.5 | 8 |
| | 5 | 62 |
| | 10 | 78 |
| | 20 | 92 |
| | 40 | 96 |

Quantification of Platelet Composition

Real-time PCR quantification of platelet factor-4 (PF-4) was used to quantify platelets in the vena cava as a measure of thrombus formation. Results are presented as a percentage of PF-4 in ISIS 404071 or warfarin treated mice, as compared to the two PBS-treated control groups. As shown in Table 21, treatment with ISIS 404071 resulted in a dose-dependent reduction of PF-4 in comparison to the PBS control for dosages of 5 mg/kg and higher. Treatment with warfarin resulted in a reduction of PF-4 in comparison to the PBS control for dosages of 2 mg/kg and higher. Therefore, reduction of Factor 11 by the compounds provided herein is useful for inhibiting thrombus and clot formation.

TABLE 21

Analysis of thrombus formation by real-time PCR quantification of PF-4 in the $FeCl_3$ induced venous thrombosis model

| | Dose in mg/kg | PF-4 |
|---|---|---|
| PBS − $FeCl_3$ | | 0 |
| PBS + $FeCl_3$ | | 100 |
| Warfarin | 0.5 | 128 |
| | 1 | 124 |
| | 2 | 80 |
| | 3 | 21 |
| | 4 | 12 |
| | 5 | 33 |
| ISIS 404071 | 1.25 | 143 |
| | 2.5 | 120 |
| | 5 | 95 |
| | 10 | 21 |
| | 20 | 37 |
| | 40 | 20 |

Example 12: In Vivo Effect of Antisense Inhibition of Murine Factor 11 Compared to Warfarin in a Tail Bleeding Assay Treatment Tail-bleeding was measured to observe whether treatment with ISIS 404071 or warfarin causes internal hemorrhage in mice. ISIS 404071 and warfarin (COUMADIN) were evaluated in the tail bleeding assay. Six groups of BALB/c mice were treated with 1.25 mg/kg, 2.5 mg/kg, 5 mg/kg, 10 mg/kg, 20 mg/kg, or 40 mg/kg of ISIS 404071, administered subcutaneously twice a week for 3 weeks. An additional 6 groups of BALB/c mice were treated with 0.5 mg/kg, 1 mg/kg, 2 mg/kg, 3 mg/kg, 4 mg/kg, and 5 mg/kg of warfarin, administered intraperioneally daily for 6 days. A separate control group of BALB/c mice was treated with PBS, administered subcutaneously twice a week for 3 weeks.

Tail-Bleeding Assay

Two days after the final treatment of ISIS 404071, warfarin, or PBS, mice were placed in a tail bleeding chamber. Mice were anesthetized in the chamber with isoflurane and a small piece of tail (approximately 4 mm from the tip) was cut with sterile scissors. The tail cut was immediately placed in a 15 mL Falcon tube filled with approximately 10 mL of 0.9% NaCl buffer solution warmed to 37° C. The blood was collected over the course of 40 minutes. The saline filled tubes were weighed both before and after bleeding. The results are provided in Table 22.

Treatment with ISIS 404071 did not affect bleeding as compared to PBS treated mice. However, warfarin did increase bleeding in mice as compared to the PBS control. Increased doses of warfarin correlated positively with increased blood loss. These data suggest that the hemorrhagic potential of the compounds provided herein is low, especially in comparison to warfarin. These data taken with the results provided in example 11 suggest inhibition of Factor 11 with the compounds described herein are useful for providing antithrombotic activity without associated bleeding risk.

TABLE 22

Tail bleeding assay in the $FeCl_3$ induced venous thrombosis model

| Treatment | Dose in mg/kg | Blood (g) |
|---|---|---|
| PBS | 0 | 0.01 |
| Warfarin | 0.5 | 0.07 |
| | 1 | 0.35 |
| | 2 | 0.39 |
| | 3 | 0.51 |
| | 4 | 0.52 |
| | 5 | 0.76 |
| ISIS 404071 | 1.25 | 0.00 |
| | 2.5 | 0.00 |
| | 5 | 0.03 |
| | 10 | 0.00 |
| | 20 | 0.06 |
| | 40 | 0.03 |

Example 13: In Vivo Effect of Antisense Inhibition of Murine Factor 11 Compared to Warfarin on PT and aPTT Treatment PT and aPTT were measured using PPP from mice treated with ISIS 404071 or warfarin. Six groups of BALB/c mice were treated with 1.25 mg/kg, 2.5 mg/kg, 5 mg/kg, 10 mg/kg, 20 mg/kg, or 40 mg/kg of ISIS 404071, administered subcutaneously twice a week for 3 weeks. An additional 6 groups of BALB/c mice were treated with 0.5 mg/kg, 1 mg/kg, 2 mg/kg, 3 mg/kg, 4 mg/kg, and 5 mg/kg of warfarin, administered intraperioneally daily for 6 days. In a control group, BALB/c mice were treated with PBS, administered subcutaneously mice twice a week for 3 weeks. Two days after the final dose was administered, PPP was collected and PT and aPTT assays were performed.

PT and aPTT Assay

PT and aPTT values provided in Table 16 are reported as International Normalized Ratio (INR) values. INR values for PT and aPTT were determined by dividing the PT or aPTT value for each experimental group (i.e. 5 mg/kg, 10 mg/kg, 25 mg/kg, and 50 mg/kg treatment with ISIS 404071) by the PT or aPTT for the PBS treated group. This ratio was then raised to the power of the International Sensitivity Index (ISI) of the tissue factor used. As shown in Table 23, PT in warfarin treated mice is significantly prolonged at every dosage. aPTT in warfarin treated mice was prolonged, particularly at dosages of 1 mg/kg and higher. ISIS 404071 did not significantly affect PT, but did prolong aPTT; however, not as significantly as in warfarin treated mice. These data suggest that ISIS 404071 affects the contact activation pathway, but not the extrinsic pathway of blood coagulation whereas warfarin affects both the contact activation pathway and the extrinsic pathway of blood coagulation.

TABLE 23

Effect of ISIS 404071 and warfarin on PT and aPTT in BALB/c mice

| Treatment | Dose in mg/kg | PT INR | aPTT INR |
|---|---|---|---|
| Warfarin | 0.5 | 1.41 | 1.10 |
| | 1 | 2.03 | 1.31 |
| | 2 | 2.77 | 1.54 |
| | 3 | 22.76 | 2.90 |
| | 4 | 6.74 | 2.18 |
| | 5 | 9.20 | 2.29 |
| ISIS 404071 | 1.25 | 0.99 | 0.98 |
| | 2.5 | 1.01 | 1.03 |
| | 5 | 1.07 | 1.09 |
| | 10 | 1.08 | 1.29 |
| | 20 | 1.09 | 1.32 |
| | 40 | 0.98 | 1.64 |

Example 14: In Vivo Effect of Antisense Inhibition of Murine Factor 11 in the $FeCl_3$ Induced Venous Thrombosis (VT) Model as Compared to Apixaban Treatment ISIS 404071 and Apixaban were evaluated in the $FeCl_3$ induced VT mouse model. Six groups of BALB/c mice were treated with 1.25 mg/kg, 2.5 mg/kg, 5 mg/kg, 10 mg/kg, 20 mg/kg, or 40 mg/kg of ISIS 404071, administered subcutaneously twice a week for 3 weeks. Two days after receiving the last dose of ISIS 404071, mice were anesthetized with 150 mg/kg ketamine mixed with 10 mg/kg xylazine administered by intraperitoneal injection. An additional 6 groups of BALB/c mice were treated with 0.5 mg/kg, 1 mg/kg, 2 mg/kg, 3 mg/kg, 4 mg/kg, and 5 mg/kg of Apixaban, administered subcutaneously one time. Twenty minutes after receiving Apixaban, mice were anesthetized with 150 mg/kg ketamine mixed with 10 mg/kg xylazine administered by intraperitoneal injection. Two control groups of BALB/c mice were treated with PBS, administered subcutaneously twice a week for 3 weeks. Two days after the last dose of PBS, mice in both groups were anesthetized with 150 mg/kg ketamine mixed with 10 mg/kg xylazine administered by intraperitoneal injection. Thrombus formation was induced with $FeCl_3$ in all of the mice except the first control group.

In mice undergoing $FeCl_3$ treatment, thrombus formation was induced by applying a piece of filter paper (2×4 mm) pre-saturated with 10% $FeCl_3$ solution directly on the vena cava. After 3 minutes of exposure, the filter paper was removed. Thirty minutes after the filter paper application, a fixed length of the vein containing the thrombus was dissected out for platelet analysis. Liver was collected for RNA analysis.

RNA Analysis

RNA was extracted from liver tissue for real-time PCR analysis of Factor 11. Results are presented as percent inhibition of Factor 11, relative to PBS control. As shown in Table 24, treatment with ISIS 404071 resulted in significant dose-dependent reduction of Factor 11 mRNA in comparison to the PBS control. Conversely, treatment with Apixaban did not result in significant reduction of Factor 11 as compared to the PBS control.

TABLE 24

Dose-dependent reduction of Factor 11 mRNA in the $FeCl_3$ induced venous thrombosis model

| | Dose in mg/kg | % inhibition |
|---|---|---|
| Apixaban | 0.5 | 5 |
| | 2 | 8 |
| | 5 | 12 |
| | 10 | 2 |
| | 20 | 0 |
| ISIS 404071 | 1.25 | 15 |
| | 2.5 | 44 |
| | 5 | 63 |
| | 10 | 76 |
| | 25 | 91 |
| | 50 | 95 |

Quantification of Platelet Composition

Real-time PCR quantification of platelet factor-4 (PF-4) was used to quantify platelets in the vena cava as a measure of thrombus formation. As shown in Table 25, treatment with ISIS 404071 resulted in reduction of PF-4 in comparison to the PBS control. Treatment with Apixaban also resulted in reduction of PF-4, in comparison to the PBS control. Results are presented as a percentage of PF-4 in ISIS 404071 or Apixaban treated mice, as compared to the two PBS-treated control groups.

TABLE 25

Analysis of thrombus formation by real-time PCR quantification of PF-4 in the $FeCl_3$ induced venous thrombosis model

| Treatment | Dose in mg/kg | PF-4 |
|---|---|---|
| PBS − $FeCl_3$ | | 0 |
| PBS + $FeCl_3$ | | 100 |
| Apixaban | 0.5 | 67 |
| | 2 | 46 |
| | 5 | 15 |
| | 10 | 5 |
| | 20 | 26 |
| ISIS 404071 | 1.25 | 42 |
| | 2.5 | 87 |
| | 5 | 60 |
| | 10 | 28 |
| | 25 | 14 |
| | 50 | 4 |

Example 15: In Vivo Effect of Antisense Inhibition of Murine Factor 11 Compared to Apixaban in the Tail Bleeding Assay Treatment Tail bleeding was measured to observe whether treatment with ISIS 404071 or warfarin causes internal hemorrhage in mice. ISIS 404071 and Apixaban were evaluated in the tail bleeding model. Six groups of BALB/c mice were treated with 1.25 mg/kg, 2.5 mg/kg, 5 mg/kg, 10 mg/kg, 20 mg/kg, or 40 mg/kg of ISIS 404071, administered subcutaneously twice a week for 3 weeks. An additional 6 groups of BALB/c mice were treated with 0.5 mg/kg, 1 mg/kg, 2 mg/kg, 3 mg/kg, 4 mg/kg, and 5 mg/kg of Apixaban, administered in a single subcutaneous dose. A separate control group of BALB/c mice was treated with PBS, administered subcutaneously twice a week for 3 weeks.

Tail-Bleeding Assay

Two days after the final treatment of ISIS 404071, Apixaban, or PBS, mice were placed in a tail bleeding chamber. Mice were anesthetized in the chamber and a small piece of tail (approximately 4 mm from the tip) was cut with sterile scissors. The cut tail was immediately placed in a 15 mL Falcon tube filled with approximately 10 mL of 0.9% NaCl buffer solution warmed to 37° C. The blood was collected over the course of 40 minutes. The saline filled tubes were weighed before and after bleeding.

As shown in Table 26, treatment with ISIS 404071 did not affect bleeding as compared to PBS treated mice. However, Apixaban did increase bleeding in mice as compared to the PBS control. Increased doses of Apixaban correlated positively with increased blood loss. These data suggest that the hemorrhagic potential of the compounds provided herein is low, especially in comparison to Apixaban. These data taken with the results provided in example 14 suggest inhibition of Factor 11 with the compounds described herein are useful for providing antithrombotic without associated bleeding risk.

TABLE 26

Tail bleeding assay in BABL/c mice

| | mg/kg | Blood (g) |
|---|---|---|
| PBS | 0 | 0.06 |
| Apixaban | 0.5 | 0.03 |
| | 2 | 0.34 |
| | 5 | 0.37 |
| | 10 | 0.40 |
| | 20 | 0.52 |
| ISIS 404071 | 1.25 | 0.00 |
| | 2.5 | 0.03 |
| | 5 | 0.00 |
| | 10 | 0.04 |
| | 25 | 0.01 |
| | 50 | 0.01 |

Example 16: Ex Vivo Effect of Antisense Inhibition of Murine Factor 11 in Combination with LOVENOX Treatment Three groups of BALB/c mice were treated with 10 mg/kg, 20 mg/kg, or 40 mg/kg of ISIS 404071, administered subcutaneously twice a week for 3 weeks. A control mouse group was treated with PBS, administered twice a week for 3 weeks. Five days after the last dose, the mice were sacrificed and plasma was collected. The low-molecular-weight (LMW) heparin, LOVENOX, was administered to the plasma ex vivo at varying concentrations of 0 μg/ml, 2.5 μg/ml, 5.0 μg/ml, and 7.5 μg/ml. PT and aPTT were measured 20 minutes after LOVENOX was administered.

PT and aPTT Assay

As shown in Table 27, treatment with LOVENOX increases PT in a dose-dependent manner. Treatment with ISIS 404071 does not significantly increase PT. PT is not significantly affected by treatment with ISIS 404071. There is no evidence of a combinational effect on PT in ISIS 404071 and LOVENOX treated plasma.

TABLE 27

Effect of combination of ISIS 404071 and LOVENOX on PT INR in murine plasma

| ISIS 404071 | LOVENOX (mg/ml) | | | |
|---|---|---|---|---|
| (mg/kg) | 0 | 2.5 | 5.0 | 7.5 |
| 0 | 1.00 | 1.02 | 1.10 | 1.12 |
| 10 | 0.97 | 1.07 | 1.10 | 1.12 |
| 20 | 1.00 | 1.10 | 1.07 | 1.10 |
| 40 | 0.97 | 1.02 | 1.07 | 1.10 |

As shown in Table 28, treatment with LOVENOX increases aPTT in a dose-dependent manner. Treatment with ISIS 404071 also increases aPTT in a dose-dependent manner. Furthermore, the combined treatment of ISIS 404071 and LOVENOX appears to have a synergistic effect on aPTT.

TABLE 28

Effect of combination of ISIS 404071 and LOVENOX on aPTT INR in murine plasma

| ISIS 404071 | LOVENOX (mg/ml) | | | |
|---|---|---|---|---|
| mg/kg | 0 | 2.5 | 5.0 | 7.5 |
| 0 | 1.00 | 1.53 | 2.10 | 2.70 |
| 10 | 1.14 | 1.76 | 2.39 | 3.20 |
| 20 | 1.28 | 1.95 | 2.83 | 3.65 |
| 40 | 1.52 | 2.66 | n.d. | 4.78 |

n.d. = no data

Example 17: In Vivo Effect of Antisense Inhibition of Murine Factor 11 in Combination with LOVENOX in the $FeCl_3$ Induced Venous Thrombosis (VT) Model Treatment The combination of ISIS 404071 and LOVENOX were evaluated in the $FeCl_3$ induced VT mouse model. Four groups of BALB/c mice were treated with 15 mg/kg, 30 mg/kg, 45 mg/kg, or 60 mg/kg of LOVENOX, administered subcutaneously once daily for 3 days. An additional 4 groups of BALB/c mice were treated with 20 mg/kg of ISIS 404071, administered subcutaneously twice weekly for 3 weeks. After the last dose of ISIS 404071, mice were treated with 15 mg/kg, 30 mg/kg, 45 mg/kg, or 60 mg/kg of LOVENOX, administered subcutaneously once daily for 3 days. Two control groups of BALB/c mice were treated with PBS, administered subcutaneously twice a week for 3 weeks. Thrombus formation was induced with $FeCl_3$ in all of the mice except the first control group. All mice were anesthetized with 150 mg/kg of ketamine mixed with 10 mg/kg of xylazine administered by intraperitoneal injection.

In mice undergoing $FeCl_3$ treatment, thrombus formation was induced by applying a piece of filter paper (2×4 mm) pre-saturated with 10% $FeCl_3$ solution directly on the vena cava. After 3 minutes of exposure, the filter paper was removed. Thirty minutes after the filter paper application, a fixed length of the vein containing the thrombus was dissected out for platelet analysis.

Quantification of Platelet Composition

Real-time PCR quantification of PF-4 was used to quantify platelets in the vena cava as a measure of thrombus formation. As shown in Table 29, treatment with LOVENOX resulted in a reduction of PF-4 in comparison to the PBS control. Treatment with LOVENOX in combination with ISIS 404071 resulted in a higher reduction of PF-4 in comparison to LOVENOX alone.

TABLE 29

Analysis of thrombus formation by real-time PCR quantification of PF-4 in the $FeCl_3$ induced venous thrombosis model

| Treatment | mg/kg | PF-4 |
|---|---|---|
| PBS − $FeCl_3$ | | 0 |
| PBS + $FeCl_3$ | | 100 |
| LOVENOX | 15 | 57 |
| | 30 | 33 |
| | 45 | 10 |
| | 60 | 5 |
| LOVENOX (+ISIS 404071) | 15 | 0 |
| | 30 | 0 |
| | 45 | 11 |
| | 60 | 5 |

Example 18: In Vivo Effect of Antisense Inhibition of Murine Factor 11 in Combination with LOVENOX on Bleeding Treatment Tail-bleeding was measured to observe whether treatment with ISIS 404071 and LOVENOX causes internal hemorrhage in mice. ISIS 404071 was administered subcutaneously at a dosage of 20 mg/kg twice a week for 3 weeks to 4 groups of BALB/c mice, and LOVENOX was administered subcutaneously at varying dosages of 15 mg/kg, 30 mg/kg, 45 mg/kg, and 60 mg/kg once daily on the last three days of ISIS 404071 treatment. In a fifth group, ISIS 404071 was administered subcutaneously to BALB/c mice at a dosage of 20 mg/kg twice a week for 3 weeks. In a sixth group, PBS was administered subcutaneously twice a week for three weeks to BALB/c mice, as a control.

Tail-Bleeding Assay

Two days after receiving their final treatment, mice were placed in a tail bleeding chamber. Mice were anesthetized in the chamber with isoflurane and a small piece of tail (approximately 4 mm from the tip) was cut with sterile scissors. The cut tail was immediately placed in a 15 mL Falcon tube filled with approximately 10 mL of 0.9% NaCl buffer solution warmed to 37° C. The blood was collected over the course of 40 minutes. The saline filled tubes were weighed both before and after bleeding.

As shown in Table 30, LOVENOX increased bleeding in mice compared to the PBS treated mice. Increased doses of LOVENOX correlated positively with increased blood loss. ISIS 404071 combined with LOVENOX did not significant increase bleeding beyond the increased blood loss shown in LOVENOX only treated mice.

TABLE 30

Tail bleeding assay comparing LOVENOX and the combination of LOVENOX and ISIS 404071

| | Dose in mg/kg | Blood (g) |
|---|---|---|
| PBS | | 0.05 |
| LOVENOX | 15 | 0.11 |
| | 30 | 0.20 |
| | 45 | 0.27 |
| | 60 | 0.47 |
| LOVENOX (+ISIS 404071) | 15 | 0.14 |
| | 30 | 0.19 |
| | 45 | 0.36 |
| | 60 | 0.61 |

Example 19: In Vivo Effect of Antisense Inhibition of Murine Factor 11 in Combination with LOVENOX on PT and aPTT Treatment PT and aPTT were measured using PPP from mice treated with ISIS 404071 in combination with LOVENOX. In the first cohort, ISIS 404071 was administered subcutaneously to BALB/c mice at a dosage of 25 mg/kg twice a week for 3 weeks. Plasma was collected from these mice 5 days after receiving the last dose of ISIS 404071. In the second cohort, LOVENOX was administered subcutaneously to BALB/c mice at a dosage of 20 mg/kg once daily for three days. Plasma was collected from these mice 4 hours after receiving the last dose of LOVENOX. In the third cohort, ISIS 404071 was administered subcutaneously to BALB/c mice at a dosage of 20 mg/kg twice a week for 3 weeks, and 2 days after receiving the last dose of ISIS 404071, LOVENOX was administered subcutaneously at a dosage of 20 mg/kg once daily. Plasma was collected from these mice 4 hours after the last dose of LOVENOX. In a fourth cohort, PBS was administered subcutaneously twice a week for three weeks, as a control. Plasma was collected from these mice 5 days after the last dose.

PT and aPTT Assay

PT and aPTT values provided in Table 31 are reported as International Normalized Ratio (INR) values. As shown in Table 31, PT is not significantly affected by treatment with ISIS 404071, LOVENOX, or treatment with ISIS 40471 combined with LOVENOX. These data suggest that there is no combinational effect on PT by ISIS 404071 combined with LOVENOX. Also shown in Table 31, treatment with LOVENOX and treatment with ISIS 404071 combined with LOVENOX increase aPTT. These data suggest that the combined treatment of ISIS 404071 and LOVENOX has an additive effect on aPTT.

TABLE 31

Effect of combination of ISIS 404071 and LOVENOX on PT and aPTT in murine plasma

| | PT INR | aPTT INR |
|---|---|---|
| ISIS 404071 | 0.95 | 1.31 |
| LOVENOX | 1.04 | 2.04 |
| 404071 + LOVENOX | 1.04 | 2.58 |

Example 20: In Vivo Effect of Antisense Inhibition of Murine Factor 11 in Combination with Apixaban on PT and aPTT Treatment PT and aPTT were measured using PPP from mice treated with ISIS 404071 in combination with Apixaban. In the first cohort, ISIS 404071 was administered subcutaneously to BALB/c mice at a dosage of 25 mg/kg twice a week for 3 weeks. Plasma was collected from these mice 5 days after receiving the last dose of ISIS 404071. In the second cohort, Apixaban was administered subcutaneously to BALB/c mice at a dosage of 6 mg/kg twice daily for three days. Plasma was collected from these mice 20 minutes after receiving the last dose of Apixaban. In the third cohort, ISIS 404071 was administered subcutaneously to BALB/c mice at a dosage of 20 mg/kg twice a week for 3 weeks, and Apixaban was administered subcutaneously at a dosage of 6 mg/kg twice daily on the last three days of ISIS 404071 treatment. Plasma was collected from these mice 20 minutes after receiving the last dose of Apixaban. In a fourth cohort, PBS was administered subcutaneously twice a week for three weeks, as a control. Plasma was collected 5 days after the last dose of PBS.

PT and aPTT Assay

PT and aPTT values provided in Table 32 are reported as International Normalized Ratio (INR) values. As shown in Table 32, PT is not significantly affected by treatment with ISIS 404071. However, Apixaban and Apixaban combined with ISIS 404071 increased PT. Also shown in Table 32, Apixaban, ISIS 404071, and ISIS 404071 combined with Apixaban increase aPTT.

TABLE 32

Effect of combination of ISIS 404071 and Apixaban on PT and aPTT in murine plasma

| | PT INR | aPTT INR |
|---|---|---|
| ISIS 404071 | 0.95 | 1.31 |
| Apixaban | 3.25 | 1.44 |
| 404071 + Apixaban | 3.50 | 2.26 |

Example 21: In Vivo Effect of Antisense Inhibition of Murine Factor 11 in Combination with Warfarin on PT and aPTT Treatment PT and aPTT were measured using PPP from mice treated with ISIS 404071 in combination with warfarin. Two groups of BALB/c mice were treated with either 25 mg/kg or 50 mg/kg of ISIS 404071, administered subcutaneously twice a week for 3 weeks. Plasma was collected from each group 5 days after the last dose was administered. In a third group, BALB/c mice were treated with 2 mg/kg of warfarin once daily for 5 days. Plasma was collected 6 hours after the last dose of warfarin was administered. Two additional groups of BALB/c mice were treated with either 25 mg/kg or 50 mg/kg of ISIS 404071, administered subcutaneously twice a week for 3 weeks and warfarin was administered subcutaneously at a dosage of 2 mg/kg once daily on the last 5 days of ISIS 404071 treatment. Plasma was collected from each group 6 hours after the last warfarin treatment. In a final group of BALB/c mice, PBS was administered subcutaneously twice a week for three weeks, as a control. Plasma was collected 5 days after the last PBS treatment.

PT and aPTT Assay

PT and aPTT values provided in Table 33 are reported as International Normalized Ratio (INR) values. As shown in Table 33, PT is not affected by treatment with PBS or ISIS 404071 at either dosage. However, treatment with 2 mg/kg warfarin, 25 mg/kg ISIS 404071 in combination with 2 mg/kg warfarin, and 50 mg/kg ISIS 404071 in combination with 2 mg/kg warfarin increase PT. These data suggest that the combined treatment of ISIS 404071 and warfarin has an additive effect on PT. Also shown in Table 33, aPTT is affected by treatment with ISIS 404071 and warfarin. The combination of ISIS 404071 and warfarin show an increase in aPTT greater than either drug alone. These data suggest that the combined treatment of ISIS 404071 and warfarin has a synergistic effect on aPTT.

TABLE 33

Effect of combination of ISIS 404071 and warfarin on PT and aPTT in murine plasma

| | Dose in mg/kg | PT INR | aPTT INR |
|---|---|---|---|
| ISIS 404071 | 25 | 0.98 | 1.37 |
| | 50 | 0.93 | 1.49 |
| Warfarin | 2 | 21.33 | 2.52 |
| ISIS 404071 (+Warfarin) | 25 | 25.77 | 4.45 |
| | 50 | 36.33 | 4.75 |

Example 22: In Vivo Antithrombotic Effect of Antisense Inhibition of Murine Factor 11 on Mesenteric Vein Thrombosis in Mice Treatment In a first cohort, ISIS 404071 was administered subcutaneously to C57BL/6 mice twice a week for three weeks at a dose of 50 mg/kg. In a second cohort, a control oligonucleotide, ISIS 405277 (AAGGACCTACACTATGGAAT; antisense oligonucleotide for Factor 2), incorporated herein as SEQ ID NO: 12 was administered subcutaneously to C57Bl/6 mice twice a week for three weeks at a dose of 50 mg/kg.

Platelet Preparation

Blood was collected from the retro-orbital venous plexus of naïve C57BL/6 mice by puncture and collected in polypropylene tubes containing 300 μl of heparin (30 U/ml). Platelet rich plasma (PRP) was obtained by centrifugation at 1000 rpm for 5 min. The PRP was transferred to fresh tubes containing 2 μl of Prostaglandin $I_2$ ($PGI_2$) (2 μg/ml) and incubated at 37° C. for 5 min. After centrifugation at 2600 rpm, pellets were resuspended in 1 ml modified Tyrode's-HEPES buffer (137 mM NaCl, 0.3 mM $Na_2HPO_4$, 2 mM KCl, 12 mM $NaHCO_3$, 5 mM HEPES, 5 mM glucose, 0.35% BSA, pH 7.2) containing 2 μl of $PGI_2$ and incubated at 37° C. for 5 min. The suspended pellet was centrifuged at 2600 rpm for 5 min. To remove $PGI_2$, the washing step was repeated twice and platelets were fluorescently labeled with calcein AM 2.5 μg/mL (Molecular Probes, Eugene, Oreg.) for 10 min at room temperature.

Intravital Microscopy for Thrombosis

Fluorescently-labeled platelets were injected intravenously in ISIS 404071 treated and control oligonucleotide treated C57BL/6 mice. The mice were anaesthetized with 2.5% avertin, and an incision was made through the abdominal wall to expose mesenteric veins 250-300-μm in diameter and having a shear rate of approximately 150 $s^{-1}$. The exposed mesentery was kept moist throughout the experiment by periodic superfusion with warmed (37° C.) PBS. The mesentery was transluminated with a 12V, 100 W, DC stabilized source. Veins were visualized using a Zeiss (Germany) Axiovert 135 inverted microscope (Objective 32×) connected to an SVHS video recorder (AG-6730; Panasonic, Tokyo, Japan) using a CCD video camera (Hamamatsu Photonic Systems, Hamamatsu City, Japan). Centerline erythrocyte velocity ($V_{rbc}$) was measured using an optical Doppler velocimeter (Microcirculation Research Institute, Texas A&M College of Medicine, College Station, Tex.). Venular shear rate (τ) was calculated based on Poiseuille's Law for a newtonian fluid, $\tau=8(V_{mean}/D_v)$, where $D_v$ is the diameter of the venule and $V_{mean}$ is estimated from the measured $V_{rbc}$ using the empirical correlation $V_{mean}=V_{rbc}/1.6$.

Results Analysis

Mesenteric vein thrombosis was performed two days after the last antisense oligonucleotide injection. Thrombosis was induced by applying Whatman paper soaked in a 10% $FeCl_3$ solution for 5 minutes on the mesenteric vein. The vein was monitored for 40 minutes, or until occlusion. The elapsed time before the first thrombus 30-50 μm in diameter and the elapsed time before blood stopped flowing for 30 seconds were observed.

Thrombus formation (30 μm in diameter) occurred in mice treated with ISIS 404071 at 14.8±1.7 minutes. Thrombus formation (30 μm in diameter) occurred in control mice at 8.9±0.6 minutes. Occlusive thrombi formed in control mice at 19.3±0.8 min and all injured venules occluded. In contrast, the majority of the veins in ISIS 404071 treated mice did not occlude when observation was terminated 40 minutes after injury and those veins showing occlusion. The only vein showing occlusion in the ISIS 404071 treated mice occluded at 29.5 minutes and reopened after 5 minutes, prior to the end of the study.

Example 23: In Vivo Sense-Oligonucleotide-Antidote for Antisense Inhibition of Murine Factor 11 in BALB/c Mice Treatment The effect of the specific sense oligonucleotide to ISIS 404071 as an antidote was tested in BALB/c mice. In a first cohort, ISIS 404071 was administered subcutaneously to BALB/c mice twice a week for three weeks at a dose of 40 mg/kg. In a second cohort, ISIS 404057 was administered subcutaneously to BALB/c mice twice a week for three weeks at a dose of 40 mg/kg. The ISIS 404071 specific antidote, ISIS 418026 (CCTCTGAAAGTGGATTACCA; complementary to ISIS 404071), incorporated herein as SEQ ID NO: 13, was administered to both cohorts subcutaneously in a single injection of 90 mg/kg 48 hours after the final treatment of ISIS 404071 or 404057. In a third cohort, ISIS 404071 was administered subcutaneously to BALB/c mice twice a week for three weeks at a dose of 40 mg/kg. Following the last treatment of ISIS 404071, mice were injected subcutaneously injected with PBS. In a fourth cohort, ISIS 404057 was administered subcutaneously to BALB/c mice twice a week for three weeks at a dose of 40 mg/kg. Following the last treatment of ISIS 404057, mice were injected subcutaneously injected with PBS. Following antidote administration, a set of 4 mice from each cohort were sacrificed at 12 hours, 1 day, 2 days, 3 days, 7 days, and 14 days. Whole liver was collected for RNA analysis and PPP was collected for aPTT analysis.

RNA Analysis

RNA was extracted from liver tissue for real-time PCR analysis of Factor 11. Results are presented as percent inhibition of Factor 11, relative to PBS control. As shown in Table 34, mice treated with ISIS 404071 without antidote showed progressive decrease in inhibition over the 14 day observation period. However, mice treated with ISIS 404071 and antidote showed an accelerated decrease in inhibition over the 14 day observation period in comparison to mice which did not receive antidote. Also shown in Table 34, treatment with ISIS 418026 had no effect on inhibition of Factor 11 mRNA expression in ISIS 404057 treated mice.

TABLE 34

Percent inhibition of mouse Factor 11 mRNA compared to PBS control

| | 12 hours | 1 day | 2 days | 3 days | 7 days | 14 days |
|---|---|---|---|---|---|---|
| ISIS 404071 | 93 | 90 | 89 | 88 | 81 | 67 |
| ISIS 404071 + ISIS 418026 | 90 | 87 | 72 | 66 | 57 | 31 |
| ISIS 404057 | n.d. | n.d. | n.d. | 95 | n.d. | n.d. |
| ISIS 404057 + ISIS 418026 | n.d. | n.d. | n.d. | 97 | n.d. | n.d. |

n.d. = no data aPTT Assay

As shown in Table 35, mice treated with ISIS 404071 and antidote (ISIS 418026) showed progressive decrease of aPTT over the 14 day observation period compared to mice treated with ISIS 404071 without antidote.

TABLE 35

Effect of antidote treatment on aPTT INR

| | 12 hours | 1 day | 2 day | 3 day | 7 day | 14 day |
|---|---|---|---|---|---|---|
| ISIS 404071 | 1.51 | 1.30 | 1.35 | 1.27 | 1.18 | 1.05 |
| ISIS 404071 + ISIS 418026 | 1.45 | 1.23 | 1.16 | 1.15 | 1.10 | 0.95 |

Example 24: In Vivo Factor 7a Protein-Antidote for Antisense Inhibition of Murine Factor 11 in BALB/c Mice Treatment The effect of human Factor 7a (Factor VIIa) protein as an antidote for ISIS 404071 was tested in BALB/c mice. Two experimental groups of BALB/c mice were treated with 20 mg/kg of ISIS 404071, administered subcutaneously twice a week for 3 weeks. Two control groups of BALB/c mice were treated with PBS, administered subcutaneously twice a week for 3 weeks. Thrombus formation was induced with $FeCl_3$ in all of the mice except the first control group. Fifteen minutes before $FeCl_3$ treatment, the first experimental group was treated with 5 μg/kg of human Factor 7a protein antidote (product no. 407act, American Diagnostica Inc.). Two days after their last dose, all mice were anesthetized with 150 mg/kg of ketamine mixed with 10 mg/kg of xylazine administered by intraperitoneal injection.

In mice undergoing $FeCl_3$ treatment, thrombus formation was induced by applying a piece of filter paper (2×4 mm) pre-saturated with 10% $FeCl_3$ solution directly on the vena cava. After 3 minutes of exposure, the filter paper was removed. Thirty minutes after the filter paper application, a fixed length of the vein containing the thrombus was dissected out for platelet analysis.

Quantification of Platelet Composition

Real-time PCR quantification of platelet factor-4 (PF-4) was used to quantify platelets in the vena cava as a measure of thrombus formation. Results are presented as a percentage of PF-4 in antidote treated and untreated mice, as compared to the two PBS-treated control groups. As shown in Table 36, animals treated with human Factor 7a protein antidote expressed more PF-4 in comparison to animals treated with ISIS 404071 alone. These data indicate that human Factor 7a is successful in rescuing the effect of antisense oligonucleotide inhibition.

TABLE 36

Analysis of thrombus formation by real-time PCR quantification of PF-4 in the $FeCl_3$ induced venous thrombosis model

| Treatment | PF-4 |
|---|---|
| PBS − $FeCl_3$ | 0 |
| PBS + $FeCl_3$ | 100 |
| ISIS 404071 | 18 |
| ISIS 404071 + hFV7a | 68 |

Example 25: In Vivo Antisense Inhibition of Murine Factor 11 in the Collagenase-Induced Intracerebral Hemorrhage Model Treatment ISIS 404071 and warfarin (COUMADIN) were examined in the collegenase-induced intracerebral hemorrhage model. In a first cohort, ISIS 404071 was administered subcutaneously to BALB/c mice twice a week for two weeks at a dose 40 mg/kg. In a second cohort, warfarin was administered intraperioneally to mice twice a week for two weeks at a dose of 2 mg/kg. In a third cohort, ISIS 421208 (TCGGAAGCGACTCTTATATG, 8 mismatches to murine Factor 11, incorporated herein as SEQ ID NO: 14) was administered subcutaneously to BALB/c mice twice a week for two weeks at a dose 40 mg/kg. In a fourth cohort, PBS was administered to BALB/c mice twice a week for two weeks.

Two days after receiving their final dose, all mice in all cohorts were anesthetized with 5 μg/g of avertin. Next, the mice were injected at −1 mm AP, 1 mm R ML, −4 mm DV from bregma flat skull with a 10 μL Hamilton syringe containing 0.075 U collagenase (150 U/mL). Collagenase was delivered over 5 minutes and the needle was kept in place for an additional 5 minutes to prevent reflux. The mice were then analyzed for hemorrhagic size, neurologic deficit score, and mortality.

Table 37 presents the hemorrhage volume detected in mice after collagenase treatment, Table 38 presents the neurologic deficit score of the mice, and Table 39 presents the mortality rate of the mice. Neurological deficit is measured by a standard scoring system where no deficiency is zero and severe deficit is five. Collectively, the data suggest that ISIS 404071 did not have a significant effect on the hemorrhagic size, neurologic deficit score, or mortality of the mice. Thus, risk of intracerebral hemorrhage (a risk factor for warfarin treated individuals) is significantly reduced in ISIS 404071 treated mice in comparison to warfarin treated mice.

TABLE 37

Hemorrhagic volume after collagenase treatment

| | Volume ($mm^3$) |
|---|---|
| PBS | 51 |
| ISIS 421208 | 41 |
| ISIS 404071 | 38 |

TABLE 38

Neurologic Deficit Score after collagenase treatment

| | Score |
|---|---|
| PBS | 2.4 |
| ISIS 421208 | 2.0 |
| ISIS 404071 | 3.8 |

TABLE 39

Mortality after collagenase treatment

| | % mortality |
|---|---|
| PBS | 0 |
| ISIS 421208 | 0 |
| ISIS 404071 | 20 |
| Warfarin | 80 |

Example 26: In Vivo Effect of Antisense Inhibition of Murine Factor 11 in Combination with PLAVIX in the $FeCl_3$ Induced Venous Thrombosis (VT) Model Treatment The combination of ISIS 404071 and PLAVIX was evaluated in the $FeCl_3$ induced VT mouse model. Four groups of eight BALB/c mice, weighing approximately 25 g each, were treated with 6.25 mg/kg, 12.50 mg/kg, 25.00 mg/kg, or 50.00 mg/kg of PLAVIX. Mice were given two doses of PLAVIX on day one and one dose of PLAVIX on day two, two hours before surgery.

An additional four groups of eight BALB/c mice, weighing approximately 25 g each, were treated with 20 mg/kg of ISIS 404071, administered subcutaneously twice a week for three weeks. After the last dose of ISIS 404071, mice were treated with 6.25 mg/kg, 12.50 mg/kg, 25.00 mg/kg, or 50.00 mg/kg of PLAVIX. Two doses of PLAVIX were administered to the mice on day one and one dose of PLAVIX was administered on day two, two hours before surgery.

Two control groups of eight BALB/c mice, weighing approximately 25 g each, were not treated with ISIS 404071 or PLAVIX. An additional two control groups of eight BALB/c mice, weighing approximately 25 g each, were treated with 20 mg/kg of ISIS 404071, administered subcutaneously twice a week for three weeks, but were not treated with PLAVIX. Thrombus formation was induced with $FeCl_3$ in all of the mice except the first and third control groups. All mice were anesthetized with 150 mg/kg of ketamine mixed with 10 mg/kg of xylazine administered by intraperitoneal injection.

In mice undergoing $FeCl_3$ treatment, thrombus formation was induced by applying a piece of filter paper (2×4 mm) pre-saturated with 10% $FeCl_3$ solution directly on the inferior vena cava. After 3 minutes of exposure, the filter paper was removed. Thirty minutes after the filter paper application, a fixed length of the vein containing the thrombus was dissected out for platelet analysis.

Quantification of Platelet Composition

Real-time PCR quantification of PF-4 was used to quantify platelets in the vena cava as a measure of thrombus formation. As shown in Table 40, treatment with PLAVIX resulted in a reduction of PF-4 in comparison to the PBS control. Treatment with PLAVIX in combination with ISIS 404071 resulted in a higher reduction of PF-4 in comparison to PLAVIX alone. Therefore, the combination of anti-platelet therapy with Factor 11 ASO increases antithrombotic activity. Data is presented as percent of PF-4 mRNA as compared to the PBS+$FeCl_3$ control.

TABLE 40

Analysis of thrombus formation by real-time PCR quantification of PF-4 in the FeCl3 induced venous thrombosis model

| Treatment | ISIS 404071 mg/kg | PLAVIX mg/kg | PF-4 |
|---|---|---|---|
| PBS − $FeCl_3$ | 0 | 0 | 29 |
| PBS + $FeCl_3$ | 0 | 0 | 100 |
| PLAVIX only | 0 | 6.25 | 59 |
| | 0 | 12.50 | 37 |
| | 0 | 25.00 | 30 |
| | 0 | 50.00 | 30 |
| ISIS 404071 − $FeCl_3$ | 20 | 0 | 27 |
| ISIS 404071 + $FeCl_3$ | 20 | 0 | 40 |
| PLAVIX (+ISIS 404071) | 20 | 6.25 | 35 |
| | 20 | 12.50 | 38 |
| | 20 | 25.00 | 25 |
| | 20 | 50.00 | 35 |

Example 27: In Vivo Effect of Antisense Inhibition of Murine Factor 11 in Combination with PLAVIX on Bleeding Treatment Tail-bleeding was measured to observe whether treatment with ISIS 404071 in combination with PLAVIX causes an increase in bleeding tendency. ISIS 404071 was administered subcutaneously at a dosage of 20 mg/kg twice a week for 3 weeks to 5 groups of eight BALB/c mice. After the last dose of ISIS 404071, mice were treated with 0 mg/kg, 6.25 mg/kg, 12.50 mg/kg, 25.00 mg/kg, or 50.00 mg/kg of PLAVIX. Two doses of PLAVIX were administered to the mice on day one and one dose of PLAVIX was administered on day two, two hours before bleeding.

An additional 5 groups of eight BABL/c mice were treated similarly, except they did not receive ISIS 404071 injections.

Tail-Bleeding Assay

Two hours after receiving their final treatment, mice were placed in a tail bleeding chamber. Mice were anesthetized in the chamber with isoflurane and a small piece of tail (approximately 4 mm from the tip) was cut with sterile scissors. The cut tail was immediately placed in a 15 mL Falcon tube filled with approximately 10 mL of 0.9% NaCl buffer solution warmed to 37° C. The blood was collected for the course of 40 minutes. The saline filled tubes were weighed both before and after bleeding.

Taken with the results of Example 26, these data show that the combination of anti-platelet therapy with Factor 11 ASO increases antithrombotic activity without increased bleeding risk.

TABLE 41

Tail bleeding assay comparing PLAVIX and the combination of PLAVIX and ISIS 404071

| Treatment | ISIS 404071 mg/kg | PLAVIX mg/kg | Blood (g) |
|---|---|---|---|
| No treatment | 0 | 0 | 0.040 |
| PLAVIX only | 0 | 6.25 mg/kg | 0.075 |
| | 0 | 12.50 mg/kg | 0.205 |
| | 0 | 25.00 mg/kg | 0.524 |
| | 0 | 50.00 mg/kg | 0.628 |
| ISIS 404071 only | 20 mg/kg | 0 | 0 |
| PLAVIX (+ISIS 404071) | 20 mg/kg | 6.25 mg/kg | 0.065 |
| | 20 mg/kg | 12.50 mg/kg | 0.300 |
| | 20 mg/kg | 25.00 mg/kg | 0.401 |
| | 20 mg/kg | 50.00 mg/kg | 0.577 |

Example 28: In Vivo Effect of a Factor Xa Small Molecule Inhibitor in Combination with PLAVIX on Bleeding Treatment Tail-bleeding was measured to observe whether treatment with a Factor 10a small molecule in combination with PLAVIX causes an increase in bleeding tendency. Five groups of eight BALB/c mice were treated with 0 mg/kg, 6.25 mg/kg, 12.50 mg/kg, 25.00 mg/kg, or 50.00 mg/kg of PLAVIX. Mice were given two doses of PLAVIX on day one and one dose of PLAVIX on day two, two hours before bleeding.

An additional five groups of eight BALB/c mice were treated with 0 mg/kg, 6.25 mg/kg, 12.50 mg/kg, 25.00 mg/kg, or 50.00 mg/kg of PLAVIX. Mice were given two doses of PLAVIX on day one and one dose of PLAVIX on day two, two hours before bleeding. These mice were also treated with 0.5 mg/kg of Apixaban, a small molecule Factor 10a inhibitor, intraperitoneally one time 20 minutes before bleeding.

Tail-Bleeding Assay

Two hours after receiving their final treatment, mice were placed in a tail bleeding chamber. Mice were anesthetized in the chamber with isoflurane and a small piece of tail (approximately 4 mm from the tip) was cut with sterile scissors. The cut tail was immediately placed in a 15 mL Falcon tube filled with approximately 10 mL of 0.9% NaCl buffer solution warmed to 37° C. The blood was collected for the course of 40 minutes. The saline filled tubes were weighed both before and after bleeding.

As shown below in Table 42, these data show that the combination of anti-platelet therapy with a small molecule Factor 10a inhibitor, such as Apixaban, increases bleeding risk. Therefore, treatment with the combination of anti-platelet therapy with a Factor 11 ASO provides a better safety profile in comparison to the safety profile of a combination of anti-platelet therapy with a small molecule Factor 10a inhibitor.

TABLE 42

Tail bleeding assay comparing PLAVIX, Apixaban, and the combination of PLAVIX and Apixaban

| Treatment | Apixaban mg/kg | PLAVIX mg/kg | Blood (g) |
|---|---|---|---|
| No treatment | 0 | 0 | 0.002 |
| PLAVIX only | 0 | 6.25 mg/kg | 0.061 |
| | 0 | 12.50 mg/kg | 0.149 |

TABLE 42-continued

| Tail bleeding assay comparing PLAVIX, Apixaban, and the combination of PLAVIX and Apixaban | | | |
|---|---|---|---|
| Treatment | Apixaban mg/kg | PLAVIX mg/kg | Blood (g) |
| | 0 | 25.00 mg/kg | 0.246 |
| | 0 | 50.00 mg/kg | 0.258 |

TABLE 42-continued

| Tail bleeding assay comparing PLAVIX, Apixaban, and the combination of PLAVIX and Apixaban | | | |
|---|---|---|---|
| Treatment | Apixaban mg/kg | PLAVIX mg/kg | Blood (g) |
| Apixaban only | 0.5 mg/kg | 0 | 0.004 |
| PLAVIX (+Apixaban) | 0.5 mg/kg | 6.25 mg/kg | 0.258 |
| | 0.5 mg/kg | 12.50 mg/kg | 0.252 |
| | 0.5 mg/kg | 25.00 mg/kg | 0.361 |
| | 0.5 mg/kg | 50.00 mg/kg | 0.363 |

Example 29: Time Course of In Vivo, Antisense-Mediated Reduction of Murine Factor 11 and Corresponding Anticoagulation in Blood Treatment The time course of antisense-mediated reduction of murine Factor 11 mRNA was observed in BALB/c mice. One dose of 50 mg/kg ISIS 404071 was administered subcutaneously to BALB/c mice. Following ISIS 404071 administration, mice were sacrificed at 12 hours, 1 day, 2 days, 3 days, 4 days, 7 days, 14 days, 28 days, and 56 days. Whole liver was collected for RNA analysis and PPP was collected for aPTT analysis. A control group of mice was treated with one subcutaneous dose of PBS.

RNA Analysis

RNA was extracted from liver tissue for real-time PCR analysis of Factor 11. Results are presented relative to PBS control. Mice treated with ISIS 404071 showed significant Factor 11 mRNA down-regulation by day 1. Mice began regaining Factor 11 mRNA expression by day 14. Mice regained full Factor 11 mRNA expression by day 28 and results from day 56 indicate that Factor mRNA was maintained at pre-treatment levels. Therefore, ISIS 404071 treated mice did not experience a rebound effect.

The rebound effect has been previously observed in antibody-mediated reduction of Factor 11 (Blood, First Edition Paper, prepublished online Oct. 22, 2008; Prevention of vascular graft occlusion and thrombus-associated thrombin generation by inhibition of factor XI). Because over expression of Factor 11 can be damaging by leading to increased coagulation, these data suggest that antisense-mediated inhibition of Factor 11 is safer than antibody-mediated inhibition of Factor 11 since antisense-mediated inhibition of Factor 11 does not rebound.

aPTT Assay aPTT values provided in Table 43 are reported as International Normalized Ratio (INR) values. INR values for aPTT were determined by dividing the aPTT value for ISIS 404071 treated mice by the aPTT for the PBS treated group. This ratio was then raised to the power of the International Sensitivity Index (ISI) of the tissue factor used. As shown in Table 43, mice treated with ISIS 404071 showed progressive decrease of aPTT until day 4 and then progressive increase to pre-treatment levels from day 7 to day 28.

TABLE 43

| Effect of ISIS 404071 treatment on aPTT INR* | | | | | | | | | |
|---|---|---|---|---|---|---|---|---|---|
| | 12 hours | day 1 | day 2 | day 3 | day 4 | day 7 | day 14 | day 28 | day 56 |
| ISIS 404071 | 0 | 1.02 | 1.12 | 1.29 | 1.30 | 1.25 | 1.11 | 1.02 | 0 |

*values in Table 43 are approximate

Example 30: Antisense Inhibition of Human Factor 11 in HepG2 Cells by Oligonucleotides Designed by Microwalk Additional gapmers were designed based on ISIS 416850 and ISIS 416858 (see Table 8 above). These gapmers were shifted slightly upstream and downstream (i.e. "microwalk") of ISIS 416850 and ISIS 416858. The microwalk gapmers were designed with either 5-8-5 MOE or 6-8-6 MOE motifs.

These microwalk gapmers were tested in vitro. Cultured HepG2 cells at a density of 20,000 cells per well were transfected using electroporation with 8,000 nM antisense oligonucleotide. After a treatment period of approximately 24 hours, RNA was isolated from the cells and Factor 11 mRNA levels were measured by quantitative real-time PCR. Factor 11 mRNA levels were adjusted according to total RNA content, as measured by RIBOGREEN. Results are presented as percent inhibition of Factor 11, relative to untreated control cells.

ISIS 416850 and ISIS 416858, as well as selected gapmers from Tables 1 and 8 (i.e., ISIS 412206, ISIS 412223, ISIS 412224, ISIS 412225, ISIS 413481, ISIS 413482, ISIS 416825, ISIS 416848, ISIS 416849, ISIS 416850, ISIS 416851, ISIS 416852, ISIS 416853, ISIS 416854, ISIS 416855, ISIS 416856, ISIS 416857, ISIS 416858, ISIS 416859, ISIS 416860, ISIS 416861, ISIS 416862, ISIS 416863, ISIS 416864, ISIS 416865, ISIS 416866, and ISIS 416867) were retested in vitro along with the microwalk gapmers under the same condition as described above.

The chimeric antisense oligonucleotides in Table 44 were designed as 5-10-5 MOE, 5-8-5 and 6-8-6 MOE gapmers. The first two listed gapmers in Table 44 are the original gapmers (ISIS 416850 and ISIS 416858) from which ISIS 445493-445543 were designed via microwalk, and are designated by an asterisk. The 5-10-5 gapmers are 20 nucleotides in length, wherein the central gap segment is comprised of ten 2'-deoxynucleotides and is flanked on both sides (in the 5' and 3' directions) by wings comprising five nucleotides each. The 5-8-5 gapmers are 18 nucleotides in length, wherein the central gap segment is comprised of eight 2'-deoxynucleotides and is flanked on both sides (in the 5' and 3' directions) by wings comprising five nucleotides each. The 6-8-6 gapmers are 20 nucleotides in length, wherein the central gap segment is comprised of eight 2'-deoxynucleotides and is flanked on both sides (in the 5' and 3' directions) by wings comprising six nucleotides each. For each of the motifs (5-10-5, 5-8-5 and 6-8-6), each nucleotide in the 5' wing segment and each nucleotide in the 3' wing segment has a 2'-MOE modification. The internucleoside linkages throughout each gapmer are phosphorothioate (P═S) linkages. All cytidine residues throughout each gapmer are 5-methylcytidines. "Human Target start site" indicates the 5'-most nucleotide to which the gapmer is targeted in the human sequence. "Human Target stop site" indicates the 3'-most nucleotide to which the gapmer is targeted in the human sequence. Each gapmer listed in Table 44 is targeted to SEQ ID NO: 1 (GENBANK Accession No. NM_000128.3). Each gapmer is Table 44 is also fully cross-reactive with the rhesus monkey Factor 11 gene sequence, designated herein as SEQ ID NO: 274 (exons 1-15 GENBANK Accession No. NW_001118167.1). 'Rhesus monkey start site' indicates the 5'-most nucleotide to which the gapmer is targeted in the rhesus monkey sequence. 'Rhesus monkey stop site' indicates the 3'-most nucleotide to which the gapmer is targeted to the rhesus monkey sequence.

As shown in Table 44, all of the microwalk designed gapmers targeted to the target region beginning at the target start site 1275 and ending at the target stop site 1317 (i.e. nucleobases 1275-1317) of SEQ ID NO: 1 exhibited at least 60% inhibition of Factor 11 mRNA. Similarly, all of the re-tested gapmers from Tables 1 and 8 exhibited at least 60% inhibition.

Several of the gapmers exhibited at least 70% inhibition, including ISIS numbers: ISIS 412206, 412224, 412225, 413481, 413482, 416825, 416848, 416849, 416850, 416851, 416852, 416853, 416854, 416855, 416856, 416857, 416858, 416859, 416860, 416861, 416862, 416863, 416864, 416865, 416866, 416867, 445494, 445495, 445496, 445497, 445498, 445499, 445500, 445501, 445502, 445503, 445504, 445505, 445506, 445507, 445508, 445509, 445510, 445511, 445512, 445513, 445514, 445515, 445516, 445517, 445518, 445519, 445520, 445521, 445522, 445523, 445524, 445525, 445526, 445527, 445528, 445529, 445530, 445531, 445532, 445533, 445534, 445535, 445536, 445537, 455538, 445539, 445540, 445541, 445542, and 445543.

Several of the gapmers exhibited at least 80% inhibition, including ISIS numbers: ISIS 412206, 412224, 412225, 413481, 413482, 416825, 416848, 416849, 416850, 416851, 416852, 416853, 416854, 416855, 416856, 416857, 416858, 416859, 416860, 416861, 416862, 416863, 416864, 416865, 416866, 416867, 445494, 445495, 445496, 445497, 445498, 445500, 445501, 445502, 445503, 445504, 445505, 445506, 445507, 445508, 445509, 445510, 445513, 445514, 445519, 445520, 445521, 445522, 445525, 445526, 445529, 445530, 445531, 445532, 445533, 445534, 445535, 445536, 455538, 445541, and 445542.

Several of the gapmers exhibited at least 90% inhibition, including ISIS numbers: ISIS 412206, 416825, 416850, 416857, 416858, 416861, 445522, and 445531.

TABLE 44

Inhibition of human Factor 11 mRNA levels by chimeric antisense oligonucleotides targeted to SEQ ID NO: 1 (GENBANK Accession No. NM_000128.3)

| ISIS No. | Human Start Site | Human Stop Site | Sequence (5' to 3') | Percent inhibition | Motif | SEQ ID No. | Rhesus monkey Start Site | Rhesus monkey Stop Site |
|---|---|---|---|---|---|---|---|---|
| *416850 | 1278 | 1297 | TGCACAGTTTCT GGCAGGCC | 91 | 5-10-5 | 215 | 1277 | 1296 |
| *416858 | 1288 | 1307 | ACGGCATTGGT GCACAGTTT | 90 | 5-10-5 | 223 | 1287 | 1306 |
| 416825 | 680 | 699 | GCCCTTCATGTC TAGGTCCA | 90 | 5-10-5 | 190 | 679 | 698 |
| 412206 | 738 | 757 | CCGTGCATCTTT CTTGGCAT | 91 | 5-10-5 | 34 | 737 | 756 |
| 412223 | 1275 | 1294 | ACAGTTTCTGG CAGGCCTCG | 62 | 5-10-5 | 51 | 1274 | 1293 |
| 445493 | 1275 | 1294 | ACAGTTTCTGG CAGGCCTCG | 69 | 6-8-6 | 51 | 1274 | 1293 |
| 445518 | 1275 | 1292 | AGTTTCTGGCA GGCCTCG | 75 | 5-8-5 | 242 | 1274 | 1291 |
| 416848 | 1276 | 1295 | CACAGTTTCTG GCAGGCCTC | 87 | 5-10-5 | 213 | 1275 | 1294 |
| 445494 | 1276 | 1295 | CACAGTTTCTG GCAGGCCTC | 85 | 6-8-6 | 213 | 1275 | 1294 |
| 445519 | 1276 | 1293 | CAGTTTCTGGC AGGCCTC | 81 | 5-8-5 | 243 | 1275 | 1292 |
| 416849 | 1277 | 1296 | GCACAGTTTCT GGCAGGCCT | 88 | 5-10-5 | 214 | 1276 | 1295 |
| 445495 | 1277 | 1296 | GCACAGTTTCT GGCAGGCCT | 89 | 6-8-6 | 214 | 1276 | 1295 |
| 445520 | 1277 | 1294 | ACAGTTTCTGG CAGGCCT | 82 | 5-8-5 | 244 | 1276 | 1293 |

TABLE 44-continued

Inhibition of human Factor 11 mRNA levels by chimeric antisense oligonucleotides targeted to SEQ ID NO: 1 (GENBANK Accession No. NM_000128.3)

| ISIS No. | Human Start Site | Human Stop Site | Sequence (5' to 3') | Percent inhibition | Motif | SEQ ID No. | Rhesus monkey Start Site | Rhesus monkey Stop Site |
|---|---|---|---|---|---|---|---|---|
| 445496 | 1278 | 1297 | TGCACAGTTTCT GGCAGGCC | 87 | 6-8-6 | 215 | 1277 | 1296 |
| 445521 | 1278 | 1295 | CACAGTTTCTG GCAGGCC | 87 | 5-8-5 | 245 | 1277 | 1294 |
| 416851 | 1279 | 1298 | GTGCACAGTTT CTGGCAGGC | 89 | 5-10-5 | 216 | 1278 | 1297 |
| 445497 | 1279 | 1298 | GTGCACAGTTT CTGGCAGGC | 81 | 6-8-6 | 216 | 1278 | 1297 |
| 445522 | 1279 | 1296 | GCACAGTTTCT GGCAGGC | 91 | 5-8-5 | 246 | 1278 | 1295 |
| 413481 | 1280 | 1299 | GGTGCACAGTT TCTGGCAGG | 82 | 5-10-5 | 114 | 1279 | 1298 |
| 445498 | 1280 | 1299 | GGTGCACAGTT TCTGGCAGG | 83 | 6-8-6 | 114 | 1279 | 1298 |
| 445523 | 1280 | 1297 | TGCACAGTTTCT GGCAGG | 73 | 5-8-5 | 267 | 1279 | 1296 |
| 416852 | 1281 | 1300 | TGGTGCACAGT TTCTGGCAG | 87 | 5-10-5 | 217 | 1280 | 1299 |
| 445499 | 1281 | 1300 | TGGTGCACAGT TTCTGGCAG | 75 | 6-8-6 | 217 | 1280 | 1299 |
| 445524 | 1281 | 1298 | GTGCACAGTTT CTGGCAG | 75 | 5-8-5 | 247 | 1280 | 1297 |
| 416853 | 1282 | 1301 | TTGGTGCACAG TTTCTGGCA | 84 | 5-10-5 | 218 | 1281 | 1300 |
| 445500 | 1282 | 1301 | TTGGTGCACAG TTTCTGGCA | 81 | 6-8-6 | 218 | 1281 | 1300 |
| 445525 | 1282 | 1299 | GGTGCACAGTT TCTGGCA | 85 | 5-8-5 | 248 | 1281 | 1298 |
| 416854 | 1283 | 1302 | ATTGGTGCACA GTTTCTGGC | 86 | 5-10-5 | 219 | 1282 | 1301 |
| 445501 | 1283 | 1302 | ATTGGTGCACA GTTTCTGGC | 83 | 6-8-6 | 219 | 1282 | 1301 |
| 445526 | 1283 | 1300 | TGGTGCACAGT TTCTGGC | 81 | 5-8-5 | 249 | 1282 | 1299 |
| 416855 | 1284 | 1303 | CATTGGTGCAC AGTTTCTGG | 85 | 5-10-5 | 220 | 1283 | 1302 |
| 445502 | 1284 | 1303 | CATTGGTGCAC AGTTTCTGG | 83 | 6-8-6 | 220 | 1283 | 1302 |
| 445527 | 1284 | 1301 | TTGGTGCACAG TTTCTGG | 70 | 5-8-5 | 250 | 1283 | 1300 |
| 412224 | 1285 | 1304 | GCATTGGTGCA CAGTTTCTG | 84 | 5-10-5 | 52 | 1284 | 1303 |
| 445503 | 1285 | 1304 | GCATTGGTGCA CAGTTTCTG | 89 | 6-8-6 | 52 | 1284 | 1303 |
| 445528 | 1285 | 1302 | ATTGGTGCACA GTTTCTG | 73 | 5-8-5 | 251 | 1284 | 1301 |
| 416856 | 1286 | 1305 | GGCATTGGTGC ACAGTTTCT | 84 | 5-10-5 | 221 | 1285 | 1304 |

TABLE 44-continued

Inhibition of human Factor 11 mRNA levels by chimeric antisense oligonucleotides targeted to SEQ ID NO: 1 (GENBANK Accession No. NM_000128.3)

| ISIS No. | Human Start Site | Human Stop Site | Sequence (5' to 3') | Percent inhibition | Motif | SEQ ID No. | Rhesus monkey Start Site | Rhesus monkey Stop Site |
|---|---|---|---|---|---|---|---|---|
| 445504 | 1286 | 1305 | GGCATTGGTGC ACAGTTTCT | 87 | 6-8-6 | 221 | 1285 | 1304 |
| 445529 | 1286 | 1303 | CATTGGTGCAC AGTTTCT | 85 | 5-8-5 | 252 | 1285 | 1302 |
| 416857 | 1287 | 1306 | CGGCATTGGTG CACAGTTTC | 91 | 5-10-5 | 222 | 1286 | 1305 |
| 445505 | 1287 | 1306 | CGGCATTGGTG CACAGTTTC | 89 | 6-8-6 | 222 | 1286 | 1305 |
| 445530 | 1287 | 1304 | GCATTGGTGCA CAGTTTC | 83 | 5-8-5 | 253 | 1286 | 1303 |
| 445506 | 1288 | 1307 | ACGGCATTGGT GCACAGTTT | 86 | 6-8-6 | 223 | 1287 | 1306 |
| 445531 | 1288 | 1305 | GGCATTGGTGC ACAGTTT | 90 | 5-8-5 | 254 | 1287 | 1304 |
| 416859 | 1289 | 1308 | GACGGCATTGG TGCACAGTT | 85 | 5-10-5 | 224 | 1288 | 1307 |
| 445507 | 1289 | 1308 | GACGGCATTGG TGCACAGTT | 85 | 6-8-6 | 224 | 1288 | 1307 |
| 445532 | 1289 | 1306 | CGGCATTGGTG CACAGTT | 89 | 5-8-5 | 255 | 1288 | 1305 |
| 413482 | 1290 | 1309 | GGACGGCATTG GTGCACAGT | 88 | 5-10-5 | 115 | 1289 | 1308 |
| 445508 | 1290 | 1309 | GGACGGCATTG GTGCACAGT | 81 | 6-8-6 | 115 | 1289 | 1308 |
| 445533 | 1290 | 1307 | ACGGCATTGGT GCACAGT | 87 | 5-8-5 | 256 | 1289 | 1306 |
| 416860 | 1291 | 1310 | CGGACGGCATT GGTGCACAG | 89 | 5-10-5 | 225 | 1290 | 1309 |
| 445509 | 1291 | 1310 | CGGACGGCATT GGTGCACAG | 84 | 6-8-6 | 225 | 1290 | 1309 |
| 445534 | 1291 | 1308 | GACGGCATTGG TGCACAG | 82 | 5-8-5 | 257 | 1290 | 1307 |
| 416861 | 1292 | 1311 | GCGGACGGCAT TGGTGCACA | 90 | 5-10-5 | 226 | 1291 | 1310 |
| 445510 | 1292 | 1311 | GCGGACGGCAT TGGTGCACA | 88 | 6-8-6 | 226 | 1291 | 1310 |
| 445535 | 1292 | 1309 | GGACGGCATTG GTGCACA | 83 | 5-8-5 | 258 | 1291 | 1308 |
| 416862 | 1293 | 1312 | AGCGGACGGCA TTGGTGCAC | 89 | 5-10-5 | 227 | 1292 | 1311 |
| 445511 | 1293 | 1312 | AGCGGACGGCA TTGGTGCAC | 77 | 6-8-6 | 227 | 1292 | 1311 |
| 445536 | 1293 | 1310 | CGGACGGCATT GGTGCAC | 82 | 5-8-5 | 259 | 1292 | 1309 |
| 416863 | 1294 | 1313 | CAGCGGACGGC ATTGGTGCA | 86 | 5-10-5 | 228 | 1293 | 1312 |
| 445512 | 1294 | 1313 | CAGCGGACGGC ATTGGTGCA | 79 | 6-8-6 | 228 | 1293 | 1312 |

TABLE 44-continued

Inhibition of human Factor 11 mRNA levels by chimeric antisense oligonucleotides targeted to SEQ ID NO: 1 (GENBANK Accession No. NM_000128.3)

| ISIS No. | Human Start Site | Human Stop Site | Sequence (5' to 3') | Percent inhibition | Motif | SEQ ID No. | Rhesus monkey Start Site | Rhesus monkey Stop Site |
|---|---|---|---|---|---|---|---|---|
| 445537 | 1294 | 1311 | GCGGACGGCAT TGGTGCA | 78 | 5-8-5 | 260 | 1293 | 1310 |
| 412225 | 1295 | 1314 | GCAGCGGACGG CATTGGTGC | 86 | 5-10-5 | 53 | 1294 | 1313 |
| 445513 | 1295 | 1314 | GCAGCGGACGG CATTGGTGC | 85 | 6-8-6 | 53 | 1294 | 1313 |
| 445538 | 1295 | 1312 | AGCGGACGGCA TTGGTGC | 80 | 5-8-5 | 261 | 1294 | 1311 |
| 416864 | 1296 | 1315 | GGCAGCGGACG GCATTGGTG | 88 | 5-10-5 | 229 | 1295 | 1314 |
| 445514 | 1296 | 1315 | GGCAGCGGACG GCATTGGTG | 81 | 6-8-6 | 229 | 1295 | 1314 |
| 445539 | 1296 | 1313 | CAGCGGACGGC ATTGGTG | 79 | 5-8-5 | 262 | 1295 | 1312 |
| 416865 | 1297 | 1316 | TGGCAGCGGAC GGCATTGGT | 86 | 5-10-5 | 230 | 1296 | 1315 |
| 445515 | 1297 | 1316 | TGGCAGCGGAC GGCATTGGT | 75 | 6-8-6 | 230 | 1296 | 1315 |
| 445540 | 1297 | 1314 | GCAGCGGACGG CATTGGT | 74 | 5-8-5 | 263 | 1296 | 1313 |
| 416866 | 1298 | 1317 | CTGGCAGCGGA CGGCATTGG | 84 | 5-10-5 | 231 | 1297 | 1316 |
| 445516 | 1298 | 1317 | CTGGCAGCGGA CGGCATTGG | 79 | 6-8-6 | 231 | 1297 | 1316 |
| 445541 | 1298 | 1315 | GGCAGCGGACG GCATTGG | 80 | 5-8-5 | 264 | 1297 | 1314 |
| 416867 | 1299 | 1318 | ACTGGCAGCGG ACGGCATTG | 85 | 5-10-5 | 232 | 1298 | 1317 |
| 445517 | 1299 | 1318 | ACTGGCAGCGG ACGGCATTG | 74 | 6-8-6 | 232 | 1298 | 1317 |
| 445542 | 1299 | 1316 | TGGCAGCGGAC GGCATTG | 83 | 5-8-5 | 265 | 1298 | 1315 |
| 445543 | 1300 | 1317 | CTGGCAGCGGA CGGCATT | 74 | 5-8-5 | 266 | 1299 | 1316 |

Example 31: Dose-Dependent Antisense Inhibition of Human Factor 11 in HepG2 Cells Gapmers from Example 30 exhibiting in vitro inhibition of human Factor 11 were tested at various doses in HepG2 cells. Cells were plated at a density of 20,000 cells per well and transfected using electroporation with 123.46 nM, 370.37 nM, 1,111.11 nM, 3,333.33 nM and 10,000 nM concentrations of antisense oligonucleotide, as specified in Table 45. After a treatment period of approximately 16 hours, RNA was isolated from the cells and Factor 11 mRNA levels were measured by quantitative real-time PCR. Human Factor 11 primer probe set RTS 2966 was used to measure mRNA levels. Factor 11 mRNA levels were adjusted according to total RNA content, as measured by RIBOGREEN. Results are presented as percent inhibition of Factor 11, relative to untreated control cells. As illustrated in Table 45, Factor 11 mRNA levels were reduced in a dose-dependent manner in antisense oligonucleotide treated cells.

The half maximal inhibitory concentration ($IC_{50}$) of each oligonucleotide was calculated by plotting the concentrations of antisense oligonucleotides used versus the percent inhibition of Factor 11 mRNA expression achieved at each concentration, and noting the concentration of antisense oligonucleotide at which 50% inhibition of Factor 11 mRNA expression was achieved compared to the PBS control. $IC_{50}$ values are presented in Table 45.

TABLE 45

Dose-dependent antisense inhibition of human Factor 11 in HepG2 cells via transfection of oligonucleotides using electroporation

| ISIS No. | 123.47 nM | 370.37 nM | 1,111.11 nM | 3,333.33 nM | 10,000.0 nM | $IC_{50}$ (μM) |
|---|---|---|---|---|---|---|
| 416849 | 5 | 5 | 26 | 57 | 68 | 2.7 |
| 416850 | 0 | 12 | 36 | 74 | 73 | 2.8 |
| 416851 | 13 | 35 | 36 | 64 | 72 | 1.5 |
| 416856 | 12 | 23 | 35 | 59 | 83 | 1.6 |
| 416857 | 2 | 20 | 35 | 62 | 72 | 2.3 |
| 416858 | 0 | 27 | 36 | 64 | 70 | 2.2 |
| 416860 | 0 | 28 | 39 | 41 | 40 | n.d. |
| 416861 | 0 | 15 | 27 | 66 | 80 | 2.0 |
| 445498 | 3 | 1 | 27 | 50 | 58 | 4.8 |
| 445503 | 0 | 0 | 22 | 36 | 60 | 5.9 |
| 445504 | 8 | 20 | 38 | 53 | 68 | 2.7 |
| 445505 | 12 | 30 | 39 | 59 | 77 | 1.8 |
| 445522 | 0 | 0 | 44 | 63 | 74 | 2.9 |
| 445531 | 8 | 16 | 52 | 61 | 77 | 1.8 |
| 445532 | 5 | 12 | 39 | 60 | 70 | 2.0 |

n.d. = no data

Example 32: Dose-Dependent Antisense Inhibition of Human Factor 11 in HepG2 Cells by Oligonucleotides Designed by Microwalk Additional gapmers were designed based on ISIS 416850 and ISIS 416858 (see Table 8 above). These gapmers are shifted slightly upstream and downstream (i.e. microwalk) of ISIS 416850 and ISIS 416858. Gapmers designed by microwalk have 3-8-3 MOE, 4-8-4 MOE, 2-10-2 MOE, 3-10-3 MOE, or 4-10-4 MOE motifs.

These gapmers were tested at various doses in HepG2 cells. Cells were plated at a density of 20,000 cells per well and transfected using electroporation with 375 nM, 750 nM, 1,500 nM, 3,000 nM, 6,000 nM and 12,000 nM concentrations of antisense oligonucleotide, as specified in Table 47. After a treatment period of approximately 16 hours, RNA was isolated from the cells and Factor 11 mRNA levels were measured by quantitative real-time PCR. Human Factor 11 primer probe set RTS 2966 was used to measure mRNA levels. Factor 11 mRNA levels were adjusted according to total RNA content, as measured by RIBOGREEN. Results are presented as percent inhibition of Factor 11, relative to untreated control cells.

ISIS 416850, ISIS 416858, ISIS 445522, and ISIS 445531 (see Table 45 above) were re-tested in vitro along with the microwalk gapmers under the same conditions described above.

The chimeric antisense oligonucleotides in Table 46 were designed as 3-8-3 MOE, 4-8-4 MOE, 2-10-2 MOE, 3-10-3 MOE, or 4-10-4 MOE gapmers. The 3-8-3 gapmer is 14 nucleotides in length, wherein the central gap segment is comprised of eight 2'-deoxynucleotides and is flanked on both sides (in the 5' and 3' directions) by wings comprising three nucleotides each. The 4-8-4 gapmer is 16 nucleotides in length, wherein the central gap segment is comprised of eight 2'-deoxynucleotides and is flanked on both sides (in the 5' and 3' directions) by wings comprising four nucleotides each. The 2-10-2 gapmer is 14 nucleotides in length, wherein the central gap segment is comprised of ten 2'-deoxynucleotides and is flanked on both sides (in the 5' and 3' directions) by wings comprising two nucleotides each. The 3-10-3 gapmer is 16 nucleotides in length, wherein the central gap segment is comprised of ten 2'-deoxynucleotides and is flanked on both sides (in the 5' and 3' directions) by wings comprising three nucleotides each. The 4-10-4 gapmer is 18 nucleotides in length, wherein the central gap segment is comprised of ten 2'-deoxynucleotides and is flanked on both sides (in the 5' and 3' directions) by wings comprising four nucleotides each. For each of the motifs (3-8-3, 4-8-4, 2-10-2, 3-10-3, and 4-10-4), each nucleotide in the 5' wing segment and each nucleotide in the 3' wing segment has a 2'-MOE modification. The internucleoside linkages throughout each gapmer are phosphorothioate (P=S) linkages. All cytidine residues throughout each gapmer are 5-methylcytidines. “Human Target start site” indicates the 5'-most nucleotide to which the gapmer is targeted in the human sequence. “Human Target stop site” indicates the 3'-most nucleotide to which the gapmer is targeted in the human sequence. Each gapmer listed in Table 46 is targeted to SEQ ID NO: 1 (GENBANK Accession No. NM_000128.3). Each gapmer is Table 46 is also fully cross-reactive with the rhesus monkey Factor 11 gene sequence, designated herein as SEQ ID NO: 274 (exons 1-15 GENBANK Accession No. NW_001118167.1). ‘Rhesus monkey start site’ indicates the 5'-most nucleotide to which the gapmer is targeted in the rhesus monkey sequence. ‘Rhesus monkey stop site’ indicates the 3'-most nucleotide to which the gapmer is targeted to the rhesus monkey sequence.

TABLE 46

Chimeric antisense oligonucleotides targeted to SEQ ID NO: 1 (GENBANK Accession No. NM_000128.3) and designed by microwalk of ISIS 416850 and ISIS 416858

| ISIS No. | Human Target Start Site | Human Target Stop Site | Sequence (5' to 3') | Motif | SEQ ID No. | Rhesus monkey Start Site | Rhesus monkey Stop Site |
|---|---|---|---|---|---|---|---|
| 449707 | 1280 | 1295 | CACAGTTT CTGGCAGG | 4-8-4 | 268 | 1279 | 1294 |
| 449708 | 1281 | 1294 | ACAGTTT CTGGCAG | 3-8-3 | 269 | 1280 | 1293 |
| 449709 | 1279 | 1296 | GCACAGTT TCTGGCAGGC | 4-10-4 | 246 | 1278 | 1295 |
| 449710 | 1280 | 1295 | CACAGTTT CTGGCAGG | 3-10-3 | 268 | 1279 | 1294 |

TABLE 46-continued

Chimeric antisense oligonucleotides targeted to SEQ ID NO: 1 (GENBANK Accession No. NM_000128.3) and designed by microwalk of ISIS 416850 and ISIS 416858

| ISIS No. | Human Target Start Site | Human Target Stop Site | Sequence (5' to 3') | Motif | SEQ ID No. | Rhesus monkey Start Site | Rhesus monkey Stop Site |
|---|---|---|---|---|---|---|---|
| 449711 | 1281 | 1294 | ACAGTTT CTGGCAG | 2-10-2 | 269 | 1280 | 1293 |

Dose-response inhibition data is given in Table 47. As illustrated in Table 47, Factor 11 mRNA levels were reduced in a dose-dependent manner in antisense oligonucleotide treated cells. The $IC_{50}$ of each antisense oligonucleotide was also calculated and presented in Table 47. The first two listed gapmers in Table 47 are the original gapmers (ISIS 416850 and ISIS 416858) from which the remaining gapmers were designed via microwalk and are designated by an asterisk.

TABLE 47

Dose-dependent antisense inhibition of human Factor 11 in HepG2 cells via transfection of oligonucleotides using electroporation

| ISIS No. | 375 nM | 750 nM | 1,500 nM | 3,000 nM | 6,000 nM | 12,000 nM | $IC_{50}$ (μM) |
|---|---|---|---|---|---|---|---|
| *416850 | 40 | 59 | 69 | 87 | 90 | 95 | 0.56 |
| *416858 | 31 | 35 | 78 | 85 | 90 | 93 | 0.83 |
| 445522 | 59 | 71 | 83 | 82 | 81 | 92 | n.d. |
| 445531 | 44 | 64 | 78 | 86 | 91 | 93 | 0.44 |
| 449707 | 7 | 35 | 63 | 73 | 85 | 91 | 1.26 |
| 449708 | 0 | 0 | 22 | 33 | 61 | 85 | 4.46 |
| 449709 | 52 | 71 | 80 | 87 | 92 | 95 | 0.38 |
| 449710 | 2 | 21 | 52 | 70 | 82 | 87 | 1.59 |
| 449711 | 6 | 14 | 1 | 7 | 32 | 52 | 11.04 |

n.d. = no data

Example 33: Tolerability of Antisense Oligonucleotides Targeting Human Factor 11 in CD1 Mice CD1 mice were treated with ISIS antisense oligonucleotides targeting human Factor 11 and evaluated for changes in the levels of various metabolic markers.

Treatment

Groups of five CD1 mice each were injected subcutaneously twice a week for 2, 4, or 6 weeks with 50 mg/kg of ISIS 416825, ISIS 416826, ISIS 416838, ISIS 416850, ISIS 416858, ISIS 416864, ISIS 416892, ISIS 416925, ISIS 416999, ISIS 417002, or ISIS 417003. A control group of five mice was injected subcutaneously with PBS for 2 weeks. All experimental groups (i.e. ASO treated mice at 2, 4, 6 weeks) were compared to the control group (i.e. PBS, 2 weeks).

Three days after the last dose was administered to all groups, the mice were sacrificed. Organ weights were measured and blood was collected for further analysis.

Organ Weight

Liver, spleen, and kidney weights were measured at the end of the study, and are presented in Tables 48, 49, and 50 as a percent of the PBS control, normalized to body weight. Those antisense oligonucleotides which did not affect more than six-fold increases in liver and spleen weight above the PBS controls were selected for further studies.

TABLE 48

Percent change in liver weight of CD1 mice after antisense oligonucleotide treatment

| ISIS No. | 2 weeks | 4 weeks | 6 weeks |
|---|---|---|---|
| 416825 | +5 | +22 | +13 |
| 416826 | +10 | +32 | +33 |
| 416838 | +8 | −6 | 0 |
| 416850 | +5 | +3 | +6 |
| 416858 | +7 | +1 | +10 |
| 416864 | −2 | +2 | −5 |
| 416925 | +14 | +14 | +33 |
| 416999 | +13 | +30 | +47 |
| 417002 | +14 | +8 | +35 |
| 416892 | +35 | +88 | +95 |
| 417003 | +8 | +42 | +32 |

TABLE 49

Percent change in spleen weight of CD1 mice after antisense oligonucleotide treatment

| ISIS No. | 2 weeks | 4 weeks | 6 weeks |
|---|---|---|---|
| 416825 | −12 | +19 | +21 |
| 416826 | −12 | −5 | +22 |
| 416838 | +21 | −8 | +9 |

TABLE 49-continued

| Percent change in spleen weight of CD1 mice after antisense oligonucleotide treatment | | | |
|---|---|---|---|
| ISIS No. | 2 weeks | 4 weeks | 6 weeks |
| 416850 | −4 | +6 | +48 |
| 416858 | −2 | +8 | +28 |
| 416864 | −10 | −2 | −6 |
| 416925 | −7 | +33 | +78 |
| 416999 | +7 | +22 | +38 |
| 417002 | +29 | +26 | +108 |
| 416892 | +24 | +30 | +65 |
| 417003 | +12 | +101 | +98 |

TABLE 50

| Percent change in kidney weight of CD1 mice after antisense oligonucleotide treatment | | | |
|---|---|---|---|
| ISIS No. | 2 weeks | 4 weeks | 6 weeks |
| 416825 | −12 | −12 | −11 |
| 416826 | −13 | −7 | −22 |
| 416838 | −2 | −12 | −8 |
| 416850 | −10 | −12 | −11 |
| 416858 | +1 | −18 | −10 |
| 416864 | −4 | −9 | −15 |
| 416925 | −4 | −14 | −2 |
| 416999 | −9 | −6 | −7 |
| 417002 | +3 | −5 | −2 |
| 416892 | +2 | −3 | +19 |
| 417003 | −9 | −2 | −1 |

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Measurements of alanine transaminase (ALT) and aspartate transaminase (AST) are expressed in IU/L and the results are presented in Tables 51 and 52. Plasma levels of bilirubin and albumin were also measured using the same clinical chemistry analyzer and expressed in mg/dL. The results are presented in Tables 53 and 54. Those antisense oligonucleotides which did not affect an increase in ALT/AST levels above seven-fold of control levels were selected for further studies. Those antisense oligonucleotides which did not increase levels of bilirubin more than two-fold of the control levels were selected for further studies.

TABLE 51

| Effect of antisense oligonucleotide treatment on ALT (IU/L) in CD1 mice | | | |
|---|---|---|---|
| | 2 weeks | 4 weeks | 6 weeks |
| PBS | 36 | n.d. | n.d. |
| ISIS 416825 | 64 | 314 | 507 |
| ISIS 416826 | 182 | 126 | 1954 |
| ISIS 416838 | 61 | 41 | 141 |
| ISIS 416850 | 67 | 58 | 102 |
| ISIS 416858 | 190 | 57 | 216 |
| ISIS 416864 | 44 | 33 | 92 |
| ISIS 416925 | 160 | 284 | 1284 |
| ISIS 416999 | 61 | 160 | 1302 |
| ISIS 417002 | 71 | 138 | 2579 |
| ISIS 416892 | 66 | 1526 | 1939 |
| ISIS 417003 | 192 | 362 | 2214 |

n.d. = no data

TABLE 52

| Effect of antisense oligonucleotide treatment on AST (IU/L) in CD1 mice | | | |
|---|---|---|---|
| | 2 weeks | 4 weeks | 6 weeks |
| PBS | 68 | n.d. | n.d. |
| ISIS 416825 | 82 | 239 | 301 |
| ISIS 416826 | 274 | 156 | 1411 |
| ISIS 416838 | 106 | 73 | 107 |
| ISIS 416850 | 72 | 88 | 97 |
| ISIS 416858 | 236 | 108 | 178 |
| ISIS 416864 | 58 | 46 | 101 |
| ISIS 416925 | 144 | 206 | 712 |
| ISIS 416999 | 113 | 130 | 671 |
| ISIS 417002 | 96 | 87 | 1166 |
| ISIS 416892 | 121 | 1347 | 1443 |
| ISIS 417003 | 152 | 249 | 839 |

n.d. = no data

TABLE 53

| Effect of antisense oligonucleotide treatment on bilirubin (mg/dL) in CD1 mice | | | |
|---|---|---|---|
| | 2 weeks | 4 weeks | 6 weeks |
| PBS | 0.28 | n.d. | n.d. |
| ISIS 416825 | 0.41 | 0.69 | 0.29 |
| ISIS 416826 | 0.39 | 0.20 | 0.37 |
| ISIS 416838 | 0.57 | 0.24 | 0.20 |
| ISIS 416850 | 0.46 | 0.23 | 0.22 |
| ISIS 416858 | 0.57 | 0.24 | 0.16 |
| ISIS 416864 | 0.40 | 0.26 | 0.22 |
| ISIS 416925 | 0.45 | 0.25 | 0.25 |
| ISIS 416999 | 0.48 | 0.18 | 0.28 |
| ISIS 417002 | 0.50 | 0.25 | 0.29 |
| ISIS 416892 | 0.38 | 2.99 | 0.50 |
| ISIS 417003 | 0.33 | 0.15 | 0.24 |

n.d. = no data

TABLE 54

| Effect of antisense oligonucleotide treatment on albumin (mg/dL) in CD1 mice | | | |
|---|---|---|---|
| | 2 weeks | 4 weeks | 6 weeks |
| PBS | 3.7 | n.d. | n.d. |
| ISIS 416825 | 3.6 | 3.4 | 3.5 |
| ISIS 416826 | 3.3 | 3.4 | 3.4 |
| ISIS 416838 | 3.5 | 3.8 | 3.6 |
| ISIS 416850 | 3.6 | 3.5 | 3.1 |
| ISIS 416858 | 3.4 | 3.5 | 2.8 |
| ISIS 416864 | 3.5 | 3.6 | 3.5 |
| ISIS 416925 | 3.5 | 3.5 | 3.2 |
| ISIS 416999 | 3.4 | 3.3 | 3.2 |
| ISIS 417002 | 3.2 | 3.4 | 3.4 |
| ISIS 416892 | 3.2 | 4.0 | 4.4 |
| ISIS 417003 | 3.4 | 3.4 | 3.2 |

n.d. = no data

Kidney Function

To evaluate the effect of ISIS oligonucleotides on kidney function, plasma concentrations of blood urea nitrogen (BUN) and creatinine were measured using an automated clinical chemistry analyzer (Hitachi Olympus AU400e, Melville, N.Y.). Results are presented in Tables 55 and 56, expressed in mg/dL. Those antisense oligonucleotides which did not affect more than a two-fold increase in BUN levels compared to the PBS control were selected for further studies.

TABLE 55

Effect of antisense oligonucleotide treatment on BUN (mg/dL) in CD1 mice

| | 2 weeks | 4 weeks | 6 weeks |
|---|---|---|---|
| PBS | 30 | n.d. | n.d. |
| ISIS 416825 | 29 | 35 | 31 |
| ISIS 416826 | 24 | 34 | 27 |
| ISIS 416838 | 25 | 38 | 30 |
| ISIS 416850 | 25 | 30 | 23 |
| ISIS 416858 | 21 | 29 | 19 |
| ISIS 416864 | 22 | 31 | 28 |
| ISIS 416925 | 21 | 30 | 17 |
| ISIS 416999 | 22 | 27 | 22 |
| ISIS 417002 | 19 | 23 | 19 |
| ISIS 416892 | 19 | 28 | 23 |
| ISIS 417003 | 23 | 26 | 24 |

n.d. = no data

TABLE 56

Effect of antisense oligonucleotide treatment on creatinine (mg/dL) in CD1 mice

| | 2 weeks | 4 weeks | 6 weeks |
|---|---|---|---|
| PBS | 0.14 | n.d. | n.d. |
| ISIS 416825 | 0.14 | 0.21 | 0.17 |
| ISIS 416826 | 0.15 | 0.20 | 0.15 |
| ISIS 416838 | 0.09 | 0.27 | 0.14 |
| ISIS 416850 | 0.13 | 0.22 | 0.19 |
| ISIS 416858 | 0.13 | 0.23 | 0.10 |
| ISIS 416864 | 0.11 | 0.22 | 0.16 |
| ISIS 416925 | 0.12 | 0.25 | 0.13 |
| ISIS 416999 | 0.07 | 0.18 | 0.13 |
| ISIS 417002 | 0.06 | 0.16 | 0.10 |
| ISIS 416892 | 0.11 | 0.20 | 0.17 |
| ISIS 417003 | 0.17 | 0.24 | 0.18 |

n.d. = no data

Hematology Assays

Blood obtained from all mice groups were sent to Antech Diagnostics for hematocrit (HCT), mean corpuscular volume (MCV), mean corpuscular hemoglobin (MCH), and mean corpuscular hemoglobin concentration (MCHC) measurements and analyses, as well as measurements of the various blood cells, such as WBC (neutrophils, lymphocytes, and monocytes), RBC, and platelets, and total hemoglobin content. The results are presented in Tables 57-67. Percentages given in the tables indicate the percent of total blood cell count. Those antisense oligonucleotides which did not affect a decrease in platelet count of more than 50% and/or an increase in monocyte count of more than three-fold were selected for further studies.

TABLE 57

Effect of antisense oligonucleotide treatment on HCT (%) in CD1 mice

| | 2 weeks | 4 weeks | 6 weeks |
|---|---|---|---|
| PBS | 50 | n.d. | n.d. |
| ISIS 416825 | 49 | 46 | 40 |
| ISIS 416826 | 47 | 41 | 37 |
| ISIS 416838 | 42 | 44 | 39 |
| ISIS 416850 | 44 | 44 | 38 |
| ISIS 416858 | 50 | 45 | 46 |
| ISIS 416864 | 50 | 45 | 42 |
| ISIS 416925 | 51 | 47 | 47 |
| ISIS 416999 | 51 | 42 | 40 |
| ISIS 417002 | 44 | 44 | 51 |
| ISIS 416892 | 48 | 42 | 45 |
| ISIS 417003 | 48 | 41 | 43 |

n.d. = no data

TABLE 58

Effect of antisense oligonucleotide treatment on MCV (fL) in CD1 mice

| | 2 weeks | 4 weeks | 6 weeks |
|---|---|---|---|
| PBS | 61 | n.d. | n.d. |
| ISIS 416825 | 58 | 53 | 51 |
| ISIS 416826 | 56 | 52 | 53 |
| ISIS 416838 | 56 | 54 | 48 |
| ISIS 416850 | 57 | 51 | 50 |
| ISIS 416858 | 59 | 51 | 50 |
| ISIS 416864 | 57 | 52 | 51 |
| ISIS 416925 | 61 | 52 | 47 |
| ISIS 416999 | 60 | 49 | 48 |
| ISIS 417002 | 61 | 50 | 52 |
| ISIS 416892 | 59 | 49 | 53 |
| ISIS 417003 | 60 | 48 | 45 |

n.d. = no data

TABLE 59

Effect of antisense oligonucleotide treatment on MCH (pg) in CD1 mice

| ISIS No. | 2 weeks | 4 weeks | 6 weeks |
|---|---|---|---|
| PBS | 18 | n.d. | n.d. |
| ISIS 416825 | 17 | 16 | 15 |
| ISIS 416826 | 17 | 16 | 16 |
| ISIS 416838 | 17 | 17 | 15 |
| ISIS 416850 | 17 | 16 | 15 |
| ISIS 416858 | 17 | 16 | 15 |
| ISIS 416864 | 18 | 16 | 16 |
| ISIS 416925 | 17 | 16 | 15 |
| ISIS 416999 | 17 | 16 | 15 |
| ISIS 417002 | 17 | 16 | 16 |
| ISIS 416892 | 18 | 16 | 16 |
| ISIS 417003 | 17 | 16 | 16 |

n.d. = no data

TABLE 60

Effect of antisense oligonucleotide treatment on MCHC (%) in CD1 mice

| | 2 weeks | 4 weeks | 6 weeks |
|---|---|---|---|
| PBS | 30 | n.d. | n.d. |
| ISIS 416825 | 29 | 31 | 31 |
| ISIS 416826 | 29 | 31 | 30 |
| ISIS 416838 | 30 | 31 | 32 |
| ISIS 416850 | 30 | 31 | 31 |

TABLE 60-continued

| Effect of antisense oligonucleotide treatment on MCHC (%) in CD1 mice | | | |
|---|---|---|---|
| | 2 weeks | 4 weeks | 6 weeks |
| ISIS 416858 | 30 | 32 | 31 |
| ISIS 416864 | 31 | 31 | 31 |
| ISIS 416925 | 30 | 32 | 32 |
| ISIS 416999 | 27 | 32 | 31 |
| ISIS 417002 | 29 | 32 | 31 |
| ISIS 416892 | 30 | 32 | 30 |
| ISIS 417003 | 29 | 32 | 33 |

n.d. = no data

TABLE 61

| Effect of antisense oligonucleotide treatment on WBC count (cells/nL) in CD1 mice | | | |
|---|---|---|---|
| | 2 weeks | 4 weeks | 6 weeks |
| PBS | 6 | n.d. | n.d. |
| ISIS 416825 | 8 | 8 | 6 |
| ISIS 416826 | 5 | 6 | 8 |
| ISIS 416838 | 4 | 6 | 5 |
| ISIS 416850 | 4 | 5 | 5 |
| ISIS 416858 | 6 | 7 | 4 |
| ISIS 416864 | 7 | 6 | 5 |
| ISIS 416925 | 6 | 6 | 11 |
| ISIS 416999 | 4 | 9 | 7 |
| ISIS 417002 | 8 | 8 | 16 |
| ISIS 416892 | 5 | 8 | 9 |
| ISIS 417003 | 7 | 9 | 10 |

n.d. = no data

TABLE 62

| Effect of antisense oligonucleotide treatment on RBC count (cells/pL) in CD1 mice | | | |
|---|---|---|---|
| | 2 weeks | 4 weeks | 6 weeks |
| PBS | 8 | n.d. | n.d. |
| ISIS 416825 | 9 | 9 | 8 |
| ISIS 416826 | 8 | 8 | 7 |
| ISIS 416838 | 8 | 8 | 8 |
| ISIS 416850 | 8 | 9 | 8 |
| ISIS 416858 | 9 | 9 | 9 |
| ISIS 416864 | 9 | 9 | 8 |
| ISIS 416925 | 9 | 9 | 10 |
| ISIS 416999 | 9 | 9 | 8 |
| ISIS 417002 | 9 | 9 | 10 |
| ISIS 416892 | 7 | 9 | 9 |
| ISIS 417003 | 8 | 9 | 10 |

n.d. = no data

TABLE 63

| Effect of antisense oligonucleotide treatment on neutrophil count (%) in CD1 mice | | | |
|---|---|---|---|
| | 2 weeks | 4 weeks | 6 weeks |
| PBS | 16 | n.d. | n.d. |
| ISIS 416825 | 15 | 43 | 23 |
| ISIS 416826 | 26 | 33 | 23 |
| ISIS 416838 | 19 | 33 | 31 |
| ISIS 416850 | 15 | 21 | 16 |
| ISIS 416858 | 14 | 24 | 27 |
| ISIS 416864 | 13 | 27 | 20 |
| ISIS 416925 | 12 | 39 | 33 |
| ISIS 416999 | 12 | 25 | 22 |
| ISIS 417002 | 14 | 31 | 36 |

TABLE 63-continued

| Effect of antisense oligonucleotide treatment on neutrophil count (%) in CD1 mice | | | |
|---|---|---|---|
| | 2 weeks | 4 weeks | 6 weeks |
| ISIS 416892 | 19 | 43 | 28 |
| ISIS 417003 | 10 | 39 | 24 |

n.d. = no data

TABLE 64

| Effect of antisense oligonucleotide treatment on lymphocyte count (%) in CD1 mice | | | |
|---|---|---|---|
| | 2 weeks | 4 weeks | 6 weeks |
| PBS | 81 | n.d. | n.d. |
| ISIS 416825 | 82 | 53 | 71 |
| ISIS 416826 | 70 | 61 | 67 |
| ISIS 416838 | 76 | 64 | 60 |
| ISIS 416850 | 82 | 73 | 76 |
| ISIS 416858 | 83 | 73 | 65 |
| ISIS 416864 | 84 | 71 | 74 |
| ISIS 416925 | 86 | 58 | 57 |
| ISIS 416999 | 86 | 72 | 69 |
| ISIS 417002 | 83 | 64 | 51 |
| ISIS 416892 | 79 | 52 | 64 |
| ISIS 417003 | 86 | 54 | 66 |

n.d. = no data

TABLE 65

| Effect of antisense oligonucleotide treatment on monocyte count (%) in CD1 mice | | | |
|---|---|---|---|
| | 2 weeks | 4 weeks | 6 weeks |
| PBS | 3 | n.d. | n.d. |
| ISIS 416825 | 2 | 5 | 4 |
| ISIS 416826 | 3 | 5 | 8 |
| ISIS 416838 | 2 | 2 | 6 |
| ISIS 416850 | 3 | 6 | 6 |
| ISIS 416858 | 2 | 3 | 7 |
| ISIS 416864 | 2 | 2 | 5 |
| ISIS 416925 | 2 | 4 | 8 |
| ISIS 416999 | 2 | 4 | 8 |
| ISIS 417002 | 3 | 4 | 12 |
| ISIS 416892 | 3 | 6 | 7 |
| ISIS 417003 | 2 | 6 | 8 |

n.d. = no data

TABLE 66

| Effect of antisense oligonucleotide treatment on platelet count (cells/nL) in CD1 mice | | | |
|---|---|---|---|
| | 2 weeks | 4 weeks | 6 weeks |
| PBS | 2126 | n.d. | n.d. |
| ISIS 416825 | 1689 | 1229 | 942 |
| ISIS 416826 | 1498 | 970 | 645 |
| ISIS 416838 | 1376 | 1547 | 1229 |
| ISIS 416850 | 1264 | 1302 | 1211 |
| ISIS 416858 | 2480 | 1364 | 1371 |
| ISIS 416864 | 1924 | 1556 | 933 |
| ISIS 416925 | 1509 | 1359 | 1211 |
| ISIS 416999 | 1621 | 1219 | 1057 |
| ISIS 417002 | 1864 | 1245 | 1211 |
| ISIS 416892 | 1687 | 636 | 1004 |
| ISIS 417003 | 1309 | 773 | 922 |

n.d. = no data

TABLE 67

| Effect of antisense oligonucleotide treatment on hemoglobin content (g/dL) in CD1 mice | | | |
|---|---|---|---|
| | 2 weeks | 4 weeks | 6 weeks |
| PBS | 15.1 | n.d. | n.d. |
| ISIS 416825 | 14.5 | 14.1 | 12.1 |
| ISIS 416826 | 13.4 | 12.8 | 11.0 |
| ISIS 416838 | 12.4 | 13.6 | 12.6 |
| ISIS 416850 | 13.1 | 13.5 | 11.6 |
| ISIS 416858 | 14.8 | 14.2 | 14.1 |
| ISIS 416864 | 15.2 | 13.9 | 13.0 |
| ISIS 416925 | 14.9 | 14.8 | 15.3 |
| ISIS 416999 | 14.2 | 13.3 | 12.8 |
| ISIS 417002 | 14.7 | 14.0 | 15.7 |
| ISIS 416892 | 13.0 | 13.5 | 13.1 |
| ISIS 417003 | 13.7 | 13.4 | 14.0 |

n.d. = no data

Example 34: Measurement of Half-Life of Antisense Oligonucleotide in CD1 Mice Liver CD1 mice were treated with ISIS antisense oligonucleotides targeting human Factor 11 and the oligonucleotide half-life as well as the elapsed time for oligonucleotide degradation and elimination from the liver was evaluated.

Treatment

Groups of fifteen CD1 mice each were injected subcutaneously twice per week for 2 weeks with 50 mg/kg of ISIS 416825, ISIS 416826, ISIS 416838, ISIS 416850, ISIS 416858, ISIS 416864, ISIS 416892, ISIS 416925, ISIS 416999, ISIS 417002, or ISIS 417003. Five mice from each group were sacrificed 3 days, 28 days and 56 days following the final dose. Livers were harvested for analysis.

Measurement of Oligonucleotide Concentration

The concentration of the full-length oligonucleotide as well as the total oligonucleotide concentration (including the degraded form) was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 270) was added prior to extraction. Tissue sample concentrations were calculated using calibration curves, with a lower limit of quantitation (LLOQ) of approximately 1.14 μg/g. Half-lives were then calculated using WinNonlin software (PHARSIGHT).

The results are presented in Tables 68 and 69, expressed as μg/g liver tissue. The half-life of each oligonucleotide is presented in Table 70.

TABLE 68

| Full-length oligonucleotide concentration (μg/g) in the liver of CD1 mice | | | | |
|---|---|---|---|---|
| ISIS No. | Motif | day 3 | day 28 | day 56 |
| 416825 | 5-10-5 | 151 | 52 | 7 |
| 416826 | 5-10-5 | 186 | 48 | 8 |
| 416838 | 5-10-5 | 170 | 46 | 10 |
| 416850 | 5-10-5 | 238 | 93 | 51 |
| 416858 | 5-10-5 | 199 | 102 | 18 |
| 416864 | 5-10-5 | 146 | 38 | 25 |
| 416999 | 2-13-5 | 175 | 26 | 0 |
| 417002 | 2-13-5 | 119 | 24 | 1 |
| 417003 | 2-13-5 | 245 | 42 | 4 |

TABLE 68-continued

| Full-length oligonucleotide concentration (μg/g) in the liver of CD1 mice | | | | |
|---|---|---|---|---|
| ISIS No. | Motif | day 3 | day 28 | day 56 |
| 416925 | 3-14-3 | 167 | 39 | 5 |
| 416892 | 3-14-3 | 135 | 31 | 6 |

TABLE 69

| Total oligonucleotide concentration (μg/g) in the liver of CD1 mice | | | | |
|---|---|---|---|---|
| ISIS No. | Motif | day 3 | day 28 | day 56 |
| 416825 | 5-10-5 | 187 | 90 | 39 |
| 416826 | 5-10-5 | 212 | 61 | 12 |
| 416838 | 5-10-5 | 216 | 98 | 56 |
| 416850 | 5-10-5 | 295 | 157 | 143 |
| 416858 | 5-10-5 | 273 | 185 | 56 |
| 416864 | 5-10-5 | 216 | 86 | 112 |
| 416999 | 2-13-5 | 232 | 51 | 0 |
| 417002 | 2-13-5 | 206 | 36 | 1 |
| 417003 | 2-13-5 | 353 | 74 | 4 |
| 416925 | 3-14-3 | 280 | 72 | 8 |
| 416892 | 3-14-3 | 195 | 54 | 6 |

TABLE 70

| Half-life of antisense oligonucleotides in the liver of CD1 mice | | |
|---|---|---|
| ISIS No. | Motif | Half-life (days) |
| 416825 | 5-10-5 | 16 |
| 416826 | 5-10-5 | 13 |
| 416838 | 5-10-5 | 13 |
| 416850 | 5-10-5 | 18 |
| 416858 | 5-10-5 | 26 |
| 416864 | 5-10-5 | 13 |
| 416999 | 2-13-5 | 9 |
| 417002 | 2-13-5 | 11 |
| 417003 | 2-13-5 | 10 |
| 416925 | 3-14-3 | 12 |
| 416892 | 3-14-3 | 12 |

Example 35: Tolerability of Antisense Oligonucleotides Targeting Human Factor 11 in Sprague-Dawley Rats Sprague-Dawley rats were treated with ISIS antisense oligonucleotides targeting human Factor 11 and evaluated for changes in the levels of various metabolic markers.

Treatment

Groups of four Sprague Dawley rats each were injected subcutaneously twice per week for 6 weeks with 50 mg/kg of ISIS 416825, ISIS 416826, ISIS 416838, ISIS 416850, ISIS 416858, ISIS 416848, ISIS 416864, ISIS 416892, ISIS 416925, ISIS 416999, ISIS 417002, or ISIS 417003. A control group of four Sprague Dawley rats was injected subcutaneously with PBS twice per week for 6 weeks. Body weight measurements were taken before and throughout the treatment period. Urine samples were taken before the start of treatment. Three days after the last dose, urine samples were taken and the rats were sacrificed. Organ weights were measured and blood was collected for further analysis.

Body Weight and Organ Weight

Body weights of the rats were measured at the onset of the study and subsequently twice per week. The body weights are presented in Table 71 and are expressed as a percent change over the weights taken at the start of the study. Liver, spleen, and kidney weights were measured at the end of the study and are presented in Table 71 as a percent of the saline control normalized to body weight. Those antisense oligonucleotides which did not affect more than a six-fold increase in liver and spleen weight above the PBS control were selected for further studies.

TABLE 71

Percent change in organ weight of Sprague Dawley rats after antisense oligonucleotide treatment

| ISIS No. | Liver | Spleen | Kidney | Body weight |
|---|---|---|---|---|
| 416825 | +20 | +245 | +25 | −18 |
| 416826 | +81 | +537 | +44 | −40 |
| 416838 | +8 | +212 | −0.5 | −23 |
| 416850 | +23 | +354 | +47 | −33 |
| 416858 | +8 | +187 | +5 | −21 |
| 416864 | +16 | +204 | +16 | −24 |
| 416925 | +44 | +371 | +48 | −32 |
| 416999 | +51 | +405 | +71 | −37 |
| 417002 | +27 | +446 | +63 | −29 |
| 416892 | +38 | +151 | +32 | −39 |
| 417003 | +51 | +522 | +25 | −40 |

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Measurements of alanine transaminase (ALT) and aspartate transaminase (AST) are expressed in IU/L and the results are presented in Table 72. Those antisense oligonucleotides which did not affect an increase in ALT/AST levels above seven-fold of control levels were selected for further studies. Plasma levels of bilirubin and albumin were also measured with the same clinical analyzer and the results are also presented in Table 72, expressed in mg/dL. Those antisense oligonucleotides which did not affect an increase in levels of bilirubin more than two-fold of the control levels by antisense oligonucleotide treatment were selected for further studies.

TABLE 72

Effect of antisense oligonucleotide treatment on metabolic markers in the liver of Sprague-Dawley rats

| | ALT (IU/L) | AST (IU/L) | Bilirubin (mg/dL) | Albumin (mg/dL) |
|---|---|---|---|---|
| PBS | 9 | 5 | 20 | 2 |
| ISIS 416825 | 89 | 17 | 4 | 2 |
| ISIS 416826 | 611 | 104 | 115 | 6 |
| ISIS 416838 | 5 | 2 | 4 | 2 |
| ISIS 416850 | 80 | 5 | 1 | 4 |
| ISIS 416858 | 13 | 4 | 4 | 2 |
| ISIS 416864 | 471 | 68 | 3 | 4 |
| ISIS 416925 | 102 | 20 | 13 | 5 |
| ISIS 416999 | 92 | 28 | 54 | 5 |
| ISIS 417002 | 44 | 11 | 12 | 3 |
| ISIS 416892 | 113 | 183 | 1 | 8 |
| ISIS 417003 | 138 | 23 | 50 | 6 |

Kidney Function

To evaluate the effect of kidney function, plasma concentrations of blood urea nitrogen (BUN) and creatinine were measured using an automated clinical chemistry analyzer (Hitachi Olympus AU400e, Melville, N.Y.). Results are presented in Table 73, expressed in mg/dL. Those antisense oligonucleotides which did not affect more than a two-fold increase in BUN levels compared to the PBS control were selected for further studies. The ratio of urine protein to creatinine in total urine samples was also calculated before and after antisense oligonucleotide treatment and is presented in Table 74. Those antisense oligonucleotides which did not affect more than a five-fold increase in urine protein/creatinine ratios compared to the PBS control were selected for further studies.

TABLE 73

Effect of antisense oligonucleotide treatment on metabolic markers in the kidney of Sprague-Dawley rats

| | BUN | Creatinine |
|---|---|---|
| PBS | 4 | 8 |
| ISIS 416825 | 7 | 17 |
| ISIS 416826 | 25 | 6 |
| ISIS 416838 | 4 | 5 |
| ISIS 416850 | 5 | 7 |
| ISIS 416858 | 8 | 4 |
| ISIS 416864 | 5 | 6 |
| ISIS 416925 | 7 | 5 |
| ISIS 416999 | 2 | 4 |
| ISIS 417002 | 11 | 1 |
| ISIS 416892 | 188 | 1 |
| ISIS 417003 | 9 | 9 |

TABLE 74

Effect of antisense oligonucleotide treatment on urine protein/creatinine ratio in Sprague Dawley rats

| | Before | After |
|---|---|---|
| PBS | 1.2 | 1.3 |
| 416825 | 1.1 | 5.4 |
| 416826 | 1.0 | 11.4 |
| 416838 | 1.2 | 3.7 |
| 416850 | 1.0 | 4.0 |
| 416858 | 0.9 | 4.4 |
| 416864 | 1.2 | 4.0 |
| 416925 | 1.0 | 4.3 |
| 416999 | 1.3 | 9.1 |
| 417002 | 1.0 | 2.4 |
| 416892 | 0.8 | 21.3 |
| 417003 | 0.9 | 4.8 |

Hematology Assays

Blood obtained from all rat groups were sent to Antech Diagnostics for hematocrit (HCT), mean corpuscular volume (MCV), mean corpuscular hemoglobin (MCV), and mean corpuscular hemoglobin concentration (MCHC) measurements and analyses, as well as measurements of various blood cells, such as WBC (neutrophils, lymphocytes and monocytes), RBC, and platelets as well as hemoglobin content. The results are presented in Tables 75 and 76. Those antisense oligonucleotides which did not affect a decrease in platelet count of more than 50% and an increase in monocyte count of more than three-fold were selected for further studies.

TABLE 75

Effect of antisense oligonucleotide treatment on blood cell count in Sprague-Dawley rats

| | WBC (/nL) | RBC (/pL) | Neutrophils (%) | Lymphocytes (%) | Monocytes (%) | Platelets ($10^3$/μL) |
|---|---|---|---|---|---|---|
| PBS | 21 | 6 | 37 | 7 | 26 | 18 |
| ISIS 416825 | 22 | 2 | 25 | 3 | 15 | 6 |
| ISIS 416826 | 7 | 5 | 30 | 5 | 7 | 11 |
| ISIS 416838 | 13 | 4 | 17 | 3 | 6 | 27 |
| ISIS 416850 | 16 | 7 | 48 | 8 | 11 | 26 |
| ISIS 416858 | 28 | 2 | 20 | 3 | 10 | 19 |
| ISIS 416864 | 15 | 4 | 26 | 2 | 29 | 12 |
| ISIS 416925 | 24 | 6 | 20 | 4 | 23 | 8 |
| ISIS 416999 | 12 | 5 | 23 | 3 | 20 | 12 |
| ISIS 417002 | 23 | 5 | 22 | 4 | 25 | 7 |
| ISIS 416892 | 68 | 12 | 92 | 18 | 58 | 66 |
| ISIS 417003 | 83 | 11 | 17 | 3 | 6 | 19 |

TABLE 76

Effect of antisense oligonucleotide treatment on hematologic factors (% control) in Sprague-Dawley rats

| | Hemoglobin (g/dL) | HCT (%) | MCV (fL) | MCH (pg) | MCHC (%) |
|---|---|---|---|---|---|
| PBS | 6 | 4 | 6 | 2 | 4 |
| ISIS 416825 | 2 | 2 | 4 | 2 | 4 |
| ISIS 416826 | 7 | 7 | 6 | 3 | 4 |
| ISIS 416838 | 2 | 5 | 4 | 2 | 5 |
| ISIS 416850 | 4 | 5 | 3 | 4 | 2 |
| ISIS 416858 | 2 | 3 | 2 | 2 | 1 |
| ISIS 416864 | 4 | 2 | 4 | 2 | 4 |
| ISIS 416925 | 6 | 8 | 5 | 2 | 4 |
| ISIS 416999 | 6 | 5 | 2 | 3 | 1 |
| ISIS 417002 | 5 | 7 | 7 | 3 | 5 |
| ISIS 416892 | 14 | 13 | 1 | 2 | 0 |
| ISIS 417003 | 11 | 8 | 6 | 4 | 4 |

Example 36: Measurement of Half-Life of Antisense Oligonucleotide in Sprague-Dawley Rat Liver and Kidney Sprague Dawley rats were treated with ISIS antisense oligonucleotides targeting human Factor 11 and the oligonucleotide half-life as well as the elapsed time for oligonucleotide degradation and elimination from the liver and kidney was evaluated.

Treatment

Groups of four Sprague Dawley rats each were injected subcutaneously twice a week for 2 weeks with 20 mg/kg of ISIS416825, ISIS 416826, ISIS 416838, ISIS 416850, ISIS 416858, ISIS 416864, ISIS 416892, ISIS 416925, ISIS 416999, ISIS 417002, or ISIS 417003. Three days after the last dose, the rats were sacrificed and livers and kidneys were collected for analysis.

Measurement of Oligonucleotide Concentration

The concentration of the full-length oligonucleotide as well as the total oligonucleotide concentration (including the degraded form) was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 270) was added prior to extraction. Tissue sample concentrations were calculated using calibration curves, with a lower limit of quantitation (LLOQ) of approximately 1.14 μg/g. The results are presented in Tables 77 and 78, expressed as μg/g liver or kidney tissue. Half-lives were then calculated using WinNonlin software (PHARSIGHT).

TABLE 77

Full-length oligonucleotide concentration (μg/g) in the liver and kidney of Sprague-Dawley rats

| ISIS No. | Motif | Kidney | Liver |
|---|---|---|---|
| 416825 | 5-10-5 | 632 | 236 |
| 416826 | 5-10-5 | 641 | 178 |
| 416838 | 5-10-5 | 439 | 171 |
| 416850 | 5-10-5 | 259 | 292 |
| 416858 | 5-10-5 | 575 | 255 |
| 416864 | 5-10-5 | 317 | 130 |
| 416999 | 2-13-5 | 358 | 267 |
| 417002 | 2-13-5 | 291 | 118 |
| 417003 | 2-13-5 | 355 | 199 |
| 416925 | 3-14-3 | 318 | 165 |
| 416892 | 3-14-3 | 351 | 215 |

TABLE 78

Total oligonucleotide concentration (μg/g) in the liver and kidney of Sprague-Dawley rats

| ISIS No. | Motif | Kidney | Liver |
|---|---|---|---|
| 416825 | 5-10-5 | 845 | 278 |
| 416826 | 5-10-5 | 775 | 214 |
| 416838 | 5-10-5 | 623 | 207 |
| 416850 | 5-10-5 | 352 | 346 |
| 416858 | 5-10-5 | 818 | 308 |
| 416864 | 5-10-5 | 516 | 209 |
| 416999 | 2-13-5 | 524 | 329 |
| 417002 | 2-13-5 | 490 | 183 |
| 417003 | 2-13-5 | 504 | 248 |
| 416925 | 3-14-3 | 642 | 267 |
| 416892 | 3-14-3 | 608 | 316 |

TABLE 79

Half-life (days) of ISIS oligonucleotides in the liver and kidney of Sprague-Dawley rats

| ISIS No. | Motif | Half-life |
|---|---|---|
| 416825 | 5-10-5 | 16 |
| 416826 | 5-10-5 | 13 |
| 416838 | 5-10-5 | 13 |
| 416850 | 5-10-5 | 18 |

TABLE 79-continued

| Half-life (days) of ISIS oligonucleotides in the liver and kidney of Sprague-Dawley rats | | |
|---|---|---|
| ISIS No. | Motif | Half-life |
| 416858 | 5-10-5 | 26 |
| 416864 | 5-10-5 | 13 |
| 416999 | 2-13-5 | 9 |
| 417002 | 2-13-5 | 11 |
| 417003 | 2-13-5 | 10 |
| 416925 | 3-14-3 | 12 |
| 416892 | 3-14-3 | 12 |

Example 37: Tolerability of Antisense Oligonucleotides Targeting Human Factor 11 in CD1 Mice CD1 mice were treated with ISIS antisense oligonucleotides targeting human Factor 11 and evaluated for changes in the levels of various metabolic markers.

Treatment

Groups of five CD1 mice each were injected subcutaneously twice per week for 6 weeks with 50 mg/kg of ISIS 412223, ISIS 412224, ISIS 412225, ISIS 413481, ISIS 413482, ISIS 416848, ISIS 416849, ISIS 416850, ISIS 416851, ISIS 416852, ISIS 416853, ISIS 416854, ISIS 416855, ISIS 416856, ISIS 416857, ISIS 416858, ISIS 416859, ISIS 416860, ISIS 416861, ISIS 416862, ISIS 416863, ISIS 416864, ISIS 416865, ISIS 416866, or ISIS 416867, or. A control group of ten CD1 mice was injected subcutaneously with PBS twice per week for 6 weeks. Body weight measurements were taken before and throughout the treatment period. Three days after the last dose, the mice were sacrificed, organ weights were measured, and blood was collected for further analysis.

Body Weight and Organ Weights

Body weight was measured at the onset of the study and subsequently twice per week. The body weights of the mice are presented in Table 80 and are expressed increase in grams over the PBS control weight taken before the start of treatment. Liver, spleen, and kidney weights were measured at the end of the study, and are also presented in Table 80 as percentage of the body weight. Those antisense oligonucleotides which did not affect more than six-fold increases in liver and spleen weight above the PBS control were selected for further studies.

TABLE 80

| Change in body and organ weight of CD1 mice after antisense oligonucleotide treatment | | | | |
|---|---|---|---|---|
| | Liver (%) | Kidney (%) | Spleen (%) | body weight (g) |
| PBS | 5 | 1.5 | 0.3 | 7 |
| ISIS 416850 | 6 | 1.6 | 0.4 | 12 |
| ISIS 416858 | 7 | 1.6 | 0.6 | 12 |
| ISIS 416864 | 5 | 1.6 | 0.3 | 12 |
| ISIS 412223 | 6 | 1.5 | 0.4 | 12 |
| ISIS 412224 | 6 | 1.6 | 0.5 | 10 |
| ISIS 412225 | 6 | 1.5 | 0.4 | 10 |
| ISIS 413481 | 6 | 1.5 | 0.5 | 9 |
| ISIS 413482 | 6 | 1.6 | 0.5 | 11 |
| ISIS 416848 | 6 | 1.5 | 0.4 | 11 |
| ISIS 416849 | 8 | 1.5 | 0.4 | 8 |
| ISIS 416851 | 7 | 1.5 | 0.5 | 11 |
| ISIS 416852 | 6 | 1.5 | 0.4 | 10 |
| ISIS 416853 | 8 | 1.5 | 0.7 | 13 |
| ISIS 416854 | 7 | 1.2 | 0.4 | 13 |
| ISIS 416855 | 8 | 1.4 | 0.6 | 12 |
| ISIS 416856 | 6 | 1.4 | 0.4 | 10 |
| ISIS 416857 | 7 | 1.6 | 0.5 | 10 |
| ISIS 416859 | 6 | 1.5 | 0.4 | 10 |
| ISIS 416860 | 6 | 1.4 | 0.4 | 10 |
| ISIS 416861 | 5 | 1.3 | 0.4 | 9 |
| ISIS 416862 | 6 | 1.5 | 0.4 | 10 |
| ISIS 416863 | 5 | 1.5 | 0.4 | 9 |
| ISIS 416865 | 6 | 1.5 | 0.4 | 8 |
| ISIS 416866 | 5 | 1.6 | 0.4 | 10 |
| ISIS 416867 | 5 | 1.4 | 0.4 | 9 |

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Measurements of alanine transaminase (ALT) and aspartate transaminase (AST) are expressed in IU/L and the results are presented in Table 81. Those antisense oligonucleotides which did not affect an increase in ALT/AST levels above seven-fold of control levels were selected for further studies. Plasma levels of bilirubin, cholesterol and albumin were also measured using the same clinical chemistry analyzer and are presented in Table 81 expressed in mg/dL. Those antisense oligonucleotides which did not affect an increase in levels of bilirubin more than two-fold of the control levels by antisense oligonucleotide treatment were selected for further studies.

TABLE 81

| Effect of antisense oligonucleotide treatment on metabolic markers in the liver of CD1 mice | | | | | |
|---|---|---|---|---|---|
| | ALT (IU/L) | AST (IU/L) | Bilirubin (mg/dL) | Albumin (mg/dL) | Cholesterol (mg/dL) |
| PBS | 32 | 68 | 0.25 | 3.7 | 135 |
| ISIS 416850 | 75 | 99 | 0.21 | 3.5 | 142 |
| ISIS 416858 | 640 | 547 | 0.28 | 4.4 | 181 |
| ISIS 416864 | 36 | 67 | 0.19 | 2.6 | 152 |
| ISIS 412223 | 60 | 125 | 0.20 | 3.0 | 117 |
| ISIS 412224 | 214 | 183 | 0.19 | 3.4 | 114 |
| ISIS 412225 | 40 | 69 | 0.23 | 3.3 | 128 |
| ISIS 413481 | 85 | 143 | 0.18 | 3.2 | 153 |
| ISIS 413482 | 54 | 77 | 0.24 | 3.0 | 138 |
| ISIS 416848 | 153 | 153 | 0.19 | 3.1 | 151 |
| ISIS 416849 | 1056 | 582 | 0.22 | 2.5 | 109 |
| ISIS 416851 | 47 | 76 | 0.19 | 3.1 | 106 |
| ISIS 416852 | 49 | 91 | 0.16 | 4.9 | 125 |
| ISIS 416853 | 1023 | 1087 | 0.25 | 3.1 | 164 |
| ISIS 416854 | 1613 | 1140 | 0.21 | 5.5 | 199 |
| ISIS 416855 | 786 | 580 | 0.25 | 4.2 | 162 |
| ISIS 416856 | 130 | 129 | 0.23 | 5.2 | 109 |
| ISIS 416857 | 370 | 269 | 0.22 | 3.7 | 94 |
| ISIS 416859 | 214 | 293 | 0.20 | 4.2 | 160 |
| ISIS 416860 | 189 | 160 | 0.23 | 3.5 | 152 |
| ISIS 416861 | 38 | 85 | 0.27 | 4.3 | 133 |
| ISIS 416862 | 225 | 172 | 0.36 | 3.9 | 103 |
| ISIS 416863 | 41 | 101 | 0.24 | 3.6 | 118 |
| ISIS 416865 | 383 | 262 | 0.27 | 4.1 | 95 |
| ISIS 416866 | 36 | 120 | 0.29 | 4.3 | 113 |
| ISIS 416867 | 45 | 82 | 0.21 | 3.3 | 144 |

Kidney Function

To evaluate the effect of ISIS oligonucleotides on kidney function, plasma concentrations of blood urea nitrogen (BUN) were measured using an automated clinical chemistry analyzer and results are presented in Table 82 expressed in mg/dL. Those antisense oligonucleotides which did not affect more than a two-fold increase in BUN levels compared to the PBS control were selected for further studies.

TABLE 82

Effect of antisense oligonucleotide treatment on BUN levels (mg/dL) in the kidney of CD1 mice

| | BUN |
|---|---|
| PBS | 22 |
| ISIS 416850 | 24 |
| ISIS 416858 | 23 |
| ISIS 416864 | 24 |
| ISIS 412223 | 28 |
| ISIS 412224 | 29 |
| ISIS 412225 | 23 |
| ISIS 413481 | 23 |
| ISIS 413482 | 27 |
| ISIS 416848 | 23 |
| ISIS 416849 | 23 |
| ISIS 416851 | 21 |
| ISIS 416852 | 21 |
| ISIS 416853 | 22 |
| ISIS 416854 | 27 |
| ISIS 416855 | 23 |
| ISIS 416856 | 21 |
| ISIS 416857 | 17 |
| ISIS 416859 | 18 |
| ISIS 416860 | 25 |
| ISIS 416861 | 23 |
| ISIS 416862 | 21 |
| ISIS 416863 | 22 |
| ISIS 416865 | 20 |
| ISIS 416866 | 22 |
| ISIS 416867 | 20 |

Hematology Assays

Blood obtained from all the mice groups were sent to Antech Diagnostics for hematocrit (HCT) measurements, as well as measurements of various blood cells, such as WBC (neutrophils, lymphocytes, and monocytes), RBC, and platelets, as well as total hemoglobin content analysis. The results are presented in Tables 83 and 84. Those antisense oligonucleotides which did not affect a decrease in platelet count of more than 50% and an increase in monocyte count of more than three-fold were selected for further studies.

TABLE 83

Effect of antisense oligonucleotide treatment on hematologic factors in CD1 mice

| | RBC ($10^6/\mu L$) | Hemoglobin (g/dL) | HCT (%) | WBC ($10^3/\mu L$) |
|---|---|---|---|---|
| PBS | 10 | 15 | 51 | 7 |
| ISIS 416850 | 10 | 15 | 49 | 5 |
| ISIS 416858 | 9 | 14 | 50 | 8 |
| ISIS 416864 | 10 | 15 | 52 | 5 |
| ISIS 412223 | 9 | 15 | 48 | 7 |
| ISIS 412224 | 10 | 15 | 50 | 9 |
| ISIS 412225 | 9 | 15 | 50 | 7 |
| ISIS 413481 | 9 | 13 | 45 | 7 |
| ISIS 413482 | 10 | 15 | 50 | 8 |
| ISIS 416848 | 9 | 14 | 47 | 7 |
| ISIS 416849 | 9 | 14 | 48 | 9 |
| ISIS 416851 | 9 | 14 | 47 | 6 |
| ISIS 416852 | 9 | 14 | 49 | 5 |
| ISIS 416853 | 11 | 17 | 56 | 8 |
| ISIS 416854 | 9 | 13 | 43 | 12 |
| ISIS 416855 | 9 | 14 | 50 | 6 |
| ISIS 416856 | 9 | 14 | 47 | 5 |
| ISIS 416857 | 10 | 15 | 53 | 6 |
| ISIS 416859 | 10 | 15 | 49 | 6 |
| ISIS 416860 | 10 | 15 | 51 | 7 |
| ISIS 416861 | 9 | 14 | 48 | 7 |
| ISIS 416862 | 9 | 14 | 49 | 6 |
| ISIS 416863 | 9 | 14 | 48 | 7 |
| ISIS 416865 | 9 | 14 | 50 | 7 |
| ISIS 416866 | 9 | 15 | 51 | 6 |
| ISIS 416867 | 10 | 14 | 47 | 8 |

TABLE 84

Effect of antisense oligonucleotide treatment on blood cell count in CD1 mice

| | Neutrophil (cells/μL) | Lymphocyte (cells/μL) | Monocytes (cells/μL) | Platelets ($10^3/\mu L$) |
|---|---|---|---|---|
| PBS | 1023 | 6082 | 205 | 940 |
| ISIS 416850 | 1144 | 4004 | 156 | 916 |
| ISIS 416858 | 2229 | 5480 | 248 | 782 |
| ISIS 416864 | 973 | 3921 | 141 | 750 |
| ISIS 412223 | 1756 | 4599 | 200 | 862 |
| ISIS 412224 | 2107 | 6284 | 195 | 647 |
| ISIS 412225 | 1547 | 4969 | 293 | 574 |
| ISIS 413481 | 1904 | 4329 | 204 | 841 |
| ISIS 413482 | 1958 | 5584 | 275 | 818 |
| ISIS 416848 | 1264 | 5268 | 180 | 953 |
| ISIS 416849 | 1522 | 6967 | 253 | 744 |
| ISIS 416851 | 1619 | 4162 | 194 | 984 |
| ISIS 416852 | 1241 | 3646 | 189 | 903 |
| ISIS 416853 | 2040 | 5184 | 225 | 801 |
| ISIS 416854 | 2082 | 9375 | 455 | 1060 |
| ISIS 416855 | 1443 | 4236 | 263 | 784 |
| ISIS 416856 | 1292 | 3622 | 151 | 753 |
| ISIS 416857 | 1334 | 3697 | 215 | 603 |
| ISIS 416859 | 1561 | 4363 | 229 | 826 |
| ISIS 416860 | 1291 | 4889 | 161 | 937 |
| ISIS 416861 | 1122 | 5119 | 219 | 836 |
| ISIS 416862 | 1118 | 4445 | 174 | 1007 |
| ISIS 416863 | 1330 | 5617 | 226 | 1131 |
| ISIS 416865 | 1227 | 5148 | 315 | 872 |
| ISIS 416866 | 1201 | 4621 | 211 | 1045 |
| ISIS 416867 | 1404 | 6078 | 188 | 1006 |

Example 38: Measurement of Half-Life of Antisense Oligonucleotide in CD1 Mouse Liver Fifteen antisense oligonucleotides which had been evaluated in CD1 mice (Example 37) were further evaluated. CD1 mice were treated with ISIS antisense oligonucleotides and the oligonucleotide half-life as well the elapsed time for oligonucleotide degradation and elimination in the liver was evaluated.

Treatment

Groups of fifteen CD1 mice each were injected subcutaneously twice per week for 2 weeks with 50 mg/kg of ISIS 412223, ISIS 412225, ISIS 413481, ISIS 413482, ISIS 416851, ISIS 416852, ISIS 416856, ISIS 416860, ISIS 416861, ISIS 416863, ISIS 416866, ISIS 416867, ISIS 412224, ISIS 416848 or ISIS 416859. Five mice from each group were sacrificed 3 days, 28 days, and 56 days after the last dose, livers were collected for analysis.

Measurement of Oligonucleotide Concentration

The concentration of the full-length oligonucleotide was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 270) was added prior to extraction. Tissue sample concentrations were calculated using calibration curves, with a lower limit of quantitation (LLOQ) of approximately 1.14 μg/g. The results are presented in Table 85 expressed as μg/g liver tissue. The half-life of each oligonucleotide was also presented in Table 85.

TABLE 85

Full-length oligonucleotide concentration and half-life in the liver of CD1 mice

| ISIS No | Motif | day 3 | day 28 | day 56 | Half-Life (days) |
|---|---|---|---|---|---|
| 412223 | 5-10-5 | 276 | 127 | 52 | 21.9 |
| 412224 | 5-10-5 | 287 | 111 | 31 | 16.6 |
| 412225 | 5-10-5 | 279 | 91 | 47 | 20.7 |
| 413481 | 5-10-5 | 185 | 94 | 31 | 20.6 |
| 413482 | 5-10-5 | 262 | 95 | 40 | 19.5 |
| 416848 | 5-10-5 | 326 | 147 | 68 | 23.5 |
| 416851 | 5-10-5 | 319 | 147 | 68 | 23.8 |
| 416852 | 5-10-5 | 306 | 145 | 83 | 28.4 |
| 416856 | 5-10-5 | 313 | 115 | 46 | 19.2 |
| 416859 | 5-10-5 | 380 | 156 | 55 | 19.0 |
| 416860 | 5-10-5 | 216 | 96 | 36 | 20.6 |
| 416861 | 5-10-5 | 175 | 59 | 39 | 24.5 |
| 416863 | 5-10-5 | 311 | 101 | 48 | 19.8 |
| 416866 | 5-10-5 | 246 | 87 | 25 | 16.0 |
| 416867 | 5-10-5 | 246 | 87 | 35 | 18.9 |

Example 39: Tolerability of Antisense Oligonucleotides Targeting Human Factor 11 in Sprague-Dawley Rats Fifteen antisense oligonucleotides which had been evaluated in CD1 mice (Example 37) were further evaluated in Sprague-Dawley rats for changes in the levels of various metabolic markers.

Treatment

Groups of four Sprague Dawley rats each were injected subcutaneously twice per week for 6 weeks with 50 mg/kg of ISIS 412223, ISIS 412224, ISIS 412225, ISIS 413481, ISIS 413482, ISIS 416848, ISIS 416851, ISIS 416852, ISIS 416856, ISIS 416859, ISIS 416860, ISIS 416861, ISIS 416863, ISIS 416866, or ISIS 416867. A control group of four Sprague Dawley rats was injected subcutaneously with PBS twice per week for 6 weeks. Body weight measurements were taken before and throughout the treatment period. Three days after the last dose, urine samples were collected and the rats were then sacrificed, organ weights were measured, and blood was collected for further analysis.

Body Weight and Organ Weights

The body weights of the rats were measured at the onset of the study and subsequently twice per week. The body weights are presented in Table 86 and are expressed as increase in grams over the PBS control weight taken before the start of treatment. Liver, spleen and kidney weights were measured at the end of the study, and are also presented in Table 86 as a percentage of the body weight. Those antisense oligonucleotides which did not affect more than six-fold increases in liver and spleen weight above the PBS control were selected for further studies.

TABLE 86

Change in body and organ weights of Sprague Dawley rats after antisense oligonucleotide treatment

| | Body weight (g) | Liver (%) | Kidney (%) | Spleen (%) |
|---|---|---|---|---|
| PBS | 179 | 4 | 0.9 | 0.2 |
| ISIS 412223 | 126 | 5 | 1.0 | 0.5 |
| ISIS 412224 | 165 | 5 | 1.0 | 0.5 |
| ISIS 412225 | 184 | 4 | 1.0 | 0.5 |
| ISIS 413481 | 147 | 5 | 0.9 | 0.3 |
| ISIS 413482 | 158 | 5 | 1.0 | 0.6 |
| ISIS 416848 | 117 | 5 | 1.1 | 0.8 |
| ISIS 416851 | 169 | 5 | 0.9 | 0.3 |
| ISIS 416852 | 152 | 5 | 1.0 | 0.4 |
| ISIS 416856 | 156 | 5 | 1.0 | 0.4 |
| ISIS 416859 | 128 | 4 | 1.0 | 0.4 |
| ISIS 416860 | 123 | 5 | 1.0 | 0.5 |
| ISIS 416861 | 182 | 5 | 0.9 | 0.3 |
| ISIS 416863 | 197 | 5 | 1.0 | 0.4 |
| ISIS 416866 | 171 | 5 | 1.0 | 0.5 |
| ISIS 416867 | 129 | 5 | 1.0 | 0.5 |

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Measurements of alanine transaminase (ALT) and aspartate transaminase (AST) are expressed in IU/L and the results are presented in Table 87. Those antisense oligonucleotides which did not affect an increase in ALT/AST levels above seven-fold of control levels were selected for further studies. Plasma levels of bilirubin and albumin were also measured using the same clinical chemistry analyzer and results are presented in Table 87 and expressed in mg/dL. Those antisense oligonucleotides which did not affect an increase in levels of bilirubin more than two-fold of the control levels by antisense oligonucleotide treatment were selected for further studies.

TABLE 87

Effect of antisense oligonucleotide treatment on metabolic markers in the liver of Sprague-Dawley rats

| | ALT (IU/L) | AST (IU/L) | Bilirubin (mg/dL) | Albumin (mg/dL) |
|---|---|---|---|---|
| PBS | 42 | 71 | 0.13 | 4 |
| ISIS 412223 | 85 | 180 | 0.14 | 5 |
| ISIS 412224 | 84 | 132 | 0.12 | 4 |
| ISIS 412225 | 48 | 108 | 0.15 | 5 |
| ISIS 413481 | 54 | 80 | 0.22 | 4 |
| ISIS 413482 | 59 | 157 | 0.14 | 4 |
| ISIS 416848 | 89 | 236 | 0.14 | 3 |
| ISIS 416851 | 64 | 91 | 0.14 | 4 |
| ISIS 416852 | 49 | 87 | 0.15 | 4 |
| ISIS 416856 | 123 | 222 | 0.13 | 4 |
| ISIS 416859 | 114 | 206 | 0.21 | 5 |
| ISIS 416860 | 70 | 157 | 0.15 | 4 |
| ISIS 416861 | 89 | 154 | 0.15 | 5 |
| ISIS 416863 | 47 | 78 | 0.13 | 4 |
| ISIS 416866 | 41 | 78 | 0.16 | 4 |
| ISIS 416867 | 47 | 126 | 0.17 | 4 |

Kidney Function

To evaluate the effect of ISIS oligonucleotides on the kidney function, plasma concentrations of blood urea nitrogen (BUN) and creatinine were measured using an automated clinical chemistry analyzer (Hitachi Olympus AU400e, Melville, N.Y.). Results are presented in Table 88, expressed in mg/dL. Those antisense oligonucleotides which did not affect more than a two-fold increase in BUN levels compared to the PBS control were selected for further studies. The total urine protein and ratio of urine protein to creatinine in total urine samples after antisense oligonucleotide treatment was calculated and is also presented in Table 88. Those antisense oligonucleotides which did not affect more than a five-fold increase in urine protein/creatinine ratios compared to the PBS control were selected for further studies.

TABLE 88

Effect of antisense oligonucleotide treatment on metabolic markers in the kidney of Sprague-Dawley rats

| | BUN (mg/dL) | Creatinine (mg/dL) | Total urine protein (mg/dL) | Urine protein/creatinine ratio |
|---|---|---|---|---|
| PBS | 19 | 38 | 60 | 1.7 |
| ISIS 412223 | 24 | 46 | 224 | 4.6 |
| ISIS 412224 | 24 | 44 | 171 | 3.8 |
| ISIS 412225 | 23 | 58 | 209 | 4.0 |
| ISIS 413481 | 26 | 45 | 148 | 3.6 |
| ISIS 413482 | 23 | 34 | 157 | 4.8 |
| ISIS 416848 | 26 | 64 | 231 | 3.9 |
| ISIS 416851 | 24 | 70 | 286 | 4.0 |
| ISIS 416852 | 25 | 60 | 189 | 3.0 |
| ISIS 416856 | 23 | 48 | 128 | 2.7 |
| ISIS 416859 | 24 | 44 | 144 | 3.3 |
| ISIS 416860 | 23 | 58 | 242 | 4.6 |
| ISIS 416861 | 22 | 39 | 205 | 5.1 |
| ISIS 416863 | 29 | 73 | 269 | 3.8 |
| ISIS 416866 | 22 | 85 | 486 | 6.2 |
| ISIS 416867 | 22 | 70 | 217 | 3.1 |

Hematology Assays

Blood obtained from all rat groups were sent to Antech Diagnostics for hematocrit (HCT) measurements, as well as measurements of the various blood cells, such as WBC (neutrophils and lymphocytes), RBC, and platelets, and total hemoglobin content. The results are presented in Tables 89 and 90. Those antisense oligonucleotides which did not affect a decrease in platelet count of more than 50% and an increase in monocyte count of more than three-fold were selected for further studies.

TABLE 89

Effect of antisense oligonucleotide treatment on hematologic factors in Sprague-Dawley rats

| | RBC ($10^6$/mL) | Hemoglobin (g/dL) | HCT (%) | WBC ($10^3$/mL) |
|---|---|---|---|---|
| PBS | 6.9 | 13.2 | 42 | 9 |
| ISIS 412223 | 7.2 | 13.1 | 41 | 20 |
| ISIS 412224 | 7.4 | 13.4 | 42 | 20 |
| ISIS 412225 | 7.4 | 13.4 | 42 | 15 |
| ISIS 413481 | 7.5 | 14.2 | 43 | 14 |
| ISIS 413482 | 7.1 | 13.2 | 40 | 13 |
| ISIS 416848 | 6.0 | 11.1 | 35 | 17 |
| ISIS 416851 | 7.4 | 13.7 | 42 | 11 |
| ISIS 416852 | 7.2 | 13.4 | 42 | 13 |
| ISIS 416856 | 7.7 | 14.1 | 43 | 19 |
| ISIS 416859 | 7.8 | 14.0 | 45 | 16 |
| ISIS 416860 | 7.8 | 14.1 | 45 | 17 |
| ISIS 416861 | 7.7 | 14.6 | 45 | 15 |
| ISIS 416863 | 7.6 | 14.1 | 45 | 17 |
| ISIS 416866 | 7.8 | 14.0 | 44 | 20 |
| ISIS 416867 | 7.8 | 14.0 | 45 | 14 |

TABLE 90

Effect of antisense oligonucleotide treatment on blood cell count in Sprague-Dawley rats

| | Neutrophil (/mL) | Lymphocyte (/mL) | Platelets ($10^3$/mL) |
|---|---|---|---|
| PBS | 988 | 7307 | 485 |
| ISIS 412223 | 1826 | 16990 | 567 |
| ISIS 412224 | 1865 | 16807 | 685 |
| ISIS 412225 | 1499 | 13204 | 673 |
| ISIS 413481 | 1046 | 12707 | 552 |
| ISIS 413482 | 1125 | 11430 | 641 |
| ISIS 416848 | 1874 | 14316 | 384 |
| ISIS 416851 | 1001 | 9911 | 734 |
| ISIS 416852 | 836 | 11956 | 632 |
| ISIS 416856 | 3280 | 14328 | 740 |
| ISIS 416859 | 1414 | 14323 | 853 |
| ISIS 416860 | 1841 | 13986 | 669 |
| ISIS 416861 | 1813 | 12865 | 1008 |
| ISIS 416863 | 1720 | 14669 | 674 |
| ISIS 416866 | 1916 | 16834 | 900 |
| ISIS 416867 | 3044 | 10405 | 705 |

Example 40: Measurement of Half-Life of Antisense Oligonucleotide in the Liver and Kidney of Sprague-Dawley Rats Sprague Dawley rats were treated with ISIS antisense oligonucleotides targeting human Factor 11 and the oligonucleotide half-life as well as the elapsed time for oligonucleotide degradation and elimination from the liver and kidney was evaluated.

Treatment

Groups of four Sprague Dawley rats each were injected subcutaneously twice per week for 2 weeks with 20 mg/kg of ISIS 412223, ISIS 412224, ISIS 412225, ISIS 413481, ISIS 413482, ISIS 416848, ISIS 416851, ISIS 416852, ISIS 416856, ISIS 416859, ISIS 416860, ISIS 416861, ISIS 416863, ISIS 416866, or ISIS 416867. Three days after the last dose, the rats were sacrificed, and livers and kidneys were harvested.

Measurement of Oligonucleotide Concentration

The concentration of the full-length oligonucleotide as well as the total oligonucleotide concentration (including the degraded form) was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 270) was added prior to extraction. Tissue sample concentrations were calculated using calibration curves, with a lower limit of quantitation (LLOQ) of approximately 1.14 μg/g. The results are presented in Tables 91 and 92, expressed as μg/g liver or kidney tissue. Half-lives were then calculated using WinNonlin software (PHARSIGHT).

TABLE 91

Full-length oligonucleotide concentration (μg/g) in the liver and kidney of Sprague-Dawley rats

| ISIS No | Motif | Kidney | Liver |
|---|---|---|---|
| 412223 | 5-10-5 | 551 | 97 |
| 412224 | 5-10-5 | 487 | 107 |
| 412225 | 5-10-5 | 202 | 119 |
| 413481 | 5-10-5 | 594 | 135 |
| 413482 | 5-10-5 | 241 | 95 |
| 416848 | 5-10-5 | 488 | 130 |
| 416851 | 5-10-5 | 264 | 193 |
| 416852 | 5-10-5 | 399 | 108 |
| 416856 | 5-10-5 | 378 | 84 |
| 416859 | 5-10-5 | 253 | 117 |
| 416860 | 5-10-5 | 247 | 94 |
| 416861 | 5-10-5 | 187 | 159 |
| 416863 | 5-10-5 | 239 | 82 |
| 416866 | 5-10-5 | 210 | 98 |
| 416867 | 5-10-5 | 201 | 112 |

TABLE 92

Total oligonucleotide concentration (μg/g) in the liver and kidney of Sprague-Dawley rats

| ISIS No | Motif | Kidney | Liver |
|---|---|---|---|
| 412223 | 5-10-5 | 395 | 86 |
| 412224 | 5-10-5 | 292 | 78 |
| 412225 | 5-10-5 | 189 | 117 |
| 413481 | 5-10-5 | 366 | 96 |
| 413482 | 5-10-5 | 217 | 91 |
| 416848 | 5-10-5 | 414 | 115 |
| 416851 | 5-10-5 | 204 | 178 |
| 416852 | 5-10-5 | 304 | 87 |
| 416856 | 5-10-5 | 313 | 80 |
| 416859 | 5-10-5 | 209 | 112 |
| 416860 | 5-10-5 | 151 | 76 |
| 416861 | 5-10-5 | 165 | 144 |
| 416863 | 5-10-5 | 203 | 79 |
| 416866 | 5-10-5 | 145 | 85 |
| 416867 | 5-10-5 | 157 | 98 |

TABLE 93

Half-life (days) of ISIS oligonucleotides in the liver and kidney of Sprague-Dawley rats

| ISIS No | Motif | Half-life |
|---|---|---|
| 412223 | 5-10-5 | 22 |
| 412224 | 5-10-5 | 17 |
| 412225 | 5-10-5 | 21 |
| 413481 | 5-10-5 | 21 |
| 413482 | 5-10-5 | 20 |
| 416848 | 5-10-5 | 24 |
| 416851 | 5-10-5 | 24 |
| 416852 | 5-10-5 | 28 |
| 416856 | 5-10-5 | 19 |
| 416859 | 5-10-5 | 19 |
| 416860 | 5-10-5 | 21 |
| 416861 | 5-10-5 | 25 |
| 416863 | 5-10-5 | 20 |
| 416866 | 5-10-5 | 16 |
| 416867 | 5-10-5 | 19 |

Example 41: Tolerability of Antisense Oligonucleotides Targeting Human Factor 11 in CD1 Mice ISIS oligonucleotides with 6-8-6 MOE and 5-8-5 MOE motifs targeting human Factor 11 were administered in CD1 mice evaluated for changes in the levels of various metabolic markers.

Treatment

Groups of five CD1 mice each were injected subcutaneously twice per week for 6 weeks with 50 mg/kg of ISIS 416850, ISIS 445498, ISIS 445503, ISIS 445504, ISIS 445505, ISIS 445509, ISIS 445513, ISIS 445522, ISIS 445530, ISIS 445531, or ISIS 445532. A control group of five CD1 mice was injected subcutaneously with PBS twice per week for 6 weeks. Body weight measurements were taken before and at the end of the treatment period. Three days after the last dose, the mice were sacrificed, organ weights were measured, and blood was collected for further analysis.

Body Weight and Organ Weight

The body weight changes in the mice are presented in Table 94 and are expressed increase in grams over the PBS control weight taken before the start of treatment. Liver, spleen and kidney weights were measured at the end of the study, and are also presented in Table 94 as percentage of the body weight. Those antisense oligonucleotides which did not affect more than six-fold increases in liver and spleen weight above the PBS control were selected for further studies.

TABLE 94

Change in body and organ weights of CD1 mice after antisense oligonucleotide treatment

| | Body weight (g) | Liver (%) | Kidney (%) | Spleen (%) |
|---|---|---|---|---|
| PBS | 10 | 5 | 1.6 | 0.3 |
| ISIS 416850 | 11 | 6 | 1.5 | 0.4 |
| ISIS 445498 | 10 | 6 | 1.6 | 0.5 |
| ISIS 445503 | 9 | 8 | 1.4 | 0.6 |
| ISIS 445504 | 11 | 6 | 1.6 | 0.4 |
| ISIS 445505 | 12 | 6 | 1.5 | 0.5 |
| ISIS 445509 | 10 | 6 | 1.6 | 0.5 |
| ISIS 445513 | 9 | 5 | 1.6 | 0.4 |
| ISIS 445522 | 11 | 6 | 1.7 | 0.4 |
| ISIS 445530 | 11 | 6 | 1.5 | 0.5 |
| ISIS 445531 | 10 | 6 | 1.5 | 0.5 |
| ISIS 445532 | 10 | 6 | 1.6 | 0.4 |

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Measurements of alanine transaminase (ALT) and aspartate transaminase (AST) are expressed in IU/L and the results are presented in Table 95. Those antisense oligonucleotides which did not affect an increase in ALT/AST levels above seven-fold of control levels were selected for further studies. Plasma levels of bilirubin and albumin were also measured and results are also presented in Table 95 and expressed in mg/dL. Those antisense oligonucleotides which did not affect an increase in levels of bilirubin more than two-fold of the control levels by antisense oligonucleotide treatment were selected for further studies.

TABLE 95

Effect of antisense oligonucleotide treatment on metabolic markers in the liver of CD1 mice

| | ALT (IU/L) | AST (IU/L) | Bilirubin (mg/dL) | Albumin (mg/dL) |
|---|---|---|---|---|
| PBS | 34 | 49 | 0.23 | 3.6 |
| ISIS 416850 | 90 | 115 | 0.20 | 3.2 |
| ISIS 445498 | 66 | 102 | 0.24 | 3.4 |
| ISIS 445503 | 1314 | 852 | 0.28 | 3.4 |
| ISIS 445504 | 71 | 107 | 0.17 | 3.4 |
| ISIS 445505 | 116 | 153 | 0.18 | 3.2 |
| ISIS 445509 | 80 | 117 | 0.17 | 3.1 |
| ISIS 445513 | 37 | 84 | 0.22 | 3.1 |
| ISIS 445522 | 51 | 110 | 0.19 | 3.4 |
| ISIS 445530 | 104 | 136 | 0.18 | 3.2 |
| ISIS 445531 | 60 | 127 | 0.16 | 3.2 |
| ISIS 445532 | 395 | 360 | 0.20 | 2.9 |

Kidney Function

To evaluate the effect of ISIS oligonucleotides on kidney function, plasma concentrations of blood urea nitrogen (BUN) were measured using an automated clinical chemistry analyzer (Hitachi Olympus AU400e, Melville, N.Y.). Results are presented in Table 96, expressed in mg/dL. Those antisense oligonucleotides which did not affect more than a two-fold increase in BUN levels compared to the PBS control were selected for further studies.

TABLE 96

Effect of antisense oligonucleotide treatment on BUN levels (mg/dL) in the kidney of CD1 mice

| | BUN |
|---|---|
| PBS | 29 |
| ISIS 416850 | 28 |
| ISIS 445498 | 28 |
| ISIS 445503 | 29 |
| ISIS 445504 | 29 |
| ISIS 445505 | 29 |
| ISIS 445509 | 29 |
| ISIS 445513 | 27 |
| ISIS 445522 | 28 |
| ISIS 445530 | 26 |
| ISIS 445531 | 27 |
| ISIS 445532 | 23 |

Hematology Assays

Blood obtained from all mice groups were sent to Antech Diagnostics for hematocrit (HCT) measurements, as well as measurements of the various blood cells, such as WBC (neutrophils and lymphocytes), RBC, and platelets, and total hemoglobin content. The results are presented in Tables 97 and 98. Those antisense oligonucleotides which did not affect a decrease in platelet count of more than 50% and an increase in monocyte count of more than three-fold were selected for further studies.

TABLE 97

Effect of antisense oligonucleotide treatment on hematologic factors in CD1 mice

| | RBC ($10^6$/mL) | Hemoglobin (g/dL) | HCT (%) | WBC ($10^3$/mL) |
|---|---|---|---|---|
| PBS | 9.6 | 15.0 | 51 | 6 |
| ISIS 416850 | 9.8 | 14.8 | 50 | 6 |
| ISIS 445498 | 9.4 | 13.9 | 47 | 5 |
| ISIS 445503 | 9.2 | 13.6 | 46 | 8 |
| ISIS 445504 | 9.6 | 14.7 | 49 | 5 |
| ISIS 445505 | 9.6 | 14.6 | 49 | 5 |
| ISIS 445509 | 10.2 | 15.3 | 51 | 5 |
| ISIS 445513, | 9.8 | 15.0 | 50 | 7 |
| ISIS 445522 | 9.7 | 14.6 | 49 | 5 |
| ISIS 445530 | 10.0 | 15.1 | 50 | 7 |
| ISIS 445531 | 9.4 | 14.5 | 48 | 9 |
| ISIS 445532 | 9.7 | 14.8 | 48 | 7 |

TABLE 98

Effect of antisense oligonucleotide treatment on blood cell count in CD1 mice

| | Neutrophil (/mL) | Lymphocyte (/mL) | Platelets ($10^3$/mL) |
|---|---|---|---|
| PBS | 1356 | 4166 | 749 |
| ISIS 416850 | 1314 | 4710 | 614 |
| ISIS 445498 | 1197 | 3241 | 802 |
| ISIS 445503 | 1475 | 6436 | 309 |
| ISIS 445504 | 959 | 3578 | 826 |
| ISIS 445505 | 818 | 3447 | 725 |
| ISIS 445509 | 1104 | 3758 | 1085 |
| ISIS 445513 | 959 | 5523 | 942 |
| ISIS 445522 | 698 | 3997 | 1005 |
| ISIS 445530 | 930 | 5488 | 849 |
| ISIS 445531 | 2341 | 6125 | 996 |
| ISIS 445532 | 1116 | 5490 | 689 |

Example 42: Tolerability of Antisense Oligonucleotides Targeting Human Factor 11 in Sprague-Dawley Rats Eight antisense oligonucleotides which had been evaluated in CD1 mice (Example 41) were further evaluated in Sprague-Dawley rats for changes in the levels of various metabolic markers.

Treatment

Groups of four Sprague Dawley rats each were injected subcutaneously twice per week for 6 weeks with 50 mg/kg of ISIS 445498, ISIS 445504, ISIS 445505, ISIS 445509, ISIS 445513, ISIS 445522, ISIS 445530, or ISIS 445531. A control group of Sprague Dawley rats was injected subcutaneously with PBS twice per week for 6 weeks. Body weight measurements were taken before and throughout the treatment period. Three days after the last dose, urine samples were collected and the rats were then sacrificed, organ weights were measured, and blood was collected for further analysis.

Body Weight and Organ Weight

The body weights of the rats were measured at the onset of the study and subsequently twice per week. The body weights are presented in Table 99 and are expressed as percent increase over the PBS control weight taken before the start of treatment. Liver, spleen and kidney weights were measured at the end of the study, and are also presented in Table 99 as a percentage of the body weight. Those antisense oligonucleotides which did not affect more than six-fold increases in liver and spleen weight above the PBS control were selected for further studies.

TABLE 99

Change in body and organ weights of Sprague Dawley rats after antisense oligonucleotide treatment (%)

| | Body weight | Liver | Spleen | Kidney |
|---|---|---|---|---|
| ISIS 445498 | −17 | +26 | +107 | −10 |
| ISIS 445504 | −15 | +22 | +116 | +6 |
| ISIS 445505 | −21 | +12 | +146 | +2 |
| ISIS 445509 | −17 | +16 | +252 | +3 |
| ISIS 445513 | −13 | +25 | +194 | +15 |
| ISIS 445522 | −13 | +26 | +184 | +19 |
| ISIS 445530 | −7 | +24 | +99 | +4 |
| ISIS 445531 | −10 | +17 | +89 | +4 |

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Plasma concentrations of ALT (alanine transaminase) and AST (aspartate transaminase) were measured and the results are presented in Table 100 expressed in IU/L. Those antisense oligonucleotides which did not affect an increase in ALT/AST levels above seven-fold of control levels were selected for further studies. Plasma levels of bilirubin and albumin were also measured using the same clinical chemistry analyzer; results are presented in Table 100 and expressed in mg/dL. Those antisense oligonucleotides which did not affect an increase in levels of bilirubin more than two-fold of the control levels by antisense oligonucleotide treatment were selected for further studies.

TABLE 100

Effect of antisense oligonucleotide treatment on metabolic marker in the liver of Sprague-Dawley rats

| | ALT (IU/L) | AST (IU/L) | Bilirubin (mg/dL) | Albumin (mg/dL) |
|---|---|---|---|---|
| PBS | 102 | 36 | 0.13 | 3.7 |
| ISIS 445498 | 417 | 124 | 0.14 | 3.7 |
| ISIS 445504 | 206 | 86 | 0.11 | 3.5 |
| ISIS 445505 | 356 | 243 | 0.15 | 3.6 |
| ISIS 445509 | 676 | 291 | 0.14 | 3.5 |
| ISIS 445513 | 214 | 91 | 0.15 | 3.5 |
| ISIS 445522 | 240 | 138 | 0.47 | 3.6 |
| ISIS 445530 | 116 | 56 | 0.11 | 3.7 |
| ISIS 445531 | 272 | 137 | 0.12 | 3.7 |

Kidney Function

To evaluate the effect of ISIS oligonucleotides on kidney function, plasma concentrations of blood urea nitrogen (BUN) and creatinine were measured using an automated clinical chemistry analyzer (Hitachi Olympus AU400e, Melville, N.Y.). Results are presented in Table 101, expressed in mg/dL. Those antisense oligonucleotides which did not affect more than a two-fold increase in BUN levels compared to the PBS control were selected for further studies. The total urine protein and ratio of urine protein to creatinine in total urine samples after antisense oligonucleotide treatment was calculated and is also presented in Table 101. Those antisense oligonucleotides which did not affect more than a five-fold increase in urine protein/creatinine ratios compared to the PBS control were selected for further studies.

TABLE 101

Effect of antisense oligonucleotide treatment on metabolic markers in the kidney of Sprague-Dawley rats

| | BUN (mg/dL) | Creatinine (mg/dL) | Urine protein/ creatinine ratio |
|---|---|---|---|
| PBS | 18 | 0.4 | 1.4 |
| ISIS 445498 | 25 | 0.5 | 3.1 |
| ISIS 445504 | 26 | 0.4 | 4.3 |
| ISIS 445505 | 24 | 0.4 | 3.8 |
| ISIS 445509 | 27 | 0.5 | 4.0 |
| ISIS 445513 | 24 | 0.4 | 4.6 |
| ISIS 445522 | 25 | 0.4 | 6.4 |
| ISIS 445530 | 22 | 0.4 | 4.2 |
| ISIS 445531 | 23 | 0.4 | 3.4 |

Hematology Assays

Blood obtained from all rat groups were sent to Antech Diagnostics for hematocrit (HCT) measurements, as well as measurements of the various blood cells, such as WBC (neutrophils, lymphocytes, and monocytes), RBC, and platelets, and total hemoglobin content. The results are presented in Tables 102 and 103. Those antisense oligonucleotides which did not affect a decrease in platelet count of more than 50% and an increase in monocyte count of more than three-fold were selected for further studies.

TABLE 102

Effect of antisense oligonucleotide treatment on hematologic factors in Sprague-Dawley rats

| | RBC (/pL) | Hemoglobin (g/dL) | HCT (%) | WBC (/nL) |
|---|---|---|---|---|
| PBS | 8.8 | 16.0 | 55 | 13 |
| ISIS 445498 | 8.5 | 14.7 | 49 | 13 |
| ISIS 445504 | 8.9 | 14.7 | 50 | 16 |
| ISIS 445505 | 9.1 | 15.0 | 50 | 21 |
| ISIS 445509 | 8.4 | 14.1 | 47 | 17 |
| ISIS 445513 | 7.8 | 13.0 | 44 | 17 |
| ISIS 445522 | 7.7 | 13.6 | 47 | 18 |
| ISIS 445530 | 8.9 | 14.7 | 50 | 12 |
| ISIS 445531 | 8.8 | 14.8 | 50 | 13 |

TABLE 103

Effect of antisense oligonucleotide treatment on blood cell count in Sprague-Dawley rats

| | Neutrophil (%) | Lymphocyte (%) | Monocytes (%) | Platelets (/nL) |
|---|---|---|---|---|
| PBS | 14 | 82 | 2.0 | 1007 |
| ISIS 445498 | 9 | 89 | 2.0 | 1061 |
| ISIS 445504 | 10 | 87 | 2.0 | 776 |
| ISIS 445505 | 10 | 87 | 2.5 | 1089 |
| ISIS 445509 | 11 | 84 | 3.8 | 1115 |
| ISIS 445513 | 14 | 82 | 3.5 | 1051 |
| ISIS 445522 | 13 | 84 | 2.8 | 1334 |
| ISIS 445530 | 11 | 87 | 2.0 | 1249 |
| ISIS 445531 | 10 | 86 | 2.8 | 1023 |

Example 43: Tolerability of Antisense Oligonucleotides Targeting Human Factor 11 in CD1 Mice ISIS oligonucleotides with 4-8-4 MOE, 3-8-3 MOE, 2-10-2 MOE, 3-10-3 MOE, and 4-10-4 MOE motifs targeting human Factor 11 were administered in CD1 mice evaluated for changes in the levels of various metabolic markers.

Treatment

Groups of five CD1 mice each were injected subcutaneously twice per week for 6 weeks with 50 mg/kg of ISIS 449707, ISIS 449708, ISIS 449409, ISIS 449710, or ISIS 449711. A control group of five CD1 mice was injected subcutaneously with PBS twice per week for 6 weeks. Body weight measurements were taken before and at the end of the treatment period. Three days after the last dose, the mice were sacrificed, organ weights were measured, and blood was collected for further analysis.

Body Weight and Organ Weight

The body weights of the mice taken at the end of the study are presented in Table 104 and are expressed in grams. Liver, spleen and kidney weights were also measured at the end of the study and are also presented in Table 104 as percentage of the body weight. Those antisense oligonucleotides which did not affect more than six-fold increases in liver and spleen weight above the PBS control were selected for further studies.

TABLE 104

Change in body and organ weights of CD1 mice after antisense oligonucleotide treatment

| | Body weight (g) | Liver (%) | Spleen (%) | Kidney (%) |
|---|---|---|---|---|
| PBS | 39 | — | — | — |
| ISIS 449707 | 42 | +11 | +63 | −5 |
| ISIS 449708 | 40 | +17 | +66 | 0 |
| ISIS 449709 | 40 | +15 | +62 | −14 |
| ISIS 449710 | 42 | +6 | +43 | −7 |
| ISIS 449711 | 42 | +18 | +63 | −12 |

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Plasma concentrations of ALT (alanine transaminase) and AST (aspartate transaminase) were measured and the results are presented in Table 105 expressed in IU/L. Those antisense oligonucleotides which did not affect an increase in ALT/AST levels above seven-fold of control levels were selected for further studies. Plasma levels of bilirubin and albumin were also measured using the same clinical chemistry analyzer and results are presented in Table 105 and expressed in mg/dL. Those antisense oligonucleotides which did not affect an increase in levels of bilirubin more than two-fold of the control levels by antisense oligonucleotide treatment were selected for further studies.

TABLE 105

Effect of antisense oligonucleotide treatment on metabolic markers in the liver of CD1 mice

| | ALT (IU/L) | AST (IU/L) | Bilirubin (mg/dL) | Albumin (mg/dL) |
|---|---|---|---|---|
| PBS | 39 | 52 | 0.22 | 3.2 |
| ISIS 449707 | 41 | 62 | 0.19 | 2.3 |
| ISIS 449708 | 66 | 103 | 0.17 | 2.8 |
| ISIS 449709 | 62 | 83 | 0.18 | 2.8 |
| ISIS 449710 | 43 | 95 | 0.18 | 2.8 |
| ISIS 449711 | 52 | 83 | 0.22 | 2.8 |

Kidney Function

To evaluate the effect of ISIS oligonucleotides on kidney function, plasma concentrations of blood urea nitrogen (BUN) and creatinine were measured using an automated clinical chemistry analyzer (Hitachi Olympus AU400e, Melville, N.Y.). Results are presented in Table 106, expressed in mg/dL. Those antisense oligonucleotides which did not affect more than a two-fold increase in BUN levels compared to the PBS control were selected for further studies.

TABLE 106

Effect of antisense oligonucleotide treatment on metabolic markers (mg/dL) in the kidney of CD1 mice

| | BUN | Creatinine |
|---|---|---|
| PBS | 28 | 0.3 |
| ISIS 449707 | 27 | 0.2 |
| ISIS 449708 | 28 | 0.2 |
| ISIS 449709 | 34 | 0.3 |
| ISIS 449710 | 29 | 0.2 |
| ISIS 449711 | 26 | 0.2 |

Hematology Assays

Blood obtained from all mice groups were sent to Antech Diagnostics for hematocrit (HCT), measurements, as well as measurements of the various blood cells, such as WBC (neutrophils, lymphocytes, and monocytes), RBC, and platelets, and total hemoglobin content. The results are presented in Tables 107 and 108. Those antisense oligonucleotides which did not affect a decrease in platelet count of more than 50% and an increase in monocyte count of more than three-fold were selected for further studies.

TABLE 107

Effect of antisense oligonucleotide treatment on hematologic factors in CD1 mice

| | RBC (/pL) | Hemoglobin (g/dL) | Hematocrit (%) | WBC (/nL) |
|---|---|---|---|---|
| PBS | 9.8 | 14.6 | 54 | 6 |
| ISIS 449707 | 8.4 | 12.4 | 45 | 6 |
| ISIS 449708 | 9.2 | 13.2 | 48 | 7 |
| ISIS 449709 | 9.2 | 13.2 | 49 | 5 |
| ISIS 449710 | 9.1 | 13.5 | 48 | 7 |
| ISIS 449711 | 9.0 | 13.3 | 48 | 6 |

TABLE 108

Effect of antisense oligonucleotide treatment on blood cell count in CD1 mice

| | Neutrophils (%) | Lymphocytes (%) | Monocytes (%) | Platelets (/nL) |
|---|---|---|---|---|
| PBS | 15 | 80 | 3 | 1383 |
| ISIS 449707 | 11 | 85 | 3 | 1386 |
| ISIS 449708 | 17 | 77 | 5 | 1395 |
| ISIS 449709 | 19 | 76 | 4 | 1447 |
| ISIS 449710 | 15 | 81 | 3 | 1245 |
| ISIS 449711 | 15 | 79 | 6 | 1225 |

Example 44: Tolerability of Antisense Oligonucleotides Targeting Human Factor 11 in Sprague-Dawley Rats Five antisense oligonucleotides which had been evaluated in CD1 mice (Example 43) were further evaluated in Sprague-Dawley rats for changes in the levels of various metabolic markers.

Treatment

Groups of four Sprague Dawley rats each were injected subcutaneously twice per week for 6 weeks with 50 mg/kg of ISIS 449707, ISIS 449708, ISIS 449709, ISIS 449710, or ISIS 449711. A control group of four Sprague Dawley rats was injected subcutaneously with PBS twice per week for 6 weeks. Body weight measurements were taken before and throughout the treatment period. Three days after the last dose, urine samples were collected and the rats were then sacrificed, organ weights were measured, and blood was collected for further analysis.

Body Weight and Organ Weight

The body weights of the rats were measured at the onset of the study and at the end of the study. The body weight changes are presented in Table 109 and are expressed as increase in grams over the PBS control weight taken before the start of treatment. Liver, spleen and kidney weights were measured at the end of the study, and are also presented in Table 109 as a percentage of the body weight. Those antisense oligonucleotides which did not affect more than six-fold increases in liver and spleen weight above the PBS control were selected for further studies.

TABLE 109

Change in body and organ weights of Sprague Dawley rats after antisense oligonucleotide treatment

| | Body weight (g) | Liver (%) | Spleen (%) | Kidney (%) |
|---|---|---|---|---|
| PBS | 478 | — | — | — |
| ISIS 449707 | 352 | +41 | +400 | +80 |
| ISIS 449708 | 382 | +31 | +259 | +40 |
| ISIS 449709 | 376 | +8 | +231 | +19 |
| ISIS 449710 | 344 | +82 | +302 | +50 |
| ISIS 449711 | 362 | +52 | +327 | +72 |

Liver Function

To evaluate the impact of ISIS oligonucleotides on hepatic function, plasma concentrations of ALT and AST were measured using an automated clinical chemistry analyzer (Hitachi Olympus AU400e, Melville, N.Y.). Plasma concentrations of alanine transaminase (ALT) and aspartate transaminase (AST) were measured and the results are presented in Table 110 expressed in IU/L. Those antisense oligonucleotides which did not affect an increase in ALT/AST levels above seven-fold of control levels were selected for further studies. Plasma levels of bilirubin and albumin were also measured and results are presented in Table 110 and expressed in mg/dL. Those antisense oligonucleotides which did not affect an increase in levels of bilirubin more than two-fold of the control levels by antisense oligonucleotide treatment were selected for further studies.

TABLE 110

Effect of antisense oligonucleotide treatment on metabolic markers in the liver of Sprague-Dawley rats

| | ALT (IU/L) | AST (IU/L) | Bilirubin (mg/dL) | Albumin (mg/dL) |
|---|---|---|---|---|
| PBS | 41 | 107 | 0.1 | 3.4 |
| ISIS 449707 | 61 | 199 | 0.2 | 3.1 |
| ISIS 449708 | 25 | 90 | 0.1 | 3.2 |
| ISIS 449709 | 63 | 126 | 0.2 | 3.1 |
| ISIS 449710 | 36 | 211 | 0.1 | 2.9 |
| ISIS 449711 | 32 | 163 | 0.1 | 2.9 |

Kidney Function

To evaluate the impact of ISIS oligonucleotides on kidney function, plasma concentrations of BUN and creatinine were measured using an automated clinical chemistry analyzer (Hitachi Olympus AU400e, Melville, N.Y.). Results are presented in Table 111, expressed in mg/dL. Those antisense oligonucleotides which did not affect more than a two-fold increase in BUN levels compared to the PBS control were selected for further studies. The total urine protein and ratio of urine protein to creatinine in total urine samples after antisense oligonucleotide treatment was calculated and is also presented in Table 111. Those antisense oligonucleotides which did not affect more than a five-fold increase in urine protein/creatinine ratios compared to the PBS control were selected for further studies.

TABLE 111

Effect of antisense oligonucleotide treatment on metabolic markers in the kidney of Sprague-Dawley rats

| | BUN (mg/dL) | Creatinine (mg/dL) | Urine protein/ creatinine ratio |
|---|---|---|---|
| PBS | 22 | 0.4 | 1.5 |
| ISIS 449707 | 24 | 0.4 | 3.2 |
| ISIS 449708 | 24 | 0.4 | 5.7 |
| ISIS 449709 | 24 | 0.4 | 3.4 |
| ISIS 449710 | 29 | 0.3 | 5.9 |
| ISIS 449711 | 28 | 0.4 | 7.3 |

Hematology Assays

Blood obtained from all rat groups were sent to Antech Diagnostics for hematocrit (HCT) measurements, as well as measurements of the various blood cells, such as WBC (neutrophils, lymphocytes, and monocytes), RBC, and platelets, and total hemoglobin content. The results are presented in Tables 112 and 113. Those antisense oligonucleotides which did not affect a decrease in platelet count of more than 50% and an increase in monocyte count of more than three-fold were selected for further studies.

TABLE 112

Effect of antisense oligonucleotide treatment on hematologic factors in Sprague-Dawley rats

| | RBC (/pL) | Hemoglobin (g/dL) | Hematocrit (%) | WBC (/nL) |
|---|---|---|---|---|
| PBS | 8.2 | 15.1 | 50 | 16 |
| ISIS 449707 | 6.0 | 12.0 | 40 | 20 |
| ISIS 449708 | 6.6 | 12.2 | 40 | 22 |
| ISIS 449709 | 6.9 | 12.6 | 41 | 14 |
| ISIS 449710 | 6.3 | 12.5 | 41 | 13 |
| ISIS 449711 | 6.4 | 12.6 | 43 | 13 |

TABLE 113

Effect of antisense oligonucleotide treatment on blood cell count in Sprague-Dawley rats

| | Neutrophils (%) | Lymphocytes (%) | Monocytes (%) | Platelets (/nL) |
|---|---|---|---|---|
| PBS | 12 | 84 | 2 | 1004 |
| ISIS 449707 | 6 | 91 | 2 | 722 |
| ISIS 449708 | 6 | 92 | 2 | 925 |
| ISIS 449709 | 5 | 91 | 3 | 631 |
| ISIS 449710 | 6 | 91 | 2 | 509 |
| ISIS 449711 | 7 | 90 | 2 | 919 |

Example 45: Dose-Dependent Pharmacologic Effect of Antisense Oligonucleotides Targeting Human Factor 11 in Cynomolgus Monkeys Several antisense oligonucleotides were tested in cynomolgus monkeys to determine the pharmacologic effects of the oligonucleotides on Factor 11 activity, anticoagulation and bleeding times, liver and kidney distributions, and tolerability. All the ISIS oligonucleotides used in this study target human Factor 11 mRNA and are also fully cross-reactive with the rhesus monkey gene sequence (see Table 44). It is expected that the rhesus monkey ISIS oligonucleotides are fully cross-reactive with the cynomolgus monkey gene sequence as well. At the time the study was undertaken, the cynomolgus monkey genomic sequence was not available in the National Center for Biotechnology Information (NCBI) database; therefore, cross-reactivity with the cynomolgus monkey gene sequence could not be confirmed.

Treatment

Groups, each consisting of two male and three female monkeys, were injected subcutaneously with ISIS 416838, ISIS 416850, ISIS 416858, ISIS 416864, or ISIS 417002 in escalating doses. Antisense oligonucleotide was administered to the monkeys at 5 mg/kg three times per a week for week 1; 5 mg/kg twice per week for weeks 2 and 3; 10 mg/kg three times per week for week 4; 10 mg/kg twice per week for weeks 5 and 6; 25 mg/kg three times per week for week 7; and 25 mg/kg twice per week for weeks 8, 9, 10, 11, and 12. One control group, consisting of two male and three female monkeys, was injected subcutaneously with PBS according to the same dosing regimen. An additional experimental group, consisting of two male and three female monkeys, was injected subcutaneously with ISIS 416850 in a chronic, lower dose regimen. Antisense oligonucleotide was administered to the monkeys at 5 mg/kg three times per week for week 1; 5 mg/kg twice per week for week 2 and 3; 10 mg/kg three times per week for week 4; and 10 mg/kg twice per week for weeks 5 to 12. Body weights were measured weekly. Blood samples were collected 14 days and 5 days before the start of treatment and subsequently once per week for Factor 11 protein activity analysis in plasma, fibrinogen measurement, PT and aPTT measurements, bleeding times, and measurement of various hematologic factors. On day 85, the monkeys were euthanized by exsanguination while under deep anesthesia, and organs harvested for further analysis.

RNA Analysis

On day 85, RNA was extracted from liver tissue for real-time PCR analysis of Factor 11 using primer probe set LTS00301 (forward primer sequence ACACGCATTAAAAAGAGCAAAGC, designated herein as SEQ ID NO 271; reverse primer sequence CAGTGTCATGGTAAAATGAAGAATGG, designated herein as SEQ ID NO: 272; and probe sequence TGCAGGCACAGCATCCCAGTGTTCTX, designated herein as SEQ ID NO. 273). Results are presented as percent inhibition of Factor 11, relative to PBS control. As shown in Table 114, treatment with ISIS oligonucleotides resulted in significant reduction of Factor 11 mRNA in comparison to the PBS control.

TABLE 114

Inhibition of Factor 11 mRNA in the cynomolgus monkey liver relative to the PBS control

| ISIS No | % inhibition |
|---|---|
| 416838 | 37 |
| 416850 | 84 |
| 416858 | 90 |
| 416864 | 44 |
| 417002 | 57 |

Protein Analysis

Plasma samples from all monkey groups taken on different days were analyzed by a sandwich-style ELISA assay (Affinity Biologicals Inc.) using an affinity-purified polyclonal anti-Factor 11 antibody as the capture antibody and a peroxidase-conjugated polyclonal anti-Factor 11 antibody as the detecting antibody. Monkey plasma was diluted 1:50 for the assay. Peroxidase activity was expressed by incubation with the substrate o-phenylenediamine. The color produced was quantified using a microplate reader at 490 nm and was considered to be proportional to the concentration of Factor 11 in the samples.

The results are presented in Table 115, expressed as percentage reduction relative to that of the PBS control. Treatment with ISIS 416850 and ISIS 416858 resulted in a time-dependent decrease in protein levels.

TABLE 115

Inhibition of Factor 11 protein in the cynomolgus monkey liver relative to the PBS control

| Days | ISIS 416838 | ISIS 416850 | ISIS 416858 | ISIS 416864 | ISIS 417002 | ISIS 416850* |
|---|---|---|---|---|---|---|
| −14 | 0 | 0 | 0 | 0 | 0 | 0 |
| −5 | 0 | 0 | 0 | 5 | 0 | 1 |
| 8 | 3 | 8 | 6 | 7 | 0 | 6 |
| 15 | 4 | 4 | 16 | 9 | 4 | 13 |
| 22 | 5 | 11 | 23 | 7 | 2 | 12 |
| 29 | 8 | 15 | 28 | 10 | 8 | 20 |
| 36 | 11 | 17 | 35 | 9 | 8 | 22 |
| 43 | 5 | 23 | 39 | 9 | 9 | 24 |
| 50 | 8 | 42 | 49 | 10 | 13 | 30 |
| 57 | 10 | 49 | 60 | 7 | 24 | 34 |
| 64 | 11 | 55 | 68 | 5 | 26 | 37 |
| 71 | 12 | 57 | 71 | 10 | 30 | 41 |
| 78 | 10 | 63 | 73 | 9 | 22 | 42 |
| 85 | 10 | 64 | 78 | 8 | 23 | 34 |

PT and aPTT Assay

Blood samples were collected in tubes containing sodium citrate. PT and aPTT were determined in duplicate with an ACL 9000 coagulation instrument (Instrumentation Laboratory, Italy). The results were interpolated on a standard curve of serial dilutions citrated control monkey plasma tested to give a reported result in percent normal.

Prothrombin Time (PT) and Activated Partial Thromboplastin Time (aPTT) were measured using platelet poor plasma (PPP) from monkeys treated with ISIS oligonucleotides. PT and aPTT values are provided in Tables 116 and 117 and are reported as International Normalized Ratio (INR) values. INR values for PT and aPTT were determined by dividing the PT or aPTT value for each experimental group by the PT or aPTT for the PBS treated group. This ratio was then raised to the power of the International Sensitivity Index (ISI) of the tissue factor used. The ISIS oligonucleotide, ISIS 416850, given with the chronic dose regimen is distinguished from the other oligonucleotides with an asterisk (*).

As shown in Table 116, PT was not significantly prolonged in monkeys treated with ISIS oligonucleotides either in the escalating dose regimen or the chronic dose regimen. However, aPTT was prolonged in a dose-dependent manner, as presented in Table 117. These data suggest that antisense reduction of Factor 11 affects the contact activation pathway, but not the extrinsic pathway of blood coagulation. Therefore, antisense reduction of Factor 11 is useful for inhibiting the formation of a thrombus or clot in response to an abnormal vessel wall, but not in response to tissue injury.

TABLE 116

Effect of ISIS antisense oligonucleotides on PT ratio in cynomolgus monkeys

| day | ISIS 416838 | ISIS 416850 | ISIS 416858 | ISIS 416864 | ISIS 417002 | ISIS 416850* |
|---|---|---|---|---|---|---|
| −14 | 1.00 | 1.00 | 1.00 | 1.00 | 1.00 | 1.00 |
| −5 | 1.00 | 1.00 | 1.00 | 1.00 | 1.00 | 1.00 |
| 8 | 1.03 | 1.00 | 1.05 | 1.02 | 1.02 | 1.03 |
| 15 | 1.03 | 1.02 | 1.07 | 1.07 | 1.04 | 1.06 |
| 22 | 1.07 | 1.02 | 1.06 | 1.03 | 1.04 | 1.06 |
| 29 | 1.03 | 1.03 | 1.08 | 1.06 | 1.01 | 1.00 |
| 36 | 1.05 | 1.02 | 1.07 | 1.06 | 1.05 | 1.06 |
| 43 | 1.03 | 1.01 | 1.08 | 1.04 | 1.03 | 1.02 |
| 50 | 1.02 | 1.02 | 1.03 | 1.01 | 0.99 | 0.98 |
| 57 | 1.04 | 1.04 | 1.09 | 1.08 | 1.03 | n.d. |
| 64 | 1.04 | 1.03 | 1.09 | 1.10 | 1.03 | n.d. |
| 71 | 1.02 | 1.03 | 1.07 | 1.07 | 0.99 | n.d. |
| 78 | 1.04 | 1.05 | 1.10 | 1.08 | 1.02 | n.d. |
| 85 | 1.05 | 1.04 | 1.07 | 1.13 | 1.02 | n.d. |

n.d. = no data

TABLE 117

Effect of ISIS antisense oligonucleotides on aPTT ratio in cynomolgus monkeys

| day | ISIS 416838 | ISIS 416850 | ISIS 416858 | ISIS 416864 | ISIS 417002 | ISIS 416850* |
|---|---|---|---|---|---|---|
| −14 | 1.00 | 1.00 | 1.00 | 1.00 | 1.00 | 1.00 |
| −5 | 1.00 | 1.00 | 1.00 | 1.00 | 1.00 | 1.00 |
| 8 | 1.07 | 1.05 | 1.03 | 1.05 | 1.05 | 1.12 |
| 15 | 1.05 | 1.05 | 1.07 | 1.03 | 1.03 | 1.07 |
| 22 | 1.20 | 1.13 | 1.18 | 1.11 | 1.16 | 1.21 |
| 29 | 1.19 | 1.13 | 1.20 | 1.13 | 1.11 | 1.26 |
| 36 | 1.20 | 1.26 | 1.36 | 1.19 | 1.18 | 1.34 |
| 43 | 1.18 | 1.17 | 1.28 | 1.07 | 1.06 | 1.22 |
| 50 | 1.25 | 1.68 | 1.55 | 1.26 | 1.18 | 1.35 |
| 57 | 1.21 | 1.59 | 1.59 | 1.19 | 1.22 | n.d. |
| 64 | 1.18 | 1.64 | 1.60 | 1.12 | 1.11 | n.d. |
| 71 | 1.15 | 1.76 | 1.70 | 1.18 | 1.16 | n.d. |
| 78 | 1.19 | 1.88 | 1.79 | 1.18 | 1.18 | n.d. |
| 85 | 1.22 | 1.99 | 1.76 | 1.25 | 1.20 | n.d. |

n.d. = no data

Protein Activity Analysis

Blood samples were collected at various time points and Factor 11 proenzyme was measured using a F11 assay based on clotting time. Clotting times were determined in duplicate with a ST4 semi-automated coagulation instrument (Diagnostica Stago, NJ). Thirty µl of citrated sample plasma diluted 1/20 in HEPES-NaCl buffer with BSA was incubated with 30 µl aPTT reagent (Automated aPTT, Organon Technika, NC) and 30 µl of citrated plasma deficient of Factor 11 (George King Bio-Medical Inc.) at 37° C. for 5 min, followed by the addition of 30 µl of 25 mM $CaCl_2$) to initiate clotting. Results were interpolated on a standard curve of serially diluted citrated control plasma.

Results are presented in Table 118 as percent inhibition of Factor 11 activity, relative to PBS control. The ISIS oligonucleotide, ISIS 416850, given with the chronic dose regimen is distinguished from the other oligonucleotides with an asterisk (*).

TABLE 118

Inhibition of Factor 11 protein by ISIS antisense oligonucleotides given in escalating dose/chronic dose regimen in cynomolgus monkeys

| Days before/after treatment | ISIS 416838 | ISIS 416850 | ISIS 416858 | ISIS 416864 | ISIS 417002 | ISIS 416850* |
|---|---|---|---|---|---|---|
| −14 | 0 | 0 | 0 | 0 | 0 | 0 |
| −5 | 0 | 0 | 0 | 5 | 0 | 1 |
| 8 | 3 | 8 | 6 | 7 | 0 | 6 |
| 15 | 4 | 4 | 16 | 9 | 4 | 13 |
| 22 | 5 | 11 | 23 | 7 | 2 | 12 |
| 29 | 8 | 15 | 28 | 10 | 8 | 20 |
| 36 | 11 | 17 | 35 | 9 | 8 | 24 |
| 43 | 5 | 23 | 39 | 9 | 9 | 24 |
| 50 | 8 | 42 | 49 | 10 | 13 | 30 |
| 57 | 10 | 49 | 60 | 7 | 24 | n.d. |
| 64 | 11 | 55 | 68 | 5 | 26 | n.d. |
| 71 | 12 | 57 | 71 | 10 | 30 | n.d. |
| 78 | 10 | 63 | 73 | 9 | 22 | n.d. |
| 85 | 10 | 64 | 78 | 8 | 23 | n.d. |

n.d. = no data

Fibrinogen Assay

Nine parts of fresh monkey plasma was collected into one part of trisodium citrate. The samples were evaluated of fibrinogen content using an ACL 9000 coagulation instrument (Instrumentation Laboratory, Italy). Results are presented in Table 119 expressed in mg/dL. The ISIS oligonucleotide, ISIS 416850, given with the chronic dose regimen is distinguished from the other oligonucleotides with an asterisk (*).

TABLE 119

Effect of ISIS antisense oligonucleotides on fibrinogen levels in cynomolgus monkeys

| Days before/after treatment | PBS | ISIS 416838 | ISIS 416850 | ISIS 416858 | ISIS 416864 | ISIS 417002 | ISIS 416850* |
|---|---|---|---|---|---|---|---|
| −14 | 296 | 251 | 310 | 277 | 300 | 291 | 274 |
| −5 | 246 | 205 | 261 | 246 | 243 | 222 | 227 |
| 8 | 245 | 209 | 281 | 246 | 227 | 221 | 232 |
| 15 | 207 | 198 | 270 | 219 | 210 | 195 | 174 |
| 22 | 219 | 183 | 243 | 222 | 184 | 199 | 192 |
| 29 | 231 | 184 | 234 | 220 | 205 | 199 | 192 |
| 36 | 235 | 182 | 232 | 225 | 202 | 191 | 185 |
| 43 | 231 | 186 | 219 | 229 | 198 | 187 | 194 |

TABLE 119-continued

| Effect of ISIS antisense oligonucleotides on fibrinogen levels in cynomolgus monkeys | | | | | | | |
|---|---|---|---|---|---|---|---|
| Days before/after treatment | PBS | ISIS 416838 | ISIS 416850 | ISIS 416858 | ISIS 416864 | ISIS 417002 | ISIS 416850* |
| 50 | 251 | 216 | 215 | 259 | 233 | 236 | 204 |
| 57 | 235 | 190 | 186 | 225 | 200 | 201 | n.d. |
| 64 | 240 | 190 | 190 | 236 | 218 | 236 | n.d. |
| 71 | 233 | 199 | 178 | 239 | 245 | 228 | n.d. |
| 78 | 234 | 189 | 177 | 234 | 250 | 221 | n.d. |
| 85 | 246 | 196 | 187 | 243 | 240 | 224 | n.d. |

n.d. = no data

Bleeding Assay

On different days during the treatment period, bleeding assay was performed using a Surgicutt Jr. device (ITC, New Jersey). Monkeys were placed in monkey chair with their arm placed in a steady support. The arm was lightly shaved and a sphygmomanometer was placed on the upper arm. The cuff of the sphygmomanometer was inflated to 40 mm Hg and this pressure was maintained throughout the procedure. The area on the upper arm to be incised was cleansed with an antiseptic swab and the Surgicutt Jr device was used to make an incision over the lateral aspect, volar surface of the forearm, parallel to and 5 cm below the antecubital crease. At the exact moment the incision was made, a stopwatch was started. Every 30 seconds, blood from the incision was blotted out using a blotting paper without directly touching the incision, so that formation of the platelet plug was not disturbed. Blood was blotted out every 30 seconds until blood no longer stained the paper. The stopwatch was then stopped and the bleeding time determined. The sphygmomanometer was removed from the animal's arm, the incision site was antiseptically swabbed and a wound closure strip applied. The results are provided in Table X, expressed in seconds. The results are provided in Table 120. The ISIS oligonucleotide, ISIS 416850, given with the chronic dose regimen is distinguished from the other oligonucleotides with an asterisk (*).

These data suggest that the hemorrhagic potential of the compounds provided herein is low.

TABLE 120

| Bleeding assay in cynomolgus monkeys | | | | | | | |
|---|---|---|---|---|---|---|---|
| Days before/after treatment | PBS | ISIS 416838 | ISIS 416850 | ISIS 416858 | ISIS 416864 | ISIS 417002 | ISIS 416850* |
| −14 | 147 | 200 | 172 | 154 | 166 | 185 | 177 |
| −5 | 153 | 150 | 127 | 149 | 111 | 175 | 93 |
| 15 | 111 | 167 | 165 | 146 | 153 | 174 | 149 |
| 22 | 113 | 165 | 151 | 100 | 133 | 194 | 143 |
| 36 | 174 | 166 | 137 | 206 | 205 | 186 | 221 |
| 43 | 157 | 120 | 216 | 111 | 146 | 120 | 156 |
| 57 | 147 | 238 | 195 | 138 | 216 | 206 | n.d. |
| 64 | 113 | 131 | 201 | 113 | 218 | 146 | n.d. |
| 78 | 114 | 145 | 203 | 186 | 170 | 163 | n.d. |
| 85 | 147 | 201 | 201 | 191 | 203 | 182 | n.d. |

Platelet Aggregation Assay

Platelet aggregation was initiated by adding 1 mmol/L ADP and/or 3 μg collagen (depending on the collection day, as outlined in Table 121) to plasma samples, and was allowed to proceed for 10 minutes. Aggregation was characterized by recording the change in the electrical resistance or impedance and the change in the initial slope of aggregation after platelet shape change. The aggregation test was performed twice per sample on each collection day and the average value was taken. The ISIS oligonucleotide, ISIS 416850, given with the chronic dose regimen is distinguished from the other oligonucleotides with an asterisk (*).

TABLE 121

| Effect of antisense oligonucleotide treatment on platelet aggregation in cynomolgus monkeys in Ohms | | | | | | | | | |
|---|---|---|---|---|---|---|---|---|---|
| | day −5 (with collagen) | day 15 (with ADP) | day 36 (with ADP) | day 43 (with collagen) | day 57 (with ADP) | day 64 (with collagen) | day 78 (with ADP) | day 85 (with ADP) | day 85 (with collagen) |
| PBS | 17 | 15 | 7 | 14 | 16 | 13 | 12 | 16 | 17 |
| ISIS 416838 | 15 | 15 | 8 | 16 | 7 | 13 | 11 | 15 | 24 |

TABLE 121-continued

Effect of antisense oligonucleotide treatment on platelet aggregation in cynomolgus monkeys in Ohms

| | day −5 (with collagen) | day 15 (with ADP) | day 36 (with ADP) | day 43 (with collagen) | day 57 (with ADP) | day 64 (with collagen) | day 78 (with ADP) | day 85 (with ADP) | day 85 (with collagen) |
|---|---|---|---|---|---|---|---|---|---|
| ISIS 416850 | 23 | 12 | 16 | 16 | 18 | 17 | 9 | 22 | 26 |
| ISIS 416858 | 22 | 19 | 17 | 16 | 11 | 14 | 8 | 18 | 23 |
| ISIS 416864 | 27 | 20 | 17.8 | 20 | 18 | 17 | 13 | 22 | 28 |
| ISIS 417002 | 21 | 16 | 13.9 | 19 | 18 | 18 | 18 | 22 | 24 |
| ISIS 416850* | 21 | 14 | 11.6 | 21 | n.d. | n.d. | n.d. | n.d. | n.d. |

n.d. = no data

Body and Organ Weights

Body weights were taken once weekly throughout the dosing regimen. The measurements of each group are given in Table 122 expressed in grams. The results indicate that treatment with the antisense oligonucleotides did not cause any adverse changes in the health of the animals, which may have resulted in a significant alteration in weight compared to the PBS control. Organ weights were taken after the animals were euthanized and livers, kidneys and spleens were harvested and weighed. The results are presented in Table 123 and also show no significant alteration in weights compared to the PBS control, except for ISIS 416858, which shows increase in spleen weight. The ISIS oligonucleotide, ISIS 416850, given with the chronic dose regimen is distinguished from the other oligonucleotides with an asterisk (*).

TABLE 122

Weekly measurements of body weights (g) of cynomolgus monkeys

| day | PBS | ISIS 416838 | ISIS 416850 | ISIS 416858 | ISIS 416864 | ISIS 417002 | ISIS 416850* |
|---|---|---|---|---|---|---|---|
| 1 | 2780 | 2720 | 2572 | 2912 | 2890 | 2640 | 2665 |
| 8 | 2615 | 2592 | 2430 | 2740 | 2784 | 2523 | 2579 |
| 15 | 2678 | 2642 | 2474 | 2760 | 2817 | 2571 | 2607 |
| 22 | 2715 | 2702 | 2514 | 2800 | 2857 | 2617 | 2661 |
| 29 | 2717 | 2689 | 2515 | 2763 | 2863 | 2622 | 2667 |
| 36 | 2738 | 2708 | 2545 | 2584 | 3327 | 2631 | 2656 |
| 43 | 2742 | 2700 | 2544 | 2607 | 3355 | 2630 | 2670 |
| 50 | 2764 | 2731 | 2613 | 2646 | 3408 | 2652 | 2679 |
| 57 | 2763 | 2737 | 2629 | 2617 | 3387 | 2654 | n.d. |
| 64 | 2781 | 2746 | 2642 | 2618 | 3384 | 2598 | n.d. |
| 71 | 2945 | 2869 | 2769 | 2865 | 2942 | 2727 | n.d. |
| 78 | 2815 | 2766 | 2660 | 2713 | 2822 | 2570 | n.d. |

n.d. = no data

TABLE 123

Organ weights (g) of cynomolgus monkeys after antisense oligonucleotide treatment

| | Liver | Spleen | Kidney |
|---|---|---|---|
| PBS | 46 | 4 | 11 |
| ISIS 416838 | 63 | 5 | 12 |
| ISIS 416580 | 64 | 4 | 16 |
| ISIS 416858 | 60 | 12 | 13 |
| ISIS 416864 | 53 | 5 | 14 |
| ISIS 417002 | 51 | 5 | 15 |

Liver Function

To evaluate the impact of ISIS oligonucleotides on hepatic function, plasma concentrations of transaminases were measured using an automated clinical chemistry analyzer (Hitachi Olympus AU400e, Melville, N.Y.). Plasma concentrations of ALT (alanine transaminase) and AST (aspartate transaminase) were measured and the results are presented in Tables 124 and 125 expressed in IU/L. Those antisense oligonucleotides which did not affect an increase in ALT/AST levels above seven-fold of control levels were selected for further studies. Plasma levels of bilirubin were also measured and results are presented in Table 126 expressed in mg/dL. Those antisense oligonucleotides which did not affect an increase in levels of bilirubin more than two-fold of the control levels by antisense oligonucleotide treatment were selected for further studies. The ISIS oligonucleotide, ISIS 416850, given with the chronic dose regimen is distinguished from the other oligonucleotides with an asterisk (*).

TABLE 124

Effect of antisense oligonucleotide treatment on ALT (IU/L) in the liver of cynomolgus monkeys

| Days before/after treatment | PBS | ISIS 416838 | ISIS 416850 | ISIS 416858 | ISIS 416864 | ISIS 417002 | ISIS 416850* |
|---|---|---|---|---|---|---|---|
| −14 | 57 | 76 | 54 | 47 | 54 | 61 | 80 |
| 22 | 39 | 36 | 41 | 28 | 37 | 36 | 42 |
| 43 | 36 | 35 | 43 | 36 | 36 | 35 | 41 |

TABLE 124-continued

Effect of antisense oligonucleotide treatment on ALT (IU/L) in the liver of cynomolgus monkeys

| Days before/after treatment | PBS | ISIS 416838 | ISIS 416850 | ISIS 416858 | ISIS 416864 | ISIS 417002 | ISIS 416850* |
|---|---|---|---|---|---|---|---|
| 64 | 38 | 40 | 60 | 47 | 43 | 42 | n.d. |
| 85 | 34 | 41 | 75 | 50 | 43 | 116 | n.d. |

n.d. = no data

TABLE 125

Effect of antisense oligonucleotide treatment on AST (IU/L) in the liver of cynomolgus monkeys

| Days before/after treatment | PBS | ISIS 416838 | ISIS 416850 | ISIS 416858 | ISIS 416864 | ISIS 417002 | ISIS 416850* |
|---|---|---|---|---|---|---|---|
| −14 | 71 | 139 | 81 | 58 | 76 | 114 | 100 |
| 22 | 43 | 39 | 45 | 38 | 41 | 44 | 39 |
| 43 | 38 | 32 | 50 | 39 | 40 | 42 | 40 |
| 64 | 35 | 33 | 56 | 50 | 46 | 37 | n.d. |
| 85 | 41 | 30 | 82. | 49 | 56 | 50 | n.d. |

n.d. = no data

TABLE 126

Effect of antisense oligonucleotide treatment on bilirubin (mg/dL) in the liver of cynomolgus monkeys

| Days before/after treatment | PBS | ISIS 416838 | ISIS 416850 | ISIS 416858 | ISIS 416864 | ISIS 417002 | ISIS 416850* |
|---|---|---|---|---|---|---|---|
| −14 | 0.24 | 0.26 | 0.21 | 0.27 | 0.31 | 0.26 | 0.28 |
| 22 | 0.16 | 0.17 | 0.13 | 0.18 | 0.22 | 0.20 | 0.19 |
| 43 | 0.17 | 0.17 | 0.13 | 0.14 | 0.17 | 0.21 | 0.18 |
| 64 | 0.19 | 0.15 | 0.14 | 0.12 | 0.16 | 0.14 | n.d. |
| 85 | 0.20 | 0.13 | 0.14 | 0.14 | 0.17 | 0.12 | n.d. |

n.d. = no data

Kidney Function

To evaluate the impact of ISIS oligonucleotides on kidney function, urine samples were collected. The ratio of urine protein to creatinine in urine samples after antisense oligonucleotide treatment was calculated and is presented in Table 127. Those antisense oligonucleotides which did not affect more than a five-fold increase in urine protein/creatinine ratios compared to the PBS control were selected for further studies.

TABLE 127

Effect of antisense oligonucleotide treatment on urine protein to creatinine ratio in cynomolgus monkeys

| | Day 80 | Day 84 |
|---|---|---|
| PBS | 0.09 | 0.10 |
| ISIS 416838 | 0.13 | 0.13 |
| ISIS 416850 | 0.09 | 0.12 |
| ISIS 416858 | 0.10 | 0.07 |
| ISIS 416864 | 0.36 | 0.34 |
| ISIS 417002 | 0.18 | 0.24 |

Measurement of Oligonucleotide Concentration

The concentration of the full-length oligonucleotide as well as the elapsed time oligonucleotide degradation and elimination from the liver and kidney were evaluated. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 270) was added prior to extraction. Tissue sample concentrations were calculated using calibration curves, with a lower limit of quantitation (LLOQ) of approximately 1.14 μg/g. Half-lives were then calculated using WinNonlin software (PHARSIGHT). The results are presented in Tables 128 and 129, expressed as μg/g liver or kidney tissue.

TABLE 128

Full-length oligonucleotide concentration (μg/g) in the liver and kidney of cynomolgus monkeys

| ISIS No. | Kidney | Liver |
|---|---|---|
| 416838 | 1339 | 1087 |
| 416850 | 2845 | 1225 |
| 416858 | 1772 | 1061 |
| 416864 | 2093 | 1275 |
| 417002 | 2162 | 1248 |

TABLE 129

| Total oligonucleotide concentration (μg/g) in the liver and kidney of cynomolgus monkeys | | |
|---|---|---|
| ISIS No. | Kidney | Liver |
| 416838 | 1980 | 1544 |
| 416850 | 3988 | 1558 |
| 416858 | 2483 | 1504 |
| 416864 | 3522 | 1967 |
| 417002 | 3462 | 1757 |

Hematology Assays

Blood obtained from all monkey groups were sent to Korea Institute of Toxicology (KIT) for HCT, MCV, MCH, and MCHC analysis, as well as measurements of the various blood cells, such as WBC (neutrophils, lymphocytes, monocytes, eosinophils, basophils, reticulocytes), RBC, platelets and total hemoglobin content. The results are presented in Tables 130-143. Those antisense oligonucleotides which did not affect a decrease in platelet count of more than 50% and an increase in monocyte count of more than three-fold were selected for further studies. The ISIS oligonucleotide, ISIS 416850, given with the chronic dose regimen is distinguished from the other oligonucleotides with an asterisk (*).

TABLE 130

Effect of antisense oligonucleotide treatment on WBC count ($\times 10^3/\mu L$) in cynomolgus monkeys

| | PBS | ISIS 416838 | ISIS 416850 | ISIS 416858 | ISIS 416864 | ISIS 417002 | ISIS 416850* |
|---|---|---|---|---|---|---|---|
| day −14 | 14 | 12 | 13 | 14 | 13 | 13 | 15 |
| day −5 | 13 | 12 | 13 | 14 | 13 | 14 | 15 |
| day 8 | 10 | 10 | 10 | 12 | 11 | 10 | 13 |
| day 15 | 10 | 10 | 9 | 11 | 10 | 10 | 16 |
| day 22 | 12 | 11 | 10 | 11 | 10 | 10 | 15 |
| day 29 | 11 | 11 | 11 | 12 | 10 | 10 | 14 |
| day 36 | 10 | 10 | 10 | 12 | 10 | 11 | 16 |
| day 43 | 10 | 10 | 9 | 11 | 10 | 10 | 15 |
| day 50 | 12 | 11 | 11 | 13 | 12 | 13 | 15 |
| day 57 | 11 | 12 | 11 | 13 | 12 | 12 | n.d. |
| day 64 | 11 | 13 | 11 | 12 | 11 | 11 | n.d. |
| day 71 | 15 | 15 | 15 | 13 | 14 | 12 | n.d. |
| day 78 | 10 | 11 | 12 | 11 | 11 | 9 | n.d. |
| day 85 | 10 | 12 | 15 | 11 | 12 | 10 | n.d. |

n.d. = no data

TABLE 131

Effect of antisense oligonucleotide treatment on RBC count ($\times 10^6/\mu L$) in cynomolgus monkeys

| | PBS | ISIS 416838 | ISIS 416850 | ISIS 416858 | ISIS 416864 | ISIS 417002 | ISIS 416850* |
|---|---|---|---|---|---|---|---|
| day −14 | 5.7 | 5.6 | 5.3 | 5.6 | 5.5 | 5.6 | 5.5 |
| day −5 | 5.7 | 5.6 | 5.5 | 5.6 | 5.6 | 5.6 | 5.5 |
| day 8 | 5.7 | 5.7 | 5.4 | 5.6 | 5.7 | 5.6 | 5.5 |
| day 15 | 5.6 | 5.6 | 5.3 | 5.4 | 5.7 | 5.4 | 5.3 |
| day 22 | 5.5 | 5.4 | 5 | 5.3 | 5.3 | 5.2 | 5.1 |
| day 29 | 5.6 | 5.3 | 4.9 | 5.3 | 5.3 | 5.2 | 5.2 |
| day 36 | 5.7 | 5.5 | 5.3 | 5.5 | 5.6 | 5.4 | 5.3 |
| day 43 | 5.7 | 5.6 | 5.2 | 5.5 | 5.5 | 5.4 | 5.2 |
| day 50 | 5.8 | 5.5 | 5.2 | 5.5 | 5.6 | 5.4 | 5.3 |
| day 57 | 5.7 | 5.5 | 5.2 | 5.6 | 5.5 | 4.9 | n.d. |
| day 64 | 5.8 | 5.6 | 5.4 | 5.7 | 5.6 | 5.4 | n.d. |
| day 71 | 5.6 | 5.5 | 5.4 | 5.6 | 5.6 | 5.5 | n.d. |
| day 78 | 5.6 | 5.4 | 5.3 | 5.4 | 5.3 | 5.4 | n.d. |
| day 85 | 5.6 | 5.5 | 5.5 | 5.5 | 5.4 | 5.4 | n.d. |

n.d. = no data

TABLE 132

Effect of antisense oligonucleotide treatment on hemoglobin (g/dL) in cynomolgus monkeys

| | PBS | ISIS 416838 | ISIS 416850 | ISIS 416858 | ISIS 416864 | ISIS 417002 | ISIS 416850* |
|---|---|---|---|---|---|---|---|
| day −14 | 13.2 | 12.9 | 12.4 | 13.2 | 12.7 | 13.0 | 12.8 |
| day −5 | 13.1 | 13.1 | 12.7 | 13.2 | 13.0 | 13.2 | 12.8 |
| day 8 | 13.1 | 12.9 | 12.4 | 12.8 | 12.7 | 12.8 | 12.5 |
| day 15 | 12.9 | 12.9 | 12.1 | 12.6 | 12.8 | 12.3 | 12.2 |
| day 22 | 12.7 | 12.5 | 11.6 | 12.4 | 12.1 | 12.1 | 11.7 |
| day 29 | 12.8 | 12.4 | 11.5 | 12.3 | 12.1 | 12.0 | 12.0 |
| day 36 | 13.0 | 12.8 | 12.2 | 12.6 | 12.5 | 12.5 | 12.3 |
| day 43 | 12.9 | 12.7 | 11.8 | 12.4 | 12.2 | 12.3 | 11.8 |
| day 50 | 12.6 | 12.3 | 11.8 | 12.2 | 12.1 | 12.3 | 11.9 |
| day 57 | 13.1 | 12.6 | 12.1 | 12.7 | 12.3 | 11.3 | n.d. |
| day 64 | 13.1 | 12.6 | 12.3 | 12.8 | 12.1 | 12.2 | n.d. |
| day 71 | 12.9 | 12.7 | 12.3 | 12.7 | 12.2 | 12.5 | n.d. |
| day 78 | 13.0 | 12.5 | 12.2 | 12.4 | 11.9 | 12.4 | n.d. |
| day 85 | 13.2 | 12.4 | 12.7 | 11.9 | 12.3 | 12.2 | n.d. |

n.d. = no data

TABLE 133

| Effect of antisense oligonucleotide treatment on hematocrit (%) in cynomolgus monkeys | | | | | | | |
|---|---|---|---|---|---|---|---|
| | PBS | ISIS 416838 | ISIS 416850 | ISIS 416858 | ISIS 416864 | ISIS 417002 | ISIS 416850* |
| day −14 | 46 | 42 | 41 | 43 | 43 | 44 | 44 |
| day −5 | 44 | 42 | 43 | 42 | 44 | 45 | 43 |
| day 8 | 44 | 43 | 43 | 43 | 44 | 44 | 43 |
| day 15 | 44 | 42 | 40 | 40 | 42 | 40 | 40 |
| day 22 | 45 | 43 | 41 | 41 | 42 | 41 | 40 |
| day 29 | 46 | 43 | 41 | 41 | 43 | 42 | 42 |
| day 36 | 46 | 43 | 42 | 40 | 42 | 42 | 41 |
| day 43 | 46 | 43 | 40 | 40 | 42 | 41 | 40 |
| day 50 | 48 | 44 | 42 | 41 | 44 | 43 | 42 |
| day 57 | 46 | 43 | 42 | 41 | 42 | 38 | n.d. |
| day 64 | 47 | 44 | 43 | 42 | 42 | 41 | n.d. |
| day 71 | 46 | 44 | 43 | 42 | 44 | 43 | n.d. |
| day 78 | 43 | 41 | 41 | 39 | 39 | 40 | n.d. |
| day 85 | 43 | 42 | 42 | 39 | 40 | 41 | n.d. |

n.d. = no data

TABLE 134

| Effect of antisense oligonucleotide treatment on MCV (fL) in cynomolgus monkeys | | | | | | | |
|---|---|---|---|---|---|---|---|
| | PBS | ISIS 416838 | ISIS 416850 | ISIS 416858 | ISIS 416864 | ISIS 417002 | ISIS 416850* |
| day −14 | 81 | 77 | 78 | 77 | 79 | 79 | 81 |
| day −5 | 78 | 76 | 77 | 75 | 79 | 80 | 78 |
| day 8 | 77 | 77 | 80 | 77 | 78 | 79 | 79 |
| day 15 | 78 | 75 | 76 | 74 | 74 | 76 | 75 |
| day 22 | 84 | 80 | 83 | 77 | 79 | 79 | 79 |
| day 29 | 83 | 81 | 83 | 78 | 80 | 81 | 82 |
| day 36 | 81 | 78 | 80 | 75 | 76 | 78 | 76 |
| day 43 | 80 | 78 | 79 | 74 | 77 | 77 | 77 |
| day 50 | 84 | 80 | 83 | 76 | 79 | 80 | 80 |
| day 57 | 82 | 79 | 80 | 74 | 77 | 80 | n.d. |
| day 64 | 81 | 79 | 79 | 73 | 75 | 76 | n.d. |
| day 71 | 84 | 80 | 80 | 75 | 79 | 78 | n.d. |
| day 78 | 78 | 76 | 79 | 72 | 74 | 75 | n.d. |
| day 85 | 77 | 77 | 77 | 72 | 74 | 76 | n.d. |

n.d. = no data

TABLE 135

| Effect of antisense oligonucleotide treatment on MCH (pg) in cynomolgus monkeys | | | | | | | |
|---|---|---|---|---|---|---|---|
| | PBS | ISIS 416838 | ISIS 416850 | ISIS 416858 | ISIS 416864 | ISIS 417002 | ISIS 416850* |
| day −14 | 23 | 23 | 23 | 24 | 23 | 24 | 24 |
| day −5 | 23 | 23 | 23 | 23 | 23 | 24 | 23 |
| day 8 | 23 | 23 | 23 | 23 | 23 | 23 | 23 |
| day 15 | 23 | 23 | 23 | 23 | 23 | 23 | 23 |
| day 22 | 23 | 23 | 24 | 24 | 23 | 23 | 23 |
| day 29 | 23 | 23 | 23 | 23 | 23 | 23 | 23 |
| day 36 | 23 | 23 | 23 | 23 | 23 | 23 | 23 |
| day 43 | 23 | 23 | 23 | 23 | 22 | 23 | 23 |
| day 50 | 22 | 23 | 23 | 23 | 22 | 23 | 23 |
| day 57 | 23 | 23 | 23 | 22 | 23 | 23 | n.d. |
| day 64 | 23 | 23 | 22 | 22 | 23 | 22 | n.d. |
| day 71 | 23 | 23 | 23 | 22 | 23 | 23 | n.d. |
| day 78 | 23 | 23 | 23 | 23 | 23 | 23 | n.d. |
| day 85 | 23 | 23 | 22 | 22 | 23 | 23 | n.d. |

n.d. = no data

TABLE 136

| Effect of antisense oligonucleotide treatment on MCHC (g/dL) in cynomolgus monkeys | | | | | | | |
|---|---|---|---|---|---|---|---|
| | PBS | ISIS 416838 | ISIS 416850 | ISIS 416858 | ISIS 416864 | ISIS 417002 | ISIS 416850* |
| day −14 | 29 | 30 | 30 | 31 | 29 | 30 | 29 |
| day −5 | 30 | 31 | 30 | 31 | 29 | 30 | 30 |
| day 8 | 30 | 30 | 29 | 30 | 29 | 29 | 29 |
| day 15 | 30 | 31 | 30 | 31 | 30 | 31 | 30 |
| day 22 | 28 | 29 | 28 | 30 | 29 | 29 | 29 |
| day 29 | 28 | 29 | 28 | 30 | 29 | 29 | 28 |
| day 36 | 28 | 30 | 29 | 31 | 30 | 30 | 30 |
| day 43 | 28 | 30 | 29 | 31 | 29 | 30 | 30 |
| day 50 | 26 | 28 | 28 | 30 | 28 | 29 | 29 |
| day 57 | 29 | 29 | 29 | 31 | 29 | 29 | n.d. |
| day 64 | 28 | 29 | 29 | 30 | 29 | 30 | n.d. |
| day 71 | 28 | 29 | 28 | 30 | 28 | 29 | n.d. |
| day 78 | 30 | 30 | 29 | 32 | 30 | 31 | n.d. |
| day 85 | 31 | 30 | 30 | 31 | 30 | 30 | n.d. |

n.d. = no data

TABLE 137

Effect of antisense oligonucleotide treatment on platelet count (×10³/μL) in cynomolgus monkeys

| | PBS | ISIS 416838 | ISIS 416850 | ISIS 416858 | ISIS 416864 | ISIS 417002 | ISIS 416850* |
|---|---|---|---|---|---|---|---|
| day −14 | 349 | 377 | 528 | 419 | 434 | 442 | 387 |
| day −5 | 405 | 425 | 573 | 463 | 456 | 466 | 434 |
| day 8 | 365 | 387 | 548 | 391 | 438 | 435 | 401 |
| day 15 | 375 | 387 | 559 | 400 | 439 | 410 | 396 |
| day 22 | 294 | 319 | 466 | 316 | 364 | 377 | 347 |
| day 29 | 311 | 337 | 475 | 336 | 397 | 410 | 370 |
| day 36 | 326 | 370 | 505 | 371 | 428 | 415 | 379 |
| day 43 | 336 | 365 | 490 | 342 | 351 | 393 | 391 |
| day 50 | 379 | 372 | 487 | 331 | 419 | 389 | 351 |
| day 57 | 345 | 371 | 528 | 333 | 409 | 403 | n.d. |
| day 64 | 329 | 358 | 496 | 295 | 383 | 436 | n.d. |
| day 71 | 322 | 365 | 465 | 286 | 394 | 490 | n.d. |
| day 78 | 309 | 348 | 449 | 262 | 366 | 432 | n.d. |
| day 85 | 356 | 344 | 458 | 267 | 387 | 418 | n.d. |

n.d. = no data

TABLE 138

Effect of antisense oligonucleotide treatment on reticulocytes (%) in cynomolgus monkeys

| | PBS | ISIS 416838 | ISIS 416850 | ISIS 416858 | ISIS 416864 | ISIS 417002 | ISIS 416850* |
|---|---|---|---|---|---|---|---|
| day −14 | 1.4 | 1.0 | 1.7 | 1.0 | 0.9 | 0.9 | 1.1 |
| day −5 | 1.0 | 0.9 | 1.2 | 0.9 | 0.9 | 0.8 | 0.8 |
| day 8 | 1.0 | 1.2 | 1.2 | 1.2 | 0.8 | 1.1 | 1.1 |
| day 15 | 1.5 | 1.2 | 1.9 | 1.6 | 0.8 | 1.1 | 1.0 |
| day 22 | 1.2 | 1.2 | 1.9 | 1.3 | 0.9 | 1.2 | 1.0 |
| day 29 | 1.6 | 1.6 | 2.5 | 1.5 | 1.3 | 1.6 | 1.4 |
| day 36 | 1.7 | 1.6 | 2.2 | 1.6 | 1.3 | 1.3 | 1.3 |
| day 43 | 1.3 | 1.2 | 1.6 | 1.3 | 1.1 | 1.1 | 1.0 |
| day 50 | 1.6 | 1.6 | 2.7 | 1.5 | 1.3 | 1.6 | 1.2 |
| day 57 | 1.8 | 1.5 | 2.0 | 1.4 | 1.0 | 4.6 | n.d. |
| day 64 | 1.3 | 1.3 | 1.7 | 1.0 | 0.8 | 1.3 | n.d. |
| day 71 | 1.6 | 1.3 | 1.8 | 1.3 | 1.0 | 1.3 | n.d. |
| day 78 | 1.5 | 1.4 | 1.8 | 1.2 | 1.2 | 1.3 | n.d. |
| day 85 | 1.5 | 1.5 | 2.3 | 1.3 | 1.5 | 1.4 | n.d. |

n.d. = no data

TABLE 139

Effect of antisense oligonucleotide treatment on neutrophils (%) in cynomolgus monkeys

| | PBS | ISIS 416838 | ISIS 416850 | ISIS 416858 | ISIS 416864 | ISIS 417002 | ISIS 416850* |
|---|---|---|---|---|---|---|---|
| day −14 | 40 | 36 | 49 | 37 | 53 | 43 | 48 |
| day −5 | 37 | 35 | 52 | 46 | 51 | 43 | 53 |
| day 8 | 54 | 42 | 57 | 51 | 52 | 46 | 53 |
| day 15 | 49 | 43 | 58 | 54 | 59 | 57 | 73 |
| day 22 | 41 | 37 | 57 | 47 | 59 | 55 | 64 |
| day 29 | 44 | 36 | 53 | 43 | 44 | 45 | 42 |
| day 36 | 37 | 39 | 57 | 47 | 58 | 61 | 72 |
| day 43 | 40 | 30 | 50 | 45 | 57 | 57 | 61 |
| day 50 | 36 | 31 | 45 | 46 | 49 | 61 | 62 |
| day 57 | 41 | 32 | 49 | 44 | 57 | 54 | n.d. |
| day 64 | 40 | 30 | 41 | 37 | 49 | 55 | n.d. |
| day 71 | 38 | 28 | 27 | 26 | 42 | 34 | n.d. |
| day 78 | 42 | 35 | 42 | 39 | 48 | 51 | n.d. |
| day 85 | 30 | 22 | 60 | 40 | 39 | 36 | n.d. |

n.d. = no data

TABLE 140

Effect of antisense oligonucleotide treatment on lymphocytes (%) in cynomolgus monkeys

| | PBS | ISIS 416838 | ISIS 416850 | ISIS 416858 | ISIS 416864 | ISIS 417002 | ISIS 416850* |
|---|---|---|---|---|---|---|---|
| day −14 | 54 | 59 | 47 | 58 | 42 | 53 | 47 |
| day −5 | 56 | 59 | 43 | 49 | 44 | 53 | 43 |
| day 8 | 43 | 54 | 39 | 45 | 45 | 50 | 44 |
| day 15 | 47 | 53 | 38 | 43 | 38 | 40 | 24 |
| day 22 | 54 | 59 | 39 | 49 | 37 | 41 | 33 |
| day 29 | 51 | 59 | 43 | 51 | 51 | 50 | 53 |
| day 36 | 58 | 57 | 39 | 49 | 38 | 35 | 26 |
| day 43 | 55 | 65 | 45 | 51 | 39 | 39 | 36 |
| day 50 | 59 | 64 | 49 | 48 | 46 | 34 | 35 |
| day 57 | 55 | 63 | 45 | 51 | 39 | 40 | n.d. |
| day 64 | 56 | 64 | 53 | 56 | 46 | 39 | n.d. |
| day 71 | 56 | 65 | 61 | 66 | 52 | 59 | n.d. |
| day 78 | 53 | 60 | 51 | 54 | 46 | 41 | n.d. |
| day 85 | 63 | 72 | 34 | 52 | 54 | 56 | n.d. |

n.d. = no data

TABLE 141

Effect of antisense oligonucleotide treatment on eosinophils (%) in cynomolgus monkeys

| | PBS | ISIS 416838 | ISIS 416850 | ISIS 416858 | ISIS 416864 | ISIS 417002 | ISIS 416850* |
|---|---|---|---|---|---|---|---|
| day −14 | 1.3 | 0.6 | 1.0 | 0.7 | 1.0 | 0.3 | 0.5 |
| day −5 | 1.5 | 0.6 | 1.6 | 1.3 | 0.9 | 0.3 | 0.7 |
| day 8 | 0.9 | 0.4 | 1.1 | 0.3 | 0.7 | 0.2 | 0.5 |
| day 15 | 0.7 | 0.3 | 1.0 | 0.3 | 0.5 | 0.1 | 0.2 |
| day 22 | 0.9 | 0.5 | 0.7 | 0.6 | 0.9 | 0.3 | 0.5 |
| day 29 | 0.9 | 0.3 | 1.2 | 0.6 | 0.9 | 0.3 | 0.8 |
| day 36 | 0.9 | 0.5 | 1.7 | 0.4 | 0.6 | 0.2 | 0.4 |
| day 43 | 0.9 | 0.6 | 1.2 | 0.3 | 0.6 | 0.2 | 0.4 |
| day 50 | 1.2 | 0.8 | 1.2 | 0.4 | 0.7 | 0.1 | 0.3 |
| day 57 | 0.7 | 0.6 | 1.0 | 0.3 | 0.4 | 0.2 | n.d. |
| day 64 | 1.0 | 0.7 | 1.3 | 0.4 | 0.7 | 0.2 | n.d. |
| day 71 | 1.6 | 0.8 | 1.8 | 0.9 | 1.1 | 0.3 | n.d. |
| day 78 | 1.0 | 0.9 | 1.0 | 0.5 | 1.2 | 0.1 | n.d. |
| day 85 | 1.3 | 1.5 | 1.2 | 0.6 | 1.6 | 0.2 | n.d. |

n.d. = no data

TABLE 142

Effect of antisense oligonucleotide treatment on monocytes (%) in cynomolgus monkeys

| | PBS | ISIS 416838 | ISIS 416850 | ISIS 416858 | ISIS 416864 | ISIS 417002 | ISIS 416850* |
|---|---|---|---|---|---|---|---|
| day −14 | 3.3 | 3.1 | 2.3 | 2.8 | 2.8 | 3.0 | 2.9 |
| day −5 | 3.8 | 3.6 | 2.8 | 2.8 | 3.3 | 3.2 | 2.4 |
| day 8 | 2.3 | 2.5 | 1.8 | 2.7 | 2.1 | 3.3 | 1.8 |
| day 15 | 2.7 | 2.4 | 2.0 | 2.2 | 2.4 | 2.3 | 1.5 |
| day 22 | 3.4 | 2.9 | 2.4 | 2.8 | 2.8 | 3.1 | 1.9 |
| day 29 | 3.3 | 3.2 | 2.7 | 3.8 | 3.4 | 3.5 | 2.7 |
| day 36 | 3.1 | 2.5 | 2.1 | 2.9 | 2.3 | 2.6 | 1.5 |
| day 43 | 3.5 | 3.3 | 2.6 | 3.1 | 2.1 | 2.8 | 1.8 |
| day 50 | 2.6 | 3.2 | 3.7 | 4.6 | 2.9 | 3.1 | 1.8 |
| day 57 | 2.6 | 3.2 | n.d.3.2 | 3.8 | 2.4 | 3.6 | n.d. |
| day 64 | 2.6 | 3.5 | n.d.3.5 | 4.4 | 2.8 | 4.0 | n.d. |

TABLE 142-continued

Effect of antisense oligonucleotide treatment on monocytes (%) in cynomolgus monkeys

| | PBS | ISIS 416838 | ISIS 416850 | ISIS 416858 | ISIS 416864 | ISIS 417002 | ISIS 416850* |
|---|---|---|---|---|---|---|---|
| day 71 | 3.4 | 4.3 | n.d.4.7 | 4.9 | 3.7 | 4.7 | n.d. |
| day 78 | 3.3 | 3.6 | n.d.4.5 | 4.9 | 3.7 | 4.7 | n.d. |
| day 85 | 4.4 | 3.7 | n.d.3.5 | 6.1 | 3.7 | 5.3 | n.d. |

n.d. = no data

TABLE 143

Effect of antisense oligonucleotide treatment on basophils (%) in cynomolgus monkeys

| | PBS | ISIS 416838 | ISIS 416850 | ISIS 416858 | ISIS 416864 | ISIS 417002 | ISIS 416850* |
|---|---|---|---|---|---|---|---|
| day −14 | 0.3 | 0.2 | 0.2 | 0.3 | 0.2 | 0.3 | 0.2 |
| day −5 | 0.3 | 0.3 | 0.2 | 0.3 | 0.2 | 0.3 | 0.3 |
| day 8 | 0.2 | 0.2 | 0.2 | 0.3 | 0.2 | 0.3 | 0.3 |
| day 15 | 0.3 | 0.3 | 0.2 | 0.2 | 0.2 | 0.2 | 0.2 |
| day 22 | 0.2 | 0.2 | 0.2 | 0.2 | 0.2 | 0.2 | 0.1 |
| day 29 | 0.3 | 0.2 | 0.2 | 0.2 | 0.3 | 0.2 | 0.3 |
| day 36 | 0.3 | 0.4 | 0.3 | 0.3 | 0.3 | 0.2 | 0.1 |
| day 43 | 0.3 | 0.4 | 0.3 | 0.3 | 0.4 | 0.3 | 0.2 |
| day 50 | 0.4 | 0.3 | 0.3 | 0.4 | 0.4 | 0.3 | 0.2 |
| day 57 | 0.2 | 0.3 | 0.4 | 0.2 | 0.3 | 0.3 | n.d. |
| day 64 | 0.3 | 0.4 | 0.4 | 0.4 | 0.4 | 0.2 | n.d. |
| day 71 | 0.2 | 0.5 | 0.3 | 0.4 | 0.4 | 0.3 | n.d. |
| day 78 | 0.2 | 0.4 | 0.3 | 0.4 | 0.3 | 0.3 | n.d. |
| day 85 | 0.3 | 0.3 | 0.3 | 0.3 | 0.4 | 0.3 | n.d. |

n.d. = no data

Cytokine and Chemokine Assays

Blood samples obtained from the monkey groups treated with PBS, ISIS 416850 and ISIS 416858 administered in the escalating dose regimen were sent to Pierce Biotechnology (Woburn, Mass.) for measurement of chemokine and cytokine levels. Levels of IL-1β, IL-6, IFN-γ, and TNF-α were measured using the respective primate antibodies and levels of IL-8, MW-1α, MCP-1, MIP-1β and RANTES were measured using the respective cross-reacting human antibodies. Measurements were taken 14 days before the start of treatment and on day 85, when the monkeys were euthanized. The results are presented in Tables 144 and 145.

TABLE 144

Effect of antisense oligonucleotide treatment on cytokine/chemokine levels (pg/mL) in cynomolgus monkeys on day −14

| | IL-1β | IL-6 | IFN-γ | TNF-α | IL-8 | MIP-1α | MCP-1 | MIP-1β | RANTES |
|---|---|---|---|---|---|---|---|---|---|
| PBS | 16 | 10 | 114 | 7 | 816 | 54 | 1015 | 118 | 72423 |
| ISIS 416850 | 3 | 30 | 126 | 14 | 1659 | 28 | 1384 | 137 | 75335 |
| ISIS 416858 | 5 | 9 | 60 | 9 | 1552 | 36 | 1252 | 122 | 112253 |

TABLE 145

| Effect of antisense oligonucleotide treatment on cytokine/chemokine levels (pg/mL) in cynomolgus monkeys on day 85 | | | | | | | | | |
|---|---|---|---|---|---|---|---|---|---|
| | IL-1β | IL-6 | IFN-γ | TNF-α | IL-8 | MIP-1α | MCP-1 | MIP-1β | RANTES |
| PBS | 7 | 4 | 102 | 34 | 87 | 23 | 442 | 74 | 84430 |
| ISIS 416850 | 13 | 17 | 18 | 27 | 172 | 41 | 2330 | 216 | 83981 |
| ISIS 416858 | 5 | 25 | 18 | 45 | 303 | 41 | 1752 | 221 | 125511 |

Example 46: Pharmacologic Effect of Antisense Oligonucleotides Targeting Human Factor 11 in Cynomolgus Monkeys Several antisense oligonucleotides chosen from the rodent tolerability studies (Examples 41-44) were tested in cynomolgus monkeys to determine their pharmacologic effects, relative efficacy on Factor 11 activity and tolerability in a cynomolgus monkey model. The antisense oligonucleotides were also compared to ISIS 416850 and ISIS 416858 selected from the monkey study described earlier (Example 45). All the ISIS oligonucleotides used in this study target human Factor 11 mRNA and are also fully cross-reactive with the rhesus monkey gene sequence (see Tables 44 and 46). It is expected that the rhesus monkey ISIS oligonucleotides are fully cross-reactive with the cynomolgus monkey gene sequence as well. At the time the study was undertaken, the cynomolgus monkey genomic sequence was not available in the National Center for Biotechnology Information (NCBI) database; therefore, cross-reactivity with the cynomolgus monkey gene sequence could not be confirmed.

Treatment

Groups, each consisting of two male and two female monkeys, were injected subcutaneously with 25 mg/kg of ISIS 416850, ISIS 449709, ISIS 445522, ISIS 449710, ISIS 449707, ISIS 449711, ISIS 449708, 416858, and ISIS 445531. Antisense oligonucleotide was administered to the monkeys at 25 mg/kg three times per week for week 1 and 25 mg/kg twice per week for weeks 2 to 8. A control group, consisting of two male and two female monkeys was injected subcutaneously with PBS according to the same dosing regimen. Body weights were taken 14 days and 7 days before the start of treatment and were then measured weekly throughout the treatment period. Blood samples were collected 14 days and 5 days before the start of treatment and subsequently several times during the dosing regimen for PT and aPTT measurements, and measurement of various hematologic factors. On day 55, the monkeys were euthanized by exsanguination while under deep anesthesia, and organs harvested for further analysis.

RNA Analysis

On day 55, RNA was extracted from liver tissue for real-time PCR analysis of Factor 11 using primer probe set LTS00301. Results are presented as percent inhibition of Factor 11, relative to PBS control. As shown in Table 146, treatment with ISIS 416850, ISIS 449709, ISIS 445522, ISIS 449710, ISIS 449707, ISIS 449708, ISIS 416858, and ISIS 445531 resulted in significant reduction of Factor 11 mRNA in comparison to the PBS control.

TABLE 146

| Inhibition of Factor 11 mRNA in the cynomolgus monkey liver relative to the PBS control | |
|---|---|
| Oligo ID | % inhibition |
| 416850 | 68 |
| 449709 | 69 |
| 445522 | 89 |
| 449710 | 52 |
| 449707 | 47 |
| 449711 | 0 |
| 449708 | 46 |
| 416858 | 89 |
| 445531 | 66 |

Protein Analysis

Plasma samples from all monkey groups taken on different days were analyzed by a sandwich-style ELISA assay (Affinity Biologicals Inc.) using an affinity-purified polyclonal anti-Factor 11 antibody as the capture antibody and a peroxidase-conjugated polyclonal anti-Factor 11 antibody as the detecting antibody. Monkey plasma was diluted 1:50 for the assay. Peroxidase activity was expressed by incubation with the substrate o-phenylenediamine. The color produced was quantified using a microplate reader at 490 nm and was considered to be proportional to the concentration of Factor 11 in the samples.

The results are presented in Table 147, expressed as percentage reduction relative to that of the PBS control. Treatment with ISIS 416850, ISIS 449709, ISIS 445522, and ISIS 416858 resulted in a time-dependent decrease in protein levels.

TABLE 147

| Inhibition of Factor 11 protein in the cynomolgus monkey liver relative to the PBS control | | | | | | | | | | |
|---|---|---|---|---|---|---|---|---|---|---|
| ISIS No. | Day −14 | Day −5 | Day 10 | Day 17 | Day 24 | Day 31 | Day 38 | Day 45 | Day 52 | Day 55 |
| 416850 | 0 | 0 | 20 | 31 | 38 | 52 | 51 | 53 | 53 | 58 |
| 449709 | 1 | 0 | 27 | 35 | 44 | 45 | 46 | 48 | 47 | 50 |
| 445522 | 2 | 0 | 36 | 50 | 61 | 70 | 73 | 77 | 80 | 82 |
| 449710 | 1 | 0 | 10 | 14 | 17 | 25 | 20 | 23 | 4 | 24 |
| 449707 | 0 | 0 | 16 | 19 | 21 | 29 | 28 | 35 | 29 | 32 |

TABLE 147-continued

| Inhibition of Factor 11 protein in the cynomolgus monkey liver relative to the PBS control | | | | | | | | | | |
|---|---|---|---|---|---|---|---|---|---|---|
| ISIS No. | Day −14 | Day −5 | Day 10 | Day 17 | Day 24 | Day 31 | Day 38 | Day 45 | Day 52 | Day 55 |
| 449711 | 0 | 1 | 5 | 3 | 6 | 9 | 2 | 4 | 3 | 5 |
| 449708 | 1 | 0 | 7 | 15 | 3 | 14 | 9 | 2 | 6 | 6 |
| 416858 | 4 | 0 | 36 | 49 | 62 | 68 | 74 | 79 | 81 | 81 |
| 445531 | 0 | 1 | 9 | 22 | 23 | 27 | 29 | 32 | 32 | 37 |

PT and aPTT Assay

PT and aPTT were measured using platelet poor plasma (PPP) from mice treated with ISIS oligonucleotides. PT and aPTT values are provided in Tables 148 and 149 and are reported as International Normalized Ratio (INR) values. INR values for PT and aPTT were determined by dividing the PT or aPTT value for each experimental group by the PT or aPTT for the PBS treated group. This ratio was then raised to the power of the International Sensitivity Index (ISI) of the tissue factor used. As shown in Table 148, PT was not significantly prolonged in mice treated with ISIS oligonucleotides. However, aPTT was significantly prolonged in groups treated with ISIS 416850, ISIS 445522, and ISIS 416858, as presented in Table 149. These data suggest that antisense reduction of Factor 11 affects the contact activation pathway, but not the extrinsic pathway of blood coagulation. Therefore, antisense reduction of Factor 11 with these ISIS oligonucleotides is useful for inhibiting the formation of a thrombus or clot in response to an abnormal vessel wall, but not in response to tissue injury.

TABLE 148

| Effect of antisense oligonucleotide treatment on PT ratio in cynomolgus monkeys | | | | | | | | | | |
|---|---|---|---|---|---|---|---|---|---|---|
| | Day −14 | Day −5 | Day 10 | Day 17 | Day 24 | Day 31 | Day 38 | Day45 | Day 52 | Day 55 |
| ISIS 416850 | 1.02 | 1.00 | 0.99 | 1.00 | 0.97 | 1.00 | 1.01 | 1.00 | 1.02 | 1.07 |
| ISIS 449709 | 1.00 | 0.96 | 0.95 | 0.95 | 0.95 | 0.95 | 0.97 | 0.97 | 0.99 | 1.03 |
| ISIS 445522 | 1.00 | 0.94 | 0.95 | 0.96 | 0.94 | 0.96 | 0.97 | 0.96 | 0.98 | 1.01 |
| ISIS 449710 | 1.03 | 0.96 | 0.98 | 1.00 | 0.97 | 0.98 | 0.99 | 0.97 | 0.98 | 1.06 |
| ISIS 449707 | 1.01 | 0.94 | 0.95 | 0.97 | 0.95 | 0.96 | 1.00 | 0.96 | 0.96 | 1.00 |
| ISIS 449711 | 1.00 | 0.95 | 0.94 | 0.95 | 0.94 | 0.98 | 1.02 | 1.01 | 1.00 | 1.07 |
| ISIS 449708 | 1.03 | 0.95 | 0.98 | 1.00 | 0.95 | 1.06 | 0.99 | 0.99 | 0.99 | 1.04 |
| ISIS 416858 | 1.01 | 0.96 | 0.96 | 0.98 | 0.95 | 1.00 | 0.97 | 1.00 | 0.99 | 1.01 |
| ISIS 445531 | 1.06 | 1.00 | 1.00 | 1.06 | 1.02 | 1.04 | 1.03 | 1.01 | 1.04 | 1.06 |

TABLE 149

| Effect of antisense oligonucleotide treatment on aPTT ratio in cynomolgus monkeys | | | | | | | | | | |
|---|---|---|---|---|---|---|---|---|---|---|
| | Day −14 | Day −5 | Day 10 | Day 17 | Day 24 | Day 31 | Day 38 | Day 45 | Day 52 | Day 55 |
| ISIS 416850 | 0.99 | 0.90 | 0.98 | 1.01 | 1.05 | 1.22 | 1.25 | 1.34 | 1.32 | 1.45 |
| ISIS 449709 | 0.99 | 0.91 | 0.99 | 1.03 | 1.05 | 1.08 | 1.08 | 1.15 | 1.09 | 1.17 |
| ISIS 445522 | 0.96 | 0.91 | 1.06 | 1.10 | 1.14 | 1.25 | 1.32 | 1.39 | 1.39 | 1.42 |
| ISIS 449710 | 1.07 | 0.98 | 1.00 | 0.97 | 1.00 | 1.04 | 1.02 | 1.06 | 1.03 | 1.07 |
| ISIS 449707 | 0.90 | 0.87 | 0.92 | 0.94 | 0.93 | 0.95 | 0.99 | 1.00 | 0.99 | 1.04 |
| ISIS 449711 | 0.94 | 0.96 | 0.92 | 0.90 | 0.92 | 0.89 | 0.93 | 0.94 | 0.92 | 0.96 |
| ISIS 449708 | 1.07 | 1.01 | 1.06 | 1.05 | 1.01 | 1.09 | 1.06 | 1.06 | 1.08 | 1.11 |
| ISIS 416858 | 1.03 | 0.96 | 1.07 | 1.13 | 1.21 | 1.32 | 1.41 | 1.49 | 1.53 | 1.61 |
| ISIS 445531 | 1.00 | 0.89 | 0.95 | 1.05 | 1.00 | 1.07 | 1.06 | 1.13 | 1.15 | 1.19 |

Body and Organ Weights

Body weights of each group are given in Table 150 expressed in grams. The results indicate that treatment with the antisense oligonucleotides did not cause any adverse changes in the health of the animals, which may have resulted in a significant alteration in weight compared to the PBS control. Organ weights were taken after the animals were euthanized on day 55, and livers, kidneys and spleens were harvested. The results are presented in Table 150 expressed as a percentage of the body weight and also show no significant alteration in weights compared to the PBS control, with the exception of ISIS 449711, which caused increase in spleen weight.

TABLE 150

Weekly measurements of body weights (g) of cynomolgus monkeys

| Days | PBS | ISIS 416850 | ISIS 449709 | ISIS 445522 | ISIS 449710 | ISIS 449707 | ISIS 449711 | ISIS 449708 | ISIS 416858 | ISIS 445531 |
|---|---|---|---|---|---|---|---|---|---|---|
| −14 | 2069 | 2061 | 2044 | 2050 | 2097 | 2072 | 2049 | 2096 | 2073 | 2079 |
| −7 | 2107 | 2074 | 2093 | 2042 | 2114 | 2083 | 2105 | 2163 | 2092 | 2092 |
| 1 | 2131 | 2083 | 2112 | 2047 | 2131 | 2107 | 2123 | 2130 | 2115 | 2125 |
| 8 | 2186 | 2072 | 2075 | 2094 | 2120 | 2088 | 2123 | 2148 | 2149 | 2119 |
| 15 | 2201 | 2147 | 2085 | 2092 | 2145 | 2120 | 2103 | 2125 | 2162 | 2109 |
| 22 | 2206 | 2139 | 2117 | 2114 | 2177 | 2142 | 2171 | 2110 | 2188 | 2143 |
| 29 | 2204 | 2159 | 2068 | 2125 | 2149 | 2155 | 2203 | 2095 | 2196 | 2148 |
| 36 | 2246 | 2136 | 2064 | 2121 | 2180 | 2158 | 2227 | 2100 | 2210 | 2191 |
| 43 | 2304 | 2186 | 2106 | 2142 | 2227 | 2197 | 2251 | 2125 | 2238 | 2233 |
| 50 | 2274 | 2143 | 2147 | 2127 | 2201 | 2185 | 2227 | 2076 | 2225 | 2197 |

TABLE 151

Organ weights (g) of cynomolgus monkeys after antisense oligonucleotide treatment

| | Liver | Spleen | Kidney |
|---|---|---|---|
| PBS | 2.3 | 0.16 | 0.48 |
| ISIS 416850 | 2.5 | 0.17 | 0.51 |
| ISIS 449709 | 2.6 | 0.21 | 0.57 |
| ISIS 445522 | 2.6 | 0.23 | 0.55 |
| ISIS 449710 | 2.6 | 0.24 | 0.58 |
| ISIS 449707 | 2.5 | 0.24 | 0.53 |
| ISIS 449711 | 2.6 | 0.32 | 0.54 |
| ISIS 449708 | 2.6 | 0.19 | 0.60 |
| ISIS 416858 | 2.6 | 0.24 | 0.47 |
| ISIS 445531 | 2.8 | 0.24 | 0.49 |

Liver Function

To evaluate the impact of ISIS oligonucleotides on hepatic function, plasma concentrations of ALT and AST were measured using an automated clinical chemistry analyzer (Hitachi Olympus AU400e, Melville, N.Y.). Plasma concentrations of alanine transaminase (ALT) and aspartate transaminase (AST) were measured and the results are presented in Tables 152 and 153 expressed in IU/L. Plasma levels of bilirubin were also measured and results are presented in Table 154 expressed in mg/dL. As observed in Tables 152-154, there were no significant increases in any of the liver metabolic markers after antisense oligonucleotide treatment.

TABLE 152

Effect of antisense oligonucleotide treatment on ALT (IU/L) in the liver of cynomolgus monkeys

| | Day −14 | Day −5 | Day 31 | Day 55 |
|---|---|---|---|---|
| PBS | 57 | 55 | 53 | 57 |
| ISIS 416850 | 48 | 42 | 45 | 55 |
| ISIS 449709 | 73 | 77 | 65 | 102 |
| ISIS 445522 | 43 | 45 | 40 | 60 |
| ISIS 449710 | 37 | 42 | 37 | 45 |
| ISIS 449707 | 54 | 56 | 52 | 63 |
| ISIS 449711 | 49 | 137 | 48 | 54 |
| ISIS 449708 | 48 | 54 | 44 | 46 |
| ISIS 416858 | 43 | 66 | 46 | 58 |
| ISIS 445531 | 84 | 73 | 57 | 73 |

TABLE 153

Effect of antisense oligonucleotide treatment on AST (IU/L) in the liver of cynomolgus monkeys

| | Day −14 | Day −5 | Day 31 | Day 55 |
|---|---|---|---|---|
| PBS | 65 | 45 | 44 | 47 |
| ISIS 416850 | 62 | 45 | 46 | 57 |
| ISIS 449709 | 62 | 51 | 45 | 71 |
| ISIS 445522 | 62 | 47 | 46 | 79 |
| ISIS 449710 | 52 | 38 | 37 | 64 |
| ISIS 449707 | 64 | 53 | 50 | 52 |
| ISIS 449711 | 58 | 78 | 47 | 47 |
| ISIS 449708 | 74 | 53 | 56 | 50 |
| ISIS 416858 | 64 | 100 | 60 | 69 |
| ISIS 445531 | 78 | 46 | 47 | 49 |

TABLE 154

Effect of antisense oligonucleotide treatment on bilirubin (mg/dL) in the liver of cynomolgus monkeys

| | Day −14 | Day −5 | Day 31 | Day 55 |
|---|---|---|---|---|
| PBS | 0.25 | 0.20 | 0.20 | 0.17 |
| ISIS 416850 | 0.26 | 0.22 | 0.26 | 0.17 |
| ISIS 449709 | 0.24 | 0.19 | 0.15 | 0.18 |
| ISIS 445522 | 0.24 | 0.20 | 0.14 | 0.18 |
| ISIS 449710 | 0.24 | 0.19 | 0.15 | 0.22 |

TABLE 154-continued

Effect of antisense oligonucleotide treatment on bilirubin (mg/dL) in the liver of cynomolgus monkeys

| | Day −14 | Day −5 | Day 31 | Day 55 |
|---|---|---|---|---|
| ISIS 449707 | 0.27 | 0.19 | 0.13 | 0.16 |
| ISIS 449711 | 0.23 | 0.16 | 0.13 | 0.13 |
| ISIS 449708 | 0.27 | 0.21 | 0.14 | 0.14 |
| ISIS 416858 | 0.25 | 0.23 | 0.16 | 0.16 |
| ISIS 445531 | 0.22 | 0.18 | 0.13 | 0.11 |

Kidney Function

To evaluate the impact of ISIS oligonucleotides on kidney function, urine samples were collected on different days. BUN levels were measured at various time points using an automated clinical chemistry analyzer (Hitachi Olympus AU400e, Melville, N.Y.) and the results are presented in Table 155. The ratio of urine protein to creatinine in urine samples after antisense oligonucleotide treatment was also calculated for day 49 and results are presented in Table 156. As observed in Tables 155 and 156, there were no significant increases in any of the kidney metabolic markers after antisense oligonucleotide treatment.

TABLE 155

Effect of antisense oligonucleotide treatment on BUN levels (mg/dL) in cynomolgus monkeys

| | Day −14 | Day −5 | Day 31 | Day 55 |
|---|---|---|---|---|
| PBS | 22 | 21 | 22 | 22 |
| ISIS 416850 | 24 | 23 | 21 | 26 |
| ISIS 449709 | 22 | 21 | 20 | 28 |
| ISIS 445522 | 23 | 22 | 22 | 22 |
| ISIS 449710 | 19 | 19 | 19 | 23 |
| ISIS 449707 | 25 | 21 | 21 | 20 |
| ISIS 449711 | 26 | 22 | 20 | 23 |
| ISIS 449708 | 25 | 23 | 23 | 23 |
| ISIS 416858 | 25 | 24 | 23 | 24 |
| ISIS 445531 | 22 | 18 | 20 | 22 |

TABLE 156

Effect of antisense oligonucleotide treatment on urine protein to creatinine ratio in cynomolgus monkeys

| | Urine protein/creatinine ratio |
|---|---|
| PBS | 0.02 |
| ISIS 416850 | 0.08 |
| ISIS 449709 | 0.05 |
| ISIS 445522 | 0.01 |
| ISIS 449710 | 0.00 |
| ISIS 449707 | 0.03 |
| ISIS 449711 | 0.01 |
| ISIS 449708 | 0.00 |
| ISIS 416858 | 0.05 |
| ISIS 445531 | 0.08 |

Hematology Assays

Blood obtained from all the monkey groups on different days were sent to Korea Institute of Toxicology (KIT) for HCT, MCV, MCH, and MCHC measurements, as well as measurements of the various blood cells, such as WBC (neutrophils and monocytes), RBC and platelets, as well as total hemoglobin content. The results are presented in Tables 157-166.

TABLE 157

Effect of antisense oligonucleotide treatment on HCT (%) in cynomolgus monkeys

| | Day −14 | Day −5 | Day 17 | Day 31 | Day 45 | Day 55 |
|---|---|---|---|---|---|---|
| PBS | 40 | 42 | 43 | 43 | 41 | 40 |
| ISIS 416850 | 41 | 44 | 42 | 42 | 42 | 40 |
| ISIS 449709 | 41 | 42 | 43 | 42 | 41 | 40 |
| ISIS 445522 | 42 | 42 | 41 | 43 | 41 | 39 |
| ISIS 449710 | 41 | 44 | 43 | 44 | 43 | 41 |
| ISIS 449707 | 40 | 43 | 42 | 43 | 43 | 42 |
| ISIS 449711 | 41 | 41 | 42 | 39 | 39 | 38 |
| ISIS 449708 | 41 | 44 | 44 | 43 | 44 | 42 |
| ISIS 416858 | 41 | 44 | 43 | 43 | 41 | 39 |
| ISIS 445531 | 41 | 42 | 43 | 41 | 41 | 41 |

TABLE 158

Effect of antisense oligonucleotide treatment on platelet count (×100/μL) in cynomolgus monkeys

| | Day −14 | Day −5 | Day 17 | Day 31 | Day 45 | Day 55 |
|---|---|---|---|---|---|---|
| PBS | 361 | 441 | 352 | 329 | 356 | 408 |
| ISIS 416850 | 462 | 517 | 467 | 507 | 453 | 396 |
| ISIS 449709 | 456 | 481 | 449 | 471 | 418 | 441 |
| ISIS 445522 | 433 | 512 | 521 | 425 | 403 | 333 |
| ISIS 449710 | 411 | 463 | 382 | 422 | 313 | 360 |
| ISIS 449707 | 383 | 464 | 408 | 408 | 424 | 399 |
| ISIS 449711 | 410 | 431 | 325 | 309 | 257 | 259 |
| ISIS 449708 | 387 | 517 | 444 | 378 | 381 | 348 |
| ISIS 416858 | 369 | 433 | 358 | 289 | 287 | 257 |
| ISIS 445531 | 379 | 416 | 380 | 376 | 345 | 319 |

TABLE 159

Effect of antisense oligonucleotide treatment on neutrophils (%) in cynomolgus monkeys

| | Day −14 | Day −5 | Day 17 | Day 31 | Day 45 | Day 55 |
|---|---|---|---|---|---|---|
| PBS | 81 | 84 | 75 | 75 | 91 | 118 |
| ISIS 416850 | 88 | 109 | 95 | 100 | 85 | 108 |
| ISIS 449709 | 73 | 101 | 89 | 81 | 77 | 115 |
| ISIS 445522 | 61 | 84 | 81 | 66 | 69 | 125 |
| ISIS 449710 | 93 | 86 | 80 | 94 | 97 | 132 |
| ISIS 449707 | 85 | 106 | 80 | 89 | 89 | 98 |
| ISIS 449711 | 64 | 71 | 52 | 58 | 45 | 70 |
| ISIS 449708 | 73 | 84 | 61 | 57 | 61 | 75 |
| ISIS 416858 | 65 | 84 | 54 | 54 | 61 | 73 |
| ISIS 445531 | 60 | 80 | 85 | 116 | 93 | 91 |

TABLE 160

Effect of antisense oligonucleotide treatment on monocytes (%) in cynomolgus monkeys

| | Day −14 | Day −5 | Day 17 | Day 31 | Day 45 | Day 55 |
|---|---|---|---|---|---|---|
| PBS | 1.9 | 2.8 | 3.1 | 2.8 | 3.9 | 2.2 |
| ISIS 416850 | 1.9 | 2.9 | 3.2 | 3.7 | 3.8 | 3.4 |
| ISIS 449709 | 4.0 | 2.0 | 3.0 | 2.8 | 3.6 | 3.4 |
| ISIS 445522 | 2.1 | 2.3 | 3.6 | 3.9 | 4.4 | 3.0 |
| ISIS 449710 | 1.3 | 2.0 | 2.5 | 2.4 | 3.4 | 1.6 |
| ISIS 449707 | 1.3 | 2.3 | 3.2 | 4.2 | 4.0 | 4.8 |
| ISIS 449711 | 1.2 | 2.3 | 5.9 | 6.9 | 7.6 | 7.8 |
| ISIS 449708 | 1.7 | 2.6 | 5.4 | 5.8 | 7.0 | 6.2 |
| ISIS 416858 | 2.0 | 2.7 | 4.0 | 4.7 | 4.6 | 4.6 |
| ISIS 445531 | 1.3 | 2.2 | 3.4 | 4.1 | 4.4 | 4.1 |

TABLE 161

Effect of antisense oligonucleotide treatment on hemoglobin content (g/dL) in cynomolgus monkeys

| | Day −14 | Day −5 | Day 17 | Day 31 | Day 45 | Day 55 |
|---|---|---|---|---|---|---|
| PBS | 12.3 | 12.5 | 12.9 | 12.7 | 12.4 | 12.1 |
| ISIS 416850 | 13.0 | 13.5 | 13.3 | 13.1 | 13.1 | 12.7 |
| ISIS 449709 | 12.8 | 12.8 | 13.2 | 13.1 | 12.6 | 12.5 |
| ISIS 445522 | 13.3 | 12.7 | 12.7 | 12.9 | 12.6 | 12.0 |
| ISIS 449710 | 13.0 | 13.2 | 13.4 | 13.1 | 13.0 | 12.7 |
| ISIS 449707 | 12.7 | 12.8 | 12.7 | 12.7 | 12.9 | 12.6 |
| ISIS 449711 | 12.7 | 12.7 | 12.5 | 11.8 | 11.5 | 11.3 |
| ISIS 449708 | 13.0 | 13.2 | 13.5 | 13.0 | 13.3 | 13.0 |
| ISIS 416858 | 12.8 | 13.0 | 13.0 | 12.8 | 12.3 | 12.0 |
| ISIS 445531 | 12.6 | 12.6 | 12.7 | 12.3 | 12.0 | 12.1 |

TABLE 162

Effect of antisense oligonucleotide treatment on WBC count ($\times 10^3/\mu L$) in cynomolgus monkeys

| | Day −14 | Day −5 | Day 17 | Day 31 | Day 45 | Day 55 |
|---|---|---|---|---|---|---|
| PBS | 10 | 10 | 11 | 12 | 11 | 12 |
| ISIS 416850 | 12 | 13 | 11 | 12 | 12 | 10 |
| ISIS 449709 | 11 | 10 | 11 | 11 | 11 | 10 |
| ISIS 445522 | 10 | 9 | 11 | 13 | 10 | 11 |
| ISIS 449710 | 11 | 11 | 12 | 12 | 11 | 15 |
| ISIS 449707 | 13 | 11 | 12 | 11 | 12 | 8 |
| ISIS 449711 | 13 | 12 | 10 | 9 | 9 | 7 |
| ISIS 449708 | 14 | 10 | 11 | 11 | 10 | 10 |
| ISIS 416858 | 10 | 11 | 10 | 9 | 8 | 9 |
| ISIS 445531 | 20 | 15 | 17 | 17 | 20 | 15 |

TABLE 163

Effect of antisense oligonucleotide treatment on RBC count ($\times 10^6/\mu L$) in cynomolgus monkeys

| | Day −14 | Day −5 | Day 17 | Day 31 | Day 45 | Day 55 |
|---|---|---|---|---|---|---|
| PBS | 5.6 | 5.6 | 5.8 | 5.8 | 5.6 | 5.5 |
| ISIS 416850 | 5.5 | 5.7 | 5.6 | 5.6 | 5.7 | 5.6 |
| ISIS 449709 | 5.8 | 5.8 | 5.9 | 5.9 | 5.7 | 5.7 |
| ISIS 445522 | 5.9 | 5.6 | 5.6 | 5.8 | 5.7 | 5.4 |
| ISIS 449710 | 5.6 | 5.8 | 5.8 | 5.8 | 5.7 | 5.6 |
| ISIS 449707 | 5.7 | 5.8 | 5.7 | 5.7 | 5.9 | 5.8 |
| ISIS 449711 | 5.6 | 5.7 | 5.6 | 5.4 | 5.4 | 5.3 |
| ISIS 449708 | 5.7 | 5.9 | 5.9 | 5.8 | 6.0 | 5.8 |
| ISIS 416858 | 5.5 | 5.5 | 5.6 | 5.6 | 5.5 | 5.3 |
| ISIS 445531 | 5.7 | 5.7 | 5.8 | 5.6 | 5.5 | 5.6 |

TABLE 164

Effect of antisense oligonucleotide treatment on MCV (fL) in cynomolgus monkeys

| | Day −14 | Day −5 | Day 17 | Day 31 | Day 45 | Day 55 |
|---|---|---|---|---|---|---|
| PBS | 72 | 74 | 75 | 73 | 73 | 73 |
| ISIS 416850 | 74 | 77 | 76 | 75 | 75 | 73 |
| ISIS 449709 | 72 | 74 | 73 | 73 | 71 | 71 |
| ISIS 445522 | 72 | 74 | 74 | 75 | 73 | 72 |
| ISIS 449710 | 75 | 77 | 75 | 75 | 75 | 73 |
| ISIS 449707 | 71 | 75 | 74 | 74 | 73 | 73 |
| ISIS 449711 | 73 | 74 | 75 | 73 | 73 | 73 |
| ISIS 449708 | 73 | 75 | 75 | 75 | 74 | 74 |
| ISIS 416858 | 75 | 79 | 78 | 76 | 75 | 75 |
| ISIS 445531 | 72 | 74 | 75 | 75 | 75 | 74 |

TABLE 165

Effect of antisense oligonucleotide treatment on MCH (pg) in cynomolgus monkeys

| | Day −14 | Day −5 | Day 17 | Day 31 | Day 45 | Day 55 |
|---|---|---|---|---|---|---|
| PBS | 22.1 | 22.4 | 22.3 | 22.1 | 22.0 | 22.0 |
| ISIS 416850 | 23.7 | 23.7 | 23.7 | 23.3 | 22.7 | 22.9 |
| ISIS 449709 | 22.4 | 22.3 | 22.5 | 22.2 | 21.0 | 22.0 |
| ISIS 445522 | 22.6 | 22.5 | 22.8 | 22.4 | 22.4 | 22.2 |
| ISIS 449710 | 23.0 | 22.8 | 23.1 | 22.6 | 21.8 | 22.7 |
| ISIS 449707 | 22.2 | 22.2 | 22.1 | 22.1 | 22.6 | 21.9 |
| ISIS 449711 | 22.6 | 22.7 | 22.2 | 22.1 | 21.7 | 21.3 |
| ISIS 449708 | 22.9 | 22.7 | 22.9 | 22.7 | 22.2 | 22.5 |
| ISIS 416858 | 23.2 | 23.5 | 23.1 | 23.0 | 22.2 | 22.8 |
| ISIS 445531 | 22.2 | 22.2 | 22.1 | 22.0 | 21.6 | 21.7 |

TABLE 166

Effect of antisense oligonucleotide treatment on MCHC (g/dL) in cynomolgus monkeys

| | Day −14 | Day −5 | Day 17 | Day 31 | Day 45 | Day 55 |
|---|---|---|---|---|---|---|
| PBS | 30.8 | 30.0 | 30.1 | 29.9 | 30.3 | 30.2 |
| ISIS 416850 | 32.0 | 30.7 | 31.3 | 31.0 | 31.0 | 30.9 |
| ISIS 449709 | 31.4 | 30.3 | 30.7 | 30.7 | 31.1 | 31.2 |
| ISIS 445522 | 31.4 | 30.4 | 30.9 | 30.0 | 30.7 | 31.0 |
| ISIS 449710 | 31.2 | 29.7 | 30.7 | 30.1 | 30.4 | 31.1 |
| ISIS 449707 | 31.4 | 29.8 | 30.0 | 29.8 | 29.8 | 30.0 |
| ISIS 449711 | 31.0 | 30.7 | 29.9 | 29.8 | 29.6 | 29.5 |
| ISIS 449708 | 31.4 | 30.2 | 30.7 | 29.9 | 30.6 | 31.8 |
| ISIS 416858 | 31.1 | 29.8 | 29.9 | 31.0 | 30.3 | 30.4 |
| ISIS 445531 | 30.9 | 30.0 | 29.5 | 29.7 | 29.0 | 29.6 |

Cytokine and Chemokine Assays

Blood samples obtained from all monkey groups were sent to Pierce Biotechnology (Woburn, Mass.) for measurements of chemokine and cytokine levels. Levels of IL-1β, IL-6, IFN-γ, and TNF-α were measured using the respective primate antibodies and levels of IL-8, MIP-1α, MCP-1, MIP-1β and RANTES were measured using the respective cross-reacting human antibodies. Measurements were taken 14 days before the start of treatment and on day 55, when the monkeys were euthanized. The results are presented in Tables 167 and 168.

TABLE 167

Effect of antisense oligonucleotide treatment on cytokine/chemokine levels (pg/mL) in cynomolgus monkeys on day −14

| | IL-1β | IL-6 | IFN-γ | TNF-α | IL-8 | MIP-1α | MCP-1 | MIP-1β | RANTES |
|---|---|---|---|---|---|---|---|---|---|
| PBS | 350 | 3 | 314 | 32 | 82 | 27 | 277 | 8 | 297 |
| ISIS 416850 | 215 | 1 | 115 | 4 | 45 | 14 | 434 | 31 | 4560 |

TABLE 167-continued

Effect of antisense oligonucleotide treatment on cytokine/chemokine levels (pg/mL) in cynomolgus monkeys on day −14

| | IL-1β | IL-6 | IFN-γ | TNF-α | IL-8 | MIP-1α | MCP-1 | MIP-1β | RANTES |
|---|---|---|---|---|---|---|---|---|---|
| ISIS 449409 | 137 | 1 | 37 | 9 | 34 | 13 | 290 | 14 | 2471 |
| ISIS 445522 | 188 | 5 | 172 | 16 | 32 | 22 | 297 | 27 | 3477 |
| ISIS 449710 | 271 | 7 | 1115 | 72 | 29 | 20 | 409 | 18 | 1215 |
| ISIS 449707 | 115 | 1 | 34 | 6 | 106 | 16 | 294 | 13 | 3014 |
| ISIS 449711 | 79 | 2 | 29 | 6 | 156 | 20 | 264 | 24 | 3687 |
| ISIS 449708 | 35 | 1 | 27 | 12 | 184 | 11 | 361 | 19 | 11666 |
| ISIS 416858 | 103 | 0 | 32 | 4 | 224 | 11 | 328 | 37 | 6521 |
| ISIS 445531 | 101 | 2 | 68 | 9 | 83 | 25 | 317 | 22 | 7825 |

TABLE 168

Effect of antisense oligonucleotide treatment on cytokine/chemokine levels (pg/mL) in cynomolgus monkeys on day 55

| | IL-1β | IL-6 | IFN-γ | TNF-α | IL-8 | MIP-1α | MCP-1 | MIP-1β | RANTES |
|---|---|---|---|---|---|---|---|---|---|
| PBS | 453 | 3 | 232 | 191 | 68 | 21 | 237 | 34 | 775 |
| ISIS 416850 | 106 | 1 | 19 | 16 | 620 | 17 | 887 | 50 | 27503 |
| ISIS 449409 | 181 | 0 | 25 | 8 | 254 | 17 | 507 | 47 | 8958 |
| ISIS 445522 | 341 | 2 | 83 | 18 | 100 | 22 | 592 | 63 | 16154 |
| ISIS 449710 | 286 | 2 | 176 | 26 | 348 | 27 | 474 | 53 | 22656 |
| ISIS 449707 | 97 | 1 | 24 | 16 | 48 | 12 | 264 | 49 | 1193 |
| ISIS 449711 | 146 | 7 | 22 | 31 | 110 | 17 | 469 | 91 | 3029 |
| ISIS 449708 | 131 | 0 | 18 | 17 | 85 | 23 | 409 | 128 | 4561 |
| ISIS 416858 | 28 | 1 | 9 | 15 | 167 | 11 | 512 | 47 | 5925 |
| ISIS 445531 | 155 | 1 | 15 | 16 | 293 | 12 | 339 | 84 | 5935 |

Example 47: Measurement of Viscosity of ISIS Antisense Oligonucleotides Targeting Human Factor 11

The viscosity of antisense oligonucleotides targeting human Factor 11 was measured with the aim of screening out antisense oligonucleotides which have a viscosity more than 40 cP at a concentration of 165-185 mg/mL.

ISIS oligonucleotides (32-35 mg) were weighed into a glass vial, 120 μL of water was added and the antisense oligonucleotide was dissolved into solution by heating the vial at 50° C. Part of (75 μL) the pre-heated sample was pipetted to a micro-viscometer (Cambridge). The temperature of the micro-viscometter was set to 25° C. and the viscosity of the sample was measured. Another part (20 μL) of the pre-heated sample was pipetted into 10 mL of water for UV reading at 260 nM at 85° C. (Cary UV instrument). The results are presented in Table 169.

TABLE 169

Viscosity and concentration of ISIS antisense oligonucleotides targeting human Factor 11

| ISIS No. | Viscosity (cP) | Concentration (mg/mL) |
|---|---|---|
| 412223 | 8 | 163 |
| 412224 | 98 | 186 |
| 412225 | >100 | 162 |
| 413481 | 23 | 144 |
| 413482 | 16 | 172 |
| 416848 | 6 | 158 |
| 416850 | 67 | 152 |
| 416851 | 26 | 187 |
| 416852 | 29 | 169 |
| 416856 | 18 | 175 |
| 416858 | 10 | 166 |
| 416859 | 10 | 161 |
| 416860 | >100 | 154 |
| 416861 | 14 | 110 |
| 416863 | 9 | 165 |
| 416866 | >100 | 166 |
| 416867 | 8 | 168 |
| 445498 | 21 | 157 |
| 445504 | 20 | 139 |
| 445505 | 9 | 155 |
| 445509 | >100 | 167 |
| 445513 | 34 | 167 |
| 445522 | 63 | 173 |
| 445522 | 58 | 174 |
| 445530 | 25 | 177 |
| 445531 | 15 | 155 |
| 445531 | 20 | 179 |

TABLE 169-continued

Viscosity and concentration of ISIS antisense oligonucleotides targeting human Factor 11

| ISIS No. | Viscosity (cP) | Concentration (mg/mL) |
|---|---|---|
| 449707 | 7 | 166 |
| 449708 | 9 | 188 |
| 449709 | 65 | 171 |
| 449710 | 7 | 186 |
| 449711 | 6 | 209 |
| 451541 | 10 | 168 |

What is claimed is:

1. A compound comprising a modified oligonucleotide, consisting of 12 to 30 linked nucleosides and having a nucleobase sequence comprising at least 12 continguous nucleobases of SEQ ID NO: 141.

2. The compound of claim 1, wherein the modified oligonucleotide has a nucleobase sequence that is at least 85% complementary to any of the nucleobase sequences of SEQ ID NO: 1 or SEQ ID NO: 2 when measured across the entire nucleobase sequence of the modified oligonucleotide.

3. The compound of claim 1, wherein the modified oligonucleotide consists of a single stranded modified oligonucleotide.

4. The compound of claim 1, wherein the modified oligonucleotide comprises at least one modified internucleoside linkage.

5. The compound of claim 4, wherein the at least one modified internucleoside linkage is a phosphorothioate internucleoside linkage.

6. The compound of claim 1, wherein the modified oligonucleotide comprises at least one modified sugar.

7. The compound of claim 6, wherein the at least one modified sugar comprises a 2'-O-methoxyethyl group.

8. The compound of claim 6, wherein the at least one modified sugar comprises a 2'-O—$CH_3$ group.

9. The compound of claim 6, wherein the at least one modified sugar is a bicyclic sugar.

10. The compound of claim 9, wherein the bicyclic sugar comprises a 4'-($CH_2$)—O-2' bridge.

11. The compound of claim 9, wherein the bicyclic sugar comprises a 4'-$(CH_2)_2$—O-2' bridge.

12. The compound of claim 9, wherein the bicyclic sugar comprises a 4'-CH($CH_3$)—O-2' bridge.

13. The compound of claim 1, wherein the modified oligonucleotide comprises:

a gap segment consisting of linked deoxynucleosides;

a 5' wing segment of linked nucleosides;

a 3' wing segment of linked nucleosides;

wherein the gap segment is positioned immediately adjacent to and between the 5' wing segment and the 3' wing segment and wherein each nucleoside of each wing segment comprises a modified sugar.

14. The compound of claim 13, wherein the modified oligonucleotide comprises:

a gap segment consisting of ten linked deoxynucleosides;

a 5' wing segment consisting of five linked nucleosides;

a 3' wing segment consisting of five linked nucleosides;

wherein the gap segment is positioned immediately adjacent to and between the 5' wing segment and the 3' wing segment, wherein each nucleoside of each wing segment comprises a 2'-O-methoxyethyl sugar, and wherein the modified oligonucleotide comprises at least one phosphorothioate internucleoside linkage.

15. The compound of claim 1, wherein the modified oligonucleotide is a salt of the modified oligonucleotide.

16. A conjugated antisense compound comprising the compound of claim 1.

17. A pharmaceutical composition comprising the compound of claim 1 and a pharmaceutically acceptable carrier or diluent.

18. The pharmaceutical composition of claim 17, comprising at least one of aspirin, clopidogrel, dipyridamole, heparin, lepirudin, ticlopidine, warfarin, apixaban, rivaroxaban, LOVENOX, and Factor Xa inhibitor.

19. The pharmaceutical composition of claim 17, wherein the pharmaceutically acceptable diluent is phosphate-buffered saline (PBS).

20. A method comprising administering the compound of claim 1 to a subject in need thereof.

* * * * *

SEQUENCE LISTING

<160> NUMBER OF SEQ ID NOS: 274

<210> SEQ ID NO 1
<211> LENGTH: 3278
<212> TYPE: DNA
<213> ORGANISM: Homo sapiens

<400> SEQUENCE: 1

```
aggcacacag gcaaaatcaa gttctacatc tgtccctgtg tatgtcactt gtttgaatac     60

gaaataaaat taaaaaaata aattcagtgt attgagaaag caagcaattc tctcaaggta    120

tatttctgac atactaagat tttaacgact ttcacaaata tgctgtactg agagagaatg    180

ttacataaca ttgagaacta gtacaagtaa atattaaagt gaagtgacca tttcctacac    240

aagctcattc agaggaggat gaagaccatt ttggaggaag aaaagcaccc ttattaagaa    300

ttgcagcaag taagccaaca aggtcttttc aggatgattt tcttatatca agtggtacat    360

ttcattttat ttacttcagt ttctggtgaa tgtgtgactc agttgttgaa ggacacctgc    420

tttgaaggag gggacattac tacggtcttc acaccaagcg ccaagtactg ccaggtagtc    480

tgcacttacc acccaagatg tttactcttc actttcacgg cggaatcacc atctgaggat    540

cccacccgat ggtttacttg tgtcctgaaa gacagtgtta cagaaacact gccaagagtg    600

aataggacag cagcgatttc tgggtattct ttcaagcaat gctcacacca aataagcgct    660

tgcaacaaag acatttatgt ggacctagac atgaagggca taaactataa cagctcagtt    720

gccaagagtg ctcaagaatg ccaagaaaga tgcacggatg acgtccactg ccactttttc    780

acgtacgcca caaggcagtt tcccagcctg gagcatcgta acatttgtct actgaagcac    840

acccaaacag ggacaccaac cagaataacg aagctcgata aagtggtgtc tggattttca    900

ctgaaatcct gtgcactttc taatctggct tgtattaggg acattttccc taatacggtg    960

tttgcagaca gcaacatcga cagtgtcatg gctcccgatg cttttgtctg tggccgaatc   1020

tgcactcatc atcccggttg cttgtttttt accttctttt cccaggaatg gcccaaagaa   1080

tctcaaagaa atctttgtct ccttaaaaca tctgagagtg gattgcccag tacacgcatt   1140

aaaaagagca aagctctttc tggtttcagt ctacaaagct gcaggcacag catcccagtg   1200

ttctgccatt cttcatttta ccatgacact gatttcttgg gagaagaact ggatattgtt   1260

gctgcaaaaa gtcacgaggc ctgccagaaa ctgtgcacca atgccgtccg ctgccagttt   1320

tttacctata ccccagccca agcatcctgc aacgaaggga agggcaagtg ttacttaaag   1380

ctttcttcaa acggatctcc aactaaaata cttcacggga gaggaggcat ctctggatac   1440

acattaaggt tgtgtaaaat ggataatgag tgtaccacca aaatcaagcc caggatcgtt   1500

ggaggaactg cgtctgttcg tggtgagtgg ccgtggcagg tgaccctgca cacaacctca   1560

cccactcaga gacacctgtg tggaggctcc atcattggaa accagtggat attaacagcc   1620
```

```
gctcactgtt tctatggggt agagtcacct aagattttgc gtgtctacag tggcatttta   1680

aatcaatctg aaataaaaga ggacacatct ttctttgggg ttcaagaaat aataatccat   1740

gatcagtata aaatggcaga aagcgggtat gatattgcct tgttgaaact ggaaaccaca   1800

gtgaattaca cagattctca acgacccata tgcctgcctt ccaaaggaga tagaaatgta   1860

atatacactg attgctgggt gactggatgg gggtacagaa aactaagaga caaaatacaa   1920

aatactctcc agaaagccaa gataccctta gtgaccaacg aagagtgcca gaagagatac   1980

agaggacata aaataaccca taagatgatc tgtgccggct acagggaagg agggaaggac   2040

gcttgcaagg gagattcggg aggccctctg tcctgcaaac acaatgaggt ctggcatctg   2100

gtaggcatca cgagctgggg cgaaggctgt gctcaaaggg agcggccagg tgtttacacc   2160

aacgtggtcg agtacgtgga ctggattctg gagaaaactc aagcagtgtg aatgggttcc   2220

caggggccat tggagtccct gaaggaccca ggatttgctg ggagagggtg ttgagttcac   2280

tgtgccagca tgcttcctcc acagtaacac gctgaagggg cttggtgttt gtaagaaaat   2340

gctagaagaa aacaaactgt cacaagttgt tatgtccaaa actcccgttc tatgatcgtt   2400

gtagtttgtt tgagcattca gtctctttgt tttgatcac gcttctatgg agtccaagaa   2460

ttaccataag gcaatatttc tgaagattac tatataggca gatatagcag aaaataacca   2520

agtagtggca gtggggatca ggcagaagaa ctggtaaaag aagccaccat aaatagattt   2580

gttcgatgaa agatgaaaac tggaagaaag gagaacaaag acagtcttca ccattttgca   2640

ggaatctaca ctctgcctat gtgaacacat ttcttttgta aagaaagaaa ttgattgcat   2700

ttaatggcag attttcagaa tagtcaggaa ttcttgtcat ttccatttta aaatatatat   2760

taaaaaaaat cagttcgagt agacacgagc taagagtgaa tgtgaagata acagaatttc   2820

tgtgtggaag aggattacaa gcagcaattt acctggaagt gataccttag gggcaatctt   2880

gaagatacac tttcctgaaa aatgatttgt gatggattgt atatttattt aaaatatctt   2940

gggaggggag gctgatggag atagggagca tgctcaaacc tccctaagac aagctgctgc   3000

tgtgactatg ggctcccaaa gagctagatc gtatatttat ttgacaaaaa tcaccataga   3060

ctgcatccat actacagaga aaaaacaatt agggcgcaaa tggatagtta cagtaaagtc   3120

ttcagcaagc agctgcctgt attctaagca ctgggatttt ctgtttcgtg caaatattta   3180

tctcattatt gttgtgatct agttcaataa cctagaattt gaattgtcac cacatagctt   3240

tcaatctgtg ccaacaacta tacaattcat caagtgtg                           3278
```

<210> SEQ ID NO 2
<211> LENGTH: 26001
<212> TYPE: DNA
<213> ORGANISM: Homo sapiens

<400> SEQUENCE: 2

```
atgccctcca taggctttca gaccttcttc aaggccaaag ggaaggcctt catggaaata     60

taattatgtg aaacacccca gaattttttc acaaactttc ctgcctataa acgccaggtc    120

ctaccactgt ccagtgtccc acttcccact gtccagtggg aagactccct ccaggacaaa    180

accacccttt ccttcaggga tgtgacgtgc tgtgctttcg ttgacagtca tgcagctgct    240

agacatgtca cttcctagct ctccattcgg gtctgtgtcc caggacctaa agaaagctaa    300

aagaagccgg gcgtggtggc tcatgcctgt catcccagca ttttgggagg ctgaggctgg    360

cggatcactg gagatcagga gtttgagacc agtctgacca gcatggtgaa accctgtctc    420

tactaaaaat acaaaaaaag aaaagaaaaa agaaaaaaaa ataagctggg cgtggtggcg    480
```

```
cgggcctgta gtcccagcta ctccggaggc ggaggcagga caatcacttg aacctggaag    540
gcggaggttg cagtgagctg agatcgcgtc attgcactcc agcctgtgcg acgagagact    600
ctgtctcaaa agaaagaaag aaagagagaa agaaagaaag aaagaaaaga aagaaagaaa    660
gaagaaagaa agaaaagaaa gaaagtaaga agcaagcaag ctgaaatagc ttattttttct    720
gttttaaaaa atagactttt agtgttcaca agtaagaata aaaaaaaaaa aagcttggcc    780
ttaggaggaa tcctatctgc ttaggcctct gagaggcagc gtcacctgaa gggaaactga    840
ctgggcaaga gccaggctct taggagctgt ctgtactttg cttcccatcc gtccgctctc    900
ccccagcagc caaagtctcc tccctccatt atattgcaaa tcaatgaatc cattagactt    960
tccatgtttt ctttttagac tttgagattc aaggtcagct agaattaatg gttaacagct   1020
gacaggtgaa agtgtggtta aatgcagctt tggctagcag gcacacaggc aaaatcaagt   1080
tctacatctg tccctgtgta tgtcacttgt ttgaatacga aataaaatta aaaaaataaa   1140
ttcagtgtat tgagaaagca agcaattctc tcaaggtata tttctgacat actaagattt   1200
taacgacttt cacaaatatg ctgtactgag agagaatgtt acataacatt gagaactagt   1260
acaagtaaat attaaagtga agtgaccatt tcctacacaa gctcattcag aggaggatga   1320
agaccatttt ggaggaagaa aagcaccctt attaagaatt gcagcaagta agccaacaag   1380
gtcttttcag gtacagtttc agaacttact atttaacatt cctctcaagc aaatacgcct   1440
tgaaatgctt tttttaaatc ataggaattt aaaaacactt tacaatagag aatgattgat   1500
ttttaaaatg tgtctgattt agctttgtag agatgttccg ctaatatcca taactaatct   1560
gagaggaaat gtggaacaac agaagagtaa cagtgtctac tcagtaacaa gcgttttacg   1620
agttaaaaag acatccaaat gcagtactga aaaatcagaa gtcttgattt gtctcactga   1680
tgactccgtt tttcctagag cagtctgttt aatgcttact ggagataaat agatttatag   1740
gtgaccaaga caatcgatta atgtatcagc cacagacttt tttaaataga aaattttcta   1800
agtaggaaat cattcatagc tctttgaaag atatagggag aggcctcaag gaaagaaaga   1860
aaggaaaaaa attgggaaag gaaacaaaga tgaaaaattg gggtggggag agcggtcaga   1920
tggtggccat gagaaggatc tgaacacaga gagcggcggg gccggcgggg aaggagggag   1980
gaggggagag cgctgcttcc ctgtgggttc cggcttctgc agagctgtaa gagttgaatg   2040
ccacacacag tcacactaag gaatgctcca ggattgggaa agaaaattca acattataat   2100
gagaacactg tgaatgctat tgaattaact actcccctct ctccctattt cttgtaagtc   2160
ttagtgtcag taaactaatt ataaatttac attttatgtt ctaaaagcat gcaccttttt   2220
ctcattgtag gatgattttc ttatatcaag tggtacattt cattttattt acttcagttt   2280
ctggtggtaa gtagagtgtt atcttaacta tgggctggga gagggaaatc acactgcaat   2340
ctccacacat gtgggagaat cccacaccat ttatgccggg aaggaaataa aatgttttta   2400
ttaacttcct gcctgaggct ccagaggttt tcaaagcagg gtaggaattg aggtgaaaaa   2460
attgtttgta ctggtaggaa tctgtgtcta tatgtgtacc atatctacat ccatgcctac   2520
atacatcatt catttaaatg atatttaaaa gcaatattaa aaagaagaaa tcttgatttg   2580
cctcactaat tagttggttt ttcataaagc agtcagttca atggaacata cacacacaca   2640
taaaatagga attttgtact gaaaaatgtt atgtaactat tcatacacag tttatgcatt   2700
tcaataattt aactaccctg ttaattctcc accctatgtc acatctgcta aatttgttta   2760
taaattactt agccaatatt aagtaggata tatcagtaca ggtattgttt agttccatga   2820
```

```
ccattcttta tttaaaatga aagctgaagc attcctttag aaaaatagct tatgtctaca   2880
tgttatattt aatttctgat actattgcta gcattttaag catagtaaat tctttttgct   2940
ggcctatgtg aaaaaaggca aacctaggtg aagatattaa aagtaaattc cacttaatat   3000
attaaattac acagctcata atttcaattt tctctgtgac aagactactg ctcaggttat   3060
aatattcctt tgttataatt atctggaaat tgtattgtta tttcattgat aaatatgtca   3120
gcgctaaata atttgatata ttttgaacac tggacccaat aactacataa acaattgacc   3180
ctgaatcagg ggttccacat ccatggattt aaacaacatt gaagtgaaat tttttaaaaa   3240
aaattatatc tgcactcaac atgtgcagag ttttttcttg tcattattcc cgaaacaaca   3300
cagtataaca acaatttgca tagtatttac attgtactag gtattataag taatctagag   3360
atgatttaaa gtacacagga ggctgtgagt aggttatatg taaatactat gccattttct   3420
atcagggact tgagcgttca tggattttgg tatctgcagg aggtctggca gccaatccct   3480
catagatatc aaggaatgat agtgtacata tttaggtcct ttatacatgc acatggaaca   3540
tttacaaata ttgaccacac acaagcctct gaaacaaggc tcaacaaatt ttaaggggtt   3600
aaaattatac tgatcatgtt attcaatcac cgtgaatggg agctagaata ataataaaaa   3660
gggaattgaa aatctgcaaa cgtttgaaaa ttgagtattt ataatcaccg tgaatgggag   3720
ctagaataat aataaaaagg gaattgaaaa tctgcaaatg tttgaaaatt gagtatttat   3780
acctttttag attaagatga atcagagatg aaatcacaat ggtaattaga aaaggaattg   3840
tacaataatg aaagtacagt atatcaaaac tttgagatgt aaccgaatca gtgttgagat   3900
caaatgtata gatttacatg tatacattag aatacagaaa agggaaaaat taatgatata   3960
agatgacaag aagatagaga atagcaactt aagtgctaag aaattagaag gcagaaagaa   4020
gaaatcgcag aaattaatta aatggaagac acacatattt gagaggtcaa cataacccct   4080
ttctagccca ttttataagg tcagggtaat cttgacacca aaatctgata ggaaaattct   4140
gaggaaaaaa agtcacaggt cttttatctt atgaacatat gtacaaatgt cctaaacaaa   4200
atattatcca acttaaccca gtagattgtt aaaaaaatta aaggatgatt acattgtgat   4260
attgtgacaa agttgggttt attccaggaa tgaaaagttg atttaacatt caaaaatcaa   4320
tagatgtgtg acttcggggt acataccgaa aaaaaagaag ggaaagcagg aactcacaca   4380
gatatacttg tacacccatc tcatagcagc attattcaca ctaacccaaa ggtggaagca   4440
gcccatgtgt ttatcaacag gtgactggat aaagtgtggt acatacatac aaaggaatat   4500
tactcaaccc taaaaagaaa ggaaattctg acacatgcta tgacatggat gaaccttgag   4560
gacattacgc taagtgaaat aagccagtca caaaagaaca aatactgtgg gatctcactg   4620
ataggaggta cttagggtag tcaatttcat caagacggaa attagaacag aggttgccag   4680
gggccgaggg gccaggggaa gggctgaggg ttggtgttta atgggcacag agcatcagct   4740
ggcgaagttg aaaagttctg gaggtggatg gtgctgatgg ttgcacagca atgtaaatac   4800
ccttagtgcc acagaactgt acactcaaga tggctacatg gcacatggta tgctatctgt   4860
cataataaaa aataaaaata attttaaatg ttaatatgtg ccgaaaaatg cttgctaaaa   4920
ttctattaat gatcaaaact ttaaataaac tggaaatgga agagaacttt catcagctat   4980
taaacgatat tttaaacaaa agcaaacaaa aatccaaacc aaaaatcttc aagaaacata   5040
atacgtaata gcggaatatt gaaagctttc ccaagggatt gagaatagga caagaatact   5100
tcccattatt tccatttact cttgactgga ggtactcgtt ggtgcggtaa ggaagggaaa   5160
taaaaggaaa acgattagga ggaacataag ctctcgtttt tcacagatga tgtgattgag   5220
```

```
tacctagaaa aatccaaaat taaccatcac ataaattatt tgagccaatt aattaaatga   5280
gtaagaagtc tcgatacaac gtcaatatac aacagcaagc acttgctcgt tcgcaaaagc   5340
agatgaacta gtttttactg acactagaag cagcatgtgt tccatgtgtt ccacatccat   5400
gcactcaaac aaccttgacg tgaaatattt tttaaaaaat tgtatctgta ctcaacgtgt   5460
gcagagtttt tttccaaaat tgttttccaa aaatttttaa atgtttatat gtttaggggg   5520
tgtaagtgca gatttcttac atacatatat tatgcggcgg tgaagtgccg gcttttggtg   5580
tacccatcac ccaagtagtg aacacagcct ccaacaggta atttttcaac gctcacccca   5640
ctcccatcct cccatctagt ggcatattga aaatcaattt gtcttgtaaa attaaataat   5700
ccaattagga gggggatata ttctaaggaa attagtgcat gatgcacaca cacacacaca   5760
cacagaacac gtgtgtgcgc atgtgcacat gagagagagt gagagagaaa ctgggtcttg   5820
ctctgtcgcc caggctggat tgcagtggta aaatcacagc tcactgcagc ctcaaactcc   5880
caggctcagg agatcctcct acctcagcct cccgagtagc tgggattaca ggtggaaaca   5940
accatgccca gctagtattt tttttttttt ttgtattttt tatagagaca gggtcttgcc   6000
atgttgccca ggctggtctt gaactcctca gctcaagcaa tctacctacc ttagcctccc   6060
aaagtgctgg gattacacgc atgagccact gcgcccactc cgcattatta aatatagaac   6120
atttatttga ttcatcagtt aatattcttc ttaaaagtac tattttaatg tagcaagatt   6180
gctttccacc aaaaggtggg gtttccacgg tggggtttcc aaattattct caatggggtg   6240
aggatgtgtg ttatcacacc cccgagccat cagatgctgt cagaaagtga tcactctgaa   6300
gtctttgttt caaataagca cagggtttgg ataaagagac gcaattagga aaggaaaaag   6360
cagaaggctc gttccagacc tggatgagat cctaaaaagc agcagctttt gccagtaaag   6420
atccttgaaa tgattcaatt accctcaaag cactccttgt ctccaagaca atcactcata   6480
agcacaattc cattgaagcc aacgtaccat tttgtgattt tcgtttccac ctgaggctgt   6540
tcattcaata aactcacata aaagtgttta ttgccttgat ttccaaattc aggcgtattt   6600
cctggtaagt agagctactt gccttgcctt tatgagatta ccacctaact agatgtatgc   6660
ccagtaaaat ccaacataac gcatgccatg tactacatca cagaatgtgt gactcagttg   6720
ttgaaggaca cctgctttga aggaggggac attactacgg tcttcacacc aagcgccaag   6780
tactgccagg tagtctgcac ttaccaccca agatgtttac tcttcacttt cacggcggaa   6840
tcaccatctg aggatcccac ccgatggtaa atgcttatgt ttctacatcg aggagacaga   6900
tttttaaagg gagattgcta ttcttaacac atttccatct aacattttat aaaatttaac   6960
attaacaact ggaagataaa ttgtctttca gttgaaatat tgttacagaa agaagtgatg   7020
gtgtttacgc aatttagaaa agaataaata tgcctccaag tgtagacttt ccagcctctc   7080
ctatagtctc atattaatgg tatgtttctt ctgtttgtct caatttttac acttcttaaa   7140
catttcacac tttgcttttc tatcgattat taatttttgt cgtgcttctc aacaaactgg   7200
aacttctccc aactatttta ttagaaaaaa ataaaatatt taaaaagaaa atttgaaaaa   7260
aagtacagta cagtgatccc cctgccacca ccaaaaccgc aatgtttgct atatttgtac   7320
agcaatatac aatatacaat acctatattt gtatacatgt ttaaccgttt gaaataattt   7380
taaaacatga cactttaccc ctaaatactt cagcatgcac tatcctacac aaaagacata   7440
cgaaatttaa caagaattcc tttatattat ttcagttttc cctcaaatat aatttatagt   7500
aattaaccag aatcttacca agagtcactc actgcattgg gtggtttgtc aggtttaaaa   7560
```

-continued

```
cattttaaac agtccaccaa ccatttgtat tcccatcctg agcttgaaaa tttaataata   7620
agcctttctg tagaattaag ttttcaacat ctttattatt gctacattca caggcattta   7680
tgtagcaccc agaacttata aaatttacta ttccagaacc tagagcaggg attggcaaat   7740
gtcttcttaa taacgcagag taaatatgtt aggctttgtg ggcaaaaccc acagtaaagc   7800
caaggatatt atttaagtat ttatgtcacc acttaaaatg taacaatttg aaaatataaa   7860
aatcattttg tatagctaac aggctaaaca gaaacacaca gatttttggt tgcattttac   7920
caacaggtcc tagttgacac attcctgttt gttcctatta gaaaggagta ttacatgcag   7980
tctcttaagt gtagggatat tgaagtaaaa aacaaactca gaatcttgct aagaaaatat   8040
ttgttttggc atgagataaa gtagtttgtt tccttctttt tggctttctg tgtgctgact   8100
tttaagatcc attattttaa aaacataaat tcctattcat taatatgtat tttttaaaaa   8160
aacaggttta cttgtgtcct gaaagacagt gttacagaaa cactgccaag agtgaatagg   8220
acagcagcga tttctgggta ttctttcaag caatgctcac accaaataag cggtaagata   8280
tgttctcaga atcaacaaat accagctgtg atgtacacat atcgccacat cggatgtggt   8340
tttaaggcta tgaaatgaaa cactgctatg tggaaataaa ccccccttaat gaagttcttt   8400
cagtgtagag tataaactag tatacataca tgcctgccct ccaacacact gtaaaaacct   8460
ctttacctca tagaaagaca tatcttacta cctcacttcc catcatttat ttatattctt   8520
tctatttccc agcctaaaat cttaaatgaa agtctttttt tttttgagac agggtctcac   8580
tctgttgtcc aggctggagt gcagtggtgc aatcacagct cactccagcc tcaacctcct   8640
gggttcaagt gatcttcctg ccttagcctc tggagtagct gggaccagag gcatgcacca   8700
acattcccag ctaatttgtt cattttttcct agagacaggg tctcactgta ttgcccaggc   8760
tggtctcaaa ctcttggcct caagtgatct gcccgcctcg gccttccaga gtgccgggat   8820
tccatggtgc ccagtcgaaa ttctttatta aacgtattaa tccaaattga aaggagcaaa   8880
tataaaggtt gaagtgacac ttgtcttaat agtgaataga tacttgaatc agttaattag   8940
cgaaataatc agtgcagtta gggagaagag aggctaggtc agaaaatcaa aatgtgaatt   9000
tacaagtcta aaattgttac agtgtaagaa ggacattggc attcttttac tgcttccatt   9060
caagaataag aattttgcag attaatataa cgaaagacct ctgaggaaag gtgggtgaaa   9120
aagttgaaag gatgagtcag gagggacagt tgcttaggtc attgccccta gaatctggaa   9180
ggtactcatg tcttctgctt ttatttccag cttgcaacaa agacatttat gtggacctag   9240
acatgaaggg cataaactat aacagctcag ttgccaagag tgctcaagaa tgccaagaaa   9300
gatgcacgga tgacgtccac tgccactttt tcacgtacgc cacaaggcag tttcccagcc   9360
tggagcatcg gtgagtgagt cccaggacat tcgagtggtc gatgaaaaac agaatcgtga   9420
tttactaaaa agcttttgcc atcaacttta tgccagaatt tattttgaac ccctaaaaga   9480
catttctata atagtactcc tagttttctt catgaaaaat acacttaaag cctaatttgg   9540
atgcatttca tttatggtaa ggagtctatc ttttaataac actgtcagaa aaatatatat   9600
acttggctaa tttcaaaagc gctacacttt taaattggca cttttgaaac agctgcaatt   9660
ggtatgattg tcagtgccct tcccagtcta aaaaatgtta cagtctaaca gaataaaaat   9720
aaaaacctac tctctctctc tctaaataac agttccttac ctaagacaaa atactcatgt   9780
aaaaagtctt atcctgctcc atactggatt ttgaaatatt tcaaggataa atctatcaca   9840
taaggattta aaaattatct gatctctaat aaccaaatct gtgttctcat ctttaaaaat   9900
ttactaggga aatagattat taatttgtat attcagaaat atttgagatg atttagattt   9960
```

```
tcatagtaaa ctgcatttat ctggaatcaa cagaaaagtg aaaaacattc aaattactaa  10020
tacttgcgtt ttaacattgg attttaacat tctgctctcc acattcacaa agaggagtga  10080
acagaaagca aacaaagcat caacgagtta tttcaaaaac aacagtggtg aaaaacacac  10140
acaccaaacc cctaaattca tgatttgact tgtaaggctt atctttagct cagctcagac  10200
gacagctttt atgtctaaga cttaacagaa tgtgaactgc aagacaagaa attggaggtt  10260
tctaagcaag ataaagttaa gtcattaaaa gtaagaagga cttagccagg cgcggtggct  10320
cacacctgta atcccagcac tttgggaggc cgaggcgggc agatcacctg aggtcaggag  10380
ttcgacacca gcctgaccaa tatggtgaaa ccccgtctct actaaaaaag aatacaaaaa  10440
ttagccaggc gcggtggtgg gcgcttgtaa tcccagctac ttgggaggct gagacaagag  10500
aatcgcttga acccaggagg cggaggttgc agtgagccaa gatcgtgcca ttgcactcca  10560
acctgggcaa cagagtgaga ctccgtctca aataaaaaaa aacaaaaaat gagaagggct  10620
tgagaagtca ttcattcatg cactctcctt cttcatgtgg tcactctctc aagctgtcat  10680
tatactgaag aagaaataaa cttacacaat tcacaggtgc ttagcaacac tgctgggacc  10740
atgcccagcc attcagcctc ccagatggat gcttcggggt ctcgcaggtc ctctctccaa  10800
aggggacttt cttaatatct catgtttttt cctccttgca gttggaagaa taagacactt  10860
ttcctttttc tttttattca gtaacatttg tctactgaag cacacccaaa cagggacacc  10920
aaccagaata acgaagctcg ataaagtggt gtctggattt tcactgaaat cctgtgcact  10980
ttctaatctg ggtaattatc gacttcttga tgatgtaatt caaccattaa atatgctgat  11040
gattacagta gatctcactc aggataccag cttatgctca cgatgaaacg gacccaaaga  11100
tctttacctt cttcatgtga tagatttcat catgtcctat acagttagat cctctattta  11160
aatttccagt ttaaaataat catgccattt tcttctaaat aaaaaaaaat taaaagatct  11220
tgggatacac ttaaattttt taatatggaa tttacacata ctgtgaccgg aatttttcctg  11280
atagctggtg aattgagtcc ctgacatagt tcttccgtcg cgcagcttgt attagggaca  11340
ttttccctaa tacggtgttt gcagacagca acatcgacag tgtcatggct cccgatgctt  11400
ttgtctgtgg ccgaatctgc actcatcatc ccggttgctt gtttttttacc ttcttttccc  11460
aggaatggcc caaagaatct caaaggtaag gagttaacaa gtaaggataa tttgttatct  11520
tctaaaaata gctgatcaaa atccatcatt aaaaattcca agtaactaaa aatttactct  11580
aaatgtcagt ataggataaa agttgcaaag aatttctagc ccctctccct ttctattccc  11640
cacctactta ccacaaaccc aacattaccg aggactcttt tttttttttt ttttttttg  11700
agatggagtc tcgctctgct gcccaggctg gagtgcggtg gcatgatttc agctcactgc  11760
aaccttcgcc tcccaggtcc aagcgattct cctgcctcag cctcctgagt agctgggact  11820
acaggcatgg gacaccacgc ccagtaattt tttttgtatt tttagtagag atggggtttc  11880
accatgttgg ccaggctggt ctcaaactcc tgacttcagg tgatccacct gcctcggcct  11940
cccaaagtgc tgagattaca gggttgggcc accgtgcccg gccagtaaat tttaaaataa  12000
atataaatat tacttcacct aaataaattt taggtacagg tacagttgtg ttacatggat  12060
atactgtgta gtggtgaagt ctgggctttc agtgtagcca aatagtatac attattccca  12120
ttagataatt tctcctgcct caccctcctc tatcctccca actctctgag tctccaatag  12180
ctttcattcc actgtctctg tgcctgtgta cactttattt agctcccact taaaagtgag  12240
aatctacaat atttgacttt ctgtttctga gttgtttcac ttgagataat agcctccagt  12300
```

```
tctatccatg ttgctgcaaa agatatgatt ttatgatttt tttatggcta agtaacattc  12360
tatagtatat tctatacacc acattttctt tatccattca tttgctgata gactcttagg  12420
ttgatccata tctttgttat tgtgaatagt gctgcagtaa acatgtgagt gtaggtatct  12480
ttgtgacatg attttttttt ctttcttttc ctttggctat gtacccagta gtgggattgc  12540
tggaggtctc caccttggca aaggggcagt tgtctagttc taaatgaaat gaagagattc  12600
catttccatt tcatgacaac taaaagacaa ttcagtccaa tgctttgttt aaaataattg  12660
aaccaggaac agaaagagct gaaaatgtca gtgaaatgtc aaacccaaag tggagagaga  12720
gagagaggtg gaaatgaatg tctccatcaa gtgggttagg gtggtggtgg agggaggttt  12780
gagaattgag tccctgtttc cttaccaatg gaaattaaca taggacatca gaaacagcat  12840
ggaaaatttc tttgattatc aaaagtacac tagctaaggt tgctgtccct cttttattta  12900
tttatttatt tgagacaggg tcttgctctg tcactcagat ttggttgcac tgggtgtgat  12960
ctcagcccac tgcagcctcc acttcctagg ctcaagcaat ccacccgtct catcctccca  13020
agttgctggg accacaggtg tgcaccacca cccccagcta atgtttgttt ttttgtagag  13080
acagagtttc gccatgttgg ccaggctggt ctagaactcc tggcctcaag caatccacct  13140
gccttggtct cccacagtgc agggattaca agcctgagcc actatgccca gcttgctatt  13200
cctcattgac aacattcact taaacaagca aacaaatatc cgtaaaatta agtcagcttt  13260
aaaacctggc ttgtatatat ctctgaattg gaactctcag agccctcagc acttgcctga  13320
ttggcctcct gttgatgaaa agttgtcctc cagacaactc agccaaggga ggccctgtgt  13380
gccttgccta tcacatgagc ctcactttcc actgagtgag gctgtcattt cagaagcacc  13440
gggtctgtca catgaaaata tatctgttac catcacttac taaacaaatt tagtagaatt  13500
tgtttggtgc ttattatgta tcaggcattg ttctgaaggc tggggatacc atttagtgaa  13560
ctaaatcgac aaaaactttg cctattggac cagagtggag atgagagaga agtgaccaga  13620
tcgatctgtg ttatcagcag acagccaata agatttgctg ataggttgga ccacggattg  13680
tgaaggagtc agtgatagca ccaagacttt tggcccaagg aactggaaag atggaaatgt  13740
caatgacaga atgtggagga tttcgcaagc agcagagtgt aggagaagca atgcccttgg  13800
ctcatctagg gcaaagggtt gaattggcaa ctggaaatag aagtcaaatt cagaagagag  13860
gtttatgtgg acatctgtgt ttaggtgtca ccaatataca gctgatactt tttaaaaatc  13920
tagtgaaatt atcaaagggt taaatgcaga gagggaagaa agtaggtcca aagatcaagc  13980
cttgggacat tggaagttta gaaataagaa agatgtcatt gtcacttgta attttgtgct  14040
agtcactgct ctttttcttt gtcttattac cttactgacc aattcctaga ataggaataa  14100
cacatttgat ctttaataca gtatgtgata ggaacatggc ttctataagc ccaaacttgg  14160
caatttaaat ttaaatttat taaaattaaa taaaactggc tgggtgcagt ggctcacgcc  14220
tgtaatccca gcactttggg aggccgaggc ggtgaatcac gaggtcagga gtacgagacc  14280
atcctggcca acatggtgaa accccgtctc tactaaaaat acaaaagtta gccaggtgtg  14340
gtggcatgtg cctgtaatcc cagctactca agaggctgag gcaggagaat cacttgaacc  14400
cgggaggcgg aggttgcagt gagccaagat cgcgacactg cactccagcc tgggtgacaa  14460
gagaaagact atgtctcaaa aaaaaaaaaa attttaaata aaactaaaaa ttcaccttcc  14520
cagctgtgtt agccacattt caagtgccca atagccacat gtagttggca gttactgtat  14580
tggatggcac aggcatagaa tatttccatc actgcagaaa gatctatgga cagtcttgct  14640
ctagactgtg attttgtcta cttaggaaaa gtcactcttt tccaggaaga tgcttccagg  14700
```

```
gtgtggagta aacgacggac ttcacccatc tccttataaa cctattgcaa ccctggatag  14760
gaggtttcta ggtagcatga agactcttga atctttaaga taggctggga gtgttgaaag  14820
gaaggaaatg aaaagggaag atactaggaa gactgacaat agagcaagct cagaaaattt  14880
ttatggaggt gatttagtta gaaaatttgt ctgcaaccta agggccatgg agtgtgactc  14940
catggtttat gggtgtaact ccgtggttta tgaagagtac tttcaaaata ggaaaatctt  15000
cacaactaag tgctagcatg agctgacttt actttctcta ggtgctgtaa aaatgttttt  15060
atgtgtttga tatgatatat ttctacttcc cttttgtttt tgttagaaat ctttgtctcc  15120
ttaaaacatc tgagagtgga ttgcccagta cacgcattaa aaagagcaaa gctctttctg  15180
gtttcagtct acaaagctgc aggcacagca tcccaggtaa actgagagtt ctgcattctg  15240
gctgagagtg accagccccg aggaggctga tacatgctga gggagggtct cactctgaca  15300
tgtggtctgc tgtctagtgt tctgccattc ttcattttac catgacactg atttcttggg  15360
agaagaactg gatattgttg ctgcaaaaag tcacgaggcc tgccagaaac tgtgcaccaa  15420
tgccgtccgc tgccagtttt ttacctatac cccagcccaa gcatcctgca acgaagggaa  15480
gtaagccata tgaagggtta tgcagacacc cttgtcccgt ctgcctgtga ggtgcattat  15540
gtttataccg ttttgtttcc aactgcaggg gcaagtgtta cttaaagctt tcttcaaacg  15600
gatctccaac taaaatactt cacgggagag gaggcatctc tggatacaca ttaaggttgt  15660
gtaaaatgga taatggtgag tataatgtca cttgaaaaaa tatagctgaa ggaattattc  15720
catgcttcat acatcacaat caagactgtc agttatagcc acagaaggga gaacattcag  15780
gaaataacaa attttgcaat tttctattat tttcactcct gtcactcaag ctgaccatgt  15840
tttaaaggta aatattgagg cttgactaaa ctgtacattg cctagtatta actaaatata  15900
tgctttaatt tgacacattt atacacctgg catttctgtt ttctttcttt cttttttttt  15960
tttttttttt tgagacacag tctcactctg ttgcccaggc tggagtgcag tgatgtggtc  16020
agtgttcact gcagcctctg gcttgaactc ctggactcga acaatcctcc caccttagct  16080
ccctgagtag ctggggctac aggcgtgcac cacaacactc ggctaatttg ttgtagagat  16140
gggatcttgc catgttgccc aggctggtct tgaactcctg ggctcaagca atcctcccgc  16200
tttggcctcc caaagttctg ggattacagg cttcagccac tgcacccagc cacaactggc  16260
atttcctaat gagacccaga ctctgccaac actcctgtta tcaaggccag taatctttcc  16320
tattatcctt tgtaagggaa ttatcgatca gcactttggt tagtcaaatt actaattttc  16380
ttccaaaaat tgtgtatcta ttcaagaaat actggagcac ctccttttta gggtctttat  16440
tcagattcca tgcagggttc tggagactta gggattggca aaggttaagg taaaacttta  16500
ctagtaacaa tgagtgtggt aggatggaaa taagtgttta gattacacga gacctgtaat  16560
aacataaaag ttacaataaa aatccaacca gcagtgtttc catcccagtg gccaatttct  16620
gagcatagtc acgagagatg ctttgtaggc aaacagaatt gttctaaggg acaaaatccc  16680
caacaggaaa gaacacacca caaacactcc tgcttaaatt accatagtaa cttaggatgg  16740
ctttactata tattgattta cataaagctg catgttctta tactgtttat tgccaaatgt  16800
ccaatattac aatacactat aaggtgcaac tgagatttaa tgaataaaat ggaagtaaca  16860
atcctgcctc gtgatagttt tagaagcaca aaaacattct gtgtcagatt atctgctgta  16920
ccgagaaggc gaatcaatcc ttaatttctg agaacttgtt ttgtagaaca taaagacgtt  16980
atattgcctc caacactggt atcctaacta acagactatg ccttcctaga gcttagaggc  17040
```

```
gctccgatga aaatctctgg atggctcaag acttcttaaa aagcaagtca attacgtcgt  17100
atctcataca ttctgttttc ctcacaataa atttccctaa gacaagaagg agcattcggc  17160
accattctgt tgtctttctt ctacttctaa gcgttagaag ggacacttag caaatgttgc  17220
tgttaagtaa tgttgacatg gtttaataaa atgggaatga gcacgtatac ctcaatacat  17280
tgcagactgc attttccccc ttccttcttc attatggttt tctctgttgg atttatagac  17340
tctggcctgt agaagttaca gaatatgcca ggtatagatt gatagctaca ggagaaaatg  17400
taagataaag gaaaataaag tcttacgtct tttcagtgca actttggagg gagtgaatta  17460
gataactagg tttttactgc gctgtatttg atgaaataac cccctaatgt gaaagggaat  17520
agctgcgtga gatatttatg gtgccttgtc tgtcactggt ctacaatgta acttaacttt  17580
ctgaagatag atagcagcac cattaaaata aacatttctt accacaaaat atgattctaa  17640
acacatattt tcagcatttc gtttaaactg agaaacagca taggatgaac ctcaaggcct  17700
ctcacctgga ccttgagtta tttctaaaat atcttagtta ctatttacct attaattttc  17760
ctaaaattta cctttatgac gcttcccacc ttgcagaaat tccagaatag atggccctcc  17820
aaaatgaatg ttcacccttc cggctctaaa atgagagcct ctgttcaggc ttccgaagtc  17880
acatcgtgct cgttctcacc tcagttgctg ttagctgctg tttccttccg aactccttct  17940
ctcatcctct cctcctattt gaaatctgcc ccagaattat acactcattt tcctaccaag  18000
gaaaaaaagg cctagaaagg ttgttttaca cccacaaaac tagtgaatgg accttctagg  18060
acccggcttc tcatcagtga ttcttctgtt aacttagact cctcccttag ctcaggacgc  18120
ggagccttct gagcacctga gcctggttat tctaaatgtg atctgggcac agcacattga  18180
catcacctgg gagcttgtta gaaagaattt caggacccac acagatgtta ctgagtcaga  18240
atctgcattt tgaaagctac acaggcaacc cacaggcaca taaattttga gtcgcatagg  18300
tgtgtgcgtg tgtgtgcgca tgtatgtgtg cgtgtgtttg tgtgcacgtg tgtgtgtgtg  18360
tgtctagaat actgctgtct acgaacaccc tattcccatc catctgtgtt ccatggctcc  18420
aaccgggagg gtgggttctt gtgtcgggca tccagtaagt agaaatagag ggcactgtcc  18480
tgtctaggca gccccaagag aaaagaaaca gagggatgag cctgagtcaa agtccctgaa  18540
aagtaccaag gaccccagag aatcccaaac tgtcaacaag gccaaaggtc agaggaagtt  18600
catagcagat cagtcttact ttggacgtgg gtggagcagg agtgactggg atcatggtca  18660
gcagagtcac tgggacaggg caggaactgg acaatggctg cagcctgcgg gcaaggtgct  18720
tgccttttct ttctaagagc agttctcaaa cgccagcagg gctggttcaa acacagatgg  18780
ctgagcttcc aggctggagt ttctcattca ctggatctga ggttgggctg aagaatgtgc  18840
atttctaaca cgttcccagg tgacgctgtt ggtctggaga ctgcacttga caaccactgg  18900
tttaaaaaca ccattcacgt tatcatttga aggagggtaa gacagccttg tagtaccaca  18960
caaggagggc tacattctta ggggtgtgta attacaagat gacttagtca attccatttt  19020
tcatgtgcat gttttgcttt ggcagcttga ttataaagtc tctgtaactc agggtcatga  19080
taaactattg acttgaggaa aggttttctt cttgttcctg aaggagcata attactgatg  19140
gaaaggaaga tgtaggaagc tgctcatcac aatgcttctg ttgcagagtg taccaccaaa  19200
atcaagccca ggatcgttgg aggaactgcg tctgttcgtg gtgagtggcc gtggcaggtg  19260
accctgcaca caacctcacc cactcagaga cacctgtgtg gaggctccat cattggaaac  19320
cagtggatat taacagccgc tcactgtttc tatgggtcag taccacggct gtttttatta  19380
gttcatcttc ttcacacatt tataaaaaat attactagca tgttaggaaa taaatacttt  19440
```

```
aaccaattag attgtcttat ttgcaaaatt aattaattgc ttcagtggta aaaaacgcaa  19500

aaaggaagag ctcatggtct cccagcatca gaacaggtgc aggtacaagg ctgcttgact  19560

gcctgctatt ccgcttccca tttaaccgca ttcacatccc caagggcctt catgttattc  19620

cctgcaagag catacctccc tctgtgcctc gctctgtgca ctgtgcccgg aactaaactc  19680

acagaggatt taccattgtc tgaatcaaat ttctaatatg tgtgtgtgtg tgtgtgcgtg  19740

tgtgtttaaa tacagaaagt ggccaggtgt ggtggttcac gcctgtcatc tcagcacttt  19800

gggtggctga ggtgggagga ttgctcaatg ccaggagtct gaggtcagcc tgggcaacat  19860

agtgagacct cgtctctaaa aaatatttaa aaactagcct ggcatggtgt tttgtgtgcc  19920

tgtagcacca gctgctcaga agtctgaggt aggaggattg cttgagccca agagttcaag  19980

ggtgcagtga gttactacag tgccactgtg ctccagcctg agcaacagag caagacccta  20040

tctctaagta aataaataaa atacagaacg agttcggtat gcatcctcac attggattcc  20100

ttacttaggt cactttcagc gttggccaaa caaaaaggct ccagctgggg gtatatatat  20160

tccagggaag ttaagttggc caaactttcc gtttgctact tcagtatcct ccgagttgtt  20220

tccagacaca gttttgtgtg ctttttagtt ttggttttct tttttaatca atctgcagca  20280

cactcatgtt aaactcaaga acacatgtga ggccaagagt tcccgttacc tgtcacatat  20340

gggaatggag tagcagaaag cctagtttct gtcacagcta gttactggcg agattgagac  20400

tgagtccagc ggtcttcgtg tgtgtgtgtg cgtgtgtgtc tgtgcagtgt gcgtgtgtgt  20460

gcgtgtctgt gtgtgcgtgt gcgggtgtgt gcgtgtgtgt gtgttggagc acggagggag  20520

tgctcattca tttttgtgt ataatggatt ttctttatag ggtgaatatg ttttttatcc  20580

cgaaaaatct taggataaaa tcactttttt ctacctaaat gtccatcatt ggcagaaaat  20640

attagtaata attaaacagc cacacacttc acaatgtctg ggaattattt ttagtaaagg  20700

aaatttcttt ccctctgttg tttgctcctt agggtagagt cacctaagat tttgcgtgtc  20760

tacagtggca ttttaaatca atctgaaata aaagaggaca catctttctt tggggttcaa  20820

gaaataataa tccatgatca gtataaaatg gcagaaagcg ggtatgatat tgccttgttg  20880

aaactggaaa ccacagtgaa ttacacaggt acggagaatt ttatccggaa agttgtctcc  20940

aatggtgaac tggataaaat gtttaacact actagactta cggcctgacc ctgccaatct  21000

ctccatgcgt tatcatcatg aaagggagag ggcctggaat gctagtcatt cactctgcta  21060

aggctgacac actttcctgg ctattgaaac ttattttggg aatgtgggta aagagatacg  21120

ttttcctgag tcttcttcag gtgcatagaa tgacataatt tcataatact ttggaatagt  21180

aaagataatt tagtctaaag ataatttatt aaagataatt tagggatgaa ggattgaagg  21240

ttagaacaat taagcaactt gtgcaggatc aaagtgagtt ggatgaggag ttagcggtga  21300

gggtgaggct tgtctctctc tcgccctctc atcctggcac atgtgcgata tcgtgctgaa  21360

cctgagggag gaaaatacac gacaacaagg caaaaaatga atatagtaaa caaagaaaac  21420

acagataatg tacagtggaa gaagagtctc ttctggaaaa gaggatatat tttgcgtctc  21480

atatttaaac cacgattttt taaatttaga ttctcaacga cccatatgcc tgccttccaa  21540

aggagataga aatgtaatat acactgattg ctgggtgact ggatgggggt acagaaaact  21600

aagaggtaaa aatgatgttg ttatatgtgc tccatcctag aaatgaagag cggaaccttt  21660

tctgccctgt caagtcatgt agctgaagca caactcgagt cacactactc agttgcagga  21720

agcggattaa taaagatgga gaggcaaaaa tcacccaagt gaggctggtg cctcatatgt  21780
```

```
ttgattggaa attttaaatg tgactaaatc tctttaaaga ctaattatat ttaatgaagt  21840
ttaatgtgaa gcctagcact tttcagtaaa tgttctagcc tgctatccaa ttactttctt  21900
gggaagtcat tccagttaga gtcataatta atttttgaac ttaattaaca ttaacaaaat  21960
ggtacacgca atagtgggaa taatgtcttc ttcatacttg taattataaa aggtctgtga  22020
agtaaatcta acatttttc cttctagatt tttatataga catgagtttt gtgttgttgt  22080
tgttttgaga tggactctcg ctctgtcgcc caggctggag tgcagtggca cgatctcggc  22140
tcactgttac ctccacctcc cgggttcaag tgattctcct gcctcagcct cccgagtagc  22200
tgggattata ggtacccaac caccacccca agctaatttt ttgtattttt agtagagacg  22260
gggtttcatc atgttagcca ggatggtctc aatctcctga cctcgtgatc cacctgcctc  22320
ggccttccaa agtgctggaa ttacaggcgt gagcccccac acccgtccat gatttttatt  22380
ttaaatatat gtggcccagc accactggtg gctcacgcct gtaatcccag cactttggga  22440
ggccaagatg ggtggatcac ttgaggtcag gagttcaaga ctggcctggc caacatggtg  22500
aaaccctgtc tctactaaaa atacaaaaat tagctgggca tggtggtgtg tgcctgtaat  22560
cccagctact cgggaggctg aggcaagata atcgcttgaa cttgggaggt ggaggtagca  22620
gtgagctgag attgcaccac tgcactccag cctgggcgac agaaagagac tccgtctcaa  22680
ttaaaaatat atatatatat atatttatat gtatgcatat atgtttatgt gtattgtgta  22740
tggttattct acaaacgaac caaaaaaatt tttttcagac aaaatacaaa atactctcca  22800
gaaagccaag atacccttag tgaccaacga agagtgccag aagagataca gaggacataa  22860
aataacccat aagatgatct gtgccggcta cagggaagga gggaaggacg cttgcaaggt  22920
aacagagtgt tcttagccaa tggaatatat gcaaattgga atgcttaatg cgttggggtt  22980
tttttgtttg ttttgttttt tttgtttgtt ttttttgag acagagtctc gctctgttgc  23040
ccaggctgga gtgcagtggc tcgatctcag ctcactgcaa gctctgcctc ccaggttcac  23100
gccattctcc tgcctcagcc tcccaaatag ctgggactac aggcgccagc taccaagccc  23160
agctagcgtc tttttttttt ttagttttag tagagacggg gtttcaccat gttggccagg  23220
atggtctcga tctcctgacc tcatgatctg cctgcctggg cctcccaaag tgctgggatt  23280
acaggcgtga gccaccgcgc cgggccgctt aatgcatttt aaaaagcagt cttctgccaa  23340
tgagcaggga acacagtgta tttgtttgac ttagactgaa atcaaaagca aggagattga  23400
ctggatgaac gcaagcaccc aggttctctg cagtatatta aggggccaag acaacatttt  23460
aggcaaaatc agcctgagca agatgtgctg aagatgggaa gcgtctgagt tgatctgtgc  23520
accttttctt gtctcccctc gttctaggga gattcgggag gccctctgtc ctgcaaacac  23580
aatgaggtct ggcatctggt aggcatcacg agctggggcg aaggctgtgc tcaaagggag  23640
cggccaggtg tttacaccaa cgtggtcgag tacgtggact ggattctgga gaaaactcaa  23700
gcagtgtgaa tgggttccca ggggccattg gagtccctga aggacccagg atttgctggg  23760
agagggtgtt gagttcactg tgccagcatg cttcctccac agtaacacgc tgaaggggct  23820
tggtgtttgt aagaaaatgc tagaagaaaa caaactgtca caagttgtta tgtccaaaac  23880
tcccgttcta tgatcgttgt agtttgtttg agcattcagt ctctttgttt ttgatcacgc  23940
ttctatggag tccaagaatt accataaggc aatatttctg aagattacta tataggcaga  24000
tatagcagaa aataaccaag tagtggcagt ggggatcagg cagaagaact ggtaaaagaa  24060
gccaccataa atagatttgt tcgatgaaag atgaaaactg gaagaaagga gaacaaagac  24120
agtcttcacc attttgcagg aatctacact ctgcctatgt gaacacattt cttttgtaaa  24180
```

```
gaaagaaatt gattgcattt aatggcagat tttcagaata gtcaggaatt cttgtcattt  24240
ccattttaaa atatatatta aaaaaaatca gttcgagtag acacgagcta agagtgaatg  24300
tgaagataac agaatttctg tgtggaagag gattacaagc agcaatttac ctggaagtga  24360
taccttaggg gcaatcttga agatacactt tcctgaaaaa tgatttgtga tggattgtat  24420
atttatttaa aatatcttgg gaggggaggc tgatggagat agggagcatg ctcaaacctc  24480
cctaagacaa gctgctgctg tgactatggg ctcccaaaga gctagatcgt atatttattt  24540
gacaaaaatc accatagact gcatccatac tacagagaaa aaacaattag ggcgcaaatg  24600
gatagttaca gtaaagtctt cagcaagcag ctgcctgtat tctaagcact gggattttct  24660
gtttcgtgca aatatttatc tcattattgt tgtgatctag ttcaataacc tagaatttga  24720
attgtcacca catagctttc aatctgtgcc aacaactata caattcatca agtgtgattt  24780
ttttttttt tttttgagat gaagtctcac cctgttgccc aagctggagt gcagtggtgt  24840
gatctcggct cactgtaaac tctacctcct ggattcaagc gattgtcctg cctcagtctc  24900
ccaagtagct gagattacag gcacatgcca ccatgcccgg ctaatttttg tatttttagt  24960
agagacgggg tttcactatg ttggccaggc tggtcttgaa ctcctgacct cgtgatctgc  25020
ccacctcggc ctctcaaagt gctgggatta caggtgtgag tcactgcgtc tggccatgga  25080
aaatatttat tgagcacaat tatgtgagag catcatgctg agctttgaag atacagtggt  25140
gagcaaacat atatcctggc ttcatgaaga ttatactcta gttaacatga gcaacaaaat  25200
aaaataatca cacaaaatat ataggttcaa gctgaaatga gtggctgcac cagattctat  25260
gagataagaa aggaagaagg acatttttca ccaagttcaa agactgggat acaaaggaat  25320
ttgtcctgac aaaggcaaaa caaaaacaac aacaaacaaa aaacccaaaa gagcaaaatg  25380
acagtagaac ataacggggc cagatcaaaa atgctgacag gttcccaaaa gaataaaatg  25440
acggtaggac atgacggggc cagatccaaa atgctgacag gttcaaacaa aattggaatt  25500
gaaaatcaga gtgcgttcaa gagtatcaaa caatactatc ttgttacttg cttattacct  25560
tagtagactg gaagcaacac ttcacacaaa aaaagggttt ggatgtaatt tcggataaga  25620
agagatgttt ctgtaaagtc tttcctgaga agcatattat ttgagaaaaa cacatatttc  25680
tgtttttagt atttcacttt gtataatgtc ttaatttttg aagagctggt atattcctat  25740
gattcattaa tgaaagttct ataagatata aaatatacaa tgaggagatc tcctcttctg  25800
taccagaaga gtgcacattc tacacactgc gtagcacctt tctcacttac gttctgtctg  25860
ggcacacttc tgattgacac gcagagggct ctctctgtct ggggatattt ctgatgggta  25920
ccgagagagc ttcctctatc ttgggttatt tctgatgcgt agagaagggc tgcctctgtc  25980
cattatggaa ggctggtgtt c                                             26001
```

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3

```
cagcctggag catcgtaaca                                                  20
```

<210> SEQ ID NO 4
<211> LENGTH: 25
<212> TYPE: DNA

<213> ORGANISM: Artificial Sequence
<220> FEATURE:
<223> OTHER INFORMATION: primer

<400> SEQUENCE: 4
tttatcgagc ttcgttattc tggtt 25

<210> SEQ ID NO 5
<211> LENGTH: 29
<212> TYPE: DNA
<213> ORGANISM: Artificial Sequence
<220> FEATURE:
<223> OTHER INFORMATION: probe

<400> SEQUENCE: 5
ttgtctactg aagcacaccc aaacaggga 29

<210> SEQ ID NO 6
<211> LENGTH: 2246
<212> TYPE: DNA
<213> ORGANISM: Mus musculus

<400> SEQUENCE: 6
ggataccggc tcacgtagaa aaaggacaag actataggaa agaaagcaaa cactccgccg 60
aggactacag caaagacaga aagtatctgc aggatgacct cattacatca ggtgttatat 120
tttatctttt ttgcctcagt ttctagtgaa tgcgttacta aggtcttcaa agacatcagc 180
tttcaaggag gtgacctgag tactgttttc acaccgagcg ccacatactg ccgcttggtc 240
tgcactcacc acccacggtg cttgctcttc acgttcatgg ctgagtcatc ttcggatgat 300
cctaccaaat ggtttgcctg catcctgaag gacagcgtca cagaaatatt gccaatggta 360
aacatgacag gcgcgatctc tggatattcc ttcaagcaat gccctcagca attaagtact 420
tgcagcaaag atgtgtacgt gaacctagac atgaagggca tgaactataa cagctctgtc 480
gtgaagaatg ctcgagaatg ccaggagaga tgcacagacg atgcccactg ccagtttttc 540
acatacgcaa cagggtattt tcccagtgtg gaccatcgta aaatgtgtct tttgaagtac 600
acccgaacgg ggacgccaac cacaataacg aagctcaatg gcgtggtatc tggattttca 660
ctgaagtcct gtggactttc aaacttggct tgtatcaggg acattttccc taacacggtg 720
ctggcagacc ttaacattga cagcgtggtg gccccagatg cttttgtctg tcgtcgcatc 780
tgcacgcatc accccacttg tttgttcttc acattctttt cccaagcatg gccgaaagaa 840
tctcagagac atctttgtct ccttaaaacc tctgaaagtg gattaccaag cacacgcatt 900
acaaagagcc acgccctttc gggcttcagt ctccagcact gcaggcacag tgtcccagta 960
ttctgccatc cgtcctttta caacgacact gatttcttgg gagaagagct ggacatcgtc 1020
gatgtgaaag gccaagaaac ctgtcagaaa acgtgtacca ataacgcccg ctgccagttc 1080
tttacctact atccatcgca cagactgtgc aatgagagga accgcagggg cagatgttac 1140
ctaaagcttt cctccaatgg atctccaacg agaatacttc atgggagggg aggcatctct 1200
ggatactcac tgaggctgtg caaaatggat aatgtgtgca caactaaaat caaccccaga 1260
gtggtaggag gagctgcgtc tgttcacggt gagtggccat ggcaggtgac tctgcacatc 1320
agccagggac acctgtgtgg aggctccatc attggaaacc aatggatact gacagcagct 1380
cattgtttct ctgggataga gacacctaaa aagctgcgtg tctacggtgg cattgtaaat 1440
caatcagaaa taaatgaagg gactgctttc ttcagggttc aagaaatgat aattcatgat 1500
cagtatacga cagcagaaag tgggtatgat attgccctgt taaaactgga atcagccatg 1560
aattacacag attttcagcg gccaatatgc ctgccttcca aaggagatag aaacgcagtg 1620
cacacagaat gctgggtgac tggatggggg tacacagcac taagaggtga agtacaaagt 1680
actcttcaga aagccaaggt tccattggtg tcaaatgaag aatgtcagac aagatacaga 1740
agacacaaaa taaccaataa gatgatctgt gcaggctaca aagaaggagg gaaggatacg 1800
tgcaagggag attctggagg gcccctgtcc tgcaaataca atggggtctg gcacttggtg 1860
ggcatcacaa gctggggtga aggctgtggt cagaaggaga gaccgggggt ctacacgaac 1920
gtggccaagt acgtggactg gattctggag aaaactcaaa cagtctgaaa gagttcaact 1980
ggtatcactt tgtggccctg gaagattatt ccatagaaat gagcttgacg tctctgatga 2040
agacactggg atactgactc ttccactgta accaattgaa tggccttgat gtacgtaaga 2100
acacccagaa agaaaactat tattttcaga attcctgatc tgggagaacc actggttgtt 2160
ttctgcatcc agctactact caaggaaaca aatacagcaa ggagatttta aaaataaaaa 2220
cacatcagat atataaggaa aatatc 2246

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
acatgacagg cgcgatctct 20

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
tctaggttca cgtacacatc tttgc 25

<210> SEQ ID NO 9
<211> LENGTH: 26
<212> TYPE: DNA
<213> ORGANISM: Artificial Sequence
<220> FEATURE:
<223> OTHER INFORMATION: probe

<400> SEQUENCE: 9
ttccttcaag caatgccctc agcaat 26

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 10
tcctggcatt ctcgagcatt 20

<210> SEQ ID NO 11
<211> LENGTH: 20
<212> TYPE: DNA
<213> ORGANISM: Artificial Sequence
<220> FEATURE:

<223> OTHER INFORMATION: synthetic oligonucleotide

<400> SEQUENCE: 11
tggtaatcca ctttcagagg 20

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 12
aaggacctac actatggaat 20

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 13
cctctgaaag tggattacca 20

<210> SEQ ID NO 14
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 14
tcggaagcga ctcttatatg 20

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15
ttcaaacaag tgacatacac 20

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
tgagagaatt gcttgctttc 20

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 17
aaatatacct tgagagaatt 20

```
<210> SEQ ID NO 18
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 18

agtatgtcag aaatatacct                                                    20


<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19

ttaaaatctt agtatgtcag                                                    20


<210> SEQ ID NO 20
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 20

cagcatattt gtgaaagtcg                                                    20


<210> SEQ ID NO 21
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 21

tgtgtaggaa atggtcactt                                                    20


<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 22

tgcaattctt aataagggtg                                                    20


<210> SEQ ID NO 23
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 23

aaatcatcct gaaaagacct                                                    20


<210> SEQ ID NO 24
<211> LENGTH: 20
<212> TYPE: DNA
<213> ORGANISM: Artificial Sequence
<220> FEATURE:
<223> OTHER INFORMATION: synthetic oligonucleotide
```

<400> SEQUENCE: 24
tgatataaga aaatcatcct 20

<210> SEQ ID NO 25
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 25
acacattcac cagaaactga 20

<210> SEQ ID NO 26
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 26
ttcaggacac aagtaaacca 20

<210> SEQ ID NO 27
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 27
ttcactcttg gcagtgtttc 20

<210> SEQ ID NO 28
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 28
aagaataccc agaaatcgct 20

<210> SEQ ID NO 29
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 29
cattgcttga aagaataccc 20

<210> SEQ ID NO 30
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 30
ttggtgtgag cattgcttga 20

<210> SEQ ID NO 31
<211> LENGTH: 20

<212> TYPE: DNA
<213> ORGANISM: Artificial Sequence
<220> FEATURE:
<223> OTHER INFORMATION: synthetic oligonucleotide

<400> SEQUENCE: 31
aatgtctttg ttgcaagcgc 20

<210> SEQ ID NO 32
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 32
ttcatgtcta ggtccacata 20

<210> SEQ ID NO 33
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 33
gtttatgccc ttcatgtcta 20

<210> SEQ ID NO 34
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 34
ccgtgcatct ttcttggcat 20

<210> SEQ ID NO 35
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 35
cgtgaaaaag tggcagtgga 20

<210> SEQ ID NO 36
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 36
agacaaatgt tacgatgctc 20

<210> SEQ ID NO 37
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 37
gtgcttcagt agacaaatgt 20

<210> SEQ ID NO 38
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 38
tgcacaggat ttcagtgaaa 20

<210> SEQ ID NO 39
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 39
gattagaaag tgcacaggat 20

<210> SEQ ID NO 40
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 40
ccgggatgat gagtgcagat 20

<210> SEQ ID NO 41
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 41
aaacaagcaa ccgggatgat 20

<210> SEQ ID NO 42
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 42
tcctgggaaa agaaggtaaa 20

<210> SEQ ID NO 43
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 43
attctttggg ccattcctgg 20

<210> SEQ ID NO 44
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 44
aaagatttct ttgagattct 20

<210> SEQ ID NO 45
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 45
aatccactct cagatgtttt 20

<210> SEQ ID NO 46
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 46
aaccagaaag agctttgctc 20

<210> SEQ ID NO 47
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 47
ggcagaacac tgggatgctg 20

<210> SEQ ID NO 48
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 48
tggtaaaatg aagaatggca 20

<210> SEQ ID NO 49
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 49
atcagtgtca tggtaaaatg 20

<210> SEQ ID NO 50
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 50
aacaatatcc agttcttctc 20

<210> SEQ ID NO 51
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 51
acagtttctg gcaggcctcg 20

<210> SEQ ID NO 52
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 52
gcattggtgc acagtttctg 20

<210> SEQ ID NO 53
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 53
gcagcggacg gcattggtgc 20

<210> SEQ ID NO 54
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 54
ttgaagaaag ctttaagtaa 20

<210> SEQ ID NO 55
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 55
agtattttag ttggagatcc 20

<210> SEQ ID NO 56
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 56
atgtgtatcc agagatgcct 20

<210> SEQ ID NO 57
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 57
gtacactcat tatccatttt 20

<210> SEQ ID NO 58
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 58
gattttggtg gtacactcat 20

<210> SEQ ID NO 59
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 59
tcctgggctt gattttggtg 20

<210> SEQ ID NO 60
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 60
ggccactcac cacgaacaga 20

<210> SEQ ID NO 61
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 61
tgtctctgag tgggtgaggt 20

<210> SEQ ID NO 62
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 62
gtttccaatg atggagcctc 20

<210> SEQ ID NO 63
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 63
atatccactg gtttccaatg 20

<210> SEQ ID NO 64

<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 64
ccatagaaac agtgagcggc 20

<210> SEQ ID NO 65
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 65
tgactctacc ccatagaaac 20

<210> SEQ ID NO 66
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 66
cgcaaaatct taggtgactc 20

<210> SEQ ID NO 67
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 67
ttcagattga tttaaaatgc 20

<210> SEQ ID NO 68
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 68
tgaaccccaa agaaagatgt 20

<210> SEQ ID NO 69
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 69
tattatttct tgaaccccaa 20

<210> SEQ ID NO 70
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 70
aacaaggcaa tatcataccc 20

<210> SEQ ID NO 71
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 71
ttccagtttc aacaaggcaa 20

<210> SEQ ID NO 72
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 72
gaaggcaggc atatgggtcg 20

<210> SEQ ID NO 73
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 73
gtcactaagg gtatcttggc 20

<210> SEQ ID NO 74
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 74
agatcatctt atgggttatt 20

<210> SEQ ID NO 75
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 75
tagccggcac agatcatctt 20

<210> SEQ ID NO 76
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 76
ccagatgcca gacctcattg 20

<210> SEQ ID NO 77
<211> LENGTH: 20
<212> TYPE: DNA

<213> ORGANISM: Artificial Sequence
<220> FEATURE:
<223> OTHER INFORMATION: synthetic oligonucleotide

<400> SEQUENCE: 77
cattcacact gcttgagttt 20

<210> SEQ ID NO 78
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 78
tggcacagtg aactcaacac 20

<210> SEQ ID NO 79
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 79
ctagcatttt cttacaaaca 20

<210> SEQ ID NO 80
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 80
ttatggtaat tcttggactc 20

<210> SEQ ID NO 81
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 81
aaatattgcc ttatggtaat 20

<210> SEQ ID NO 82
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 82
tatctgccta tatagtaatc 20

<210> SEQ ID NO 83
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 83
gccactactt ggttattttc 20

<210> SEQ ID NO 84
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 84
aacaaatcta tttatggtgg 20

<210> SEQ ID NO 85
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 85
ctgcaaaatg gtgaagactg 20

<210> SEQ ID NO 86
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 86
gtgtagattc ctgcaaaatg 20

<210> SEQ ID NO 87
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 87
ttttcaggaa agtgtatctt 20

<210> SEQ ID NO 88
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 88
cacaaatcat ttttcaggaa 20

<210> SEQ ID NO 89
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 89
tcccaagata ttttaaataa 20

<210> SEQ ID NO 90
<211> LENGTH: 20
<212> TYPE: DNA
<213> ORGANISM: Artificial Sequence
<220> FEATURE:

<223> OTHER INFORMATION: synthetic oligonucleotide

<400> SEQUENCE: 90
aatgagataa atatttgcac 20

<210> SEQ ID NO 91
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 91
tgaaagctat gtggtgacaa 20

<210> SEQ ID NO 92
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 92
cacacttgat gaattgtata 20

<210> SEQ ID NO 93
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 93
taccttgaga gaattgcttg 20

<210> SEQ ID NO 94
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 94
gtcagaaata taccttgaga 20

<210> SEQ ID NO 95
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 95
atcttagtat gtcagaaata 20

<210> SEQ ID NO 96
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 96
gagtcacaca ttcaccagaa 20

<210> SEQ ID NO 97
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 97
gtgagcattg cttgaaagaa 20

<210> SEQ ID NO 98
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 98
cttatttggt gtgagcattg 20

<210> SEQ ID NO 99
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 99
acataaatgt ctttgttgca 20

<210> SEQ ID NO 100
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 100
ggtccacata aatgtctttg 20

<210> SEQ ID NO 101
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 101
gtctaggtcc acataaatgt 20

<210> SEQ ID NO 102
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 102
tgcccttcat gtctaggtcc 20

<210> SEQ ID NO 103
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 103
gttatagttt atgcccttca 20

<210> SEQ ID NO 104
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 104
tcagtagaca aatgttacga 20

<210> SEQ ID NO 105
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 105
tgggtgtgct tcagtagaca 20

<210> SEQ ID NO 106
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 106
agccagatta gaaagtgcac 20

<210> SEQ ID NO 107
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 107
agcaaccggg atgatgagtg 20

<210> SEQ ID NO 108
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 108
gccattcctg ggaaaagaag 20

<210> SEQ ID NO 109
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 109
ttgagattct ttgggccatt 20

<210> SEQ ID NO 110
<211> LENGTH: 20

<212> TYPE: DNA
<213> ORGANISM: Artificial Sequence
<220> FEATURE:
<223> OTHER INFORMATION: synthetic oligonucleotide

<400> SEQUENCE: 110
actgaaacca gaaagagctt 20

<210> SEQ ID NO 111
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 111
agaatggcag aacactggga 20

<210> SEQ ID NO 112
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 112
tgtcatggta aaatgaagaa 20

<210> SEQ ID NO 113
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 113
aagaaatcag tgtcatggta 20

<210> SEQ ID NO 114
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 114
ggtgcacagt ttctggcagg 20

<210> SEQ ID NO 115
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 115
ggacggcatt ggtgcacagt 20

<210> SEQ ID NO 116
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 116
aactggcagc ggacggcatt 20

<210> SEQ ID NO 117
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 117
ccttaatgtg tatccagaga 20

<210> SEQ ID NO 118
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 118
tggtggtaca ctcattatcc 20

<210> SEQ ID NO 119
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 119
ggcttgattt tggtggtaca 20

<210> SEQ ID NO 120
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 120
aacgatcctg ggcttgattt 20

<210> SEQ ID NO 121
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 121
acaggtgtct ctgagtgggt 20

<210> SEQ ID NO 122
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 122
cactggtttc caatgatgga 20

<210> SEQ ID NO 123
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 123
ctaccccata gaaacagtga 20

<210> SEQ ID NO 124
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 124
ttaggtgact ctaccccata 20

<210> SEQ ID NO 125
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 125
agacacgcaa aatcttaggt 20

<210> SEQ ID NO 126
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 126
tttcttgaac cccaaagaaa 20

<210> SEQ ID NO 127
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 127
gtggtttcca gtttcaacaa 20

<210> SEQ ID NO 128
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 128
ttggctttct ggagagtatt 20

<210> SEQ ID NO 129
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 129
ggcacagatc atcttatggg 20

<210> SEQ ID NO 130
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 130
gattcctgca aaatggtgaa 20

<210> SEQ ID NO 131
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 131
gcagagtgta gattcctgca 20

<210> SEQ ID NO 132
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 132
atcatttttc aggaaagtgt 20

<210> SEQ ID NO 133
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 133
gtgagacaaa tcaagacttc 20

<210> SEQ ID NO 134
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 134
ttagtttact gacactaaga 20

<210> SEQ ID NO 135
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 135
ctgctttatg aaaaaccaac 20

<210> SEQ ID NO 136
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 136
atacctagta caatgtaaat 20

<210> SEQ ID NO 137
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 137
ggcttgtgtg tggtcaatat 20

<210> SEQ ID NO 138
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 138
tgggaaagct ttcaatattc 20

<210> SEQ ID NO 139
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 139
atggaattgt gcttatgagt 20

<210> SEQ ID NO 140
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 140
tttcaagctc aggatgggaa 20

<210> SEQ ID NO 141
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 141
gttggtaaaa tgcaaccaaa 20

<210> SEQ ID NO 142
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 142
tcaggacaca agtaaacctg 20

<210> SEQ ID NO 143

<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 143
tgcaagctgg aaataaaagc 20

<210> SEQ ID NO 144
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 144
tgccaattta aaagtgtagc 20

<210> SEQ ID NO 145
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 145
atatttcaaa atccagtatg 20

<210> SEQ ID NO 146
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 146
ttctgaatat acaaattaat 20

<210> SEQ ID NO 147
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 147
tttactatga aaatctaaat 20

<210> SEQ ID NO 148
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 148
ggtatcctga gtgagatcta 20

<210> SEQ ID NO 149
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 149
ccagctatca ggaaaattcc 20

<210> SEQ ID NO 150
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 150
aaagctattg gagactcaga 20

<210> SEQ ID NO 151
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 151
atggaatctc ttcatttcat 20

<210> SEQ ID NO 152
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 152
atggagacat tcatttccac 20

<210> SEQ ID NO 153
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 153
gctctgagag ttccaattca 20

<210> SEQ ID NO 154
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 154
ctgggaaggt gaatttttag 20

<210> SEQ ID NO 155
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 155
tcaagagtct tcatgctacc 20

<210> SEQ ID NO 156
<211> LENGTH: 20
<212> TYPE: DNA

<213> ORGANISM: Artificial Sequence
<220> FEATURE:
<223> OTHER INFORMATION: synthetic oligonucleotide

<400> SEQUENCE: 156
tcagtttacc tgggatgctg 20

<210> SEQ ID NO 157
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 157
gacattatac tcaccattat 20

<210> SEQ ID NO 158
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 158
gtataaatgt gtcaaattaa 20

<210> SEQ ID NO 159
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 159
gtaaagtttt accttaacct 20

<210> SEQ ID NO 160
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 160
ccataatgaa gaaggaaggg 20

<210> SEQ ID NO 161
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 161
ttaagttaca ttgtagacca 20

<210> SEQ ID NO 162
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 162
tgtgtgggtc ctgaaattct 20

<210> SEQ ID NO 163
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 163
atcttgtaat tacacacccc 20

<210> SEQ ID NO 164
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 164
gtacactctg caacagaagc 20

<210> SEQ ID NO 165
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 165
agggaataac atgaaggccc 20

<210> SEQ ID NO 166
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 166
atccagttca ccattggaga 20

<210> SEQ ID NO 167
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 167
ttttccagaa gagactcttc 20

<210> SEQ ID NO 168
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 168
gtcacattta aaatttccaa 20

<210> SEQ ID NO 169
<211> LENGTH: 20
<212> TYPE: DNA
<213> ORGANISM: Artificial Sequence
<220> FEATURE:

<223> OTHER INFORMATION: synthetic oligonucleotide

<400> SEQUENCE: 169
ttaatatact gcagagaacc 20

<210> SEQ ID NO 170
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 170
agaaatatcc ccagacagag 20

<210> SEQ ID NO 171
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 171
aaatgtcttt gttgcaagcg 20

<210> SEQ ID NO 172
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 172
taaatgtctt tgttgcaagc 20

<210> SEQ ID NO 173
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 173
ataaatgtct ttgttgcaag 20

<210> SEQ ID NO 174
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 174
cataaatgtc tttgttgcaa 20

<210> SEQ ID NO 175
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 175
cacataaatg tctttgttgc 20

<210> SEQ ID NO 176
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 176
ccacataaat gtctttgttg 20

<210> SEQ ID NO 177
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 177
tccacataaa tgtctttgtt 20

<210> SEQ ID NO 178
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 178
gtccacataa atgtctttgt 20

<210> SEQ ID NO 179
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 179
aggtccacat aaatgtcttt 20

<210> SEQ ID NO 180
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 180
taggtccaca taaatgtctt 20

<210> SEQ ID NO 181
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 181
ctaggtccac ataaatgtct 20

<210> SEQ ID NO 182
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 182
tctaggtcca cataaatgtc 20

<210> SEQ ID NO 183
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 183
tgtctaggtc cacataaatg 20

<210> SEQ ID NO 184
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 184
atgtctaggt ccacataaat 20

<210> SEQ ID NO 185
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 185
catgtctagg tccacataaa 20

<210> SEQ ID NO 186
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 186
tcatgtctag gtccacataa 20

<210> SEQ ID NO 187
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 187
cttcatgtct aggtccacat 20

<210> SEQ ID NO 188
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 188
ccttcatgtc taggtccaca 20

<210> SEQ ID NO 189
<211> LENGTH: 20

<212> TYPE: DNA
<213> ORGANISM: Artificial Sequence
<220> FEATURE:
<223> OTHER INFORMATION: synthetic oligonucleotide

<400> SEQUENCE: 189
cccttcatgt ctaggtccac 20

<210> SEQ ID NO 190
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 190
gcccttcatg tctaggtcca 20

<210> SEQ ID NO 191
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 191
atgcccttca tgtctaggtc 20

<210> SEQ ID NO 192
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 192
tatgcccttc atgtctaggt 20

<210> SEQ ID NO 193
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 193
ttatgccctt catgtctagg 20

<210> SEQ ID NO 194
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 194
tttatgccct tcatgtctag 20

<210> SEQ ID NO 195
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 195
tccgtgcatc tttcttggca 20

<210> SEQ ID NO 196
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 196
atccgtgcat ctttcttggc 20

<210> SEQ ID NO 197
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 197
catccgtgca tctttcttgg 20

<210> SEQ ID NO 198
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 198
tcatccgtgc atctttcttg 20

<210> SEQ ID NO 199
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 199
gtcatccgtg catctttctt 20

<210> SEQ ID NO 200
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 200
accgggatga tgagtgcaga 20

<210> SEQ ID NO 201
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 201
aaccgggatg atgagtgcag 20

<210> SEQ ID NO 202
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 202
caaccgggat gatgagtgca 20

<210> SEQ ID NO 203
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 203
gcaaccggga tgatgagtgc 20

<210> SEQ ID NO 204
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 204
gattctttgg gccattcctg 20

<210> SEQ ID NO 205
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 205
agattctttg ggccattcct 20

<210> SEQ ID NO 206
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 206
gagattcttt gggccattcc 20

<210> SEQ ID NO 207
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 207
tgagattctt tgggccattc 20

<210> SEQ ID NO 208
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 208
tttgagattc tttgggccat 20

<210> SEQ ID NO 209
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 209
ctttgagatt ctttgggcca 20

<210> SEQ ID NO 210
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 210
tctttgagat tctttgggcc 20

<210> SEQ ID NO 211
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 211
ttctttgaga ttctttgggc 20

<210> SEQ ID NO 212
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 212
tttctttgag attctttggg 20

<210> SEQ ID NO 213
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 213
cacagtttct ggcaggcctc 20

<210> SEQ ID NO 214
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 214
gcacagtttc tggcaggcct 20

<210> SEQ ID NO 215
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 215
tgcacagttt ctggcaggcc 20

<210> SEQ ID NO 216
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 216
gtgcacagtt tctggcaggc 20

<210> SEQ ID NO 217
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 217
tggtgcacag tttctggcag 20

<210> SEQ ID NO 218
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 218
ttggtgcaca gtttctggca 20

<210> SEQ ID NO 219
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 219
attggtgcac agtttctggc 20

<210> SEQ ID NO 220
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 220
cattggtgca cagtttctgg 20

<210> SEQ ID NO 221
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 221
ggcattggtg cacagtttct 20

<210> SEQ ID NO 222

<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 222
cggcattggt gcacagtttc 20

<210> SEQ ID NO 223
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 223
acggcattgg tgcacagttt 20

<210> SEQ ID NO 224
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 224
gacggcattg gtgcacagtt 20

<210> SEQ ID NO 225
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 225
cggacggcat tggtgcacag 20

<210> SEQ ID NO 226
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 226
gcggacggca ttggtgcaca 20

<210> SEQ ID NO 227
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 227
agcggacggc attggtgcac 20

<210> SEQ ID NO 228
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 228
cagcggacgg cattggtgca 20

<210> SEQ ID NO 229
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 229
ggcagcggac ggcattggtg 20

<210> SEQ ID NO 230
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 230
tggcagcgga cggcattggt 20

<210> SEQ ID NO 231
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 231
ctggcagcgg acggcattgg 20

<210> SEQ ID NO 232
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 232
actggcagcg gacggcattg 20

<210> SEQ ID NO 233
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 233
tgcttgaagg aatatccaga 20

<210> SEQ ID NO 234
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 234
tagttcatgc ccttcatgtc 20

<210> SEQ ID NO 235
<211> LENGTH: 20
<212> TYPE: DNA

<213> ORGANISM: Artificial Sequence
<220> FEATURE:
<223> OTHER INFORMATION: synthetic oligonucleotide

<400> SEQUENCE: 235
tgttatagtt catgcccttc 20

<210> SEQ ID NO 236
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 236
aatgtccctg atacaagcca 20

<210> SEQ ID NO 237
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 237
gggaaaatgt ccctgataca 20

<210> SEQ ID NO 238
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 238
tgtgcagagt cacctgccat 20

<210> SEQ ID NO 239
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 239
ttcttgaacc ctgaagaaag 20

<210> SEQ ID NO 240
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 240
tgaattatca tttcttgaac 20

<210> SEQ ID NO 241
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 241
tgatcatgaa ttatcatttc 20

<210> SEQ ID NO 242
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 242
agtttctggc aggcctcg 18

<210> SEQ ID NO 243
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 243
cagtttctgg caggcctc 18

<210> SEQ ID NO 244
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 244
acagtttctg gcaggcct 18

<210> SEQ ID NO 245
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 245
cacagtttct ggcaggcc 18

<210> SEQ ID NO 246
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 246
gcacagtttc tggcaggc 18

<210> SEQ ID NO 247
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 247
gtgcacagtt tctggcag 18

<210> SEQ ID NO 248
<211> LENGTH: 18
<212> TYPE: DNA
<213> ORGANISM: Artificial Sequence
<220> FEATURE:

<223> OTHER INFORMATION: synthetic oligonucleotide

<400> SEQUENCE: 248
ggtgcacagt ttctggca 18

<210> SEQ ID NO 249
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 249
tggtgcacag tttctggc 18

<210> SEQ ID NO 250
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 250
ttggtgcaca gtttctgg 18

<210> SEQ ID NO 251
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 251
attggtgcac agtttctg 18

<210> SEQ ID NO 252
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 252
cattggtgca cagtttct 18

<210> SEQ ID NO 253
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 253
gcattggtgc acagtttc 18

<210> SEQ ID NO 254
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 254
ggcattggtg cacagttt 18

<210> SEQ ID NO 255
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 255
cggcattggt gcacagtt 18

<210> SEQ ID NO 256
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 256
acggcattgg tgcacagt 18

<210> SEQ ID NO 257
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 257
gacggcattg gtgcacag 18

<210> SEQ ID NO 258
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 258
ggacggcatt ggtgcaca 18

<210> SEQ ID NO 259
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 259
cggacggcat tggtgcac 18

<210> SEQ ID NO 260
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 260
gcggacggca ttggtgca 18

<210> SEQ ID NO 261
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 261
agcggacggc attggtgc 18

<210> SEQ ID NO 262
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 262
cagcggacgg cattggtg 18

<210> SEQ ID NO 263
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 263
gcagcggacg gcattggt 18

<210> SEQ ID NO 264
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 264
ggcagcggac ggcattgg 18

<210> SEQ ID NO 265
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 265
tggcagcgga cggcattg 18

<210> SEQ ID NO 266
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 266
ctggcagcgg acggcatt 18

<210> SEQ ID NO 267
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 267
tgcacagttt ctggcagg 18

<210> SEQ ID NO 268
<211> LENGTH: 16

<212> TYPE: DNA
<213> ORGANISM: Artificial Sequence
<220> FEATURE:
<223> OTHER INFORMATION: synthetic oligonucleotide

<400> SEQUENCE: 268
cacagtttct ggcagg 16

<210> SEQ ID NO 269
<211> LENGTH: 14
<212> TYPE: DNA
<213> ORGANISM: Artificial Sequence
<220> FEATURE:
<223> OTHER INFORMATION: synthetic oligonucleotide

<400> SEQUENCE: 269
acagtttctg gcag 14

<210> SEQ ID NO 270
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 270
gcgtttgctc ttcttcttgc gtttttt 27

<210> SEQ ID NO 271
<211> LENGTH: 23
<212> TYPE: DNA
<213> ORGANISM: Artificial Sequence
<220> FEATURE:
<223> OTHER INFORMATION: primer

<400> SEQUENCE: 271
acacgcatta aaaagagcaa agc 23

<210> SEQ ID NO 272
<211> LENGTH: 26
<212> TYPE: DNA
<213> ORGANISM: Artificial Sequence
<220> FEATURE:
<223> OTHER INFORMATION: primer

<400> SEQUENCE: 272
cagtgtcatg gtaaaatgaa gaatgg 26

<210> SEQ ID NO 273
<211> LENGTH: 25
<212> TYPE: DNA
<213> ORGANISM: Artificial Sequence
<220> FEATURE:
<223> OTHER INFORMATION: probe

<400> SEQUENCE: 273
tgcaggcaca gcatcccagt gttct 25

<210> SEQ ID NO 274
<211> LENGTH: 3275
<212> TYPE: DNA
<213> ORGANISM: Macaca mulatta
<220> FEATURE:
<221> NAME/KEY: misc_feature
<222> LOCATION: (1)..(3275)
<223> OTHER INFORMATION: n = A,T,C or G

<400> SEQUENCE: 274

```
aggcacacag acaaaatcaa gctctacagc tgtctgtgtg tatgtcactt gtttgaatat      60
gaattaaaat taaaatataa attcaatgta ttgagaaagc aagcaattct ctcaaggtat     120
atttctgaca tactaagatt ttaacgactt tcacaaatat gctgcaccga gagacaatgt     180
tacacaacac tgagaaccag tacaagtaaa tattaaagtt aagtgaccat ttcctacaca     240
cgctcattca gaggaggatg aggatcaatt tggaagaaga aaaacaccct tattaagaat     300
tgcagcaaat aagcaaacga ggtcttttca ggatgatttt cttatatcaa atggtacatt     360
tcattctatt tacgtcagtt tctggtgaat gtgtgactcg gttgttcaag gacatccact     420
ttgaaggagg ggacattgct acggttttca caccaagcgc caagcactgc caggtggtct     480
gcactcacca cccacgatgt ctgctcttca ctttcacggg ggaatctgca tctgaggatc     540
ctacccagtg gtttacttgt gtcctgaagg acagtgttac agaaacactg ccaagagtga     600
ataggacagg agcgatttct gggtattctt tcaagcaatg ctcacaccaa ataagcgctt     660
gcaacaaaga catttatgtg gacctagaca tgaagggcat aaactataac agctcacttg     720
ccaagagtgc tcaagaatgc caagaaagat gcacggatga catccactgc cactttttca     780
cgtatgccac aaggcagttt cccagtctgg agcatcgtaa catttgtcta ctgaagcaca     840
cccaaacggg gacaccaacc ggaataatga agctcgataa agtggtgact ggattttcac     900
tgaaatcctg tgcactttct aatctggctt gtatcaggga cgttttcccc aacacggtgt     960
ttgcggacag caacatcgat agtgtcatgg ctccagatgc ctttgtctgt cgccggatct    1020
gcactcatca tcccggttgc ttgtttttta ccttcttttc ccaggaatgg cccaaagaat    1080
ctcaaagaaa tctttgtctc cttaaaacat ctgagagtgg attacccagt acacgcatta    1140
aaaagagcaa agctctttct ggtttcagtc tccaaagctg caggcacagc atcccagtgt    1200
tctgccattc ttcattttac catgacactg atttcttggg agaagaactg gatattgttg    1260
ctgtgaaagg tcacgaggcc tgccagaaac tgtgcaccaa tgccgtccgc tgccagtttt    1320
ttacctatgc cccagctcaa gcatcttgca acgaagggaa gggcaaatgt tacttaaagc    1380
tttcttcaaa tggatctcca actaaaatac ttcgcgggac aggaggcatc tctggataca    1440
cattaaggct gtgtaaaatg gataatgagt gtaccaccaa aatcaagccc aggatcgttg    1500
gaggaactgc atctgttcgt ggtgagtggc catggcaggt gactctgcac accacctcac    1560
ccactcagag acacctgtgt ggaggctcca tcattggaaa ccagtggata ttaacggccg    1620
ctcactgttt ctatggggta gagtcaccta agattttgcg tgtctacatt ggcattttaa    1680
atcaatctga aataaaagag gatacatctt tctttggggt tcaagaaata ataatccatg    1740
atcaatataa aatggcagaa agtgggtatg atattgcctt gttgaaactg gaaaccacag    1800
tgaattacac agattctcaa cgacccatat gcctgccttc aaaaggagat agaaatgtga    1860
tatacactga ctgctgggtg actggatggg ggtacagaaa attaagagac aaaatacaga    1920
atactctcca gaaagccaag atacccttag tgaccaatga cgagtgccag aagagataca    1980
gaggacataa aataacccat aagatgatct gtgccggcta cagggaagga gggaaggatg    2040
cttgcaagnn nnnnnnnnnn nnnnnnnnnn nnnnnnnnnn nnnnnnnnnn nnnnnnnnnn    2100
nnnnnnnnnn nnnnnnnnnn nnnnnnnnnn nnnnnnnnnn nnnnnnnnnn nnnnnnnnnn    2160
nnnnnnnnnn nnnnnnnnnn nnnnnnnnnn nnnnnnnnnn nnnnnnnnnn nnnnnnnnnn    2220
nnnnnnnnnn nnnnnnnnnn nnnnnnnnnn nnnnnnnnnn nnnnnnnnnn nnnnnnnnnn    2280
nnnnnnnnnn nnnnnnnnnn nnnnnnnnnn nnnnnnnngc ttggtgctgg taggaaaatg    2340
```

-continued

```
ccagaagaaa acaaactgtc acaagctgtt atgtccaaag ctcccgttct atgatcattg   2400

tagtttgttt cagcatccag tgtctttgtt tctgatcacg cttctaagga gtccaagaat   2460

taccataagg caatatttct gatgattact atataggcag atatatcaga aaataaccaa   2520

gtagtggcag cagggatcag gtagaagaac tgataaaaga aaccaccata aatagatttg   2580

ttcaatgaaa aatgaaaact ggaagaaagg ataacaaaga cagtcttcac cattttgcag   2640

gaatctacac tctgcctgtg tgaacacatt tctttgtaaa gaaagaattt gattgcattt   2700

actggcagat tttcagaata gtcaggaatt catgttattt ccattttaaa acatgtttaa   2760

aaaaatcagt ttgagtagac acaagctaag agtgaatgtg aaggtaccag aatttctgta   2820

tggaagaggg tgacaagcag caatgtacct ggaagtggta ccttaggacc aatcttaaag   2880

atacactttc ctgaaaaatg atttgtgatg gatcgtatat ttatttaaaa tatcttggga   2940

gggagaggct gatggcgata gggaggcaag ctgaagcctc cataagacaa gctgctactg   3000

cgactgtggc ccccaaagag ctacaccgca tatttatttg acaaaagtca ccattgacta   3060

catccgtact acagagaaaa aacaatttgg gcacaaatgg atggttacag taaagtcttc   3120

agcaagcagc tccctgtatt ctaagtactg ggcttttctg tttggtgcaa atatttatct   3180

cattattgct gtgatctagt ccagtaacct agaatttgat ttgtcaccac atagctttca   3240

acctgtgcca acaattatac aattcatcaa gtgtg                              3275
```